United States Patent
Ichinohe et al.

(10) Patent No.: US 11,788,076 B2
(45) Date of Patent: *Oct. 17, 2023

(54) FULL REPLACEMENT TECHNIQUE FOR T CELL RECEPTOR USING PLATINUM TALEN

(71) Applicants: Hiroshima University, Higashi-Hiroshima (JP); Repertoire Genesis Incorporation, Ibaraki (JP)

(72) Inventors: Tatsuo Ichinohe, Hiroshima (JP); Takashi Yamamoto, Higashi-Hiroshima (JP); Tetsushi Sakuma, Higashi-Hiroshima (JP); Yasuko Honjo, Hiroshima (JP); Takakazu Kawase, Hiroshima (JP); Takahiko Miyama, Hiroshima (JP); Ryuji Suzuki, Ibaraki (JP)

(73) Assignees: Hiroshima University, Higashi-Hiroshima (JP); Repertoire Genesis Incorporation, Ibaraki (JP)

( * ) Notice: Subject to any disclaimer, the term of this patent is extended or adjusted under 35 U.S.C. 154(b) by 574 days.

This patent is subject to a terminal disclaimer.

(21) Appl. No.: 16/755,074

(22) PCT Filed: Oct. 9, 2018

(86) PCT No.: PCT/JP2018/037590
§ 371 (c)(1),
(2) Date: Apr. 9, 2020

(87) PCT Pub. No.: WO2019/073964
PCT Pub. Date: Apr. 18, 2019

(65) Prior Publication Data
US 2020/0362323 A1 Nov. 19, 2020

(30) Foreign Application Priority Data

Oct. 10, 2017 (JP) .................. 2017-197010
Sep. 7, 2018 (JP) .................. 2018-167954

(51) Int. Cl.
C12N 9/22 (2006.01)
C12N 15/64 (2006.01)
C07K 19/00 (2006.01)

(52) U.S. Cl.
CPC ............ *C12N 9/22* (2013.01); *C12N 15/64* (2013.01); *C07K 19/00* (2013.01); *C07K 2319/81* (2013.01)

(58) Field of Classification Search
CPC ..................................................... C12N 9/22
See application file for complete search history.

(56) References Cited

U.S. PATENT DOCUMENTS

2016/0186151 A1 6/2016 Yamamoto et al.
2016/0289760 A1 10/2016 Suzuki et al.

FOREIGN PATENT DOCUMENTS

| EP | 3091074 A1 | 11/2016 |
|----|-----------|---------|
| JP | 2015-528298 A | 9/2015 |
| JP | 5931022 B2 | 5/2016 |
| JP | 2016-515822 A | 6/2016 |
| JP | 2016-520320 A | 7/2016 |
| WO | 2006/026002 A2 | 3/2006 |
| WO | 2011/139371 A1 | 11/2011 |
| WO | 2014/039523 A1 | 3/2014 |
| WO | 2014/153470 A2 | 9/2014 |
| WO | 2014/191527 A1 | 12/2014 |
| WO | 2015/075939 A1 | 5/2015 |
| WO | 2016/069282 A1 | 5/2016 |
| WO | 2017/044672 A1 | 3/2017 |
| WO | 2017/070429 A1 | 4/2017 |

OTHER PUBLICATIONS

Studer. Residue mutations and their impact on protein structure and function: detecting beneficial and pathogenic changes. Biochem. J. (2013) 449, 581-594.*
Adair et al., "Human Tregs Made Antigen Specific by Gene Modification: The Power to Treat Autoimmunity and Antidrug Antibodies with Precision," *Front Immunol* 8:1117, 10 pages.
Honjo et al., "T-cell receptor gene editing by transcription activator-like effector nuclease (TALEN) as a novel tool for adoptive T-cell immunotherapy," *Journal of Germfree Life and Gnotobiology* 47(1), 5 pages, 2017.
Hull et al., "Generation of human islet-specific regulatory T cells by TCR gene transfer," *Journal of Autoimmunity* 79:63-73, 2017.
Mastaglio et al., "NY-ESO-1 TCR single edited stem and central memory T cells to treat multiple myeloma without graft-versus-host disease," *Blood* 130(5):606-618, 2017.
Miyama et al., "OS2-11B-2 TALEN-mediated T-cell receptor gene editing as a novel tool for adoptive T-cell immunotherapy," *Proceedings of the Fiftieth Annual Meeting of the Japanese Association of Germfree Life and Gnotobiology*, Tokyo, Japan, Jun. 7-10, 2017, 3 pages.
Sakuma et al., "Repeating pattern of non-RVD variations in DNA-binding modules enhances TALEN activity," *Scientific Reports* 3:3379, 2013, 8 pages.
Sakuma et al., "Engineering Customized TALENs Using the Platinum Gate TALEN Kit," *TALENs: Methods and Protocols, Methods in Molecular Biology* 1338, 11 pages, 2016.
Wright et al., "Adoptive therapy with redirected primary regulatory T cells results in antigen-specific suppression of arthritis," *PNAS* 106(45):19078-19083, 2009.

(Continued)

*Primary Examiner* — Yong D Pak
(74) *Attorney, Agent, or Firm* — Seed IP Law Group LLP

(57) ABSTRACT

The present disclosure provides a technique whereby the influence of an endogenous TCR is eliminated in TCR gene transfer. A TCR gene is edited using a genome editing enzyme, said genome editing enzyme having one characteristic that amino acids at two specific positions in DNA-binding modules contained in a DNA-binding domain thereof show repeating patterns which differ from one module to another among the four DNA-binding modules. Thus, a lowering in the expression efficiency of the transferred TCR caused by mispairing with an endogenous TCR and the occurrence of a self-reactive TCR are avoided.

5 Claims, 28 Drawing Sheets

Specification includes a Sequence Listing.

(56) References Cited

OTHER PUBLICATIONS

Genovese et al., "Abstract 209, TCR Gene Editing in a Single Step of T Cell Activation to Redirect T Cell Specificity and Prevent GvHD," *Abstracts of the ASGCT 18th Annual Meeting, Molecular Therapy* 23(1):s82-s83, May 2015.
Provasi et al., "Editing T cell specificity towards leukemia by zinc finger nucleases and lentiviral gene transfer," *Nature Medicine* 18(5), doi:10.1038/nm.2700, 11 pages, 2012.

\* cited by examiner

FULL REPLACEMENT TECHNIQUE FOR T CELL RECEPTOR USING PLATINUM TALEN

STATEMENT REGARDING SEQUENCE LISTING

The Sequence Listing associated with this application is provided in text format in lieu of a paper copy, and is hereby incorporated by reference into the specification. The name of the text file containing the Sequence Listing is 790132_405USPC_SEQUENCE_LISTING.txt. The text file is 268 KB, was created on Jun. 10, 2020, and is being submitted electronically via EFS-Web.

TECHNICAL FIELD

The present invention relates to a biotechnology engineering of T cells.

BACKGROUND ART

Demand for an antigen-specific T cell receptor (TCR) gene introduction technology as means for adoptive immunotherapy of effector T cells (Teff) against malignant tumor or viral infections has been increasing in recent years. However, the effect of co-expression of TCRs endogenous to T cells and newly introduced TCRs cannot be completely avoided with conventional developed methods.

Regulatory T cells (Treg) are a cell population that is mainly responsible for immune response regulation in vivo. While regulatory action thereof was considered nonspecific to antigens, the presence of antigen-specific Tregs exerting immunoregulatory action in response to a specific autoantigen or alloantigen has been elucidated in recent years. It is reported that antigen specific Tregs are more effective than conventional Tregs in an autoimmune disease model. However, a technology for manufacturing a Treg specific to any desired antigen, which introduces an exogenous TCR into a Treg while preventing the effect of co-expression with an endogenous TCR, has not been developed.

SUMMARY OF INVENTION

Solution to Problem

One aspect of the present disclosure provides a genome editing enzyme modified TALEN for editing an endogenous TCR gene or a composition comprising the same. T cells that do not express an endogenous TCR can be made by editing and cleaving an endogenous TCR gene with a modified TALEN. One embodiment uses a TALEN known as a Platinum TALEN as a modified TALEN. One feature of a Platinum TALEN is in amino acids at two specific positions in DNA binding modules in a DNA binding domain thereof exhibiting different repeat forms for each of the four DNA binding modules. A Platinum TALEN is characterized by having both high functionality by a functional domain and a high recognition specificity to a DNA sequence.

One aspect of the present disclosure provides a method comprising removing an endogenous TCR gene in a regulatory T cell using the modified TALEN of the invention. For example, a TCR gene of a Treg separated from peripheral blood can be cleaved using a modified TALEN to suppress the expression of an endogenous TCR. The modified TALEN of the invention can more thoroughly suppress the expression of an endogenous TCR with a high cleavage efficiency, and can suppress the risk of an off-target gene modification in a T cells low due to high recognition specificity of a sequence.

One aspect of the present disclosure can provide a method comprising introducing a TCR gene into a Treg with an endogenous TCR gene removed with the modified TALEN of the invention. The modified TALEN of the invention can be considered useful when introducing a new TCR together with editing of a TCR in view of the properties described above. Therefore, a Treg expressing a TCR exhibiting a high binding ability specifically to a desired antigen, can be made.

One aspect in the present disclosure provides a composition of a kit for editing a TCR gene. Another aspect provides a composition or a kit for manufacturing a TCR modified T cell.

The present disclosure also provides a T cell (e.g., regulatory T cell) manufactured using the method of the present disclosure. Such a regulatory T cell is useful in various situations where immune suppression is desirable. For example, the regulatory T cell of the invention can be used in the treatment or prevention of an autoimmune disease, allergic disease, or graft-versus-host disease (GVHD), rejection, or graft failure in transplantation. The present disclosure also provides an article for use in the method of the present disclosure.

The modified TALEN of the present disclosure is also useful in use in a method with the following features in view of the properties described above. The modified TALEN of the invention is useful in use in a method for expressing a T cell receptor (TCR) of an effector T cell in a T cell (e.g., regulatory T cell). In one embodiment, the method of the present disclosure comprises introducing a full or partial TCR gene into a regulatory T cell so that TCRα and TCRβ are expressed as a pair. A TCR with a high antigen binding capability can be identified and/or isolated and used in introduction into a T cell in an effector T cell responsive to a desired antigen. One feature of one embodiment of the present disclosure is to express only a TCR with high antigen binding capability obtained from an effector T cell (Teff) responsive to a desired antigen in a regulatory T cell (Treg) with a deletion of an endogenous TCR by the modified TALEN of the present disclosure. A TCR with a high antigen binding capability can be identified based on a frequency of T cell receptor (TCR) clones that are present in an effector T cell population specific to an antigen. For identification of a TCR, a method of measuring a TCR repertoire comprising unbiasedly amplifying a nucleic acid sequence of the TCR can be used. In the present disclosure, a method of identifying and/or isolating a pair of TCRα and TCRβ with a high antigen binding capability can be used. For example, an effector T cell (Teff) group that is specifically responsive to a desired antigen can be separated using n HLA tetramer or the like to obtain a gene sequence comprising an antigen recognition region of a TCRα chain/TCRβ chain expressed thereby. Furthermore, the binding capability to a desired antigen of each obtained TCR clonotype can be evaluated.

For example, the present disclosure provides the following inventions.

(Item 1)

A composition for editing a TCR gene, comprising a polypeptide comprising a DNA binding domain and a functional domain or a nucleic acid encoding the polypeptide, wherein the DNA binding domain and the functional domain are connected by a polypeptide consisting of 35 to 55 amino acids, the DNA binding domain comprises a plurality of DNA binding modules consecutively from the N-terminal side, a combination of the xth amino acid and the yth amino acid in the 4n−3th DNA binding module from the N-terminus being identical for any n, a combination of the xth amino acid and the yth amino acid in the 4n−2th DNA binding module from the N-terminus being identical for any n, a combination of the xth amino acid and the yth amino acid in the 4n−1th DNA binding module from the N-terminus being identical for any n, and a combination of the xth amino acid and the yth amino acid in the 4nth DNA binding module from the N-terminus being identical for any n, the combination of the xth amino acid and the yth amino acid in the 4n−3th DNA binding module from the N-terminus, the combination of the xth amino acid and the yth amino acid in the 4n−2th DNA binding module from the N-terminus, the combination of the xth amino acid and the yth amino acid in the 4n−1th DNA binding module from the N-terminus, and the combination of the xth amino acid and the yth amino acid in the 4nth DNA binding module from the N-terminus are different from one another, and n is a natural number from 1 to 10, x is a natural number from 1 to 40, y is a natural number from 1 to 40, and x and y are different natural numbers.

(Item 2)

The composition of the preceding item, wherein the DNA binding domain and the functional domain are connected by a polypeptide consisting of 40 to 50 amino acids, the DNA binding domain comprises 16 to 20 DNA binding modules consisting of 34 amino acids consecutively from the N-terminal side, a combination of the 4th amino acid and the 32nd amino acid in the 4n−3th DNA binding module from the N-terminus being identical for any n, a combination of the 4th amino acid and the 32nd amino acid in the 4n−2th DNA binding module from the N-terminus being identical for any n, a combination of the 4th amino acid and the 32nd amino acid in the 4n−1th DNA binding module from the N-terminus being identical for any n, and a combination of the 4th amino acid and the 32nd amino acid in the 4nth DNA binding module from the N-terminus being identical for any n, the combination of the 4th amino acid and the 32nd amino acid in the 4n−3th DNA binding module from the N-terminus, the combination of the 4th amino acid and the 32nd amino acid in the 4n−2th DNA binding module from the N-terminus, the combination of the 4th amino acid and the 32nd amino acid in the 4n−1th DNA binding module from the N-terminus, and the combination of the 4th amino acid and the 32nd amino acid in the 4nth DNA binding module from the N-terminus are different from one another, n is a natural number from 1 to 5, and an origin of the DNA binding domain is TALE.

(Item 3)

The composition of any one of the preceding items, wherein the functional domain is a DNA cleaving domain.

(Item 4)

The composition of any one of the preceding items, wherein the DNA binding domain binds specifically to a gene of TCRα or a gene of TCRβ.

(Item 5)

The composition of any one of the preceding items, wherein the DNA binding domain specifically binds to TRAC exon 1, TRBC1 exon 1, or TRBC2 exon 1.

(Item 6)

The composition of any one of the preceding items, wherein the DNA binding domain specifically binds to the nucleic acid sequence of SEQ ID NO: 80, the nucleic acid sequence of SEQ ID NO: 81, the nucleic acid sequence of SEQ ID NO: 82, the nucleic acid sequence of SEQ ID NO: 83, the nucleic acid sequence of SEQ ID NO: 84, or the nucleic acid sequence of SEQ ID NO: 85.

(Item 7)

The composition of any one of the preceding items, comprising an expression vector comprising the nucleic acid encoding the polypeptide.

(Item 8)

The composition of any one of the preceding items, wherein the nucleic acid encoding the polypeptide is comprised in a form of an mRNA.

(Item 9)

A method of editing a TCR gene, comprising introducing the composition of any one of the preceding items into a cell.

(Item 10)

The method of the preceding items, comprising:

introducing into a cell the composition of any one of the preceding items wherein the DNA binding domain specifically binds to a gene of TCRα; and introducing into a cell the composition of any one of the preceding items wherein the DNA binding domain specifically binds to a gene of TCRβ.

(Item 11)

The method of any one of the preceding items, wherein the editing of a TCR gene is removal of an endogenous TCR gene.

(Item A1)

The method of any one of the preceding items, further comprising introducing an exogenous TCR gene into the cell.

(Item A1-1)

The method of any one of the preceding items, wherein the introducing comprises knocking in the exogenous TCR gene into a genome of the cell via microhomology mediated end joining (MMEJ).

(Item A1-2)

The method of any one of the preceding items, wherein the introducing comprises introducing a vector encoding the exogenous TCR gene into the cell.

(Item A2)

The method of any one of the preceding items, wherein the exogenous TCR has specificity to NY-ESO-1.

(Item A3)

A TCR modified T cell, manufactured by the method of any one of the preceding items.

(Item A4)

A composition comprising the TCR modified T cell of any one of the preceding items for treating cancer in a subject.

(Item A5)

The composition of any one of the preceding items, wherein the cancer is NY-ESO-1 positive cancer.

(Item 12)

A composition for editing a TCR gene, comprising a nucleic acid encoding a polypeptide comprising a DNA binding domain, wherein the DNA binding domain comprises a plurality of DNA binding modules consecutively from the N-terminal side, a combination of the xth amino acid and the yth amino acid in the 4n−3th DNA binding module from the N-terminus being identical for any n, a combination of the xth amino acid and the yth amino acid in the 4n−2th DNA binding module from the N-terminus being identical for any n, a combination of the xth amino acid and the yth amino acid in the 4n−1th DNA binding module from the N-terminus being identical for any n, and a combination of the xth amino acid and the yth amino acid in the 4nth DNA binding module from the N-terminus being identical for any n, the combination of the xth amino acid and the yth amino acid in the 4n−3th DNA binding module from the N-terminus, the combination of the xth amino acid and the yth amino acid in the 4n−2th DNA binding module from the N-terminus, the combination of the xth amino acid and the yth amino acid in the 4n−1th DNA binding module from the N-terminus, and the combination of the xth amino acid and the yth amino acid in the 4nth DNA binding module from the N-terminus are different from one another, n is a natural number from 1 to 10, x is a natural number from 1 to 40, y is a natural number from 1 to 40, and x and y are different natural numbers, and the composition is used in combination with a nucleic acid encoding a polypeptide comprising a functional domain.

(Item 12A)

The composition of the preceding item, having a feature of any one or more of the preceding items.

(Item 13)

A composition for editing a TCR gene, comprising a nucleic acid encoding a polypeptide comprising a functional domain, the composition characterized by being used in combination with a nucleic acid encoding a polypeptide comprising a DNA binding domain, wherein the DNA binding domain comprises a plurality of DNA binding modules consecutively from the N-terminal side, a combination of the xth amino acid and the yth amino acid in the 4n−3th DNA binding module from the N-terminus being identical for any n, a combination of the xth amino acid and the yth amino acid in the 4n−2th DNA binding module from the N-terminus being identical for any n, a combination of the xth amino acid and the yth amino acid in the 4n−1th DNA binding module from the N-terminus being identical for any n, and a combination of the xth amino acid and the yth amino acid in the 4nth DNA binding module from the N-terminus being identical for any n, the combination of the xth amino acid and the yth amino acid in the 4n−3th DNA binding module from the N-terminus, the combination of the xth amino acid and the yth amino acid in the 4n−2th DNA binding module from the N-terminus, the combination of the xth amino acid and the yth amino acid in the 4n−1th DNA binding module from the N-terminus, and the combination of the xth amino acid and the yth amino acid in the 4nth DNA binding module from the N-terminus are different from one another, and n is a natural number from 1 to 10, x is a natural number from 1 to 40, y is a natural number from 1 to 40, and x and y are different natural numbers.

(Item 13A)

The composition of the preceding item, having a feature of any one or more of the preceding items.

(Item 14)

A combination for editing a TCR gene, comprising a nucleic acid encoding a polypeptide comprising a DNA binding domain and a nucleic acid encoding a polypeptide comprising a functional domain, wherein the DNA binding domain comprises a plurality of DNA binding modules consecutively from the N-terminal side, a combination of the xth amino acid and the yth amino acid in the 4n−3th DNA binding module from the N-terminus being identical for any n, a combination of the xth amino acid and the yth amino acid in the 4n−2th DNA binding module from the N-terminus being identical for any n, a combination of the xth amino acid and the yth amino acid in the 4n−1th DNA binding module from the N-terminus being identical for any n, and a combination of the xth amino acid and the yth amino acid in the 4nth DNA binding module from the N-terminus being identical for any n, the combination of the xth amino acid and the yth amino acid in the 4n−3th DNA binding module from the N-terminus, the combination of the xth amino acid and the yth amino acid in the 4n−2th DNA binding module from the N-terminus, the combination of the xth amino acid and the yth amino acid in the 4n−1th DNA binding module from the N-terminus, and the combination of the xth amino acid and the yth amino acid in the 4nth DNA binding module from the N-terminus are different from one another, and n is a natural number from 1 to 10, x is a natural number from 1 to 40, y is a natural number from 1 to 40, and x and y are different natural numbers (Item 14A)

The combination of the preceding item, having a feature of any one or more of the preceding items.

(Item 15)

A polypeptide comprising a DNA binding domain and a functional domain, wherein the DNA binding domain and the functional domain are connected by a polypeptide consisting of 35 to 55 amino acids, the DNA binding domain comprises a plurality of DNA binding modules consecutively from the N-terminal side, a combination of the xth amino acid and the yth amino acid in the 4n−3th DNA binding module from the N-terminus being identical for any n, a combination of the xth amino acid and the yth amino acid in the 4n−2th DNA binding module from the N-terminus being identical for any n, a combination of the xth amino acid and the yth amino acid in the 4n−1th DNA binding module from the N-terminus being identical for any n, and a combination of the xth amino acid and the yth amino acid in the 4nth DNA binding module from the N-terminus being identical for any n, the combination of the xth amino acid and the yth amino acid in the 4n−3th DNA binding module from the N-terminus, the combination of the xth amino acid and the yth amino acid in the 4n−2th DNA binding module from the N-terminus, the combination of the xth amino acid and the yth amino acid in the 4n−1th DNA binding module from the N-terminus, and the combination of the xth amino acid and the yth amino acid in the 4nth DNA binding module from the N-terminus are different from one another, n is a natural number from 1 to 10, x is a natural number from 1 to 40, y is a natural number from 1 to 40, and x and y are different natural numbers, and the DNA binding domain specifically binds to a gene of TCRα or a gene of TCRβ.

(Item 15A)

The polypeptide of the preceding item, having a feature of any one or more of the preceding items.

(Item 16)

The polypeptide of any one of the preceding items, wherein the DNA binding domain and the functional domain are connected by a polypeptide consisting of 40 to 50 amino acids, the DNA binding domain comprises 16 to 20 DNA binding modules consisting of 34 amino acids consecutively from the N-terminal side, a combination of the 4th amino acid and the 32nd amino acid in the 4n−3th DNA binding module from the N-terminus being identical for any n, a combination of the 4th amino acid and the 32nd amino acid in the 4n−2th DNA binding module from the N-terminus being identical for any n, a combination of the 4th amino acid and the 32nd amino acid in the 4n−1th DNA binding module from the N-terminus being identical for any n, and a combination of the 4th amino acid and the 32nd amino acid in the 4nth DNA binding module from the N-terminus being identical for any n, the combination of the 4th amino acid and the 32nd amino acid in the 4n−3th DNA binding module from the N-terminus, the combination of the 4th amino acid and the 32nd amino acid in the 4n−2th DNA binding module from the N-terminus, the combination of the 4th amino acid and the 32nd amino acid in the 4n−1th DNA binding module from the N-terminus, and the combination of the 4th amino acid and the 32nd amino acid in the 4nth DNA binding module from the N-terminus are different from one another, n is a natural number from 1 to 5, and an origin of the DNA binding domain is TALE.

(Item 17)

The polypeptide of any one of the preceding items, wherein the functional domain is a DNA cleaving domain.

(Item 18)

The polypeptide of any one of the preceding items, wherein the DNA binding domain specifically binds to TRAC exon 1, TRBC1 exon 1, or TRBC2 exon 1.

(Item 19)

The polypeptide of any one of the preceding items, wherein the DNA binding domain specifically binds to the nucleic acid sequence of SEQ ID NO: 80, the nucleic acid sequence of SEQ ID NO: 81, the nucleic acid sequence of SEQ ID NO: 82, the nucleic acid sequence of SEQ ID NO: 83, the nucleic acid sequence of SEQ ID NO: 84, or the nucleic acid sequence of SEQ ID NO: 85.

(Item 20)

The polypeptide of any one of the preceding items, wherein the DNA binding domain comprises the amino acid sequence of SEQ ID NO: 86, the amino acid sequence of SEQ ID NO: 87, the amino acid sequence of SEQ ID NO: 88, the amino acid sequence of SEQ ID NO: 89, the amino acid sequence of SEQ ID NO: 90, or the amino acid sequence of SEQ ID NO: 91.

(Item 21)

A nucleic acid encoding the entirety or a part of the polypeptide of any one of the preceding items.

(Item 22)

A kit for editing a TCR gene, comprising:

the composition of any one of the preceding items or the combination of any of the preceding items; and means for checking for a mutation in an endogenous TCR gene and/or means for checking for removal of an endogenous TCR gene.

(Item 23)

A kit for editing a TCR gene, comprising:

the composition of any one of the preceding items or the combination of any of the preceding items; and means for introducing an exogenous TCR gene and/or means for detecting a cell introduced with a gene.

(Item 24)

The kit of any one of the preceding items for substituting an endogenous TCR gene with an exogenous TCR gene.

(Item 25)

The kit of any one of the preceding items for the manufacture of a TCR modified regulatory T cell.

(Item 25A)

The kit of the preceding item, having a feature of any one or more of the preceding items.

(Item B1)

The kit of any one of the preceding items for the manufacture of a TCR modified T cell expressing an exogenous TCR with specificity to NY-ESO-1.

(Item X)

A cell population of cells comprising an exogenous TCR of interest, wherein a ratio of cells comprising an exogenous TCR other than the exogenous TCR of interest is less than 10% in the cell population.

(Item X1)

The cell population of any one of the preceding items, wherein the exogenous TCR has specificity to NY-ESO-1.

(Item X2)

A method of creating the cell population of any one of the preceding items, comprising:

removing an endogenous TCR from a cell; and introducing a nucleic acid encoding the exogenous TCR into the cell with the endogenous TCR removed.

(Item X2-1)

The method of any one of the preceding items, wherein the introducing comprises knocking in the exogenous TCR gene into a genome of the cell via microhomology mediated end joining (MMEJ).

(Item X2-2)

The method of any one of the preceding items, wherein the introducing comprises introducing a vector encoding the exogenous TCR gene into the cell.

(Item X3)

The method of any one of the preceding items, wherein the exogenous TCR has specificity to NY-ESO-1.

The present disclosure is intended so that one or more of the features can be provided not only as the explicitly disclosed combinations, but also as other combinations thereof. Additional embodiments and advantages of the present disclosure are recognized by those skilled in the art by reading and understanding the following detailed description, as needed.

Advantageous Effects of Invention

It is possible to reduce or avoid the decrease in the expression efficiency of an introduced TCR or manifestation of a self-reactive TCR due to mispairing with an endogenous TCRα chain or TCR chain in a T cell, whereby a specific TCR gene can be introduced into a T cell (e.g., human T cell) to express a desired TCR.

DESCRIPTION OF EMBODIMENTS

Figure 1:
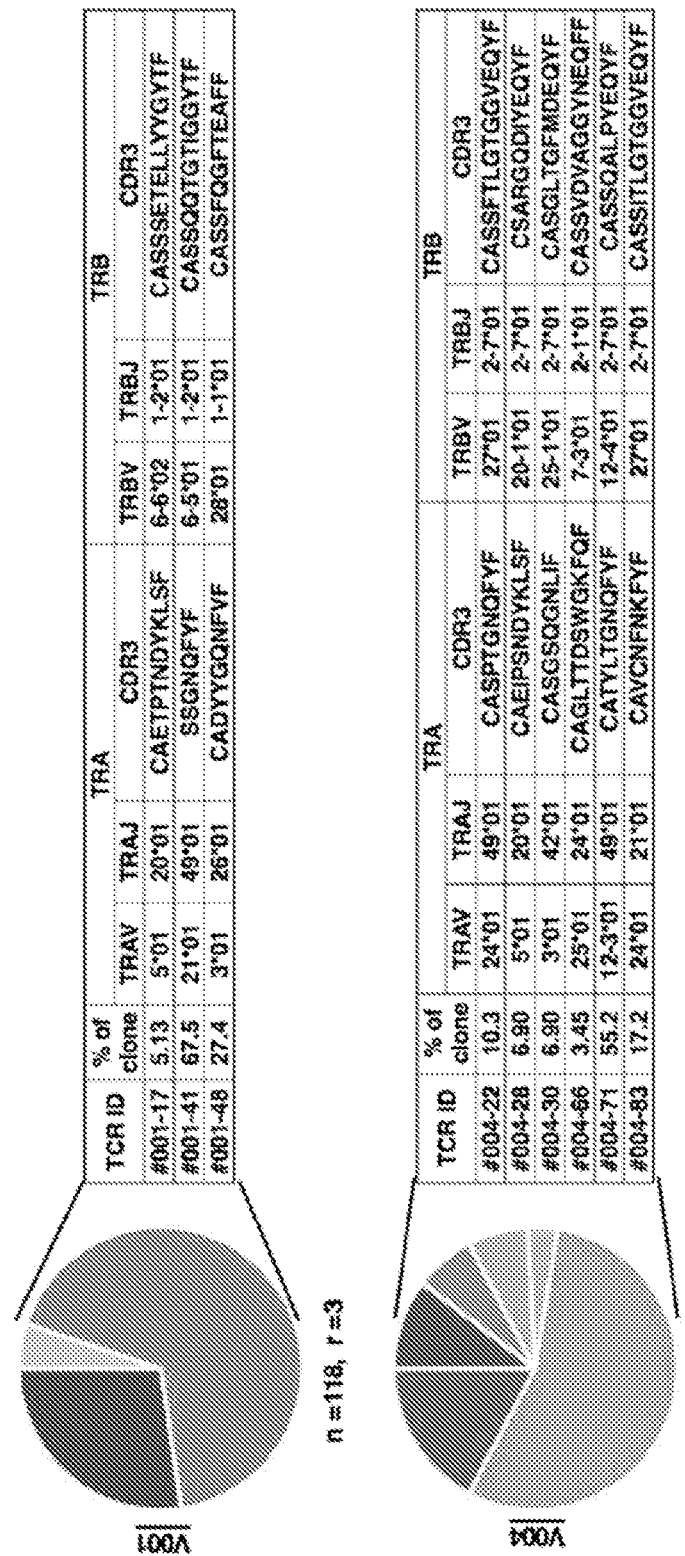
FIG. 1 is a diagram showing CMV NLV specific TCRα and TCRβ repertoires of a single cell. The figure shows a pair of CMV NLV specific TCRα and TCRβ of cells obtained from two HLA A2 antigen positive and CMV antibody positive healthy donors (V001 and V004). 118 and 29 T cells were analyzed from V001 and V004, respectively, and three types (TCR ID; 001-17, 48, and 41) and six types (TCR ID; 004-66, 22, 63, 30, 28, and 71) of respective CDR3a and CDR3β pairs were identified. CDR3 sequences corresponds to SEQ ID NO: 93 to 110, respectively.

The present invention is explained hereinafter while showing the best mode of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

1. Definitions and Explanation of Basic Technologies

The definitions of the terms and/or details of the basic technologies that are especially used herein are explained hereinafter as appropriate.

As used herein, "effector T cell" refers to a differentiated and activated T cell that recognizes an antigen presented by an antigen presenting cell such as a B cell, macrophage, or dendritic cell via a T cell receptor. An effector T cell is also denoted herein as "Teff" or the like.

As used herein, "regulatory T cell" is a CD4 positive T cell exhibiting immunosuppressive action with positive Foxp3 expression. A regulatory T cell is also referred to as "Treg" herein. CD25 strong positive and CD127 expression weak positive can also be used as an indicator of a regulatory T cell. Treg is roughly classified into endogenous T cells (Naturally Occurring Regulatory T cell; nTreg) and inducible T cells with low self-recognition capability differentiated from naïve CD4 positive T cells (Inducible Regulatory T cell; iTreg).

As used herein, "flow cytometry" refers to a technology for measuring the number and individual physical/chemical/biological attributes of a cell, individual, and other biological particles suspended in a liquid. An apparatus using this technology is referred to as a "flow cytometer".

As used herein, "clonotype" refers to a recombinant sequence derived from a T cell or a B cell encoding a T cell receptor or an immunoglobulin molecule or a portion thereof. While, the genomic sequences of normal somatic cells are the same in an individual, the sequence is rearranged in each cell in a coding sequence of a T cell or B cell receptor, so that there are a plurality of clonotypes in T cells or B cells in an individual.

As used herein a "dominant" clone refers to a clone in a clone population with the greater frequency than a certain threshold value that can be appropriately determined by those skilled in the art.

As used herein, "T cell receptor (TCR)" refers to a receptor in a T cell. A TCR is a heterodimer receptor molecule consisting of two TCR polypeptide chains. There are αβ TCRs expressed in normal T cells and γδ TCRs with a special function. α and β chain TCR molecules form a complex with a plurality of CD3 molecules (CD3ζ chain, CD3ε chain, CD3γ chain, and CD3δ chain), transmit an intracellular signal after antigen recognition, and initiate various immune responses. Endogenous antigens such as a cancer antigen derived from a cancer cell or a viral antigen proliferated in a cell with a viral infection are presented as an antigen peptide on an MHC class I molecule. Further, an antigen derived from an exogenous microorganism is taken up by an antigen-presenting cell by endocytosis and processed, and then presented on an MHC class II molecule. Such antigens are recognized by TCRs expressed by each of CD8+ T cell and CD4+ T cell. It is also known that a costimulatory molecule such as a CD28, ICOS, or OX40 molecule is important for stimulation via a TCR molecule. For αβ TCRs, which are one of the primary objectives herein, a gene product of each of α and β is understood to express specificity by a unique combination.

The biological defense mechanism using the immune system is heavily dependent on the specific immunity provided mainly by T cells and B cells. In principle, T cells and B cells can specifically recognize and attack exogenous pathogens such as viruses or bacteria without reacting to autologous cells or molecules. For this reason, T cells and B cells have a mechanism that can recognize and distinguish various antigens from other organisms in addition to autoantigens by a receptor molecule expressed on the cell surface. In T cells, T cell receptors (TCR) function as an antigen receptor. An intracellular signal is transmitted by a stimulation from such antigen receptors, production of inflammatory cytokines, chemokines or the like are promoted, cell proliferation increases, and various immune responses are initiated.

A TCR recognizes a peptide bound to a peptide binding cleft of a major histocompatibility complex (MHC) expressed on antigen presenting cells (peptide-MHC complex, pMHC) to distinguish autologous and heterologous and recognizes an antigen peptide (Cell 1994, 76, 287-299).

A TCR gene consists of numerous V regions (variable region, V), J regions (joining region, J), D regions (diversity region, D), and C regions (constant region, C) encoded by different regions in the genome. In a T cell differentiation process, such gene fragments are genetically rearranged in various combinations. α chain and γ chain TCRs express genes consisting of V-J-C, and β chain and δ chain TCRs express genes consisting of V-D-J-C. Diversity is created by rearrangement of such gene fragments. In addition, insertion or deletion of one or more bases between V and D or D and J gene fragments leads to the formation of a random amino acid sequence to create a more diverse TCR gene sequence.

A region where a TCR molecule directly binds to a pMHC complex surface (TCR footprint) is composed of diverse complementarity determining regions (CDR) within the V region, i.e., CDR1, CDR2, and CDR3 regions. The CDR3 region in particular comprises a part of a V region, a V-D region (α chain and γ chain) or a V-D-J region (β chain and δ chain) formed by a random sequence, and a part of J region, forming the most diverse antigen recognition site. Meanwhile, the other regions are known as FRs (framework region) serving the role of forming a backbone structure of a TCR molecule. In a differentiation and maturation process of a T cell in the thymus gland, a β chain TCR is genetically rearranged initially, and conjugates with a pTα molecule to form a pre-TCR complex molecule. An α chain TCR is then rearranged to form an αβ TCR molecule, and when a functional αβ TCR is not formed, rearrangement occurs in the other a chain TCR gene allele. It is known that after undergoing positive/negative selection in the thymus gland, a TCR with a suitable affinity is selected to acquire antigen specificity (Annual Review Immunology, 1993, 6, 309-326).

T cells produce one type of TCR with high specificity to a specific antigen. With numerous antigen specific T cells in the living body, a diverse TCR repertoire can be formed to effectively function as a defense mechanism against various pathogens.

As used herein, "highly functional TCR" refers to a TCR with a higher binding capability than other TCRs among TCRs with binding capability to a certain antigen. It can be determined whether a certain TCR is a highly functional TCR by, for example, incubating a cell expressing the TCR with an antigen tetramer-PE complex at a certain concentration (e.g., 10 µg/ml) and then measuring whether the TCR can bind to the antigen thereof with an affinity at which MFI (mean fluorescence intensity) in TCRαβ positive cells exceeds a certain value (e.g., 5000).

2. Preferred Embodiments

The preferred embodiments of the present disclosure are described hereinafter. It is understood that the embodiments provided hereinafter are provided to facilitate better understanding of the present disclosure, so that the scope of the present disclosure should not be limited by the following description. Thus, it is apparent that those skilled in the art can refer to the descriptions herein to make appropriate modifications within the scope of the present disclosure. It is also understood that the following embodiments of the present disclosure can be used alone or as a combination.

Each of the embodiments described below provides a comprehensive or specific example. The numerical values, shapes, materials, constituent elements, positions of arrangement and connection modes of the constituent elements, steps, order of steps, and the like in the following embodiments are one example, which is not intended to limit the Claims. Further, the constituent elements in the following embodiments that are not recited in the independent claims showing the most superordinate concept are described as an optional constituent element.

2.1.1 Modified TALEN

One aspect of the invention provides a composition for editing a TCR gene comprising a polypeptide comprising a DNA binding domain and a functional domain or a nucleic acid encoding the polypeptide. A DNA binding domain and a functional domain can be provided separately. For this reason, one embodiment of the invention provides a composition for editing a TCR gene, comprising a nucleic acid encoding a polypeptide comprising a DNA binding domain, the composition characterized by being used in combination with a nucleic acid encoding a polypeptide comprising a functional domain. Alternatively, a composition for editing a TCR gene comprising a nucleic acid encoding a polypeptide comprising a functional domain, the composition characterized by being used in combination with a nucleic acid encoding a polypeptide comprising a DNA binding domain. Another embodiment provides a combination for editing a TCR gene, comprising a nucleic acid encoding a polypeptide comprising a DNA binding domain and a nucleic acid encoding a polypeptide comprising a functional domain. The genome editing enzyme of the invention is preferably TALEN, and more preferably Platinum TALEN.

The activity of Platinum TALEN is increased more than Voytas TALEN by a periodic arrangement with variation in the 4th and 32nd amino acids among the 34 amino acids contained in a DNA binding repeat of TALEN (Sakuma et al., Sci Rep, 2013). The method of the present disclosure preferably edits an endogenous TCR gene using Platinum TALEN. Platinum TALEN is described in Japanese Laid-Open Publication No. 2016-175922, whose entire content is incorporated herein by reference. The modified TALEN of the present disclosure can have, for example, the features described below.

One embodiment of the present disclosure uses a polypeptide or a nucleic acid encoding the same that can have both high functionality by a functional domain and a high recognition specificity to a DNA sequence and is capable of safely exerting a desired function at a high probability, as well as can be manufactured by a simple operation, to modify an endogenous TCR gene.

A polypeptide, wherein a DNA binding domain and a functional domain are connected by a polypeptide consisting of 35 to 55 amino acids, and amino acids at two specific positions in a DNA binding module contained in the DNA binding domain exhibit different repeat forms for each of the four DNA binding modules, can have both high functionality by a functional domain and a high recognition specificity to a DNA sequence. A vector for expressing said polypeptide can be readily manufactured by using a vector set with a specific feature and a vector library with a specific feature.

In one embodiment of the present disclosure, the present invention can utilize a polypeptide comprising a DNA binding domain and a functional domain. The polypeptide wherein the DNA binding domain and the functional domain are connected by a polypeptide consisting of 35 to 55 amino acids, the DNA binding domain comprises a plurality of DNA binding modules consecutively from the N-terminal side, a combination of the xth amino acid and the yth amino acid in the 4n−3th DNA binding module from the N-terminus being identical for any n, a combination of the xth amino acid and the yth amino acid in the 4n−2th DNA binding module from the N-terminus being identical for any n, a combination of the xth amino acid and the yth amino acid in the 4n−1th DNA binding module from the N-terminus being identical for any n, and a combination of the xth amino acid and the yth amino acid in the 4nth DNA binding module from the N-terminus being identical for any n, the combination of the xth amino acid and the yth amino acid in the 4n−3th DNA binding module from the N-terminus, the combination of the xth amino acid and the yth amino acid in the 4n−2th DNA binding module from the N-terminus, the combination of the xth amino acid and the yth amino acid in the 4n−1th DNA binding module from the N-terminus, and the combination of the xth amino acid and the yth amino acid in the 4nth DNA binding module from the N-terminus are different from one another, and n is a natural number from 1 to 10, x is a natural number from 1 to 40, y is a natural number from 1 to 40, and x and y are different natural numbers, or a nucleic acid encoding the same can be used. A functional domain can be a DNA cleavage domain. Polynucleotides encoding polypeptides are included thereby.

The present invention can also utilize a vector library for manufacturing a vector comprising a polynucleotide encoding the polypeptide described above, wherein the vector library is comprised of a plurality of vectors having, in order from the 5' end, a first restriction enzyme cleavage site, a polypeptide encoding four DNA binding modules, and a second restriction enzyme cleavage site, wherein the combination of the first restriction enzyme cleavage site and the second restriction enzyme cleavage site is a combination of a type A restriction enzyme cleavage site and a type B restriction enzyme cleavage site, a combination of a type A restriction enzyme cleavage site and a type C restriction enzyme cleavage site, a combination of a type A restriction enzyme cleavage site and a type D restriction enzyme cleavage site, a combination of a type A restriction enzyme cleavage site and a type E restriction enzyme cleavage site, a combination of a type B restriction enzyme cleavage site and a type C restriction enzyme cleavage site, a combination of a type C restriction enzyme cleavage site and a type D restriction enzyme cleavage site, or a combination of a type D restriction enzyme cleavage site and a type E restriction enzyme cleavage site, wherein the type A restriction enzyme cleavage site to type E restriction enzyme cleavage site each result in different cleavage ends from one another by cleavage with the same restriction enzyme, and in the four DNA binding modules, a combination of the xth amino acid and the yth amino acid in the 1st DNA binding module from the 5' end being identical for any vector, a combination of the xth amino acid and the yth amino acid in the 2nd DNA binding module from the 5' end being identical for any vector, a combination of the xth amino acid and the yth amino acid in the 3rd DNA binding module from the 5' end being identical for any vector, and a combination of the xth amino acid and the yth amino acid in the 4th DNA binding module from the 5' end being identical for any vector, the combination of the xth amino acid and the yth amino acid in the 1st DNA binding module from the 5' end, the combination of the xth amino acid and the yth amino acid in the 2nd DNA binding module from the 5' end, the combination of the xth amino acid and the yth amino acid in the 3rd DNA binding module from the 5' end, and the combination of the xth amino acid and the yth amino acid in the 4th DNA binding module from the 5' end are different from one another, and x is a natural number from 1 to 40, y is a natural number from 1 to 40, and x and y are different natural numbers.

The present invention can also utilize a vector set for manufacturing the vector library described above. In this regard, the vector set comprises a plurality of vectors comprising, in order from the 5' end, a first restriction enzyme cleavage site, a DNA binding module, and a second restriction enzyme cleavage site, the first restriction enzyme cleavage site and the second restriction enzyme cleavage site resulting in different cleavage ends from each other by cleaving with the same restriction enzyme, a combination of the xth amino acid and the yth amino acid in the DNA binding module being one of four different combinations, wherein x is a natural number from 1 to 40, y is a natural number from 1 to 40, and x and y are different natural numbers.

Since the polypeptide described above materializes high functionality by a functional domain and a high recognition specificity to a DNA sequence, an alteration of a desired TCR gene can be materialized safely and at a high probability by introducing a vector comprising a polynucleotide encoding the polypeptide described above into a cell. If the vector library described above is used, a vector for expressing a polypeptide having both high functionality by a functional domain and a high recognition specificity to a DNA sequence can be prepared readily and quickly.

Examples of origins of a DNA binding domain include the plant pathogen *Xanthomonas* TALE (Transcription Activator-Like Effector), Zinc finger, and the like.

Examples of functional domains include domains encoding enzymes, transcription regulatory factors, reporter proteins, and the like. Examples of enzymes include DNA modifying enzymes such as a recombinase, nuclease, ligase, kinase, and phosphatase, and other enzymes such as lactamase. As used herein, a domain encoding a nuclease is referred to as a DNA cleavage domain. Examples of transcription regulatory factors include activators, repressors, and the like. Examples of reporter proteins include fluorescent proteins such as a green fluorescent protein (GFP), humanized *Renilla reniformis* green fluorescent protein (hrGFP), enhanced green fluorescent protein (eGFP), enhanced blue fluorescent protein (eBFP), enhanced cyan fluorescent protein (eCFP), enhanced yellow fluorescent protein (eYFP), red fluorescent protein (RFP or DsRed), and mCherry; bioluminescent proteins such as firefly luciferase and *Renilla* luciferase; enzymes converting a chemiluminescent substrate such as alkaline phosphatase, peroxidase, chloramphenicol acetyltransferase, and β-galactosidase, and the like. A DNA cleavage domain preferably approaches another DNA cleavage domain to form a multimer, and attains improved nuclease activity. Examples of such a DNA cleavage domain include those derived from FokI.

A DNA binding domain and a functional domain are connected by a polypeptide consisting of 35 to 55, preferably 40 to 50, more preferably 45 to 49, and most preferably 47 amino acids.

A DNA binding domain can comprise a plurality of DNA binding modules consecutively from the N-terminal side. One DNA binding module specifically recognizes one base pair.

The number of DNA binding modules contained in a DNA binding domain, from the viewpoint of attaining both high functionality of a functional domain and a high recognition specificity to a DNA sequence, is preferably 8 to 40, more preferably 12 to 25, and still more preferably 15 to 20. Examples of DNA binding modules include TAL effector repeat and the like. Examples of the length of a single DNA binding module include 20 to 45, 30 to 38, 32 to 36, 34, and the like. The length of a DNA binding module contained in a DNA binding domain is preferably the same for all DNA binding modules. Examples of a DNA binding module include the sequence of LTPDQVVAIAS HDGGKQALETVQRLLPVLCQDHG (SEQ ID NO: 1). For example, it is understood that if the 12th amino acid and the 13th amino acid of this sequence are H and D in this order, the DNA binding domain recognizes C as a base, and if the amino acids are N and G in this order, the DNA binding domain recognizes T as a base, and if the amino acids are N and I in this order, the DNA binding domain recognizes A as a base, and if the amino acids are N and N in this order, the DNA binding domain recognizes G as a base. Examples of DNA binding modules include a polypeptide with 85%, 90%, 95%, or 97% identity with the amino acid sequence of SEQ ID NO: 1 and substantially retains the function to recognize a base pair.

A combination of the xth amino acid and the yth amino acid in the 4n−3th DNA binding module from the N-terminus can be identical for any n. Further, a combination of the xth amino acid and the yth amino acid in the 4n−2th DNA binding module from the N-terminus can be identical for any n. Further, a combination of the xth amino acid and the yth amino acid in the 4n−1th DNA binding module from the N-terminus can be identical for any n. Further, a combination of the xth amino acid and the yth amino acid in the 4nth DNA binding module from the N-terminus can be identical for any n. In this regard, n is a natural number from 1 to 10, preferably a natural number from 1 to 7, and more preferably a natural number from 1 to 5. n is preferably a natural number that is sufficient to indicate all DNA binding modules contained in a DNA binding domain. x is a natural number from 1 to 40, preferably a natural number from 1 to 10, more preferably a natural number from 2 to 6, still more preferably a natural number from 3 to 5, and most preferably the natural number 4. y is a natural number from 1 to 40, preferably a natural number from 25 to 40, more preferably a natural number from 30 to 36, still more preferably a natural number from 31 to 33, and most preferably the natural number 32. x and y are different natural numbers. The values of x and y can be different depending on the length of the DNA binding modules used. x is preferably a numerical value indicating a position corresponding to the 2nd amino acid in a DNA binding module consisting of 34 amino acids. y is preferably a numerical value indicating a position corresponding to the 32nd amino acid in a DNA binding module consisting of 34 amino acids.

A combination of the xth amino acid and the yth amino acid in the 4n−3th DNA binding module from the N-terminus, a combination of the xth amino acid and the yth amino acid in the 4n−2th DNA binding module from the N-terminus, a combination of the xth amino acid and the yth amino acid in the 4n−1th DNA binding module from the N-terminus, and a combination of the xth amino acid and the yth amino acid in the 4nth DNA binding module from the N-terminus can be different from one another, wherein n is a natural number from 1 to 10, preferably a natural number from 1 to 7, more preferably a natural number from 1 to 5. n is preferably a natural number that is sufficient to indicate all DNA binding modules contained in a DNA binding domain. x is a natural number from 1 to 40, preferably a natural number from 1 to 10, more preferably a natural number from 2 to 6, still more preferably a natural number from 3 to 5, and most preferably the natural number 4. y is a natural number from 1 to 40, preferably a natural number from 25 to 40, more preferably a natural number from 30 to 36, still more preferably a natural number from 31 to 33, and most preferably the natural number 32. x and y are different natural numbers. Preferably, a combination of the xth amino acid and the yth amino acid in the 4n−3th DNA binding module from the N-terminus, a combination of the xth amino acid and the yth amino acid in the 4n−2th DNA binding module from the N-terminus, and a combination of the xth amino acid and the yth amino acid in the 4nth DNA binding module from the N-terminus can each be selected from the group consisting of a combination of, in order of x and y, a combination of D and D, a combination of E and A, a combination of D and A, and a combination of A and D.

Examples of vectors that can be used include plasmid vectors, cosmid vectors, viral vectors, artificial chromosome vectors, and the like. Examples of artificial chromosome vectors include yeast artificial chromosome vectors (YAC), bacterial artificial chromosome vectors (BAC), P1 artificial chromosome vectors (PAC), mouse artificial chromosome vectors (MAC), human artificial chromosome vectors (HAC), and the like. Examples of vector components include nucleic acids such as DNA and RNA, nucleic acid analogs such as GNA, LNA, BNA, PNA, and TNA, and the like. Vectors may be modified with a component other than a nucleic acid such as saccharides.

The polypeptide described above can be prepared by introducing a vector into a cell or the like to cause expression of the vector. A desired function corresponding to the functional domain e.g., DNA modification such as DNA recombination or DNA cleavage, expression of other enzymatic activity such as transcription regulation, or labeling of a DNA region with a reporter protein can be exerted in a cell by introducing a vector into a cell or the like to cause expression of the vector. If a functional domain is a DNA cleavage domain, a plurality of, preferably two vectors can be introduced into and expressed in a cell or the like to generate a base sequence specific double strand cleavage on a genomic DNA of the cell introduced with the vectors, and introduce a mutation in the genome of the cell. Examples of the origin of a cell introduced with a vector include animals such as fruit flies, zebra fish, and mammals such as mice, plants such as *Arabidopsis thaliana*, cultured cells such as ES cells and iPS cells, and the like.

(2.1.2. Manufacturing Scheme of Modified TALEN)

Figure 20:
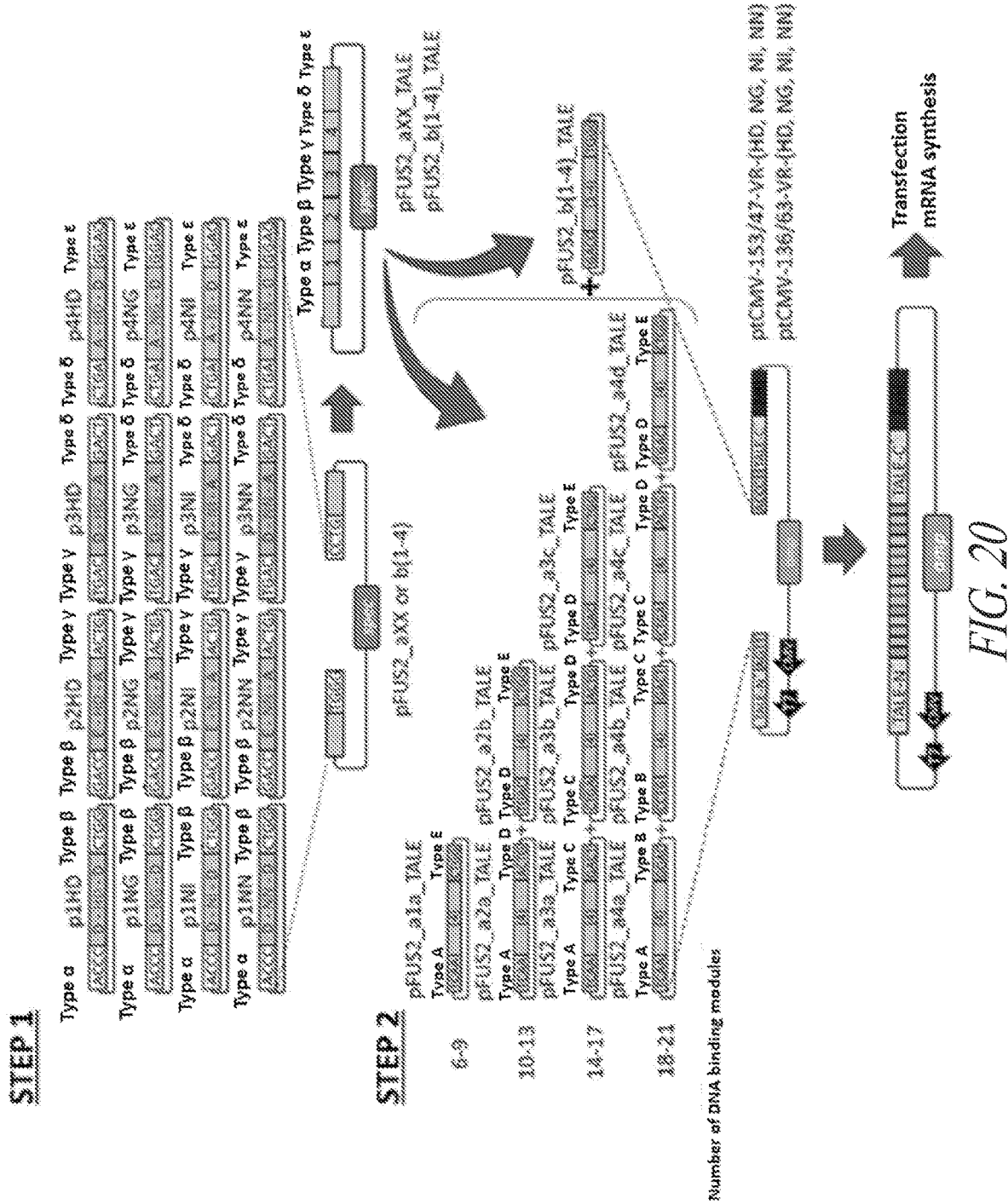
FIG. 20 is a schematic diagram showing the manufacturing method of the modified TALEN of the invention.

A Platinum TALEN corresponding to a certain recognition sequence can be prepared in advance or manufactured by combining vectors in a newly created vector library to prepare a nucleic acid encoding a Platinum TALEN. For example, Platinum TALEN corresponding to a desired recognition sequence can be manufactured using a Platinum TALEN production kit (Platinum Gate TALEN Kit). A new Platinum TALEN vector set can be manufactured in accordance with the production scheme shown in FIG. 20.

Each vector in a vector library can comprise, for example, four DNA binding modules. Four DNA binding modules in a vector can have a variation corresponding to one cycle of a periodic variation in sequences (e.g., variation in the 4th and 32nd amino acids of a binding module) of Platinum TALEN described above. Each DNA binding module specifies a corresponding recognition base in accordance with RVD thereof. There can be $4^4=256$ different base sequences that can be recognized by four DNA binding modules. While a vector library can comprehensively have vectors that recognize four base sequences, it is sufficient to have only vectors that are required for the production of a desired binding domain.

Specifically, a vector encoding a DNA domain can be produced by selecting a vector corresponding to a sequence of a DNA binding module contained in a DNA binding domain that binds to a desired recognition sequence from a vector library, digesting the selected vector with a restriction enzyme that cleaves type A restriction enzyme cleavage site to type E restriction enzyme cleavage site, and linking vector fragments obtained by the digestion. All vectors constituting a vector library have two restriction enzyme cleavage sites cleaved by the same restriction enzyme, and cleaved ends that are different from one another are generated at the restriction enzyme cleavage sites by the cleaving with the enzyme. Therefore, digestion of a selected vector and linking of vector fragments can each be performed in the same reaction solution when producing a vector encoding Platinum TALEN. For this reason, a vector encoding Platinum TALEN can be produced in a very simple manner using a vector library.

Type A to type E with regard to restriction enzyme cleavage sites are denotation used for convenience herein to show the difference in properties of restriction enzyme cleavage sites. Different types indicate that properties of restriction enzyme cleavage sites are different from each other, and same types indicate that the properties of restriction enzyme cleavage sites are the same. In a vector library, type A restriction enzyme cleavage site to type E restriction enzyme cleavage site are cleaved by the same restriction enzyme. Cleavage ends that are different from one another are produced by cleavage with the same restriction enzyme at type A restriction enzyme cleavage site to type E restriction enzyme cleavage site. Examples of such restriction enzyme cleavage sites include cleavage sites generated by a restriction enzyme (e.g., BsaI, BbsI, BsmBI, or the like) cleaving any site that is adjacent to a restriction enzyme recognition site.

A combination of the xth amino acid and yth amino acid in the first DNA binding module from the 5' end is identical for any vector constituting a vector library. Likewise, a combination of the xth amino acid and yth amino acid in the second DNA binding module from the 5' end is identical for any vector constituting a vector library. Further, combination of the xth amino acid and yth amino acid in the third DNA binding module from the 5' end is identical for any vector constituting a vector library. Furthermore, a combination of the xth amino acid and yth amino acid in the fourth DNA binding module from the 5' end is identical for any vector constituting a vector library.

2.2. Removal of Endogenous TCR Gene 2.2.1 Mechanism of Removal of Endogenous TCR The modified TALEN of the invention can be used for removing an endogenous TCR. The removal of an endogenous TCR is described hereinafter.

It can be preferable to remove an endogenous TCR upon introduction of a TCR. It is reported in Proc Natl Acad Sci USA. 2010 Jun. 15; 107(24): 10972-7 (PMID: 20534461) that a mixed dimer can be formed by introducing a TCR in the presence of an endogenous TCR, resulting in the manifestation of new antigen reactivity.

When a TCR mixed dimer (pair of an endogenous TCR chain and exogenous TCR chain) is formed, it is not only possible that the expression of the introduced TCR chain and endogenous TCR chain decreases to impair specific reactivity, but also the mixed dimer has a potentially detrimental specificity. While the aforementioned reference reports that new reactivity was manifested by introduction of a TCR and most new reactivity was allo-HLA reactive, some with autoreactive activity was found. Mol Biol Rep. 2010 December; 37(8): 3951-6 (PMID: 20373027) describes the FRET method as a technology for quantitatively detecting a TCR generated by mispairing.

An endogenous TCR can be removed by modifying an endogenous TCR gene. An endogenous TCR can be removed, for example, by knocking down an endogenous TCR gene. Antisense method, RNAi, or the like can be utilized. An endogenous TCR can also be removed by knocking out an endogenous TCR gene. An endogenous TCR can be modified, for example, by deletion of all or part of the coding region, introduction of a mutation into a regulatory region, introduction of a nonsense or missense mutation, or the like.

Preferably, an endogenous TCR gene can be modified using a genome editing technology. Genome editing is a technology for modifying a target gene by utilizing a site specific nuclease. Examples of genome editing technology include ZFN, TALEN, CRISPR/Cas9, and the like, each having a binding domain for materializing DNA sequence specific linkage to a desired sequence and a cleavage domain for cleaving a DNA at a desired site of the sequence.

ZFN is an artificial restriction enzyme comprising a zinc finger domain and a DNA cleavage domain. A zinc finger domain can be modified to recognize any DNA base sequence, which enables a zinc finger nuclease to target a single sequence in a complex genome.

The CRISPR (Clustered Regularly Interspaced Short Palindromic Repeats)/Cas9 (Crispr ASsociated protein 9) system comprises two separate molecules, i.e., guide RNA and Cas9, whereas ZFN and TALEN are basically used as a single protein. A guide RNA can be specifically bound to a target site by including a complementary sequence of a DNA target site in the guide RNA. In view of the above, a Cas9 protein is bound so as to cover the guide RNA and DNA to cleave the DNA. Cas9 itself can be reused, so that it is sufficient to produce only guide RNA depending on the target site. Thus, multiplexing is considered simple.

TALEN (Transcription Activator-Like Effector Nuclease) is an artificial enzyme prepared by fusing a restriction enzyme FokI as a DNA cleavage domain to a DNA binding domain of a TALE protein secreted from a plant pathogenic bacteria *Xanthomonas*. A DNA binding domain of a TALE protein has a repeat structure of about 34 amino acids. Such a repeat unit is referred to as a module. The 12th and 13th amino acids therein are variable. The amino acids are portions that bind to a target sequence and are referred to as a "repeat variable diresidue" (RVD). TALEN uses molecules that bind to each of the opposite strands of a target DNA as a pair of L TALEN and R TALEN. For FokI to exhibit cleavage activity, TALEN needs to form a dimer while maintaining a suitable distance. Mismatch tolerance and off-target activity in TALEN are hardly reported. Thus, TALEN is characterized by high specificity. Since an unexpected adverse effect can be triggered if off-target modification is generated upon modification of T cells, use of TALEN with high specificity is preferable in the present disclosure.

In addition to conventional TALEN, various modified TALEN have been produced. Modification of an endogenous TCR gene with such a TALEN is preferable in view of high specificity and high modification efficiency. Examples herein demonstrate that complete elimination of endogenous TCRs of a T cell was made possible by using a modified TALEN.

Figure 17:
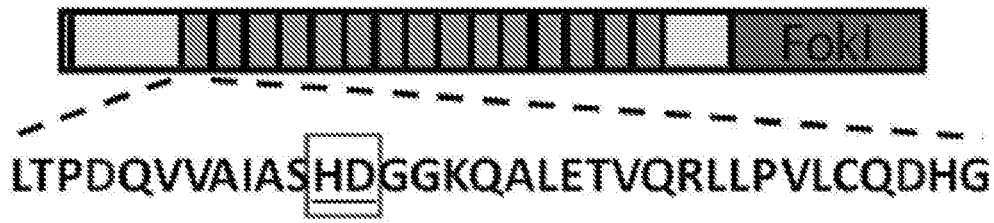
FIG. 17 is a diagram showing several examples of modified TALENs. An example of a specific sequence is shown for the portion of a binding module in a DNA binding domain. The underlines are RVD. HD (RVD corresponding to base C) is described as an example in the figure. While examples of the structures of Voytas TALEN and Zhang TALEN prepared from altering the 4th and 32nd amino acid sequences of a binding module of Voytas TALEN are shown, the amino acid residues of these portions are identical for all modules in these TALENs. Meanwhile, the 4th and 32nd amino acid sequences of a binding module periodically changes for each module in Platinum TALEN. The example of a DNA binding module of Voytas TALEN and the first sequence from the top in the example of a DNA binding module of Platinum TALEN correspond to SEQ ID NO: 1, and the rest corresponds to, from the top, SEQ ID NOs: 111 to 114 in order.
Figure 17:
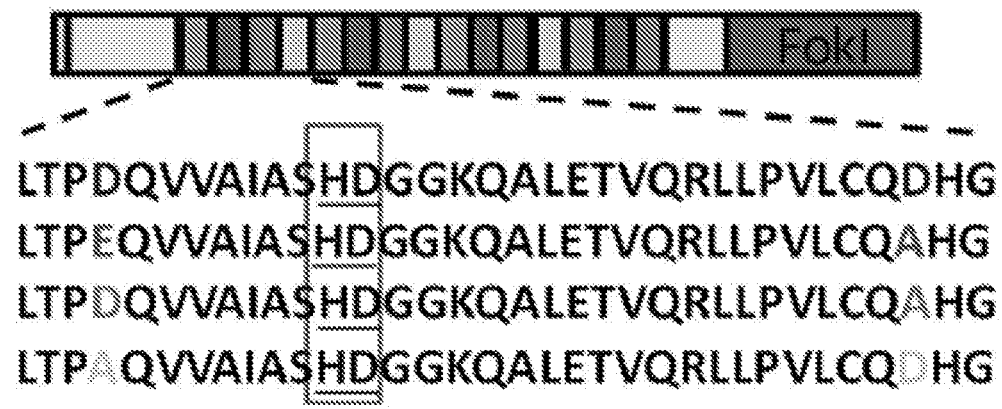
Figure 17:
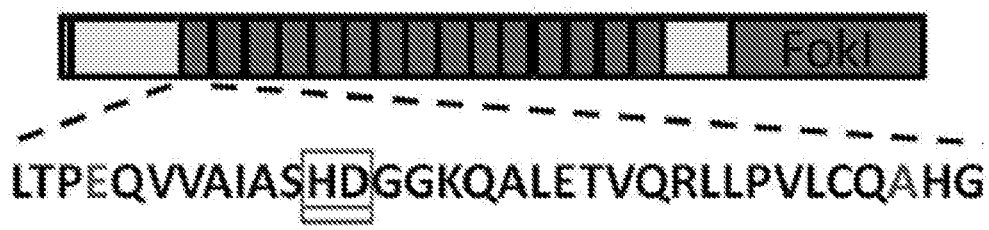
Figure 17:

Some examples of modified TALENs are shown in FIG. 17. For example, the 4th and 32nd amino acids of a module are modified in a SuperTALEN, and only specific modified repeats are assembled and used (PCT/JP2014/071116, entirely thereof is incorporated herein by reference). This SuperTALEN with two amino acids modified therein that are modified to E and A is a Zhang TALEN (type EA SuperTALEN). It is reported that activity increases for type EA shown in FIG. 17 as well as type QA.

2.2.2 Target of Modified TALEN

The genome editing enzyme (also known as modified TALEN) of the present disclosure can be designed to target a TCR gene. Therefore, a DNA binding domain can specifically bind to a gene of TCRα or gene of TCRβ. Examples of portions to which a DNA binding domain is bound on a TCR gene include, but are not limited to, TRAC exon 1, TRBC1 exon 1, TRBC2 exon 1, and the like. As described above, a DNA binding domain can be designed to have specificity to a desired sequence by selecting an RVD that is present in each module. Those skilled in the art can design a DNA binding domain specific to any target sequence disclosed herein.

A DNA binding domain can be designed to target, for example, the following sequences:

[Chemical Formula 1]
α2L:
(SEQ ID NO: 80)
TGTCTGCCTATTCACCGATT

α2R:
(SEQ ID NO: 81)
TCCTTACTTTGTGACACATT

β1L:
(SEQ ID NO: 82)
TGTTCCCACCCGAGGTCGCT

β1R:
(SEQ ID NO: 83)
TGTGGGAGATCTCTGCTTCT

β3L:
(SEQ ID NO: 84)
TGTGCCTGGCCACAGGCTTC

β3R:
(SEQ ID NO: 85)
TCACCCACCAGCTCAGCTCC.

Example 2 herein demonstrates that an endogenous TCR gene can be removed with a genome editing enzyme having a DNA binding domain targeting such a position. Base T on the left end of each target sequence is T recognized by the N-terminus domain (region outside the DNA binding repeat) of TALE. While it is understood that the base T is not included as a "recognition sequence of DNA binding repeat", it is understood that base T is included as a "target sequence of TALEN".

Examples of DNA binding domains of Platinum TALEN targeting the sequences described above include those with the following pattern sequence. Example 2 herein demonstrates that an endogenous TCR gene of a T cell was able to be removed successfully using a TALEN having such a DNA binding domain. The final repeat of a DNA binding module is a truncated repeat known as half repeat.

[Chemical Formula 2]
>TALEN_α2L binding domain (module repeat)
(SEQ ID NO: 86)
LTPDQVVAIASNNGGKQALETVQRLLPVLCQDHG

LTPEQVVAIASNGGGKQALETVQRLLPVLCQAHG

LTPDQVVAIASHDGGKQALETVQRLLPVLCQAHG

LTPAQVVAIASNGGGKQALETVQRLLPVLCQDHG

LTPDQVVAIASNNGGKQALETVQRLLPVLCQDHG

LTPEQVVAIASHDGGKQALETVQRLLPVLCQAHG

LTPDQVVAIASHDGGKQALETVQRLLPVLCQAHG

LTPAQVVAIASNGGGKQALETVQRLLPVLCQDHG

LTPDQVVAIASNIGGKQALETVQRLLPVLCQDHG

LTPEQVVAIASNGGGKQALETVQRLLPVLCQAHG

LTPDQVVAIASNGGGKQALETVQRLLPVLCQAHG

LTPAQVVAIASHDGGKQALETVQRLLPVLCQAHG

LTPDQVVAIASNIGGKQALETVQRLLPVLCQDHG

LTPEQVVAIASHDGGKQALETVQRLLPVLCQAHG

LTPDQVVAIASHDGGKQALETVQRLLPVLCQAHG

LTPAQVVAIASNNGGKQALETVQRLLPVLCQDHG

LTPDQVVAIASNIGGKQALETVQRLLPVLCQDHG

LTPEQVVAIASNGGGKQALETVQRLLPVLCQAHG

LTPEQVVAIASNGGGRPALES

[Chemical Formula 3]
>TALEN_α2R binding domain (module repeat)
(SEQ ID NO: 87)
LTPDQVVAIASHDGGKQALETVQRLLPVLCQDHG

LTPEQVVAIASHDGGKQALETVQRLLPVLCQAHG

LTPDQVVAIASNGGGKQALETVQRLLPVLCQDHG

LTPAQVVAIASNGGGKQALETVQRLLPVLCQDHG

LTPDQVVAIASNIGGKQALETVQRLLPVLCQDHG

LTPDQVVAIASNGGGKQALETVQRLLPVLCQAHG

LTPAQVVAIASNGGGKQALETVQRLLPVLCQDHG

LTPDQVVAIASNGGGKQALETVQRLLPVLCQDHG

LTPEQVVAIASNNGGKQALETVQRLLPVLCQAHG

LTPDQVVAIASNGGGKQALETVQRLLPVLCQDHG

LTPAQVVAIASNNGGKQALETVQRLLPVLCQDHG

LTPDQVVAIASNIGGKQALETVQRLLPVLCQDHG

LTPEQVVAIASHDGGKQALETVQRLLPVLCQAHG

LTPDQVVAIASNIGGKQALETVQRLLPVLCQDHG

LTPAQVVAIASHDGGKQALETVQRLLPVLCQDHG

LTPDQVVAIASNIGGKQALETVQRLLPVLCQDHG

LTPEQVVAIASNGGGKQALETVQRLLPVLCQAHG

LTPEQVVAIASNGGGRPALES

[Chemical Formula 4]
>TALEN_β1L binding domain (module repeat)
(SEQ ID NO: 88)
LTPDQVVAIASNNGGKQALETVQRLLPVLCQDHG

LTPEQVVAIASNGGGKQALETVQRLLPVLCQAHG

LTPDQVVAIASNGGGKQALETVQRLLPVLCQDHG

LTPAQVVAIASHDGGKQALETVQRLLPVLCQDHG

LTPAQVVAIASHDGGKQALETVQRLLPVLCQDHG

LTPEQVVAIASHDGGKQALETVQRLLPVLCQAHG

LTPDQVVAIASNIGGKQALETVQRLLPVLCQAHG

LTPAQVVAIASHDGGKQALETVQRLLPVLCQDHG

LTPDQVVAIASHDGGKQALETVQRLLPVLCQDHG

LTPEQVVAIASHDGGKQALETVQRLLPVLCQDHG

LTPDQVVAIASNNGGKQALETVQRLLPVLCQAHG

LTPAQVVAIASNIGGKQALETVQRLLPVLCQDHG

LTPDQVVAIASNNGGKQALETVQRLLPVLCQDHG

LTPEQVVAIASNNGGKQALETVQRLLPVLCQAHG

LTPDQVVAIASNGGGKQALETVQRLLPVLCQDHG

LTPAQVVAIASHDGGKQALETVQRLLPVLCQDHG

LTPDQVVAIASNNGGKQALETVQRLLPVLCQDHG

LTPEQVVAIASHDGGKQALETVQRLLPVLCQAHG

LTPEQVVAIASNGGGRPALES

[Chemical Formula 5]
>TALEN_β1R binding domain (module repeat)
(SEQ ID NO: 89)
LTPDQVVAIASNNGGKQALETVQRLLPVLCQDHG

LTPEQVVAIASNGGGKQALETVQRLLPVLCQAHG

LTPDQVVAIASNNGGKQALETVQRLLPVLCQAHG

LTPAQVVAIASNNGGKQALETVQRLLPVLCQDHG

LTPDQVVAIASNNGGKQALETVQRLLPVLCQDHG

LTPEQVVAIASNIGGKQALETVQRLLPVLCQAHG

LTPDQVVAIASNNGGKQALETVQRLLPVLCQAHG

LTPAQVVAIASNIGGKQALETVQRLLPVLCQDHG

LTPDQVVAIASNGGGKQALETVQRLLPVLCQDHG

LTPEQVVAIASHDGGKQALETVQRLLPVLCQAHG

LTPDQVVAIASNGGGKQALETVQRLLPVLCQAHG

LTPAQVVAIASHDGGKQALETVQRLLPVLCQDHG

LTPDQVVAIASNGGGKQALETVQRLLPVLCQDHG

LTPEQVVAIASNNGGKQALETVQRLLPVLCQAHG

LTPDQVVAIASHDGGKQALETVQRLLPVLCQAHG

LTPAQVVAIASNGGGKQALETVQRLLPVLCQDHG

LTPDQVVAIASNGGGKQALETVQRLLPVLCQAHG

LTPEQVVAIASHDGGKQALETVQRLLPVLCQAHG

LTPEQVVAIASNGGGRPALES

[Chemical Formula 6]
>TALEN_β3L binding domain (module repeat)
(SEQ ID NO: 90)
LTPDQVVAIASNNGGKQALETVQRLLPVLCQDHG

LTPEQVVAIASNGGGKQALETVQRLLPVLCQAHG

LTPDQVVAIASNNGGKQALETVQRLLPVLCQAHG

LTPAQVVAIASHDGGKQALETVQRLLPVLCQDHG

LTPDQVVAIASHDGGKQALETVQRLLPVLCQDHG

LTPEQVVAIASNGGGKQALETVQRLLPVLCQAHG

LTPDQVVAIASNNGGKQALETVQRLLPVLCQAHG

LTPAQVVAIASNNGGKQALETVQRLLPVLCQDHG

LTPDQVVAIASHDGGKQALETVQRLLPVLCQDHG

LTPEQVVAIASHDGGKQALETVQRLLPVLCQAHG

LTPDQVVAIASNIGGKQALETVQRLLPVLCQAHG

LTPAQVVAIASHDGGKQALETVQRLLPVLCQDHG

LTPDQVVAIASNIGGKQALETVQRLLPVLCQDHG

LTPEQVVAIASNNGGKQALETVQRLLPVLCQAHG

LTPDQVVAIASNNGGKQALETVQRLLPVLCQAHG

LTPAQVVAIASHDGGKQALETVQRLLPVLCQDHG

-continued
LTPDQVVAIASNGGGKQALETVQRLLPVLCQDHG

LTPEQVVAIASNGGGKQALETVQRLLPVLCQAHG

LTPEQVVAIASHDGGRPALES

[Chemical Formula 7]
>TALEN_β3R binding domain (module repeat)
(SEQ ID NO: 91)
LTPDQVVAIASHDGGKQALETVQRLLPVLCQDHG

LTPEQVVAIASNIGGKQALETVQRLLPVLCQAHG

LTPDQVVAIASHDGGKQALETVQRLLPVLCQAHG

LTPAQVVAIASHDGGKQALETVQRLLPVLCQDHG

LTPDQVVAIASHDGGKQALETVQRLLPVLCQDHG

LTPEQVVAIASNIGGKQALETVQRLLPVLCQAHG

LTPDQVVAIASHDGGKQALETVQRLLPVLCQAHG

LTPAQVVAIASHDGGKQALETVQRLLPVLCQDHG

LTPDQVVAIASNIGGKQALETVQRLLPVLCQDHG

LTPEQVVAIASNNGGKQALETVQRLLPVLCQAHG

LTPDQVVAIASHDGGKQALETVQRLLPVLCQAHG

LTPAQVVAIASNGGGKQALETVQRLLPVLCQDHG

LTPDQVVAIASHDGGKQALETVQRLLPVLCQDHG

LTPEQVVAIASNIGGKQALETVQRLLPVLCQAHG

LTPDQVVAIASNNGGKQALETVQRLLPVLCQAHG

LTPAQVVAIASHDGGKQALETVQRLLPVLCQDHG

LTPDQVVAIASNGGGKQALETVQRLLPVLCQDHG

LTPEQVVAIASHDGGKQALETVQRLLPVLCQAHG

LTPEQVVAIASHDGGRPALES

Examples of TALEN plasmids for targeting a gene of TCRα in the present disclosure include TALEN-TCR-alpha2_L19 (SEQ ID NO: 46) and TALEN-TCR-alpha2_R19 (SEQ ID NO: 47). These sequences can be used as a pair.

Examples of TALEN plasmids for targeting a gene of TCR in the present disclosure include the pair of TALEN-TCR-beta1_L19 (SEQ ID NO: 48) and TALEN-TCR-beta1_R19 (SEQ ID NO: 49) and the pair of TALEN-TCR-beta3_L19 (SEQ ID NO: 50) and TALEN-TCR-beta3_R19 (SEQ ID NO: 51).

It should be noted that the sequences specifically presented in the present disclosure can be used with an addition of a modification, as long as the desired activity is maintained. For example, sequences with at least about 70%, at least about 75%, at least about 80%, at least about 85%, at least about 90%, at least about 95%, at least about 96%, at least about 97%, at least about 98%, or at least about 99% identity to a sequence specifically presented in the present disclosure can be used.

A modified amino acid sequence can be an amino acid sequence with one or a plurality (preferably one or several, or one, two, three, or four) conservative substitutions. As used herein, "conservative substitution" refers to substitution of one or a plurality of amino acid residues with other chemical similar amino acid residues in a manner that does not substantially modify the function of a protein. Examples thereof include a substitution of a hydrophobic residue with another hydrophobic residue, a substitution of a polar residue with another polar residue having the same charge, and the like. Functionally similar amino acids that can be substituted in such a manner are known in the art for each amino acid. Specific examples of nonpolar (hydrophobic) amino acids include alanine, valine, isoleucine, leucine, proline, tryptophan, phenylalanine, methionine, and the like. Specific examples of polar (neutral) amino acids include glycine, serine, threonine, tyrosine, glutamine, asparagine, cysteine, and the like. Specific examples of positively charged (basic) amino acids include arginine, histidine, lysine, and the like. Specific examples of negatively-charged (acidic) amino acids include aspartic acid, glutamic acid, and the like.

Since the same amino acid can be encoded by a plurality of gene codons, there can be a plurality of nucleic acid sequences encoding the same amino acid sequence. A different nucleic acid sequence can be utilized, as long as the purpose is to encode an amino acid sequence.

2.3 Antigen Specific Regulatory T Cell

In one aspect, the modified TALEN of the present disclosure can be used in a method of producing a regulatory T cell specific to an antigen, comprising removing an endogenous TCR gene. For example, the present disclosure provides a method of producing a regulatory T cell specific to an antigen, comprising: determining a TCR repertoire in an effector T cell population specific to the antigen in an effector T cell donor, comprising unbiasedly amplifying a TCR gene; identifying a pair of TCRα and TCR in the effector T cell population; checking whether the identified pair of TCRα and TCRβ has affinity to an antigen; cloning a full or partial nucleic acid sequence of TCRα and a full or partial nucleic acid sequence of TCR in the identified pair of TCRα and TCRβ; removing an endogenous TCR gene of a regulatory T cell using a modified TALEN; and introducing the cloned full or partial nucleic acid sequence of TCRα and full or partial nucleic acid sequence of TCRβ into the regulatory T cell so that the TCRα and the TCRβ are expressed as a pair.

Figure 18:
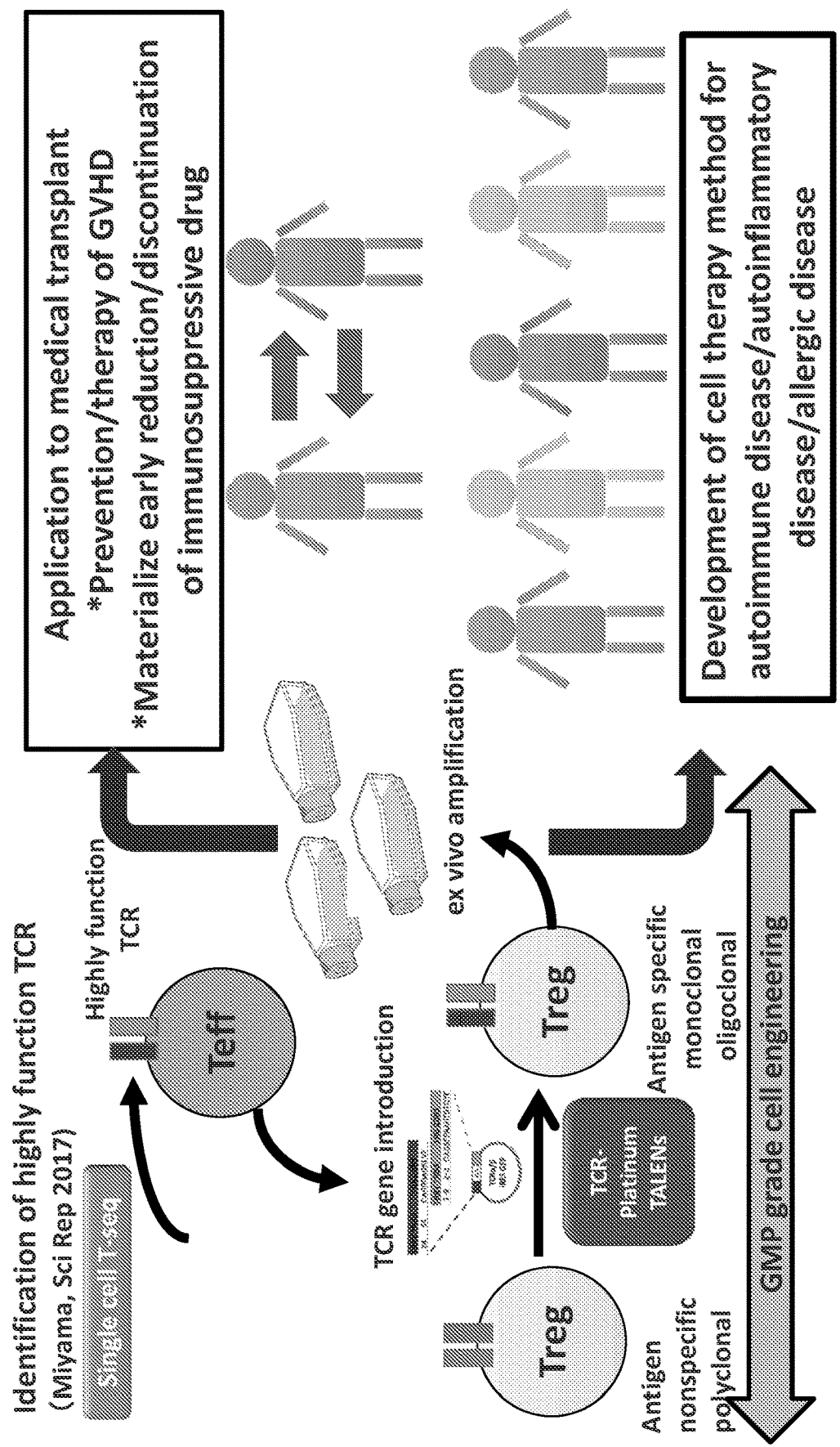
FIG. 18 is a diagram showing an example of a preferred embodiment of the invention. For example, the present disclosure can materialize an antigen specific Treg transfer therapy using a highly functional TCR.

A preferred embodiment is described in FIG. 18. A highly functional TCR is identified and introduced into an antigen nonspecific polyclonal regulatory T cell obtained from a donor, whereupon an endogenous TCR gene can be edited using a Platinum TALEN. Preferably, the TCR described above is introduced so that the TCRs described above are expressed as a pair. The obtained antigen specific monoclonal or oligoclonal regulatory T cell is amplified ex vivo and transferred into a recipient. It is understood that antigen specific regulatory T cells obtained by the present disclosure are safe due to the lack of unknown antigen reactivity, and exhibits high antigen specific immunosuppression capability by using a highly functional TCR. A recipient can be the same or different individual as the donor of a regulator T cell.

The present disclosure can also provide any article for use in the method of the present disclosure. For example, the present disclosure can provide a composition comprising a vector configured to express the TCRα and the TCRβ as a pair for use in the method of the present disclosure. A composition comprising an MHC tetramer for use in the method of the present disclosure can also be provided.

The present disclosure can also provide a composition for use in the method of the present disclosure, comprising a polypeptide comprising a DNA binding domain and a functional domain or a nucleic acid encoding the polypeptide, wherein the DNA binding domain specifically binds to a TCR gene.

A TCR repertoire of an effector T cell population identified by the method of the present disclosure or a portion thereof, or a nucleic acid encoding the same is also within the scope of the present disclosure. A composition for manufacturing a TCR modified T cell comprising a TCR repertoire of an effector T cell population or a portion thereof, or a nucleic acid encoding the same is also provided. Preferably, a TCR modified T cell comprises a TCR modified regulatory T cell.

2.4 T Cell Endogenous TCR Gene Modification

In one aspect of the present disclosure, the modified TALEN of the present disclosure can be used in a method of modifying an endogenous TCR gene in a T cell. This method can preferably comprise modifying a T cell so that an endogenous TCR is not expressed.

Said step can be performed by introducing the composition of the present disclosure into a cell. Since the modified TALEN of the present disclosure can target a gene of TCRα and/or gene of TCRβ, modified TALENs specific to each of the gene of TCRα and gene of TCRβ can be simultaneously or sequentially introduced into a cell. The TALENs can be introduced sequentially in any order. Therefore, the step of modifying a T cell can comprise introducing a composition comprising a polypeptide having a DNA binding domain specifically binding to a gene of TCRα or a nucleic acid encoding the same into a cell and introducing a composition comprising a polypeptide having a DNA binding domain specifically binding to a gene of TCR or a nucleic acid encoding the same into a cell.

Another aspect of the present disclosure can comprise introducing an exogenous TCR into a T cell (e.g., by introducing a nucleic acid). Examples of T cells targeted by the present disclosure include, but are not limited to, regulatory T cells, effector T cells, helper T cells, natural killer T cells (NKT cells), γδ T cells, and the like. Modification/introduction of a TCR of a regulatory T cell is preferable as it leads to immune regulation including antigen specific immune tolerance. Since NKT cells or γδ T cells themselves have antigen nonspecific killer activity, there is a significance in introducing antigen specific TCRαβ by the method of the present disclosure. It is demonstrated that γδ T cells can generate antigen specific effector T cells by transduction of TCRαβ into a γδ T cell, as described in J Immunol. 2009 Jan. 1; 182(1): 164-70. (PMID: 19109147). It is effective to introduce a highly functional TCR identified by the present disclosure into a γδ T cell.

T cells or T cell population can be isolated by a conventional method from a sample obtained from a subject or the like, such as peripheral blood, bone marrow, tumor tissue, hematopoietic tissue, spleen, normal tissue, or lymph of the subject. Sample collection from peripheral blood can be advantageous for the noninvasiveness and simplicity thereof. For separation of T cell population, sorting by flow cytometry as well as cell separation using magnetism can also be used.

The present disclosure can utilize a first T cell for modifying an endogenous TCR gene and a second T cell having a TCR to be introduced. In this regard, the first T cell and the second T cell can be obtained from the same subject or different subjects (first donor and second donor). Furthermore, the modified first T cell can be used to treat the same subject, or a subject (recipient) who is different from either donor. In one preferred embodiment, the first T cell is a regulatory T cell, and the second T cell is an effector T cell.

Some embodiments of the present disclosure provides a modified T cell or a composition comprising the same. One embodiment provides an endogenous TCR gene-free regulatory T cell. Said T cell can impart desired antigen specificity safely without TCR gene mispairing.

Another embodiment provides a regulatory T cell comprising a full or partial nucleic acid sequence of a gene of TCRα and a full or partial nucleic acid sequence of a gene of TCRβ, wherein the genes are included in a T cell receptor (TCR) clone in an effector T cell population in an effector T cell donor. A T cell receptor (TCR) clone in a T cell population in a donor is considered highly functional. It is understood that a regulatory T cell having such a TCR exhibits antigen specific immunosuppression. The present disclosure also provides a regulatory T cell which is free of an endogenous TCR gene and comprises a full or partial nucleic acid sequence of a gene of TCRα and a full or partial nucleic acid sequence of a TCRβ gene contained in a T cell receptor (TCR) clone that is in an effector T cell population in an effector T cell donor.

2.5 Analysis of Composition of T Cell Subpopulation

The composition of T cell subpopulations can be analyzed upon use of the modified TALEN in the present disclosure.

The composition of a desired T cell subpopulation in a T cell population or a sample can be measured using a conventional method by those skilled in the art. Generally, the number of cells which are positive for a marker identifying a cell subpopulation of interest in a T cell population or a sample, or for a marker correlated with a desired feature (e.g., CD3) can be measured using flow cytometry or the like. A desired cell subpopulation can be separated simultaneously with flow cytometry technology. Examples of advantages of flow cytometry include ease of finding the ratio accounted for by cells introduced with a desired gene, high specificity and sensitivity, high reproducibility, ability to analyze a large number of cells, short time requirement, and the like.

A flow cytometer is an instrument for measuring the optical property of a suspended matter (cell) from a homogeneous cell suspension. Cells pass through a focal point of a laser beam on a liquid flow. A flow cytometer can simultaneously measure, for individual cells, the optical properties of forward scatter, side scatter, and fluorescence of one or more different wavelengths from 500 to 4000 cells per second upon passage, and quickly and accurately measure biological properties such as the size and internal structure of the cells, and the amount of various antigens or nucleic acids within the cell membrane/cytoplasm/nucleus.

Scatter is light scattered to the surrounding from a collision with a cell. Forward scatter (FSC) is detected in front with respect to the laser beam axis, and scatter intensity is proportional to the surface area of a cell. Specifically, it is understood that cells are large for relatively larger FSC values, and cells are small for smaller FSC values. Side scatter (SSC) is detected at a position that is at 90 degrees (perpendicular) to the laser beam axis, and the scatter intensity is proportional to the state of cell granule or intracellular structure. Specifically, it is understood that the internal structure of a cell is more complex for a relatively large SSC value, and the internal structure of a cell is simpler for smaller SSC values.

Results of flow cytometry can be typically expressed as a dot plot, with FSC in the X axis and SSC in the Y axis. Each cell is indicated by a dot (point) in a diagram. The position thereof is determined by the relative values of FSC and SSC. Lymphocytes which have a relatively small size and simple internal structure are displayed on the bottom left section, granulocytes which have a large size and granules inside are displayed on the top right section, and monocytes which have a large size but a simple internal structure are displayed between lymphocytes and granulocytes, with each forming a population separated from one another.

Fluorescence refers to light generated when a fluorescent pigment labeling a cell is excited by an irradiated laser beam and releases energy. Flow cytometers (e.g., product name: Becton & Dickinson FACSCalibur) typically irradiate a 488 nm single wavelength laser beam and a 635 nm single wavelength laser beam. Although cells themselves have a property of emitting weak fluorescence (autofluorescence), actual specific detection of molecules of cells with fluorescence requires attachment of a fluorescent pigment to the cells or molecules thereof in advance in some form. For example, FITC (Fluorescein isothiocyanate) absorbs 488 nm excitation light and primarily emits 530 nm fluorescence (green). If antibodies are labeled with FITC in advance, this would result in a difference in the amount of bound antibodies in accordance with the amount of antigens on the cell surface and thus a difference in the fluorescence intensity of FITC, so that the amount of antigens on the cell surface can be estimated. FACSCalibur that can be used as an example is equipped with four fluorescence detectors, which can detect difference fluorescence wavelength regions. If a plurality of fluorescent pigments emitting lights of different wavelengths are prepared, up to four different antigens can be simultaneously detected. As fluorescent pigments other than FITC that are excited by a 488 nm single wavelength laser beam, PE (phycoerythrin) primarily emits 585 nm fluorescence, and PerCP (peridinin chlorophyll protein) and PE-Cy5 (carbocyanin-5) primarily emits 670 nm fluorescence. APC (allophycocyanin), which is a fluorescent pigment excited by a 635 nm single wavelength laser beam, primarily emits 670 nm fluorescence. These fluorescent pigments are combined with various antibodies and used in double or triple staining of cells. CD3, CD4, CD8, CD25, and TCR that are expressed on the surface of T lymphocytes, Foxp3 molecules expressed inside cells, and the like can be detected with a monoclonal antibody specifically reacting therewith.

Strictly speaking, there are two types of flow cytometers, i.e., instrument that only analyzes cells and instrument capable of separating (sorting) analyzed cells. The latter is known as "FACS". As used herein, "FACS" is an abbreviated of fluorescence-activated cell sorter, referring to an apparatus used in a method of analyzing surface antigens of free cells such as lymphocytes using a laser beam or sorting for a specific cell by the presence/absence of a surface antigen or the like.

Results of flow cytometry can be displayed as a histogram, dot plot, or the like. As used herein, "histogram" refers to a graph representing light signal intensity of each parameter on the X axis and cell count on the Y axis in measurement of fluorescence using a flow cytometer. With such a mode, a total of 10000 or more cells in total can be counted.

As used herein, "dot plot" refers to a plot of fluorescence intensity of two types of fluorescent pigments on the X and Y axes. With double- or triple-stained cells, the cells can be analyzed using a display method in which each fluorescence intensity is placed on the X or Y axis and individual cells correspond to each point on a two dimensional graph.

For example, peripheral blood or bone marrow liquid is collected, and then erythrocytes are removed by the hemolytic method or specific gravity centrifugation, then the residual is reacted with a fluorescently labeled antibody (antibody to antigen of interest and a control antibody thereof) and sufficiently washed for observation using flow cytometry. The detected scattered light or fluorescence is converted to an electric signal and analyzed by a computer. The result can distinguish lymphocytes, mononuclear cells, and granulocytes by representing the intensity of FSC as the cell size and the intensity of SSC as intracellular structure. The cell population of interest is gated thereafter as needed to examine the manner of antigen expression in the cells.

In practicing the method of the present disclosure, those skilled in the art can suitably identify a surface marker of the shown cells to fractionate or count the cells. CD antigens were agreed upon at an international workshop to be classified as clusters (clustering) mainly by the biochemical feature (especially molecular weight) of an antigen recognized thereby as the standard. This is known as CD classification. Many types of monoclonal antibodies that recognize a specific leukocyte differentiation antigen are named thereby under a unified convention, which is CD followed by a number, i.e., CD number (i.e., CD1, CD2, and the like).

Since CD3 molecules are present in the cell membrane and form a complex with a TCR, such molecules can be used as a marker for TCR expression.

It was found that CD4+ T cells highly expressing interleukine-2 receptor a chain, CD25 molecule, have a function of suppressing autoimmune diseases. CD4 and CD25 are used as regulatory T cell markers. Recently, it was found that a transcription factor Foxp3 is a master gene of Treg differentiation, so that Foxp3 is now widely used as a molecular marker identifying CD4+CD25+ Treg. CD127 is used as a cell surface marker for Treg other than Foxp3. It was found that Treg is abundant in the CD4+CD25 strong positive CD127 negative or weak positive T cell fraction.

2.6. Analysis of TCR Repertoire

The modified TALEN of the present disclosure can be used in modifying a TCR based on information obtained by TCR repertoire analysis.

One embodiment of the present disclosure provides a method comprising determining a TCR repertoire of a T cell population. For identification of a TCR clone that is in an effector T cell population which is specific to an antigen in a donor, it was found that a highly functional TCR clone can be identified by measuring the frequency of presence of each TCR clone ($\alpha$ chain or $\beta$ chain) that is in an effector T cell population. The modified TALEN of the present disclosure is useful in terms of the ability to prevent interference by an endogenous TCR gene upon introducing a TCR clone into a T cell. For this reason, the modified TALEN of the present disclosure can be used in a method comprising identifying a highly functional TCR clone and introducing said TCR clone (full or partial nucleic acid sequence thereof). A composition for use in such a method is also provided.

An example of a method of determining a TCR repertoire is a method of analyzing the ratio of T cells expressing individual V$\beta$, chains by flow cytometry using a specific V$\beta$, chain specific antibody for how much of individual V chains is used by a T cell in a sample (FACS analysis).

TCR repertoire analysis through a molecular biological approach has been conceived based on information on a TCR gene obtained from a human genome sequence. This includes a method of extracting RNA from a cell sample and synthesizing a complementary DNA, and then subjecting a TCR gene to PCR amplification for quantification.

A nucleic acid can be extracted from a cell sample by using a tool that is known in the art such as RNeasy Plus Universal Mini Kit (QIAGEN). Total RNA can be extracted and purified from a cell dissolved in a TRIzol LS reagent by using an RNeasy Plus Universal Mini Kit (QIAGEN).

A complementary DNA can be synthesized from an extracted RNA by using any reverse transcriptase known in the art such as Superscript III™ (Invitrogen).

Those skilled in the art can appropriately perform PCR amplification of a TCR gene using any polymerase known in the art. However, an "unbiased" amplification of a gene with large variation such as a TCR gene can result in an advantageous effect for accurate measurement.

A method of designing numerous individual TCR V chain specific primers as primers used for PCR amplification and quantifying each by real-time PCR or the like, or a method of concurrently amplifying such specific primers (Multiple PCR) have been used. However, even for quantification of each V chain using an endogenous control, an accurate analysis cannot be conducted if many primers are used. Furthermore, Multiple PCR has a disadvantage in that a difference in amplification efficiencies among primers leads to a bias during PCR amplification. To overcome such a disadvantage of Multiple PCR, Tsuruta et al. reported Adaptor-ligation PCR for adding an adapter to the 5' terminus of a double stranded complementary DNA of a TCR gene, then amplifying all γδ TCR genes with a common adapter primer and a C region specific primer (Journal of Immunological Methods, 1994, 169, 17-23). This was also applied to amplification of an αβ TCR gene to develop Reverse dot blot (Journal of Immunological Methods, 1997, 201, 145-15.) and Microplate hybridization assay (Human Immunology, 1997, 56, 57-69) for quantification with individual V chain specific oligoprobes.

A preferred embodiment of the present disclosure determines TCR diversity by amplifying, without changing the frequency of presence, TCR genes comprising all isotype and subtype genes with one set of primers consisting of one type of forward primer and one type of reverse primer as described in WO 2015/075939 (Repertoire Genesis Inc., the entire document is incorporated herein by reference). The following primer design is advantageous for unbiased amplification.

Focus was placed on the genetic structure of a TCR or BCR gene. An adaptor sequence is added, without setting a primer to highly diverse V regions, to the 5' terminal thereof to amplify all V region comprising genes. Such an adaptor can have any length or sequence in a base sequence. About 20 base pairs are optimal, but a sequence from 10 bases to 100 bases can be used. An adaptor added to the 3' terminal is removed with a restriction enzyme. In addition, all TCR genes are amplified by amplifying with a reverse primer specific to a C region which has a common sequence with an adaptor primer with the same sequence as a 20 base pair adaptor.

A complementary strand DNA is synthesized with a reverse transcriptase from a TCR or BCR gene messenger RNA and then a double stranded complementary DNA is synthesized. A double stranded complementary DNA comprising V regions with different lengths is synthesized by a reverse transcription reaction or a double strand synthesizing reaction. Adaptors consisting of 20 base pairs and 10 base pairs are added to the 5' terminal section of such genes by a DNA ligase reaction.

The genes can be amplified by setting a reverse primer to a C region of an α chain, β chain, γ chain or δ chain of TCRs. As reverse primers set in a C region, primers are set which match the sequences of each of Cβ, Cα, Cγ and Cδ of TCRs and have a mismatch to an extent that other C region sequences are not primed. A reverse primer of a C region is optimally produced while considering the base sequence, base composition, DNA melting temperature (Tm), or presence/absence of a self-complementary sequence, so that amplification with an adaptor primer is possible. A primer can be set in a region other than the base sequence that is different among allelic sequences in a C region sequence to uniformly amplify all alleles. A plurality of stages of nested PCR are performed in order to enhance the specificity of an amplification reaction.

The length (number of bases) of a primer candidate sequence is not particularly limited for a sequence not comprising a sequence that is different among allelic sequences for each primer. However, the number of bases is 10 to 100, preferably 15 to 50, and more preferably 20 to 30.

Use of such unbiased amplification is advantageous and preferred for identification of a low frequency ($1/10,000$ to $1/100,000$ or less) gene. A TCR repertoire can be determined from read data that is obtained by sequencing a TCR gene amplified in this manner.

PCR amplification on a TCR gene from a human sample and utilization of next generation sequence analysis techniques can now materialize large-scale high efficiency TCR repertoire analysis, which obtains and analyzes more detailed gene information at a clone level from conventional small scale TCR repertoire analysis obtaining limited information such as V chain usage frequency or the like.

The sequencing approach is not limited, as long as a sequence of a nucleic acid sample can be determined. While any approach known in the art can be utilized, it is preferable to use next generation sequencing (NGS). Examples of next generation sequencing include, but are not limited to, pyrosequencing, sequencing by synthesis, sequencing by ligation, ion semiconductor sequencing, and the like.

The obtained read data can be mapped to a reference sequence comprising V, D, and J genes to derive the unique number of reads and determine TCR diversity.

One embodiment prepares a reference database to be used for each of V, D, and J gene regions. Typically, a nucleic acid sequence data set for each allele or each region published by the IMGT is used, but is not limited thereto. Any data set with a unique ID assigned to each sequence can be used.

The obtained read data (including those subjected to appropriate processing such as trimming as needed) is used as the input sequence set to search for homology with a reference database for each gene region, and an alignment with the closest reference allele and the sequence thereof are recorded. In this regard, an algorithm with high tolerance for a mismatch except for C is used for homology search. When a common homology search program BLAST is used, shortening of the window size, reduction in mismatch penalty, and reduction in gap penalty are set for each region. The closest reference allele is selected by using a homology score, alignment length, kernel length (length of consecutively matching base sequence) and number of matching bases as indicators, which are applied in accordance with a defined order or priority. For an input sequence with determined V and J used in the present disclosure, a CDR3 sequence is extracted with the front of CDR3 on reference V and end of CDR3 on reference J as guides. This is translated into an amino acid sequence for use in classification of a D region. When a reference database of a D region is prepared, a combination of results of homology search and results of amino acid sequence translation is used as a classification result.

In view of the above, each allele of V, D and J is assigned for each sequence in an input set. The frequency of appearance by each of V, D and J or frequency of appearance of a combination thereof is subsequently calculated in the entire input set to derive a TCR repertoire. The frequency of appearance is calculated in a unit of allele or unit of gene name depending on the precision required in classification. The latter is made possible by translating each allele into a gene name.

After V region, J region, and C region are assigned to read data, matching reads can be added to calculate the number of reads detected in a sample and the ratio to the total number of reads (frequency) for each unique read (read without the same sequence). A diversity index or similarly index can be calculated with a statistical analysis software such as ESTIMATES or R (vegan) by using data such as number of samples, read type, or the number of reads. In a preferred embodiment, TCR repertoire analysis software (Repertoire Genesis Inc.) is used.

A preferred embodiment of the present disclosure measures TCR diversity using large-scale high efficiency TCR repertoire analysis. As used herein, "large-scale high efficiency repertoire analysis" is described in WO 2015/075939 (the entire disclosure thereof is incorporated herein by reference as needed) and is referred to as "large-scale high efficiency TCR repertoire analysis" when targeting TCR. This method comprises: (1) providing a nucleic acid sample comprising a nucleic acid sequence of a T cell receptor (TCR) which is amplified in an unbiased manner; (2) determining the nucleic acid sequence comprised in the nucleic acid sample; and (3) calculating a frequency of appearance of each gene or a combination thereof based on the determined nucleic acid sequence to derive a TCR repertoire of the effector T cell population.

In another embodiment, (1) providing a nucleic acid sample comprising a nucleic acid sequence of a TCR which is amplified in an unbiased manner can comprise:

(1-1) synthesizing a complementary DNA by using an RNA sample derived from a target cell as a template;

(1-2) synthesizing a double stranded complementary DNA by using the complementary DNA as a template;

(1-3) synthesizing an adaptor-added double stranded complementary DNA by adding a common adaptor primer sequence to the double stranded complementary DNA;

(1-4) performing a first PCR amplification reaction by using the adaptor-added double stranded complementary DNA, a common adaptor primer consisting of the common adaptor primer sequence, and a first TCR C region specific primer, wherein the first TCR C region specific primer is designed to comprise a sequence that is sufficiently specific to a C region of interest of the TCR and not homologous with other genetic sequences, and comprise a mismatching base between subtypes downstream when amplified;

(1-5) performing a second PCR amplification reaction by using a PCR amplicon of (1-4), the common adaptor primer, and a second TCR C region specific primer, wherein the second TCR C region specific primer is designed to have a sequence that is a complete match with the TCR C region in a sequence downstream the sequence of the first TCR C region specific primer, but comprise a sequence that is not homologous with other genetic sequences, and comprise a mismatching base between subtypes downstream when amplified; and (1-6) performing a third PCR amplification reaction by using a PCR amplicon of (1-5), an added common adaptor primer in which a nucleic acid sequence of the common adaptor primer comprises a first additional adaptor nucleic acid sequence, and an adaptor-added third TCR C region specific primer in which a second additional adaptor nucleic acid sequence is added to a third TCR C region specific sequence;

wherein the third TCR C region specific primer is designed to have a sequence that is a complete match with the TCR C region in a sequence downstream to the sequence of the second TCR C region specific primer, but comprise a sequence that is not homologous with other genetic sequences, and comprise a mismatching base between subtypes downstream when amplified. The specific detail of this method is described in WO 2015/075939. Those skilled in the art can perform analysis by appropriately referring to this document and the Examples of the present specification and the like.

2.7. TCR Pair Identification

The modified TALEN of the present disclosure can also be utilized for identifying a TCR pair and introducing a desired TCR.

In one embodiment of the present disclosure, a pair of a TCRα chain and a TCRβ chain is identified as a TCR clone that is in a T cell population. A TCR is understood to exert antigen specificity as a pair of α chain and β chain. The use of the identified pair can further ensure that antigen specificity is imparted to a T cell due to introduction of a pair of TCRs. Therefore, the step of identifying a TCR clone can comprise amplifying a gene of TCRα and a gene of TCRβ derived from the same cell and identifying a pair of TCRα and TCRβ in a T cell population. In another embodiment, the method can further comprise checking whether the identified pair of TCRα and TCRβ has affinity to an antigen. In still another embodiment, the method can further comprise cloning a full or partial nucleic acid sequence of TCRα and a full or partial nucleic acid sequence of TCRβ in the identified pair of TCRα and TCRβ.

The modified TALEN of the present disclosure is preferable because the modified TALEN can prevent mispairing that can be generated by an endogenous TCR, so that antigen specificity of an identified pair can be suitably exerted upon introduction of the pair into a T cell.

For example, the technology described in Nature Medicine 19, 1542 to 1546 (2013) can be used as a technology for such pair identification. A human TCR cDNA is amplified from a single cell, cloned in an expression vector, and transduced into a TCR negative T cell (e.g., TG40 cell strain). TCR antigen specificity is evaluated by staining the T cell with an MHC tetramer or monitoring CD69 expression. Such a process can be performed in its entirety in 10 days or less.

Pair identification from a single cell is theoretically possible with a technology of simultaneously amplifying an α chain and a β chain by multiplex PCR such as those described in, for example, J Clin Invest. 2011 January; 121 (1): 288-95. doi: 10.1172/JCI44752. Epub 2010 Dec. 6. (PMID: 21135507), PloS one [23 May 2012, 7(5): e37338] (PMID: 22649519), and the like.

Some TCR pairing technologies have already been commercialized, which are described in the introduction of Trends Biotechnol. 2017 March; 35(3): 203-214. doi: 10.1016/j.tibtech.2016.09.010. Epub 2016 Oct. 26. (PMID: 28341036), and the like. Table 2 in said document describes a general single cell sequencing technology. For example, a technology using continuous-flow microfluidics (Fluidigm, Kolodziejczyk, A. A. et al. (2015) The technology and biology of single-cell RNA sequencing. Mol. Cell 58, 610-620), plate-based technology (Cellular Research/BD Biosciences, 65. Fan, H. C. et al. (2015) Expression profiling. Combinatorial labeling of single cells for gene expression cytometry. Science 347, 1258367), technology using droplet based microfluidics (10× Genomics, 76. Murphy, K. M. et al. (2016) Janeway's Immunobiology. (9th), Garland Science), and the like are described. In addition, a TCR high throughput pairing technology that does not require isolation of a single cell can also be used, such as the technology described in Sci Transl Med. 2015 Aug. 19; 7(301): 301ra131. doi: 10.1126/scitranslmed.aac5624. (PMID: 26290413). Those skilled in the art can identify a pair of TCRs using such an approach.

Examples of representative technologies for identifying a pair of TCRs include analysis of TCRs derived from a single cell, such as analysis after sorting with a flow cytometer, and single cell RNA-seq using a droplet generator. A single cell analysis kit using the SMART method is sold as a SMARTer® Human scTCR a/b Profiling Kit. An RNA with an unknown sequence on the 5' end side or an RNA without a common sequence can be amplified by a reverse transcription (RT) reaction, template switching (TS) reaction, and PCR reaction. An improved method of such methods can also be used.

If an antigen peptide of interest is known or expected in the analysis after sorting with a flow cytometer, it is possible to sort, by FACS, T cells with a TCR that reacts to the antigen peptide using a tetramer, determine an α chain and a β chain, and identify a pair of TCRs that react to the antigen peptide in a single cell analysis of about 100 to 300 cells. Even if the antigen peptide is unknown, the method can determine a primary pair when a combination can be considered from information for an α chain with high prevalence and β chain with high prevalence confirmed from analysis data for only α chain and only β chain.

Single cell RNA-seq used in a droplet creation apparatus can analyze up to 10000 single cells and analyze up to 10000 or more single cells at once without a two-stage analysis performed in a method using a flow cytometer when the antigen peptide described above is unknown.

Different approaches described above can be used for different purposes. While the objective of the step can be achieved by pair identification with a droplet based method capable of analyzing many cells, the objective of the step can also be achieved by analyzing about 100 to 300 single cells by creating a tetramer when an antigen peptide is known or expected. If the objective is to find a highly functional TCR, analysis of at most several hundred single cells is very cost-effective. If the objective is to comprehensively analyze low frequency TCRs (TCRs of naïve fraction, shared TCRs, or the like), it is understood that analysis using droplets is costly but advantageous.

Recently, single cell RNA-Seq methods have been developed and used in various studies (Hashimshony T et al: Cell Rep, 2(3): 666-673, 2012, Hashimshony T et al: Genome Biol, 17: 77, 2016). Various separation apparatuses such as FACS sorting, microwells, and microfluidic circuits are used for single cell analysis. A method using a droplet separation apparatus can create a single cell library in a highly efficient and simple manner.

TCRs can be analyzed at a single cell level by single cell RNA-Seq using a droplet creation apparatus. A droplet method can create a single cell library of 10000 cells in about 30 minutes by rapidly encapsulating a cell and a carrier of a solid phase oligoprobe in an approximately 100 μm water-in-oil droplet. In 2016's Cell journal, Mocosko et al. reported a Drop-Seq method using oligobeads (Macosko EZ et al: Cell, 161(5): 1202-1214, 2015), and Klein et al. reported an InDrop method using a hydrogel (Klein A M et al: Cell, 161(5): 1187-1201, 2015). Both methods attach a poly(T) probe to which a cell barcode (CBC) and a unique molecular index (UMI) are added to a carrier, and encapsulate a cell and an oligo-carrier in a droplet using a microchip. Subsequently, cDNA synthesis, PCR, and sequencing are performed to materialize scRNA-Seq.

Furthermore, Gene Capture Drop-Seq™ for highly efficiently determining a TCR pair gene has been developed by improving the Drop-Seq method. Gene Capture Drop-Seq™ is a technology for highly efficiently determining a TCR pair gene by attaching barcode labeled-α and β chain TCR oligomers to microbeads and selectively capturing TCR mRNA within a droplet. A method of determining a pair gene by simultaneously sequencing a cell barcode sequence and a CDR3 sequence using a gene-specific probe can efficiently identify a large number of pair genes without a high-spec sequencer. This technology is a useful single cell analysis method that can also be applied in subset analysis focused on expression of a specific gene or determination of a heavy chain and light chain pair of an antigen gene. Those skilled in the art can identify a pair of TCRα chain and TCRβ chain as a TCR clone that is present in a T cell population by using a technology such as those described above.

2.8. Highly Functional TCR

The modified TALEN of the present disclosure can be used to provide a highly functional TCR.

Figure 2:
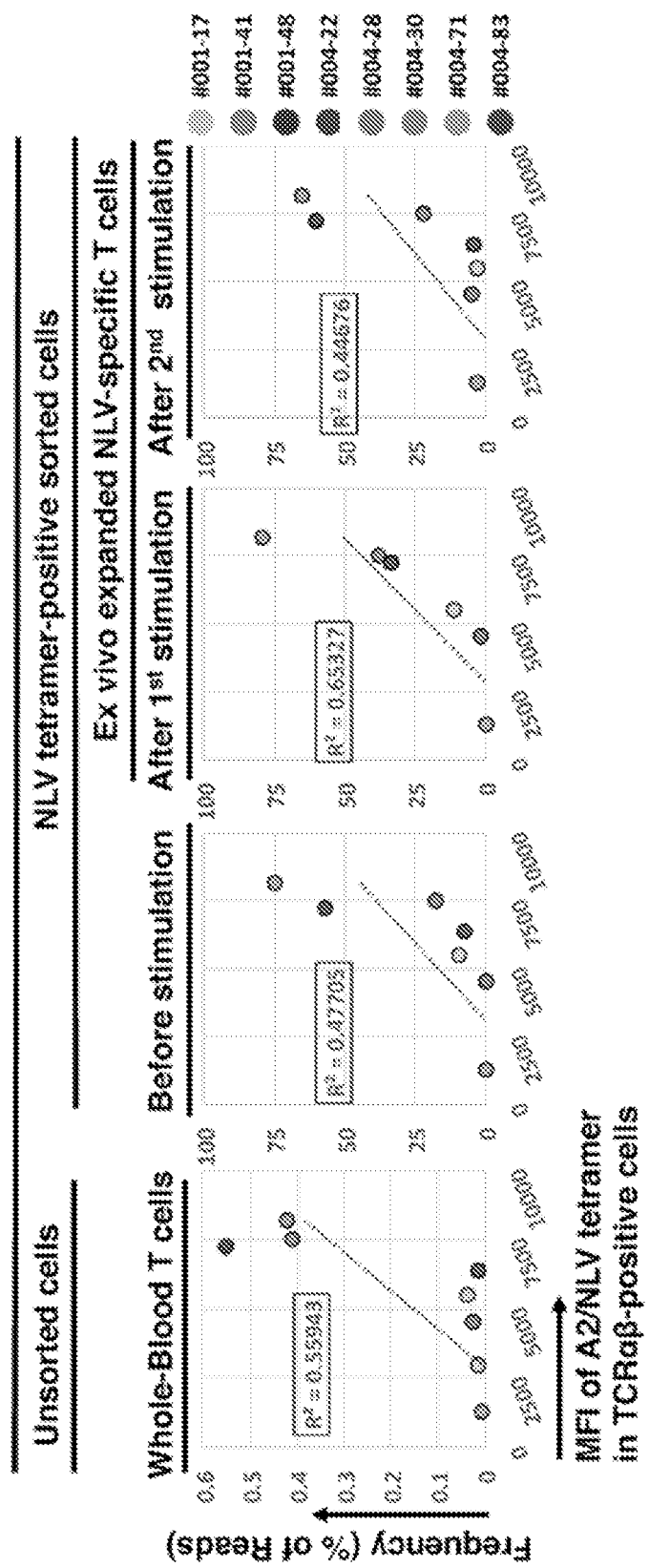
FIG. 2 is a scatter diagram showing the relationship between the frequency of each TCR pair in a TCR repertoire and affinity to an antigen. The vertical axis is the frequency in reads, and the horizontal axis indicates the binding affinity.

It was found that a TCR of a T cell clonotype shared frequently among different individuals is consistently detected in repertoires of all functional T cell subset (naïve, SCM, CM, EM, and EFF) and antigen specific T cell repertoires. It was found that a more dominant antigen specific TCR has higher epitope binding affinity and is derived from a clonotype that is more highly shared, as demonstrated in Example 1 herein (FIG. 2). Furthermore, such an antigen specific TCR is demonstrated to retain antigen affinity when introduced into other T cells in Example 1.

It is demonstrated that epitope binding affinity was higher for a dominant CMV NLV specific clonotype, and a dominant clonotype shares and comprises a TCR clonotype that is present at a relatively high frequency among different individuals (see, for example, Scientific Reports 7, Article number: 3663 (2017); the entire document is incorporated herein by reference for any purpose). It is shown that a more dominant CMV pp65 specific clonotype has a higher epitope binding affinity, and is derived from a clonotype that is more highly shared. This observation suggests that functional TCR clonotypes which are present in a given individual are relative small in numbers, but these clonotypes are shared at a high frequency among different individuals.

One embodiment of the present disclosure provides steps comprising introducing a TCR clone (full or partial nucleic acid sequence) that is present in a T cell population into a T cell. As described above, a clone that is predominantly present in an antigen specific T cell population of an individual has high antigen affinity. Use of such a clone is advantageous in imparting antigen specificity to a cell to be modified. However, a clone that is present in an antigen specific T cell population is comprised of a relatively small number of clonotypes. Any clone included therein can be utilized in impartation of antigen specificity even if the clone cannot be considered dominant. Preferably, a T cell population is an antigen specific effector T cell population.

A clone to be introduced can be a clone that is present at a greater frequency than the mean frequency of presence of each clone in an antigen specific T cell population. For example, a clone to be introduced can be present at a frequency that is 1 standard deviation or more, 2 standard deviation or more, or 3 standard deviation or more greater than the mean frequency of presence of each clone in an antigen specific T cell population.

A TCR clone to be introduced can be present at a frequency of about 1, about 2, about 5, about 8, about 10%, about 12%, or about 15% or greater in a T cell population.

As described above, the modified TALEN of the present disclosure is useful in that it can prevent interference by an endogenous TCR gene when introducing a TCR clone into a T cell. The modified TALEN of the present disclosure can be used in a method comprising identifying the aforementioned highly functional TCR clone and introducing said TCR clone (full or partial nucleic acid sequence thereof). A composition for use in such a method is also provided.

2.9. Introduction of Exogenous TCR

In one embodiment of the present disclosure, the modified TALEN of the present disclosure can be used in a method comprising introducing a TCR into a T cell. A T cell is preferably a regulatory T cell. Since the modified TALEN of the present disclosure can eliminate the effect of an endogenous TCR, it is suitable for use in such a method. Some embodiments of the present disclosure provide a composition comprising a modified TALEN for use in a method comprising introducing a TCR to a T cell.

The introducing step can be a step of introducing a full or partial nucleic acid sequence of a gene of TCRα and a full or partial nucleic acid sequence of a gene of TCRβ. Preferably, a highly functional TCR described herein is introduced into a T cell. A highly functional TCR can be identified as a pair of TCRs. Preferably, a TCR is introduced so that such a TCRα chain and a TCRβ chain are expressed as a pair.

Introduction of TCRs so that they are expressed as a pair is described in Cancer Immunol Immunother. 2016 June; 65(6): 631-49 (PMID: 27138532) and the like. There are technologies for introducing TCRs so that they are expressed as a pair other than a method of forming a disulfide bond by Cys formation (introduction of a Cys residue) such as codon optimization/introduction of a leucine zipper into an intracellular region/sugar chain modification of TCR.

Examples of existing technologies for avoiding mispairing applied to TCR introducing vectors include:
1) introduction of Cys (Blood. 109: 2331, 2007.);
2) Leucin zipper (Proc Natl Acad Sci. 91: 11408, 1994.);
3) equal expression of α/β chains using a 2A sequence (optionally codon optimization) (J Mol Med 88: 1113, 2010);
4) removal of specific N-glycosylation site (J Exp Med. 206: 463, 2009.);
5) use of intracellular domain of mice or the like (Cancer Res. 66: 8878, 2006; J Immunol. 184: 6223, 2010);
6) use of a single chain TCR (α-β-Constant) (Blood. 115: 5154, 2010);
and the like.

A TCR can be introduced using a vector that enables such expression. For example, a vector can be configured to comprise a nucleic acid sequence encoding Cys so that a disulfide bond is formed between TCRα and TCRβ to be expressed, to codon optimize the coding sequence of TCRα and TCRβ, to introduce a leucine zipper into an intracellular region of TCRα and TCRβ, or to express TCRα and TCR with modification of a sugar chain.

In the present disclosure, full nucleic acids of a TCR clone that has been identified can be introduced, or only a part of the nucleic acids can be introduced as long as the binding affinity is maintained. In one embodiment, a part of a nucleic acid sequence of a gene of TCRα comprising a sequence corresponding to a CDR3 region of Vα-Jα can be introduced. A part of a nucleic acid sequence of a gene of TCRβ comprising a sequence corresponding to a CDR3 region of Vβ-D-Jβ can be introduced. A part of a nucleic acid sequence of a gene of TCRα comprising a cDNA sequence of Vα-Jα-Cα can be introduced. A part of a nucleic acid sequence of a gene of TCR comprising a cDNA sequence of Vβ-D-Jβ-Cβ can be introduced.

In one embodiment of the present disclosure, removal of an endogenous TCR gene and introduction of a TCR can be performed in two steps for complete substitution of an endogenous TCR. For example, a method is provided, comprising: removing one of genes of endogenous TCRα and endogenous TCRβ in a T cell, introducing a full or partial nucleic acid sequence of a gene of TCRα and a full or partial nucleic acid sequence of a gene of TCRβ into a T cell; and removing the other one of the genes of endogenous TCRα and endogenous TCRβ in the T cell, and reintroducing a full or partial nucleic acid sequence of a gene of TCRα and a full or partial nucleic acid sequence of a gene of TCRβ in the T cell.

An exogenous TCR can be knocked in and introduced into a genome without using a viral vector for complete substitution of an endogenous TCR. A knock-in technology using homologous recombination (HR) is known. A method mediated by microhomology-mediated end joining (MMEJ) can also be used instead of homologous recombination (HR). MMEJ is one of the DNA repairing mechanisms of eukaryotes. This is a mechanism of repairing by binding complementary sequences (5 to 25 base pairs) to each other between both cleaved ends generated upon double strand cleavage. When inserting an exogenous gene by utilizing the MMEJ repair mechanism, a recognition sequence of artificial nuclease is added to a donor vector, so that the sequence complementarily binds with a target site of a chromosome and a cleaved end of a vector upon double strand cleavage. A gene can be knocked into a target site by introducing the donor vector with an artificial nuclease (TALEN, CRISPR/Cas, and the like) (referred to as TAL-PITCh method and CRIS-PITCh method, respectively) (Nature Communications volume 5, Article number: 5560 (2014)). When an exogenous TCR is introduced using a viral vector, there is a theoretical risk of carcinogenicity while the probability may not be a practical issue. Thus, it can be advantageous to avoid using a viral vector in terms of avoiding such a risk.

2.10 Cell Population

One embodiment of the present disclosure provides a cell population of cells comprising an exogenous TCR of interest, the cell population having a reduced ratio of cells comprising an exogenous TCR other than the exogenous TCR of interest. The ratio of cells comprising an exogenous TCR other than the exogenous TCR of interest in the cell population of the invention is, for example, less than about 20%, about 15%, about 12%, about 10%, about 7%, about 5%, about 3%, about 2%, or about 1%, or the cell population of the invention is substantially free of cells comprising an exogenous TCR other than the exogenous TCR of interest. Non-limiting examples of exogenous TCR of interest include those specific to NY-ESO-1.

Exogenous TCRs other than the exogenous TCR of interest include TCRs other than a pair of α chain and β chain of the exogenous TCR of interest, such as TCRs expressed as a result of unintended pairing (mispairing) of an introduced TCR chain and an endogenous TCR. It has been reported that creation of a cell population of cells comprising an exogenous TCR generates mispairing with an endogenous TCR, which has the potential for loss of antigen specificity and/or manifestation of unintended antigen specificity. While a method of reducing such mispairing has been studied, it is reported that the ratio of TCR mispairing is reduced to only about 12 to 22%, even if endogenous TCR expression is suppressed with siRNA and Cys modifications are used in a TCR introducing vector (Okamoto et al., Molecular Therapy-Nucleic Acids (2012) 1, e63).

One embodiment of the present disclosure provides a method of creating the aforementioned cell population, comprising: removing an endogenous TCR from a cell; and introducing a nucleic acid encoding an exogenous TCR into the cell with the endogenous TCR removed. The steps of removing an endogenous TCR and introducing a nucleic acid encoding an exogenous TCR into the cell with the endogenous TCR removed in this method are described herein, or a technology that is well known to those skilled in the art can be used. For example, an endogenous TCR can be removed with the modified TALEN described herein. For example, a nucleic acid encoding an exogenous TCR can be introduced using the vector with a Cys modification described herein.

2.11 Other Application Examples

The modified TALEN of the present disclosure is also useful in manipulating the specificity of a T cell. A T cell manipulated to express an exogenous TCR so that mispairing/off-target does not occur using the modified TALEN of the present disclosure can be utilized in adoptive immunotherapy or the like.

The regulatory T cell of the present disclosure can be used in treatment, therapy, or prevention of autoimmune disease, allergic disease, or graft-versus-host disease (GVHD), rejection, or graft failure in transplantation because it is understood that antigen specific regulatory T cells are effective in suppressing immune responses to the antigen.

Examples of autoimmune diseases include, but are not limited to, rheumatoid arthritis (RA), Sjogren's syndrome, systemic lupus erythematosus (SLE), antiphospholipid syndrome, polymyositis/dermatomyositis, systemic sclerosis, mixed connective tissue disease, vasculitis syndrome, type I diabetes, Graves' disease, Hashimoto Disease, idiopathic Addison's disease, autoimmune hepatitis, Goodpasture syndrome, glomerulonephritis, autoimmune hemolytic anemia (AIHA), autoimmune thrombocytopenic purpura, autoimmune neutropenia, myasthenia gravis, pemphigus, vitiligo, idiopathic azoospermia, and the like. Examples of allergic diseases include, but are not limited to, hay fever, allergic rhinitis, bronchial asthma, atopic dermatitis, and the like. In addition, the antigen specific regulatory T cell of the present disclosure can be used for the treatment or prevention of diseases in which an abnormal immune response to a specific antigen is involved in the onset or progression of the pathological condition.

3. Kit

The present disclosure also provides a kit for editing a TCR gene. A kit can comprise: a composition or combination comprising the modified TALEN of the present disclosure; means for checking for a mutation in an endogenous TCR gene; and/or means for checking for removal of an endogenous TCR gene.

In another embodiment, a kit can comprise: a composition or combination comprising the modified TALEN of the present disclosure; means for introducing an exogenous TCR gene; and/or means for detecting a cell introduced with a gene. Furthermore, a kit can be for substituting an endogenous TCR gene with an exogenous TCR gene. A kit can also be used for the manufacture of a TCR modified T cell. The TCR modified T cell is, for example, a TCR modified regulatory T cell.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present invention has been described while showing preferred embodiments to facilitate understanding. While the present invention is described hereinafter based on the Examples, the above descriptions and the following Examples are provided for the sole purpose of exemplification, not limitation of the present invention. Thus, the scope of the present invention is not limited to the embodiments and Examples that are specifically described herein and is limited only by the scope of claims.

EXAMPLES

The Examples are described hereinafter. The subjects used in the following Examples were handled, when needed, in compliance with the ethical guidelines for human genomic gene/analysis studies specified by the national government, ethical guidelines for medical studies involving humans, and the standards stipulated by the Hiroshima University. Even where it is not explicitly stated, animal experiments were conducted, when applicable, in accordance with the spirit of animal protection and relevant laws and regulations.

Example 1: Identification/Cloning of High Affinity Clone (Summary)

The objective of this Example is to demonstrate that an immunologically dominant clone is a high affinity clone, and demonstrate a method of identifying/cloning such a clone.

The distribution of the frequency of presence of TCR clones in an antigen specific T cell population after stimulating a T cell population with an antigen was measured, and each TCR clone was cloned. It was found from measuring the binding capability of each TCR clone to an antigen that a dominant clone in a T cell population had high antigen binding capability. Information related to this Example is also described in Scientific Reports 7, Article number: 3663 (2017). The entire document is incorporated herein by reference for any purpose.

(Materials and Methods)

[Donor Sample]

This Example was conducted in accordance with the principles of the Declaration of Helsinki. All experiments using human samples were conducted in accordance with the protocol approved by the ethics committee of the Hiroshima University. Peripheral blood mononuclear cells (PBMC) were obtained from five healthy donors who provided written consent. All donors were screened for the CMV serum conditions and subjected to genotyping for HLA-A, -B, -C, -DRB1, -DQB1, and -DPB1 alleles using a high resolution Luminex technology. The PBMCs were isolated using a standard Ficoll gradient separation protocol and then stored in liquid nitrogen.

[Flow Cytometry Analysis and Cell Sorting]

The expression of cell surface molecules was determined using the following fluorescently labeled monoclonal antibodies (mAb): allophycocyanin (APC) conjugated or fluorescein isothiocyanate (FITC) conjugated anti-CD8, allophycocyanin-hilite7 (APC-H7) conjugated anti-CD3, phycoerythrin-cyanine7 (PE-Cy7) conjugated anti-CD45R0 mAb, brilliant violet 510 (BV510) conjugated anti-CD62L mAb, brilliant violet 421 (BV421) conjugated anti-CD197 mAb, APC conjugated anti-CD95, and APC conjugated anti-TCR4. These antibodies were purchased from BD Bioscience (San Jose, Calif.). CMV pp65 specific T cells were reacted with phycoerythrin (PE) conjugated HLA-A*02-peptide tetramer as described in Kuzushima, K. et al. Tetramer-assisted identification and characterization of epitopes recognized by HLA A*2402-restricted Epstein-Barr virus-specific CD8+ T cells. Blood 101, 1460-1468 (2003). The CD8 binding site on MHC-I of the tetramer was intact. The inventors selected the NLVPMVATV (SEQ ID NO: 2) sequence of HLA-A*02 restricted CMV pp65 peptide (NLV peptide) as a model antigen. The MHC tetramer staining was performed for 15 minutes at room temperature, and then cell surface was stained for 30 minutes at 4° C. The concentration of tetramers used in all the experiments was 10 µg/ml, except for serial dilution experiments. Nonspecific tetrameter straining was checked using a negative control tetramer (HLA-A2-HIV (KLTPLCVTL (SEQ ID NO: 3)) tetramer-PE).

Flow cytometry analysis and cell sorting were performed using FACSCanto II (BD Biosciences, San Jose, Calif.) and FACSAria (BD Biosciences, San Jose, Calif.). All flow cytometry data was analyzed using the FlowJo software (Tree Star, Ashland, Oreg.). Dead cells and damaged cells were removed using 7-AAD, and doublet cells were removed using FSC-A/FSC-H and SSC-A/SSC-H. CD3+ CD8+ T cells were further fractionated into the following functional subsets: naïve, CD45RO−CD62L+CCR7+ CD95−; SCM, CD45RO−CD62L+CCR7+CD95+; CM, CD45RO+CD62L+CCR7+; EM, CD45RO+CD62L−CCR7−; and EFF, CD45RO−CD62L−CCR7−.

[Cell Culture]

PBMCs and sorted CD8+ T cells were cultured in X-VIVO 20 (Lonza, Walkersville, Md.) containing 10% AB serum, 2 mmol/l L-glutamine, and 1% penicillin/streptomycin. B-lymphoblastoid cell line (B-LCL) was cultured in RPMI 1640 (Sigma-Aldrich, St Louis, Mo.) containing 10% FBS, 2 mmol/l L-glutamine, and 1% penicillin/streptomycin. All cells were cultured in a humidifying incubator at 37° C. under a 5% $CO_2$ containing atmosphere.

Phytohemagglutinin (PHA) blasts were generated by culturing PBMCs in a CTL medium containing 5 µg/ml PHA-L (Sigma-Aldrich, St Louis, Mo.). On the next day, IL-2 (Peprotech, Rocky Hill, N.J.) was added to the final concentration of 50 U/ml. Half of the medium was then replaced twice with a fresh medium containing IL-2 (50 U/ml) and IL-7 (Peprotech, Rocky Hill, N.J.) (20 ng/ml) each week. PHA blasts were used after 14 days from starting the culture.

Jurkat cells engineered to lack TCR expression by CRISPR-Cas9 were established as follows. Briefly, after CRISPR-Cas9 mediated knockout of the endogenous TCRα chain, CD3 negative cells were enriched by flow sorting. The sorted cells were transduced with an episome vector comprising a TCRα chain, and then CD3 positive cells (Jurkat cells with a transduced α chain and an endogenous β chain) were enriched by flow sorting. The endogenous TCRβ of the sorted cells was knocked out with CRISPR-Cas9, and then CD3 negative cells (Jurkat cells without endogenous TCRα and TCRβ) were enriched. Single cell cloning of Jurkat cells was performed using a single cell sorting method by flow cytometry. Finally, a TCR chain was transduced into the cloned Jurkat cells, and Jurkat clones that were endogenous TCRα negative, endogenous TCRβ negative, and transduced TCRα negative were then selected. TCRα negative of a clone was confirmed by transducing TCRβ into the clone. TCRβ negative of a clone was confirmed by transducing TCRα into the clone. The clone was also transduced with a pMX-CD8α expression vector, and brightly stained with an anti-CD8 mAb.

[In Vitro Stimulation of CMV Pp65 Specific T Cell]

CD8+ T cells were isolated from PBMCs using CD8 microbeads. CD4+ T cells were removed from the rest of the cells using a CD4+ T-cell isolation kit (Miltenyi Biotec, Auburn, Calif.). The remaining CD4/CD8 double negative cells were used as antigen presenting cells (APC). After irradiation of radiation (35 Gy), the APCs were exposed to an NLV peptide for 2 hours at room temperature, and co-cultured with the same number of CD8+ T cells in a CTL medium containing IL-2 and IL-7. Synthetic NLV peptides were purchased from GenScript (Piscataway, N.J.). Half of the medium was exchanged twice each week.

[Semi-Quantitative Analysis of TCR Repertoire Using High Throughput NGS]

Comprehensive TC repertoire analysis using NGS and unbiased gene amplification method using adaptor ligation PCR was performed as summarized hereinafter. Total RNA was extracted from PBMC ($5\times10^6$) or sorted T cells, and converted into cDNA using a BSL-18E primer comprising $poly(T)_{18}$ and NotI sites. A double stranded (ds) DNA was then synthesized, and the end was blunted using a T4 DNA polymerase (Invitrogen). A P10EA/P20EA adaptor was ligated to the 5' terminus of the dsDNA, and then cleaved by NotI. After removing the adapter and primer, PCR was performed using a TRA constant region specific primer or a TRB constant region specific primer and P20EA. Second PCR was performed using a constant region specific P20EA primer with the same PCR conditions. The product of the second PCR was used for high throughput sequencing using an Illumina Miseq platform. After removing sequences with a low quality score, TCR repertoire analysis was performed using a bioinformatics software created by Repertoire Genesis Incorporation (Ibaraki, Japan). More details of individual procedures are described in the following sections.

[Unbiased Amplification of TCR Gene]

Total RNA was extracted from PBMCs or sorted T cells using an RNeasy Lipid Tissue Mini Kit (Qiagen, Hilden, Germany) in accordance with the manufacturer's instruction. The amount of RNA and purity were measured using Agilent 2200 TapeStation (Agilent Technologies, Palo Alto, Calif.). 1 μg of total RNA was converted into cDNA using Superscript III reverse transcriptase (Invitrogen, Carlsbad, Calif.). A BSL-18E primer comprising poly(T)$_{18}$ and NotI sites was used for cDNA synthesis. After the cDNA synthesis, a double stranded (ds) cDNA was synthesized using Escherichia coli DNA polymerase I (Invitrogen), E. coli DNA Ligase (Invitrogen), and RNase H (Invitrogen). The ends of the dscDNA were blunted using T4 DNA polymerase (Invitrogen). A P10EA/P20EA adaptor was ligated to the 5' end of the dscDNA, and then cleaved by NotI. After removing the adaptor and primer with a MinElute Reaction Cleanup kit (Qiagen), PCR was performed using a primer of P20EA and one of a TCRα chain constant region specific primer (CA1) or TCR chain constant region specific primer (CB1). The PCR conditions were 20 cycles of 95° C. (30 seconds), 55° C. (30 seconds), and 72° C. (1 minute). Second PCR was performed using a primer of P20EA and one of CA2 and CB2 under the same PCR conditions.

The primers used are shown in the following Table.

TABLE 1

Primer for next generation sequendng of rearranged T cell receptor gene segment

| Primer | Sequence | MID Tag |
|---|---|---|
| BSL-18E | AAAGCGGCCGCATGCTTTTTTTTTTTT TTTTTVN | |
| P20EA | TAATACGACTCCGAATTCCC | |
| P10EA | GGGAATTCGG | |
| CA1 | TGTTGAAGGCGTTTGCACATGCA | |
| CA2 | GTGCATAGACCTCATGTCTAGCA | |
| CB1 | GAACTGGACTTGACAGCGGAACT | |
| CB2 | AGGCAGTATCTGGAGTCATTGAG | |
| HuVaF-01~10 | CCATCTCATCCCTGCGTGTCTCCGACTCAG- (MID)-ATAGGCAGACAGACTTGTCACTG | MID1~MID11 |
| HuVbF-01~10 | CCATCTCATCCCTGCGTGTCTCCGACTCAG- (MID)-ACACCAGTGTGGCCTTTTGGGTG | MID15~MID24 |
| B-P20EA | *CCTATCCCCTGTGTGCCTTGGCAGTC*TAATA CGACTCCGAATTCCC | |

Correspond to, from the top, SEQ ID NOs: 4 to 13.
V: A/C/G, N: A/C/G/T, and sequences of adaptor A and B are respectively indicated by bold and bold italic.
The Key sequence (TCAG) is indicated by underlines.
The MID tag sequences used for identification of a sample source are the following.
MID1, ACCAGTGCGT; MID2, ACGCTCGACA; MID3, AGACGCACTC; MID4, AGCACTGTAG; MID5, ATCAGACACG; MID6, ATATCGCGAG; MID7, CGTGTCTCTA; MID8, CTCGCGTGTC; MID10, TCTCTATGCG; MID11, TGA-TACGTCT; MID15, TACGACGTA; MID16, TCACGTACTA; MID17, CGTCTAGTAC; MID18, TCTACGTAGC; MID19, TGTACTACTC; MID20, ACGACTACAG; MID21, CGTAGACTAG; MID22, TACGAGTATG; MID23, TACTCTCGTG; MID24, AGAGACGAG (Each corresponding to SEQ ID ID NOs: 14 to 33 in the order of description)

[Amplicon Sequencing Using Roche 454 Sequencing System]

Amplicons for NGS were prepared from the product of second PCR using a P20EA primer and a fused tag primer (Table 1). The fused tag primer comprised an A adapter sequence (CCATCTCATCCCTGCGTGTCTCCGAC (SEQ ID NO: 34)), a 4 base sequence key (TCAG), and a molecule identification (MID) tag sequence (10 nucleotides). TCR constant region specific sequences were designed in accordance with the manufacturer's instruction. After PCR amplification, amplicons were evaluated using agarose gel electrophoresis. Incomplete fragments or primers were removed using Agencourt AMPure XP (Beckman Coulter, Brea, Calif.) in accordance with the manufacturer's instruction. The amount of purified amplicons was quantified using a Quant-iT PicoGreen dsDNA Assay Kit (Life Technologies, Carlsbad, Calif.). Each amplicon obtained from 10 samples by different fused tag primers was mixed at an equal molar concentration. Emulsion PCR (emPCR) was performed with a GS Junior Titanium emPCR Lib-L kit (Roche 454 Life Sciences, Branford, Conn.) in accordance with the manufacturer's instruction by using the amplicon mixture.

[Assignment of TRV and TRJ Segments]

All sequence reads were classified in accordance with the MID tag sequence thereof. Artificially added sequences (tags, adapters, and keys) and sequences with a low quality score were removed from both ends of sequence reads using the software provided with 454 Sequencing System. The remaining sequences were used in the assignment of TRAV and TRAJ of TCRα sequences and TRBV and TRBJ of TCRβ sequences. Sequences were assigned by determining the sequence with the highest percentage identity in a data set of reference sequences (54 TRAV, 61 TRAJ, 65 TRBV, and 14 TRBJ genes (including pseudogenes and open reading frame (ORF) reference sequences)) that are available from the ImMunoGeneTics Information System (IMGT) database. Data processing, assignment, and data aggregation were automatically performed using a repertoire analysis software (Repertoire Genesis, RG) independently developed by Repertoire Genesis Incorporation (Osaka, Japan). RG first assigns TRV and TRJ alleles to a query using BLASTN and IMGT data set. Identity between a query and reference sequence was calculated in this step. Parameters that increase the sensitivity and accuracy (E value threshold, minimum kernel, and high score segment pair (HSP) score) were optimized for each repertoire analysis. Next, RG estimates a CDR3 region of the query by examining a translated reading frame. RG then calculates the distribution of TRV-CDR3-TRJ patterns and generates graphs (e.g., TRV-TRJ use histogram or CDR3 length distribution chart). These steps were automatically performed after inputting the query.

[Data Analysis]

A translated nucleotide sequence of a CDR3 region spanned a range from conserved Cys104 to conserved Phe118 or Gly119 in accordance with the IMGT nomenclature. A unique sequence read (USR) was defined as 0% identity to the deduced amino acid sequence of a CDR3 domain of TRV, TRJ and other sequence reads. The RG software automatically counted the number of copies of the same UCR in each sample, and then ranked the UCRs in order of the number of copies. The percentage frequency of sequence reads of TRAV, TRAJ, TRBV, and TRBJ genes was calculated.

[Single Cell Sorting and RT-PCR]

To identify and characterize a CMV NLV specific TCRαβ pair expressed by a single cell, the inventors used a modified hTEC10 system (Kobayashi, E. et al. A new cloning and expression system yields and validates TCRs from blood lymphocytes of patients with cancer within 10 days. Nat. Med. 19, 1542-1546 (2013), Hamana, H., shiaoka, K., Kishi, H., Ozawa, T. & Muraguchi, A. A novel, rapid and efficient method of cloning functional antigen specific T-cell receptors from single human and mouse T-cells. Biochem. Biophys. Res. Commun. 474, 709-714 (2016)) as follows. CD8/NLV tetramer double positive cells were sorted in each well of a 96-well PCR plate. cDNA was synthesized/amplified using multiplex RT-PCR. Gene specific primers used for amplifying a sequence encoding a TCRα chain and TCRβ chain were designed from a leader peptide sequence obtained from the IMGT database. PCR reactions are described in detail in the following [RT-PCR analysis of TCRA and TCRB pairs]. TCR repertoire analysis was performed using the IMGT/V-Quest tool.

[RT-PCR Analysis of TCRA and TCRB Pairs]

RT-PCR was performed in a reaction mixture comprising 0.1 μl of 40 U/μl RNase Inhibitor (NEB, Ipswich, Mass.), 0.1 μl of 200 U/μl PrimeScript II RNase (TaKaRa, Otsu, Japan), 0.4 μl of primer mixture, 0.025 μl of 2.5 U/μl PrimeStar HS DNA Polymerase (TaKaRa), 0.4 μl of 2.5 mM dNTP, and 2.5 μl of 5× PrimeStar GC buffer (TaKaRa). DEPC treated $H_2O$ was added, such that the final volume was 5 μl. The RT reaction was performed for 40 minutes at 45° C., and then the following PCR reaction was performed. 30 cycles of 1 minute at 98° C., then 10 seconds at 98° C., 5 seconds at 55° C., and 1 minute at 72° C. A PCR reactant was diluted 10-fold with water and then used as a template DNA for nested PCR. Nested PCR for amplifying TCRA and TCRB was performed with a different 96-well PCR plate. The reaction mixture included 2 μl of DNA template from the first PCR reaction, 0.4 μl of 10 μM of respective specific primer set (for TCRα, A-AD and A-RV2 primers, and for TCRβ, B-AD and B1-RV2 primers and B2-RV2 primer), 0.1 μl of 2.5 U/μl PrimeSTAR HS DNA Polymerase, 1.6 μl of 2.5 mM dNTP, 10 μl of 5× PrimeSTAR GC Buffer, 0.1 μl of 2.5 U/μl, and $H_2O$ (added until reaching a final volume of 20 μl). The PCR cycle was the following: 35 cycles of 1 minute at 98° C., then 10 seconds at 98° C., 5 seconds at 55° C., and 1 minute at 72° C. TCRA and TCRB PCR products were analyzed by Sanger sequencing.

[Studying the Binding Capability of Cloned TCR)

1) Each of the cloned TCRαβ pair genes (CMV pp65, NLVPMVATV: NLV specific) described above was transferred into a TCRαβ deficient Jurkat cell using a retroviral vector (pMXs-IRES GFP).
2) GFP positive cells were separated from the Jurkat cells introduced with each TCR gene using a cell sorter (Aria II).
3) The Jurkat cells introduced with each TCR were stained with serially diluted NLV tetramers at concentrations of 2, 4, 6, 8, and 10 μg/ml.
4) The fluorescence intensity (MFI) of tetramer positive cells was measured using flow cytometry to analyze the binding capability of each TCR with a tetramer.

(Results)

The results are shown in FIGS. 1 and 2. For donors V001 and V004, T cell clones with the clonotypes shown in FIG. 1 were identified as antigen specific clonotypes. It was found that a population of antigen specific clones is comprised of a very small number of clones.

FIG. 2 shows the comparison of frequency of presence of each TCR clone measured by the method described above and bindability to antigens. A linear correlation is observed between the frequency and binding affinity from the results. It is understood that dominant clones within the antigen specific T cell population are high affinity clones.

Example 1-2

The step of [Semi-quantitative analysis of TCR repertoire using high throughput NGS] in Example 1 was performed by the following procedure using a different sequencer (Miseq, Illumina).

[Summary of Changes in the Experimental Protocol]

The same steps as Example 1 were performed from RNA-double stranded DNA synthesis. For PCR, the same steps were performed from 1st PCR to 2nd PCR, and the steps thereafter were performed as PCR for Miseq (Tag PCR and Index PCR). Changes in reagents included use of KAPA HiFi HotStart ReadyMix recommended as the PCR enzyme of next generation sequencing.

3-2-9: Sample Manipulation 7 (1st, 2nd PCR)

The flow for analyzing two genes of human TCRαβ is described.

<1st PCR>

The amount of reagent for 1 sample is shown.

Add 10 μL of 2×KAPA HiFi Hot Start Ready Mix to each of α and β tubes.

Add 7.6 μL of DW (for DNA, bottle) to each of α and β tubes. Add 0.2 μL of 10 μM P20EA primer to each of α and β tubes.

Add 0.2 μL of 10 μM CA1 primer to an α tube, and 0.2 μL of 10 μM CB1 primer to a β tube.

Add 2 μL of each dsDNA sample to a tube containing α or β solution.

Select the applicable setting (program name: KAPA20, conditions of 95° C. 3 min, 20 cycles (98° C. 20 sec, 65° C. 30 sec, 72° C. 1 min), 72° C. 2 min, lastly 12° C. forever) in a thermal cycler.

<2nd PCR>

The amount of reagent for 1 sample is shown.

Add 10 μL of 2×KAPA HiFi Hot Start Ready Mix to each of α and β tubes.

Add 6 μL of DW to each of α and β tubes.

Add 1 μL of 10 μM P20EA primer to each of α and β tubes.

Add 1 μL of 10 μM CA2 primer to an α tube, and 1 μL of 10 μM CB2 primer to a β tube.

Add 2 μL of a and β 1st PCR product to 2nd PCR tubes for α and β PCR, respectively.

Select the applicable setting (program name: KAPA20, conditions of 95° C. 3 min, 20 cycles (98° C. 20 sec, 65° C. 30 sec, 72° C. 1 min), 72° C. 2 min, lastly 12° C. forever) in a thermal cycler.

<DNA Purification 1>

3-2-10: Sample Manipulation 8 (AMpure Purification 1)

Use BECKMAN COULTER's Agencourt AMPure XP in this step.

Admix AMPure XP beads thoroughly until the mixture is homogenous, and dispense 8 μL into a tube.

Add 10 μL of 2nd PCR product to the tube into which AMPure XP beads have been dispensed, and place the tube on MM-Separater M96 to collect magnetic beads.

Remove the supernatant, rinse with 200 μL of 70% ethanol, place the supernatant on the MM-Separater M96 to collect magnetic beads.

Completely remove the supernatant, dispense 30 μL of DW (for DNA, bottle), vortex, and place on MM-Separator M96 to collect magnetic beads.

Collect 25 μL of supernatant.

<Tag PCR>

3-2-11: Sample Manipulation 9 (Tag PCR)

Add 10 μL of 2×KAPA HiFi Hot Start Ready Mix to each of α and β tubes.

Add 4.2 μL of DW (for DNA, bottle) to each of α and β tubes. Add 0.4 μL of 10 μM P22EA-ST1-R primer to each of a and β tubes.

Add 0.4 μL of 10 μM CA-ST1-R primer to an α tube, and 0.4 μL of 10 μM CB-ST1-R primer to a β tube.

Add 5 µL of each 2nd PCR purified sample to each tube containing α and β reagent mixture.

Select the applicable setting (program name: KAPA20, conditions of 95° C. 3 min, 20 cycles (98° C. 20 sec, 65° C. 30 sec, 72° C. 1 min), 72° C. 2 min, lastly 12° C. forever) in a thermal cycler.

<DNA Purification 2>

3-2-14: Sample Manipulation 11 (AMpure Purification 2)*

*The manipulation in this section is the same as the protocol "3-2-10: Sample manipulation 8 (AMpure purification 1)"

<Design of Index PCR for Analyzing a Plurality of Specimens in One Sequencing>

3-2-15: Sample Manipulation 12 (Creation of Sheet Required for Index PCR)

3-2-15-1: The Main Point

Index PCR is performed to add an index sequence and P5/P7 sequence (portion binding to flowcell) to each sample.

Determine the order of arrangement of samples and primers in advance (matrix), and create a sample sheet with Illumina Experiment Manager.

An existing product of Illumina (Nextera XT Index Kit v2 Set A) is used as the index primer.

<Index PCR>

3-2-16: Sample Manipulation 13 (Index PCR)

The amount of reagent for 1 sample is indicated in this protocol.

Add 10 µL of 2×KAPA HiFi Hot Start Ready Mix to a tube.

Add 4 µL of DW (for DNA, bottle) to a tube.

Dispense 14 µL in an 8-strip PCR tube.

Dispense N primer 2 µL at a time.

Dispense S primer 2 µL at a time.

Dispense Tag PCR purified sample to a predetermined tube 2 µL at a time.

Select the applicable setting (program name: INDEX12, conditions of 95° C. 3 min, 12 cycles (95° C. 30 sec, 55° C. 30 sec, 72° C. 30 sec), 72° C. 5 min, lastly 4° C. forever) in a thermal cycler.

<Electrophoresis>

3-2-17: Sample Manipulation 14 (Electrophoresis and Evaluation 2)

About 650 bp for TCR genes

Prepare 1.5% agarose gel, and use Atlas ClearSight for staining.

Place gel in an electrophoresis vessel, and subject 4 µL of index PCR product to electrophoresis (30 minutes at 100 V) with a 100 bp DNA ladder and 10× Dye. Evaluate results of amplification using a UV transilluminator or digital camera.

if too thin, PCR conditions need to be changed (increased to 15 cycles) by returning to the protocol "3-2-16: Sample manipulation 13 (Index PCR)".

<Measurement of Concentration 1>

3-3-3: Sample Manipulation 1 (DNA Concentration Measurement by Qubit)

Dilute DW (for DNA, bottle) 10-fold using an Index PCR product.

Dilute the dye included in a Qubit dsDNA HS Assay kit 200-fold with the included buffer.

Add 190 µL of diluted dye solution to two 500 µL dedicated tubes (for Standard) and 198 µL of diluted dye solution is added for specimens.

Add 10 µL each of Standard #1 and Standard #2 included in the Qubit dsDNA HS Assay kit to the 500 µL dedicated tubes (two tubes) to which 190 µL of diluted dye solution have been added.

Add 2 µL of Index PCR product to the 500 µL dedicated tubes (10 tubes) to which 198 µL of diluted dye solution have been added.

Activate Qubit. Select the measurement mode "dsDNA", and then select "High Sensitivity".

Move to the measurement screen and select "Read standards" at the bottom.

Measure Standard #1 and Standard #2 in order. Confirm that the value is several "10s" or "10s of thousands"

Set the amount of specimen input to 2 µL for measurement.

Since the range of measurement is 0.1 to 50 ng/µL, measurement is redone after dilution if the value is beyond the range.

Based on the measurement results, dispense specimens in separate tubes so that equal amount of DNA can be mixed from a plurality of specimens (generally, 50 to 60 specimens are simultaneously measured in Miseq sequencing) to prepare a pooled specimen.

<DNA Purification 3>

3-2-18: Sample Manipulation 15 (AMpure Purification 3)

The manipulation in this section is the same as the manipulation in the protocol "3-2-10: Sample manipulation 8 (AMpure purification 1)", but is adjusted in accordance with the amount of the pooled specimen.

<Concentration Measurement 2>

Same manipulation as 3-3-3: Sample manipulation 1 (Dilution and DNA concentration measurement by Qubit).

Since the specimen concentration used in sequencing with Miseq is 4 nM (1.72 ng for 650 bp), the specimen is diluted to the designated concentration after measurement.

<Sequencing Run Using Miseq>

3-3: MiSeq Sequence Analysis 3-3-4: Sample Manipulation 2 (Denaturation of Phi-X and DNA Library)

Mix 5 µL of 0.2 N—NaOH with 5 µL of pooled specimen (DNA) prepared to be 4 nM.

Mix 5 µL of 0.2 N—NaOH with 5 µL of PhiX (sequence stabilization reagent; contains random bases) prepared to be 4 nM.

Dispense Hyb-Buffer in each mixture and mix so that the final concentration is 10 µM, DNA:PhiX=4:1 (PhiX is 20%) for final adjustments.

3-3-5: Sample Manipulation 3 (Miseq Run)

Illumina's Miseq is used for sequence analysis. MiSeq Reagent Kit v3 (600 cycles) MS-102-3003 is used as the primary sequencing reagent. The manipulation method includes dispensing a specimen that has undergone final adjustment into a designated well in a frozen reagent cassette and placing the cassette in the equipment.

Information such as primer sequences is described below.

TABLE 2

| Name | Sequence | Length |
|---|---|---|
| BSL-18E | AAAGCGGCCGCATGCTTTTTTTTTTTTTT TTVN | 35 |
| P10A | GGGAATTCGG | 10 |
| P20EA | TAATACGACTCCGAATTCCC | 20 |
| P22EA-ST1-R | GTCTCGTGGGCTCGGAGATGTGTATAAGAGA CAGCTAATACGACTCCGAATTCCC | 55 |
| Tag-1 | GTCTCGTGGGCTCGGAGATGTGTATAAGAGA CA | 33 |

TABLE 2-continued

| Name | Sequence | Length |
|---|---|---|
| Tag-2 | TCGTCGGCAGCGTCAGATGTGTATAAGAGACAG | 33 |
| CA1 | TGTTGAAGGCGTTTGCACATGCA | 23 |
| CA2 | GTGCATAGACCTCATGTCTAGCA | 23 |
| CA-ST1-R | TCGTCGGCAGCGTCAGATGTGTATAAGAGACAGGAGGGTCAGGGTTCTGGA | 51 |
| CB1 | GAACTGGACTTGACAGCGGAACT | 23 |
| CB2 | AGGCAGTATCTGGAGTCATTGAG | 23 |
| CB-ST1-R | TCGTCGGCAGCGTCAGATGTGTATAAGAGACAGAGGCTCAAACACAGCGACCTC | 52 |

(Corresponding to, from the top, SEQ ID NOs: 4, 6, 5, 35 to 37, 7, 8, 38, 9, 10, and 39)

See https://support.illumina.com/content/dam/illumina-support/documents/documentation/chemistry documentation/experiment-design/illumina-adapter-sequences_1000000002694-01.pdf for more information on Index PCR primers.

Example 1-3

The portion of [Single cell sorting and RT-PCR] and [RT-PCR analysis of TCRA and TCRB pairs] in Example 1 can also be performed by the following procedures. This procedure was developed by improving Drop-Seq method as a Gene Capture Drop-Seq™ that highly efficiently determines TCR pair genes. A single cell TCR pair gene determination method using Gene Capture Drop-Seq™ and a manufacturing method of TCR specific oligobeads are described. More details of this procedure are described in Yodosha, "Jikken Igaku/Bessatsu" [*Experimental Medicine/Extra Issue*] Single Cell Analysis Protocol (issue published on Oct. 10, 2017). The entire document is incorporated herein by reference.

[Preparation]
(Equipment)
Dolomite Bio's single cell RNA-Seq system (FIG. 19A) (three P pumps, three sets of flow meters, cell agitator, digital microscope, single cell RNA-Seq chip)
MiSeq sequencer (Illumina)
Qubit 3.0 fluorometer (Thermo Fisher Scientific)

A single cell separation apparatus (Dolomite Bio) is comprised of three P pumps, three sets of flow meters, cell agitator, digital microscope, and single cell RNA-Seq chip. The apparatus is equipped with a monitor so that droplet formation can be viewed in real time, and is designed to be highly extensible thus enabling various assemblies.

Figure 19B:
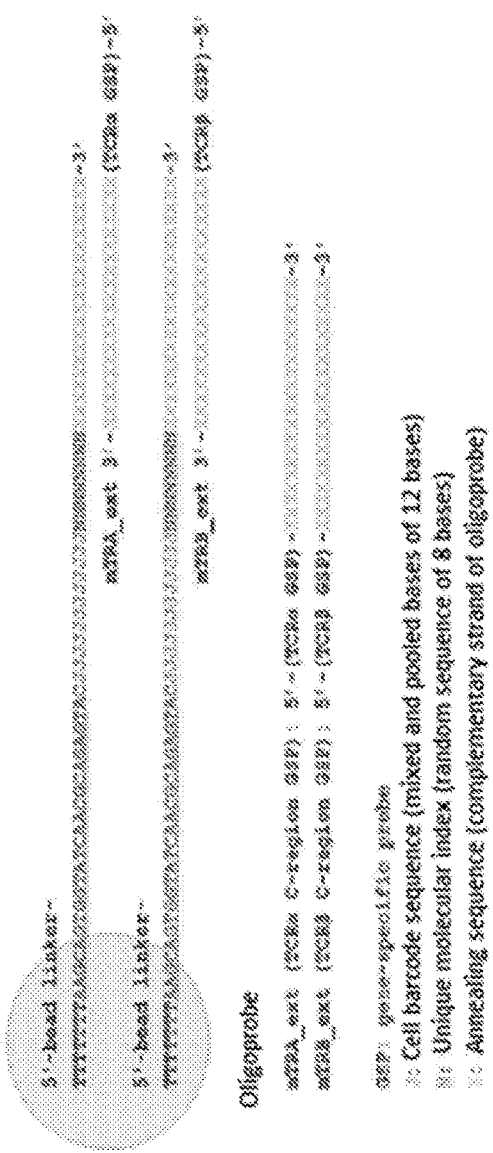
FIG. 19B shows an outline of Oligobeads. The SMART sequence in the Oligobeads corresponds to SEQ ID NO: 45.
Figure 19A:
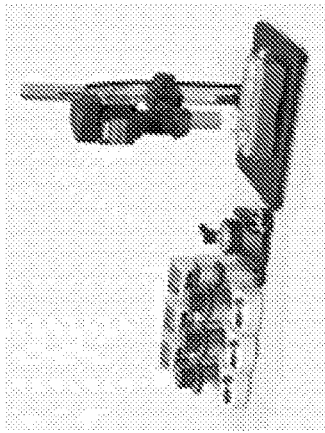
FIG. 19A shows a single cell RNA-Seq system from Dolomite Bio.

(Reagents)
1. Beads Oligo Creation
TE 10 mM Tris-HCl, pH 8.0, 1 mM EDTA
TE/TW 10 mM Tris-HCl, pH 8.0, 1 mM EDTA, 0.1% Tween20
TE/SDS 10 mM Tris-HCl, pH 8.0, 1 mM EDTA, 0.5% SDS
Bst reaction stopper 100 mM KCl, 10 mM Tris-HCl (pH 8.0), 50 mM EDTA, 0.1% Tween20
NaOH detergent I 150 mM NaOH, 0.5% Brij35P
NaOH detergent II 100 mM NaOH, 0.5% Brij35P
Neutral buffer 100 mM NaCl, 100 mM Tris-HCl (pH 8.0), 10 mM EDTA, 0.1% Tween20
Oligo immobilized beads (custom synthesis, Chemgene)[1] (FIG. 19B)

[1] Synthesis of oligobeads was commissioned to ChemGene in the US. The oligobeads for RNA-Seq of Mocosko et al. consist of the SMART sequence (SEQ ID NO: 45) followed by 12 base mixed and pooled bases (cell barcode sequence, J), 8 base random sequence (unique molecular index, N), and 30 base Poly (T) sequence. An annealing sequence is added instead of a Poly (T) sequence to Gene Capture. Both a TCRα chain C region specific probe and a TCR chain C region specific probe are bound to a single bead by an extension reaction.

Synthetic DNA
Bst 3.0 DNA Polymerase (NEB)
Exonuclease I (NEB)

Probe oligos are bound to beads by an extension reaction. Oligobeads of a gene of interest can be created by synthesizing a gene-specific probe (GSP) with an annealing sequence and performing an extension reaction. Two genes forming a pair have the same cell barcode sequence, so that a pair gene can be determined from the sequence.

2. Cell Separation
Serum medium RPMI 1640 (Wako Pure Chemical), 10% FCS, penicillin/streptomycin (Wako Pure Chemical), 50 μM 2-mercaptoethanol
ACK lysis buffer 0.15 M $NH_4Cl$, 0.01 M $KHCO_3$, 0.1 mM $Na_2$ EDTA, pH 7.2 to 7.4
70 μm cell strainer (Corning)
MACS magnetic cell separator (Miltenyi Biotec)
$CD8a^+$ T Cell Biotin-Antibody Cocktail (Miltenyi Biotec)
Anti-Biotin MicroBeads (Miltenyi Biotec)
MACS LS column (Miltenyi Biotec)
MACS buffer PBS, 2 mM EDTA, 0.5% BSA 3. Single Cell Separation
100 μm filter
40 μm filter
Cell lysis solution 200 mM Tris-HCl (pH 7.5), 6% ficoll PM400 (GE Healthcare), 0.2% sarkosyl (20% N-Lauroylsarcosine sodium salt, Sigma-Aldrich), 20 mM EDTA, 1.5 M Betaine, 0.2×SSC, 5% DMSO
1 M DTT
Cell buffer PBS, 0.01% BSA
Droplet Generator Oil for EvaGreen (Bio-Rad)
Perfluorooctanol (PFO, Sigma-Aldrich)
6×SSC 4. Template Switching Reverse Transcription Reaction
Superscript IV (Thermo Fisher Scientific)
10 mM dNTPs (Promega)
RNasin® Plus RNase Inhibitor (Promega)
KAPA HiFi HotStart ReadyMix (KAPA Biosystems)
TSO oligo: GTCGCACGGTCCATCGCAGCAGT-CACAGG (1G), 1G: LNA oligo (SEQ ID NO: 40)
TSO PCR primer: GTCGCACGGTC-CATCGCAGCAGTC (SEQ ID NO: 41)
SMART PCR primer: AAGCAGTGGTAT-CAACGCAGAGT (SEQ ID NO: 42)
TSO_TAG primer:

(SEQ ID NO: 43)
GTCTCGTGGGCTCGGAGATGTGTATAAGAGACAGCGTCGCACGGTCCATCG

CAGCAGTC

SMART_TAG primer:

(SEQ ID NO: 44)
TCGTCGGCAGCGTCAGATGTGTATAAGAGACAGAAGCAGTGGTATCAACGC

AGAGT

Figure 19D:
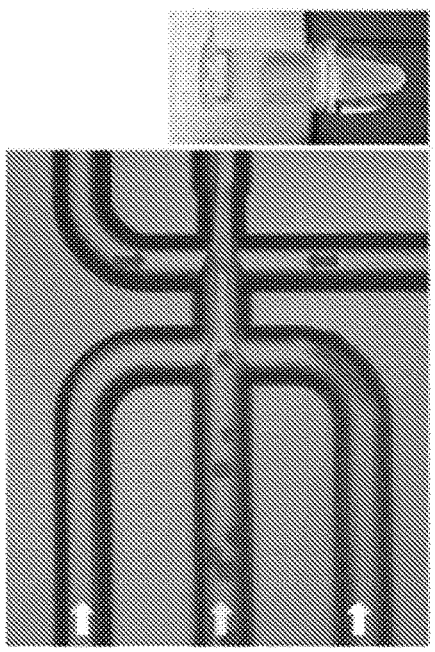
FIG. 19D shows the bead flow and droplets in a microchip. The beads flow through the center line (yellow) and mix with two cell lines (white), and is injected into an oil line (red) to form a droplet (left diagram). The beads are randomly encapsulated by a droplet while passing through. The collected droplets (white) are separated from the oil layer (transparent) and can be readily retrieved.
Figure 19C:
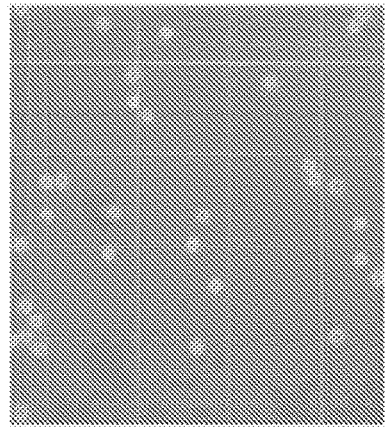
FIG. 19C shows Oligobeads under a microscope.

Nextera XT Index Kit v2 SetA (illumina)
Agencourt AMPure XP (Beckman Coulter)
EB buffer (5 mM Tris-HCl, pH 8.5)
Qubit dsDNA assay kit (Thermo Fisher Scientific)
(Cells)
T lymphoma cell line (EL-4)
Mouse splenocytes (C57BL/6)
[Protocol]
1. Creation of Oligobeads
   (1) Suspend custom oligobeads (10 μmole scale) obtained from ChemGene in 30 mL of TE/TW, centrifuge for 1 minute at 1000 g and wash (repeated twice). Beads can be readily washed and collected by suspending the beads in a buffer and centrifuging for 1 minute at 1000 g. Use a swing rotor to carefully remove the buffer so as not to suction the beads.
   (2) Count the beads using a hemocytometer (FIG. 19C). Suspend the beads in a TE/TW solution to attain 500000 beads/mL, and refrigerate the beads. The beads can be refrigerated for a long period of time in TE/TW. The beads manufactured by ChemGene use TOYOPEARL HW. The beads have a diameter of about 30 μm.
   (3) Dispense 1 mL of the bead suspension (500,000 beads) into an Eppendorf tube and centrifuge for 1 minute at 1000 g.
   (4) Suspend the beads in 500 μL of 1× Isothermal buffer (NEB) and centrifuge for 1 minute at 1000 g (for prewashing with next extension reaction buffer).
   (5) Prepare the next extension reaction solution and add the solution to the beads in (4).

TABLE 3

| Oligo extension reaction solution (μL) | |
| --- | --- |
| 10 × Isothermal buffer | 5 |
| 10 mM $MgSO_4$ | 1.5 |
| 10 mM dNTPs | 5 |
| 100 uM mTRA_ext | 5 |
| 100 uM mTRB_ext | 5 |
| DW | 26.5 |
| Total | 48 |

(6) After incubating for 2 minutes at 85° C., incubate the solution for 20 minutes at 60° C.
   (7) Add 2 μL Bst 3.0 polymerase (800 U/μL) and react with a heat rotator for 1 hour and 30 minutes at 60° C. Since beads precipitate during an enzymatic reaction, use of a heat rotator is desirable to maintain uniform reaction.
   (8) Add 1 mL of Bst reaction stopper, incubate for 30 minutes, and centrifuge for 1 minute at 1000 g (repeated twice).
   (9) For exonuclease I treatment, add 1 mL of 1× exonuclease buffer and prewash, and centrifuge for 1 minute at 1000 g (single stranded DNA is degraded to remove unreacted bead bound oligos).
   (10) Prepare the next exonuclease I reaction solution and suspend the beads.

TABLE 4

| 10 × exonuclease buffer | 5 |
| --- | --- |
| DW | 42.5 |
| Total | 47.5 |

(11) Add 2.5 μL exonuclease I (20 U/μL) so that the final concentration would be 1 U/μL and react with a heat rotator for 45 minutes at 37° C.
   (12) Suspend the beads in 1 mL of TE/SDS and centrifuge for 1 minute at 1000 g (repeated twice).
   (13) Suspend the beads in 1 mL of NaOH detergent and centrifuge for 1 minute at 1000 g (double stranded DNA that binds to beads is denatured by alkaline washing to prepare a single stranded DNA probe).
   (14) Suspend the beads in 1 mL of NaOH detergent II and centrifuge for 1 minute at 1000 g (repeated twice).
   (15) Suspend the beads in 1 mL of TE/TW and centrifuge for 1 minute at 1000 g (repeated twice). Finally, suspend the beads in TE/TW so as to attain $5 \times 10^5$ beads/mL and refrigerate until use.
2. Preparation of Cells
<Mouse T Cell Line>
   (1) Centrifuge a mouse T lymphoma cell line cultured in a serum medium for 5 minutes at 800 g, and collect the cells.
   (2) Wash the cells with 10 mL of serum medium.
   (3) Suspend the cells in 10 mL of serum medium and filter the cells through a 75 μm cell strainer. Count the cells with a hemocytometer.
<Mouse Splenocytes>
   (1) Dissect mice (C57BL/6, 6 week old) to extract the spleens. Prepare cells immediately before single cell separation as much as possible to reduce cell damage.
   (2) Gently grind the spleens at the frosted section of a slide glass on a culture dish comprising 10 mL of serum medium.
   (3) Transfer the serum medium to a 15 mL centrifuge tube and wait for debris to precipitate.
   (4) Transfer the supernatant to another centrifuge tube and centrifuge for 5 minutes at 800 g.
   (5) After removing the supernatant, add 2 mL of ACK lysis buffer. Suspend the mixture and incubate for 2 minutes at room temperature to break the red blood cells.
   (6) Add 10 mL of serum medium to stop hemolysis, and centrifuge for 5 minutes at 800 g.
   (7) Suspend the cells in 10 mL of serum medium and filter the cells through a 75 μm cell strainer. Count the cells with a hemocytometer.
<Mouse Spleen CD8 Positive Cells>
   (1) Fractionate $1 \times 10^8$ cell solution and centrifuge for 5 minutes at 800 g.
   (2) Suspend the cells in 10 mL of ice-cooled MACS buffer and then centrifuge for 5 minutes at 800 g.
   (3) Add 400 μL of $CD8a^+$ T Cell Biotin-Antibody Cocktail and incubate for 5 minutes on ice.
   (4) Add 300 μL of MACS buffer, and then add 200 μL of Anti-Biotin Microbeads. Incubate the mixture for 10 minutes on ice.
   (5) During this time, place an LS column in a magnetic separator and add 3 mL of MACS buffer to recycle the column.
   (6) Load 1 mL of cell suspension into the LS column, and aggregate the flow-through.
   (7) Further add 3 mL of MACS buffer and collect all flow-throughs.
   (8) Add 6 mL of serum medium and centrifuge for 5 minutes at 800 g.
   (9) Add 10 mL of serum medium and centrifuge for 5 minutes at 800 g.
   (10) Add 4 mL of serum medium, and count the cells.

3. Separation of Single Cells 3-1. Set-Up of Dolomite Bio's Single Cell Separator (Since Microfiber Contamination can Cause Line Clogging, it is Preferable to Use a Dust-Free Wiper for Clean Rooms to Clean the Lab Bench so that Dust or the Like would not Fall in.)

(1) Activate the compressor. Boot up a PC and dedicated controlling software (Mitos Flow Control Center).

(2) Check the connection of each line and install a microchip so that a flow channel can be viewed on a monitor under a microscope.

(3) Place filtered sterile water and control oil in a bottle in a P pump. Filter all reagents that are placed in a line in advance. Use Novec 7700 or FC40 (3M) for the run because EvaGreen Droplet Oil comprising a surfactant is expensive.

(4) Perform a test flow by setting the flow rate of cell lines and bead line to 40 µL/min and setting oil lines to 200 µL/min. The droplet size can be adjusted by changing the flow rate. While the size is about 85 µm under these conditions, the size can be adjusted to about 100 µm at 30 µL/min (cells), 30 µL/min (beads), and 166 µL/min (oil).

(5) Check that droplets are formed without any problems with a microscope.

3-2. Preparation of Beads (6) Fractionate $1.5 \times 10^5$ beads, centrifuge for 1 minute at 1000 g, and pellet down the beads.

(7) Add 500 µL of lysis buffer, prewash the beads, and centrifuge for 1 minute at 1000 g.

(8) Add 500 µL of lysis buffer and adjust the mixture to $3 \times 10^5$ beads/mL.

(9) Filter with a 70 um filter and then draw in with a 1 mL syringe.

(10) To inject beads in a 500 µL sample loop, switch the valve and slowly inject the beads while inverting the syringe. Perform the process while inverting the syringe so that the beads do not precipitate.

(11) Set the flow rate of the beads line to 40 µL/min and stand by with the valve closed.

3-3. Preparation of Cells

(12) Fractionate $1 \times 10^6$ cells suspended in a serum medium and centrifuge for 5 minutes at 800 g.

(13) Suspend the cells in 10 mL PBS/BSA and centrifuge for 5 minutes at 800 g.

(14) Suspend the cells in PBS/BSA so the concentration is $3 \times 10^5$ cells/mL and filter with a 70 µm filter and then set a bottle in a P pump. Cool the cells with ice to prevent degradation.

(15) RUN the separator at a flow rate of 40 µL/min while stirring with a stirrer bar.

3-4. Preparation of Oil

(16) Take out the bottle containing the control oil and place Droplet Generation Oil for EvaGreen for droplets in the P pump.

(17) Set the flow rate to 200 µL/min and confirm that oil is flowing and droplets are formed.

3-5. Preparation of Output Line

(18) Set an output line to a tube to collect droplets coming out from a microchip.

(19) Open the bead line to allow beads to flow in the microchip. Confirm that beads are flowing and droplets are formed while viewing the monitor screen (FIG. 19D). Droplets are formed at 4000/second under this condition. A bead is encapsulated into one of 20 droplets.

(20) Collect droplets for 15 to 20 minutes. Confirm that there are no more beads on the monitor screen. Two layers, i.e., top layer droplet and bottom layer oil, can be observed from the collected droplet solution.

4. Breakage of Droplets (1) Collect droplets into a tube and remove the bottom layer of oil. Remove oil by aspiration with the tip end. Perform the following steps as quickly as possible.

(2) Dispense all droplets in the top layer (white) in 8-strip PCR tubes.

(3) Anneal droplets for 2 minutes at 75° C. and reduce the temperature by 1° C. at a 30 second interval from 65° C. to 50° C.

(4) Transfer all the droplets into a 50 mL conical tube and add 10 mL of cooled 6×SSC solution.

(5) Add 500 µL of perfluorooctanol (PFO) and vigorously vortex.

(6) Centrifuge for 1 minute at 1000 g and carefully remove the supernatant. Beads form a white layer. Note that beads may float up in 6×SSC. If beads do not precipitate, the beads can be recentrifuged or collected with a 25 µm filter. At the same time, remove the oil layer (clear) that has accumulated at the bottom.

(7) Add 10 mL of 6×SSC and vigorously vortex, and then centrifuge again for 1 minute at 1000 g. Carefully remove the supernatant and wash the beads (repeat twice).

(8) Transfer the white beads to an Eppendorf tube and centrifuge for 1 minute at 1000 g to remove the supernatant.

5. Template Switching Reverse Transcription Reaction (1) Add 100 µL of 5×RT buffer to bead pellets and centrifuge for 1 minute at 1000 g for prewashing.

(2) Prepare the following reverse transcription reaction solution and add beads.

TABLE 5

| Reverse transcription reaction solution | |
| --- | --- |
| 5 × 1st strand buffer | 10 µL |
| 0.1M DTT | 2.5 µL |
| 10 mM dNTPs | 2.5 µL |
| 48 µM TSO[1] | 2.5 µL |
| RNasin Plus (40 U/µL) | 2.5 µL |
| DW | 28 µL |
| Total | 48 µL |

[1]To create a directional library, a template switching oligo (TSO) that is different from the bead sequence is used. A SMART oligo added to beads can also be used.

(3) Add 2 µL of SuperScript IV (200 U/µL) and incubate at 50° C. for 1 hour and 30 minutes with a heat rotator.

(4) Add 100 µL of TE/SDS solution and centrifuge for 1 minute at 1000 g to remove the supernatant.

(5) Add 100 µL of TE/TW solution and centrifuge for 1 minute at 1000 g to remove the supernatant (repeat twice).

(6) Add 100 µL of 1× exonuclease buffer and centrifuge for 1 minute at 1000 g for prewashing.
(7) Add the following exonuclease reaction solution to the beads.

TABLE 6

| Exonuclease reaction solution | |
|---|---|
| 10 × exonuclease buffer | 2 µL |
| DW | 17 µL |
| Total | 19 µL |

(8) Add 1 µL of exonuclease (20 U/µL) and incubate with a heat rotator for 30 minutes at 37° C.
(9) Add 100 µL of TE/SDS solution and centrifuge for 1 minute at 1000 g to remove the supernatant (repeat twice).
(10) Add 100 µL of TE/TW solution and centrifuge for 1 minute at 1000 g to remove the supernatant (repeat twice).

6. PCR Reaction (1) Add 100 µL of DW and centrifuge for 1 minute at 1000 g to remove the supernatant.
(2) Prepare the following pre-PCR reaction solution and add beads.

TABLE 7

| Pre-PCR reaction solution | |
|---|---|
| 2 × KAPA HiFi HotStart ReadyMix | 10 µL |
| 10 µM TSO PCRPrimer[1] | 0.4 µL |
| 10 µM SMART PCRprimer | 0.4 µL |
| DW | 9.2 µL |
| Total | 20 µL |

Pre-PCR cycle
3 minutes at 98° C. (20 seconds at 98° C., 20 seconds at 65° C., and 3 minutes at 72° C.)
18 cycles, 5 minutes at 72° C.
[1]PCR can be performed with only a SMART PCR primer when using a SMART sequence as TSO.

(3) Add 12 µL of Ampure beads to 15 µL PCR product and incubate for 5 minutes at room temperature.
(4) Incubate for 2 minutes at room temperature on a magnet plate and remove the supernatant.
(5) Wash with 200 µL of 70% ethanol (repeat twice).
(6) Completely remove the 70% ethanol and then dry up the beads for 1 minute.
(7) Add 15 µL of EB buffer (5 mM Tris-HCl, pH 8.5), vortex, and incubate for 1 minute.
(8) Incubate for 2 minutes at room temperature on a magnet plate and collect the supernatant in a new tube.
(9) Prepare the following PCR reaction solution, add 2 µL of purified pre-PCR reaction solution, and perform PCR in the next cycle.

TABLE 8

| PCR reaction solution | |
|---|---|
| 2 × KAPA HiFi HotStart ReadyMix | 10 µL |
| 10 µM TSOprimer | 1 µL |
| 10 µM SMARTprimer | 1 µL |
| DW | 6 µL |
| Total | 18 µL |

PCR cycle
3 minutes at 98° C., (20 seconds at 98° C., 20 seconds at 65° C., and 3 minutes at 72° C.)
30 cycles, 5 minutes at 72° C.

(10) Check the PCR products by 2% agarose gel electrophoresis.
(11) Collect PCR products by purification with the same Ampure beads as (3) to (8).
(12) Prepare an INDEX tag added-PCR reaction solution, add 2 µL of purified PCR reaction solution, and perform PCR in the next cycle.

TABLE 9

| Tag PCR reaction solution | |
|---|---|
| 2 × KAPA HiFi HotStart ReadyMix | 10 µL |
| 10 µM TSO_TAG primer | 1 µL |
| 10 µM SMART_TAG primer | 1 µL |
| DW | 6 µL |
| Total | 18 µL |

Tag PCR cycle
3 minutes at 98° C., (20 seconds at 98° C., 20 seconds at 65° C., and 3 minutes at 72° C.)
18 cycles, 5 minutes at 72° C.

(13) Collect PCR products by purification with the same Ampure beads as (3) to (8).
(14) Prepare a PCR reaction solution for INDEX PCR, add 2 µL of purified PCR reaction solution, and perform PCR in the next cycle.

TABLE 10

| INDEX PCR reaction solution | |
|---|---|
| 2 × KAPA HiFi HotStart ReadyMix | 10 µL |
| N-primer | 2 µL |
| S-primer | 2 µL |
| DW | 4 µL |
| Total | 18 µL |

Tag PCR cycle
3 minutes at 95° C., (30 seconds at 95° C., 20 seconds at 55° C., and 2 minutes at 72° C.)
14 cycles, 5 minutes at 72° C.

(15) Collect PCR products by purification with the same Ampure beads as (3) to (8).
(16) Measure the amount of DNA for the purified INDEX PCR product with Qubit 3.0 fluorometer using a Qubit dsDNA assay kit.
(17) Dilute the PCR product to attain 4 µM, and perform sequencing with MiSeq with a goal of 300000 to 1000000 reads.

7. TCR Repertoire

Analysis of the read total and assignment of V, D, and J region sequences with a mouse TCR reference sequence of sequence data was performed with a dedicated software for repertoire analysis developed by Repertoire Genesis. MiXCR, HighVQuest provided by IMGT, and the like are known as available TCR analysis software. Such software can also be used. Barcode matching between read sequences can be performed using Biostrings of R or a similar package.

[Discussion]

The analysis after sorting with a flow cytometer used in Example 1-1 and the droplet based approach described in Example 1-3 can be used for different objectives. If the objective is to find a highly functional TCR, analysis of at most several hundred single cells is very cost-effective. If the objective is to comprehensively analyze low frequency TCRs (TCRs of naïve fraction, shared TCRs, or the like), it is understood that analysis using droplets is costly but advantageous.

Example 2: Removal of Endogenous TCR (Summary)

This Example demonstrates complete removal of endogenous TCR genes by genome editing that targets a TCR gene.

(Materials and Method)

[Manufacture of Platinum TALEN]

(Materials and Method)

[Manufacture of Platinum TALEN]

A Platinum TALEN targeting an endogenous TCR gene was manufactured in accordance with the manufacturer's protocol (http://www.addgene.org/kits/yamamoto-platinum-gate/#protocols-and-resources) using a Platinum TALEN manufacturing kit (Platinum Gate TALEN Kit).

[mRNA Synthesis from Platinum TALEN]

(1) Plasmids of Left (L)-TALEN and Right (R)-TALEN for cleaving a TRA or TRB gene were treated with SmaI for 2 hours at 30° C.
(2) The plasmids were treated with Proteinase K for 20 minutes at 50° C. and purified with a QIAGEN PCR Purification Kit.
(3) mRNA was synthesized with an mMESSAGE MACHINE T7 Kit (Life technologies), followed by poly(A) Tailing Kit (Life technologies) and purified by LiCl precipitation method (in accordance with the Manufacturer's instruction).

In this Example, a pair of TALEN-TCR-alpha2_L19 and TALEN-TCR-alpha2_R19 was used for targeting a gene of TCRα. The full length sequences of these plasmids are represented by SEQ ID NO: 46 and SEQ ID NO: 47. The TALEN coding sequence of TALEN-TCR-alpha2_L19 is represented by SEQ ID NO: 52, and the amino acid sequence of said TALEN is represented by SEQ ID NO: 53. The TALEN coding sequence of TALEN-TCR-alpha2_R19 is represented by SEQ ID NO: 54, and the amino acid sequence of said TALEN is represented by SEQ ID NO: 55.

In this Example, a pair of TALEN-TCR-beta1_L19 and TALEN-TCR-beta1_R19, or TALEN-TCR-beta3_L19 and TALEN-TCR-beta3_R19 was used for targeting a gene of TCRβ. The full length sequences of these plasmids are represented by SEQ ID NO: 48, SEQ ID NO: 49, SEQ ID NO: 50, and SEQ ID NO: 51 in the order of description. The TALEN coding sequence of TALEN-TCR-beta1_L19 is represented by SEQ ID NO: 56, and the amino acid sequence of said TALEN is represented by SEQ ID NO: 57. The TALEN coding sequence of TALEN-TCR-beta1_R19 is represented by SEQ ID NO: 58, and the amino acid sequence of said TALEN is represented by SEQ ID NO: 59. The TALEN coding sequence of TALEN-TCR-beta3_L19 is represented by SEQ ID NO: 60, and the amino acid sequence of said TALEN is represented by SEQ ID NO: 61. The TALEN coding sequence of TALEN-TCR-beta3_R19 is represented by SEQ ID NO: 62, and the amino acid sequence of said TALEN is represented by SEQ ID NO: 63.

[Preparation of TCR Deficient T Cell Using Platinum TALEN mRNA]

(1) Jurkat cells were cultured for 3 days in RPMI 1640+ 10% FBS+2 mmol/l L-Glutamin+1% penicillin/streptomycin.
(2) By the following procedure, 10 µg each of TALEN-TCR-alpha2_L19 (TCRα-L-TALEN) mRNA and TALEN-TCR-alpha2_R19 (TCRα-R-TALEN) mRNA were introduced into cultured Jurkat cells when targeting a gene of TCRα, and a pair of TALEN-TCR-beta1_L19 (TCRβ1-L-TALEN) mRNA and TALEN-TCR-beta1_R19 (TCRβ1-R-TALEN) mRNA, or a pair of TALEN-TCR-beta3_L19 (TCRβ-L-TALEN) mRNA and TALEN-TCR-beta3_R19 (TCRβ-R-TALEN) mRNA was introduced into cultured Jurkat cells when targeting a gene of TCR (SE CellLine 4D-Nucleofector™ X Kit S).

(2-1) Cell pellets were prepared by centrifugation (400 G, 10 minutes, room temperature) of $5 \times 10^5$ to $1 \times 10^6$ Jurkat cells.
(2-2) The cell pellets were suspended in a total of 20 µl of Nucleofector solution prepared by adding 3.6 µl of Supplement to 16.4 µl of Nucleofector SE solution per reaction.
(2-3) A pair of TALEN mRNA for targeting a gene of TCRα or a TCRβ gene was added at 10 µg each.
(2-4) Nucleofection was performed using Amaxa 4D-Nucleofector (program: CL-120).

[Confirmation of Removal of Endogenous TCR]

It was confirmed that a CD3 negative fraction found by FACS after introduction of TALEN mRNA into Jurkat cells was manifested. Cells from sorting CD3 negative fractions were confirmed by FACS to be TCR (endogenous) negative. The expression intensity of CD3 obtained by FACS was analyzed with FACS analysis software (Flow Jo).

As to whether the manifested CD3/TCR negative fractions were obtained by introduction of TALEN, the presence of a cleavage fragment was checked by a T7 Endonuclease I (T7E1) assay.

[T7 Endonuclease I Assay]

(1) PCR was performed using the extracted genomic DNA. PCR was performed for 10 minutes at 94° C., then 30 seconds at 94° C., 30 seconds at 55° C., and 1 minute at 72° C. for 30 cycles, and a reaction for 5 minutes at 72° C. in a reaction mixture of a final concentration 1× buffer, 200 µM dNTP, 0.4 µM primer, 2.5 to 5 ng DNA, and Excellent Taq HS (APRO Science).
(2) The primer sequences were the following.

[Chemical Formula 8]

| Primers | Sequences |
| --- | --- |
| TCR-aLpha2-f | CTCTGCATGACTCACTAGCACTCTAT |
| TCR-aLpha2-r | GACTGACTTAGTGAGCTGGGAAAGAT |
| TCR-beta1-c1-f | CTAATATGTGTCACTACCCCACGAG |
| TCR-beta1-c1-r | GAGAGTTACACAGGCCACATAGAAAG |
| TCR-beta1-c2-f | GAGGAGACATCACCTGGAATGTTAG |
| TCR-beta1-c2-r | GATATATTAGGCTGTGCTCTGGCTCT |

Corrresponding to, from the top, SEQ ID NO: 64-69)

(3) 1% agarose gel electrophoresis was performed to extract DNA using a Gel Extraction kit (QIAGEN).
(4) 200 to 250 ng of the extracted DNA was heated for 5 minutes at 95° C., then cooled to room temperature, and reannealed.
(5) T7 Endonuclease I was added for 30 minutes of treatment at 37° C. The DNA was then studied by electrophoresis with 2% gel.

Figure 3:
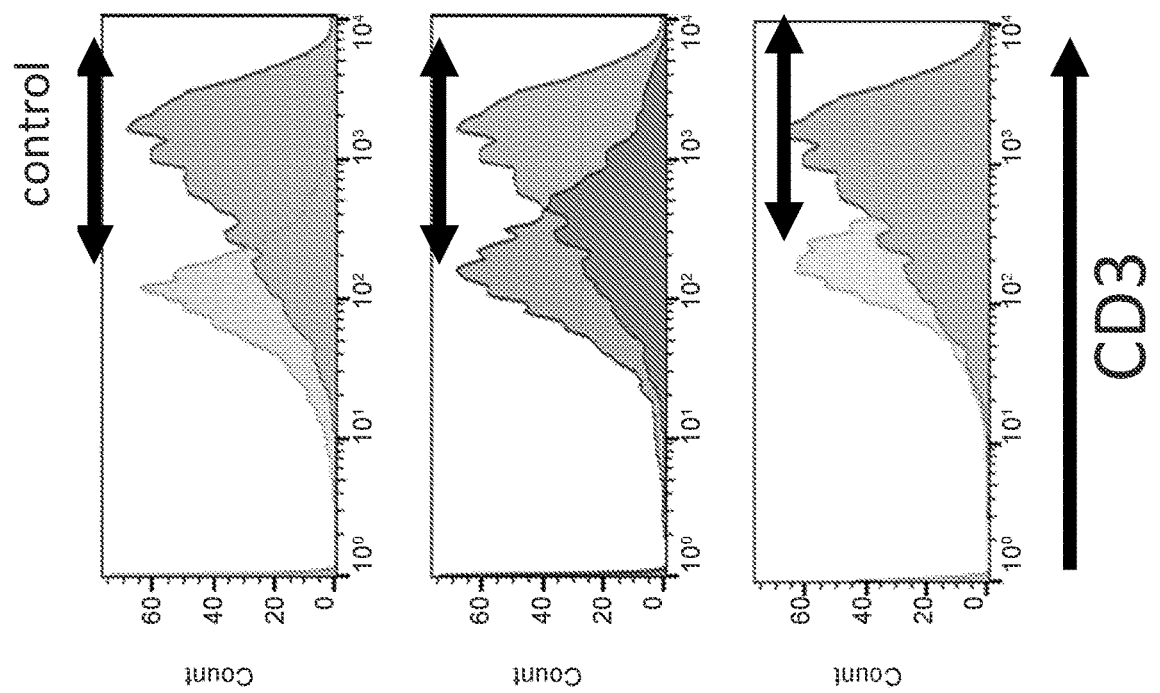
FIG. 3 is a histogram showing the change in CD3 expression compared to a control when an endogenous TCR gene is removed with TALEN (right panel). The left side of FIG. 3 shows the experimental scheme using TALEN-TCR mRNA and results of FACS analysis using GFP-A and SSC-A. CD3 expression can be utilized as a marker for TCR expression, and CD3 expression is shifted to negative compared to a control, thus indicating that an endogenous TCR gene was successfully removed.
Figure 3:
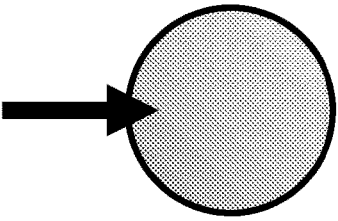
Figure 3:
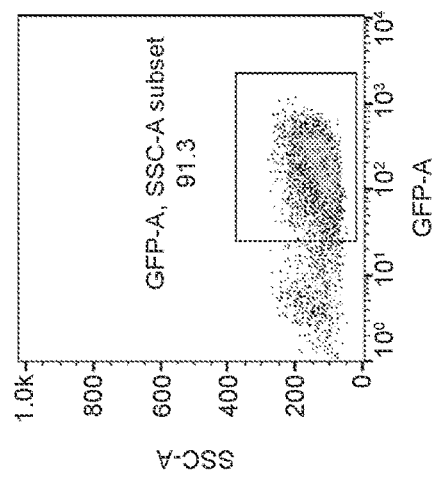
Figure 4:
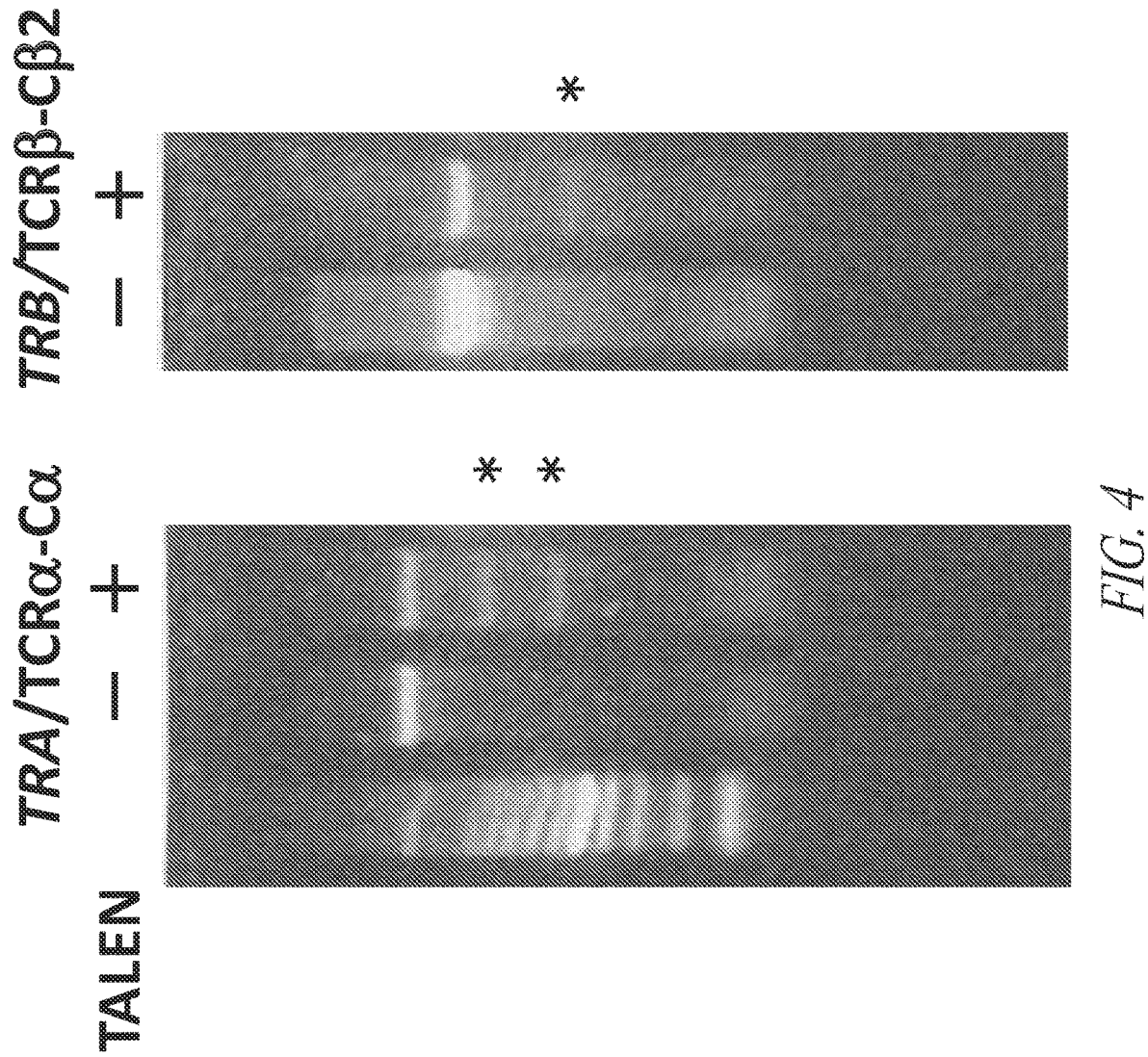
FIG. 4 is an electrophoretic diagram showing results of a T7E1 assay indicating successful cleavage of a TCR gene with TALEN. The figure shows that a TRA/TRB genes were cleaved in human T cell derived Jurkat cell strains (left and right panel, respectfully).

The results are shown in FIG. 3. It can be understood that each endogenous TCR gene was knocked out by genome editing targeting each TCR gene. FIG. 4 shows the results of a T7E1 assay. It is understood from FIG. 4 that the knockout of TCR genes is due to genome editing.

Example 3: Introduction of TCR (Summary)

This Example demonstrates that a TCR gene can be expressed in T cells without mispairing by using a cysteine mutated TCR introduction vector. A TCR gene was introduced with the removal of an endogenous TCR gene shown in Example to demonstrate that a T cell expressing only the introduced TCR can be created.

(Materials and Methods)
(1) T cells were stimulated with CD3/28 beads and cultured for 3 days with X-VIVO20+10% AB serum+2 mmol/l L-Glutamin+1% penicillin/streptomycin.
(2) TCRα-L-TALEN mRNA and TCRα-R-TALEN mRNA were introduced (P3 Primary Cell 4D-Nucleofector™ X Kit S) into the cultured T cells using an Amaxa 4D-Nucleofector by the following procedure.
  (2-1) $5 \times 10^5$ to $1 \times 10^6$ T cells were centrifuged (400 G, 10 minutes, room temperature) to prepare cell pellets.
  (2-2) The cell pellets were suspended in a total of 20 μl of Nucleofector solution prepared by adding 3.6 μl of Supplement to 16.4 μl of Nucleofector P3 solution per reaction.
  (2-3) TCRα-L-TALEN mRNA and TCRα-R-TALEN mRNA were added at 10 μg each.
  (2-4) Nuceofection (program: EO-115) was performed.
  (2-5) The mixture was continuously cultured.
  (2-6) After three days of Nucleofection, the efficiency of cleaving TCR genes was studied with respect to loss of expression of CD3 and TCRα and β by flow cytometry.
(3) CD3 negative fractions were collected by magnetic sorting or FACS (Aria II).
(4) The TCR gene of interest was introduced into the CD3 negative T cells obtained in (3) with a retroviral vector in accordance with the procedure described in detail below.
(5) On the next day, it was confirmed by FACS that a TCR positive CD3 positive fraction is manifested.
(6) The CD3 positive fraction was collected by magnetic sorting or FACS (Aria II).
(7) TCRβ3-L-TALEN mRNA and TCRβ3-R-TALEN mRNA were introduced into the CD3 positive T cells obtained in (6) by the same approach as (2).
(8) The CD3 negative fraction was collected by magnetic sorting or FACS (Aria II).
(9) The TCR gene of interest was introduced into the CD3 negative T cells obtained in (8) with a retroviral vector again by the same procedure.
(10) It was confirmed that a CD3 positive fraction is manifested. The fraction was collected by magnetic sorting or FACS (Aria II).

[Introduction of Desired TCR into TCR Deficient T Cells]

The introduction of a TCR gene in the procedure described above was performed by the following procedure.

Day 1:
(1) PLAT-GP was seeded in a 10 cm dish and cultured to 70% confluence.
(2) 10 μg of vector and 5 μg of VSV-G were added to 1.4 ml of OPTI-MEM I and incubated for 5 minutes at room temperature.
(3) 50 μl of Lipofectamine 2000 was added to 1.4 ml of OPTI-MEM I and incubated for 5 minutes at room temperature.
(4) (2) and (3) were mixed and incubated for 20 minutes at room temperature.
(5) The mixture of (4) was added to a culture of PLAT-GP and cultured for 48 hours.

Day 4-1:
(1) Supernatant was collected from PLAT-GP and centrifuged (1500 rpm×5 min, 4° C.)
(2) The supernatant was passed through a 0.45 μM filter and further centrifuged (6000 G×16 hr, 4° C.)

Day 4-2:
TCR deficient T cells in the culture were dispensed in a 24 well plate at $5 \times 10^5$/well.

Day 5:
(1) The supernatant in the centrifuge tube of Day 4-1 (2) was removed and pellets were suspended in 500 μl of X-VIVO 20 to create a viral solution.
(2) After adding the viral solution to a medium of TCR deficient cells dispensed on the previous day and centrifuging (2000 rpm×30 min, 32° C.), culture was continued for 24 hours. The next day, the infection rate was checked by the ratio of GFP positive cells (flow cytometry) among viable cells.

[Cloning of TCR Gene to a pMXs-IRES-GFP Vector]
(1) A pMXs-IRES-GFP vector was cleaved with BamHI and NotI.
(2) A primer was designed so that an overlap sequence was formed at each binding section, specifically as follows:

[Chemical Formula 9]

Vα: 5'-TGGAGGAGAACCCTGGACCT-3'

5'-GGTGAATAGGCAGACAGACTT-3'

Cα: 5'-GAGACTCTAAATCCAGTGAC-3'

5'-GGGGGCGGAATTTACGTAGCGGCCGCTCAGCTGCT-3'

Vβ: 5'-TGCCGGATCTAGCTAGTTAATTAAGGATCCGAATTCCTGCAG G-3'

5'-TTCACCCACCAGCTCAGCTC-3'

Cβ: 5'-TTCACCCACCAGCTCAGCTC-3'

5'-AGGTCCAGGGTTCTCCTCCA-3'
(Corresponding to, from the top in order, SEQ ID NOs: 70 to 77)

(3) Each fragment was amplified by PCR using the primer in (2).
(4) The fragments obtained in (1) and (3) were purified. The fragment of (1) (vector) was purified to attain 25 ng/μl.

The fragments of (2) (Vα, Cα, Vβ, Cβ) were each purified to attain 10 ng/μl.
(5) Gibson assembly reaction (NEB, Gibson Assembly Master Mix, in accordance with the Manufacture's Instruction) was performed. To 5 μl of Gibson Assembly Master Mix, 1 μl of vector, 0.75 μl of Vα, 0.75 μl of Vβ, 0.75 μl of Cα, and 0.75 μl of Cβ, were added. 1 hour at 50° C.
(6) The reaction solution in (5) was diluted 4-fold, and the samples were transformed to competent cells (JM109).
(7) DNA was purified with Miniprep and studied by sequencing.

[Introduction Vector]

Figure 5:
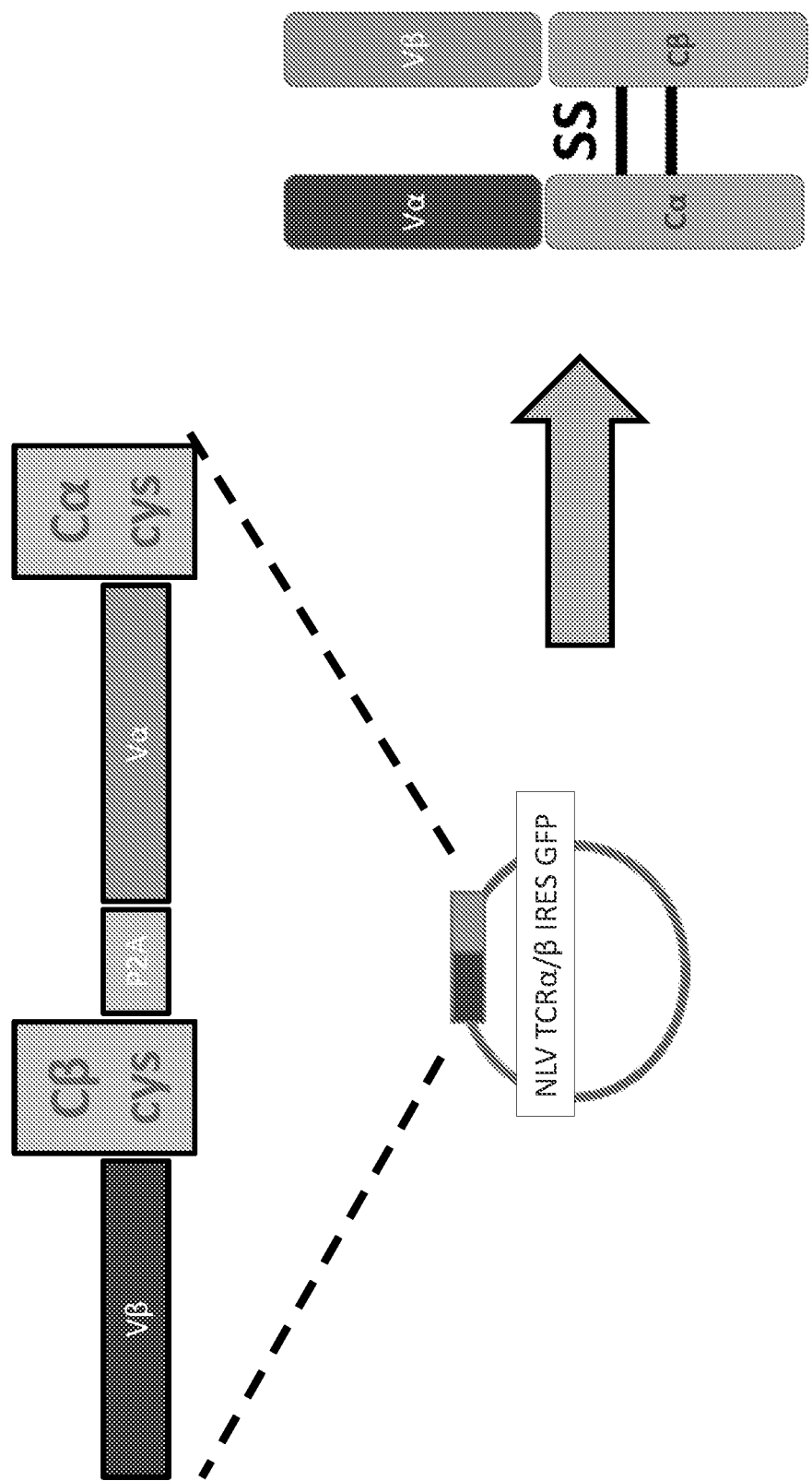
FIG. 5 is a schematic diagram of one example of an expression vector used in introduction of a TCR.

For the introduction vector, pMXs-IRES-GFP Retroviral Vector (Cell Biolabs, Inc.) was used as the backbone. A schematic diagram of a vector is shown in FIG. 5. The V region of TCRβ chain to be introduced, constant region of the TCR β chain (Cβ) P2A sequence, V region of a TCRα chain to be introduced, and constant region of the TCRα chain (Cα) were incorporated into and used at a introduced sequence portion of the pMXs-IRES-GFP Retroviral Vector in this order. Preparation of such a vector is described in Incorporation of Transmembrane Hydrophobic Mutations in the TCR Enhance Its Surface Expression and T Cell Functional Avidity Astar Haga-Friedman, Miryam Horovitz-Fried and Cyrille J. Cohen J Immunol 2012; 188: 5538-5546; Prepublished online 27 Apr. 2012.

By referring to Enhanced antitumor activity of T cells engineered to express T-cell receptors with a second disulfide bond. Cohen C J, Li Y F, El-Gamil M, Robbins P F, Rosenberg S A, Morgan R A. Cancer Res. 2007 Apr. 15; 67(8): 3898-903, an additional Cys was introduced to the C region to add one S—S bond. By referring to Incorporation of Transmembrane Hydrophobic Mutations in the TCR Enhance Its Surface Expression and T Cell Functional Avidity Astar Haga-Friedman, Miryam Horovitz-Fried and Cyrille J. Cohen J Immunol 2012; 188: 5538-5546; Prepublished online 27 Apr. 2012, a mutation to a hydrophobic amino acid was introduced into a transmembrane region.

A P2A sequence was used as a self-cleaving linker (J. H. Kim, S. R. Lee, L. H. Li, H. J. Park, J. H. Park, K. Y. Lee, et al., High cleavage efficiency of a 2A peptide derived from porcine teschovirus-1 in human cell lines, zebrafish and mice, PLoS One. 6 (2011) 1-8. doi:10.1371/journal.pone.0018556.)

The amino acid sequences of the constant regions of the TCR α chain and TCR β chain that were used are the following.

[Chemical Formula 10]
>hTCR_alpha_const
(SEQ ID NO: 78)
XIQNPDPAVYQLRDSKSSDKSVCLFTDFDSQTNVSQSKDSDVYITDKTVLD

MRSMDFKSNSAVAWSNKSDFACANAFNNSIIPEDTFFPSPESSCDVKLVEK

SFETDTNLNFQNLSVIGFRILLLKVAGFNLLMTLRLWSS

>TCR_hum_Cbeta_1
(SEQ ID NO: 79)
EDLNKVFPPEVAVFEPSEAEISHTQKATLVCLATGFFPDHVELSWWVNGKE

VHSGVSTDPQPLKEQPALNDSRYCLSSRLRVSATFWQNPRNHFRCQVQFYG

LSENDEWTQDRAKPVTQIVSAEAWGRADCGFTSVSYQQGVLSATILYEILL

GKATLYAVLVSALVLMAMVKRKDF

[TCR Transgene]
A QYD specific TCRαβ gene was obtained from a CMV pp65 QYD antigen specific CD8+ T cells in the peripheral blood of a healthy individual by using hTEC10, and was used as the transgene.

[Antigen Specificity of Treg]
The binding affinity to a QYD antigen of a T cell to which TCR was introduced was measured to confirm introduction of TCR. It was confirmed whether there is antigen specificity of Treg (QYD-Treg) by QYD tetramer staining.

Figure 6:
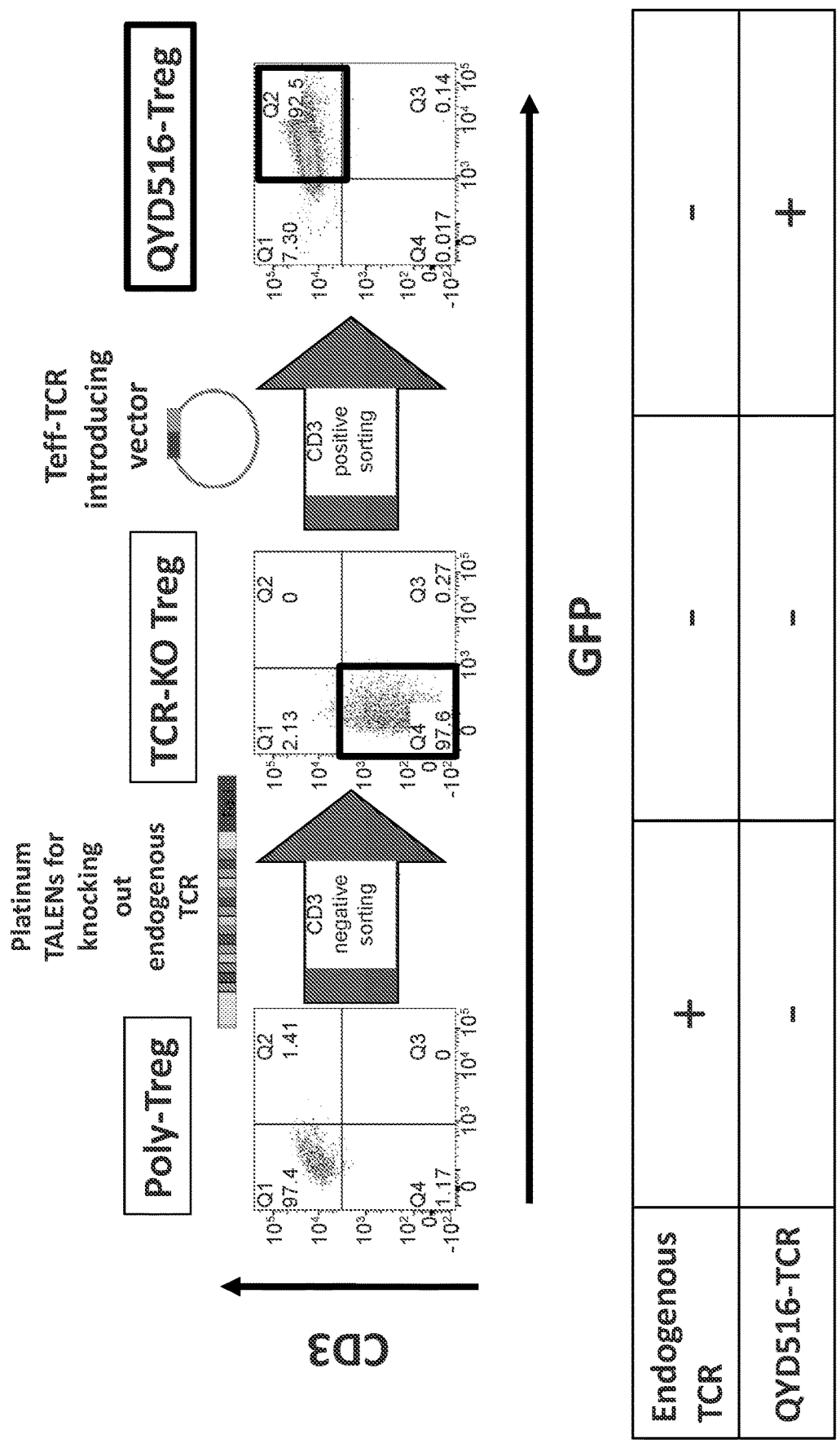
FIG. 6 is a diagram showing that polyclonal Treg TCR can be completely substituted with an antigen specific TCR by removing an endogenous TCR and introducing an exogenous antigen specific TCR.
Figure 7:
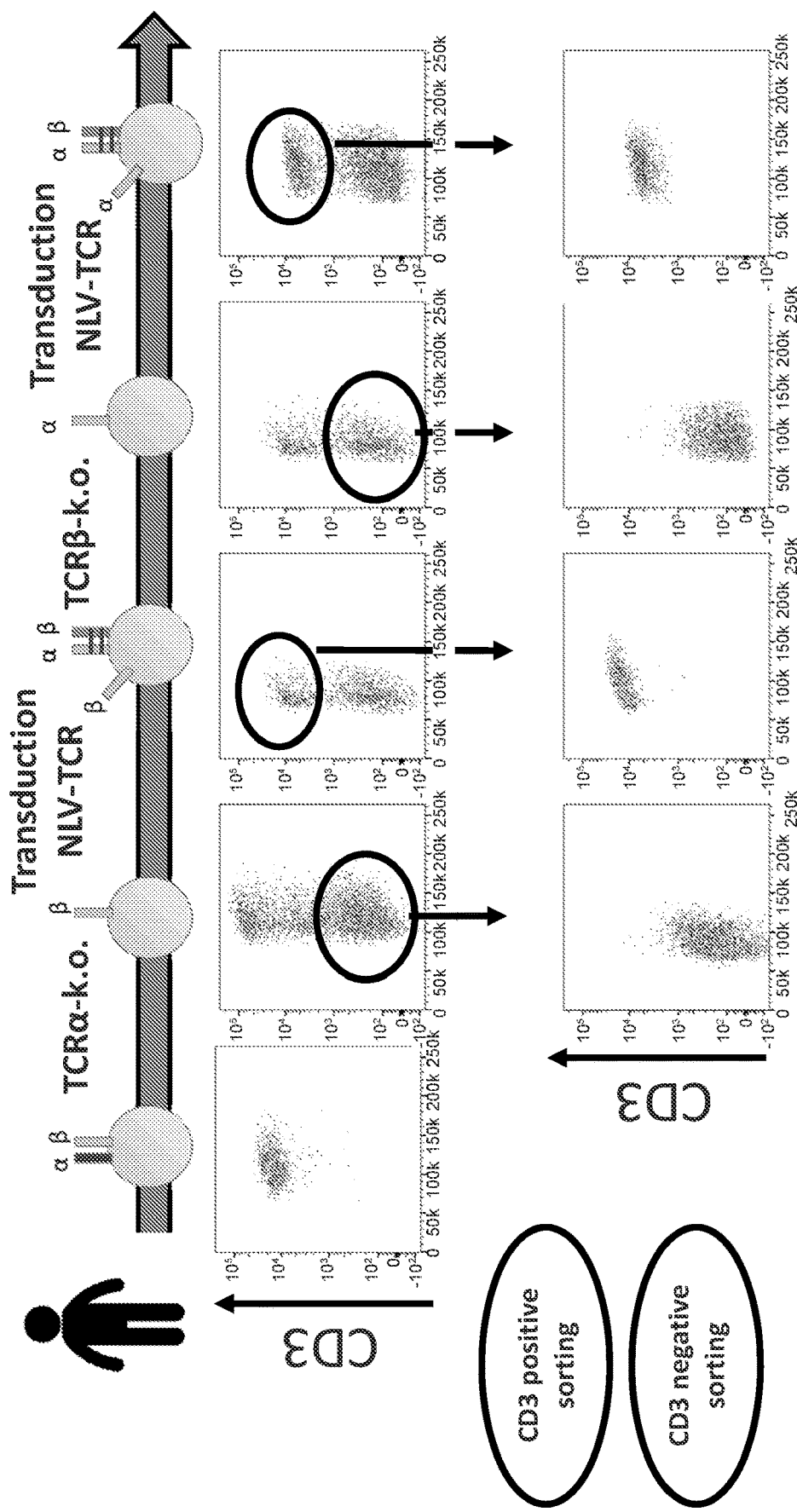
FIG. 7 is a schematic diagram showing the procedure for removing an endogenous TCR and introducing an exogenous antigen specific TCR by the method of the invention. The state of CD3 expression of cells in each step is shown. The middle row shows the distribution of CD3 expression of a cell population before sorting by CD3 expression. The bottom row shows the distribution of CD3 expression of a cell population after sorting by CD3 expression.

(Results)
The results of introduction to regulatory T cells are shown in FIGS. 5 and 6. It is understood from the results of flow cytometry that only the introduced TCR is expressed in the T cells after modification.

Figure 8:
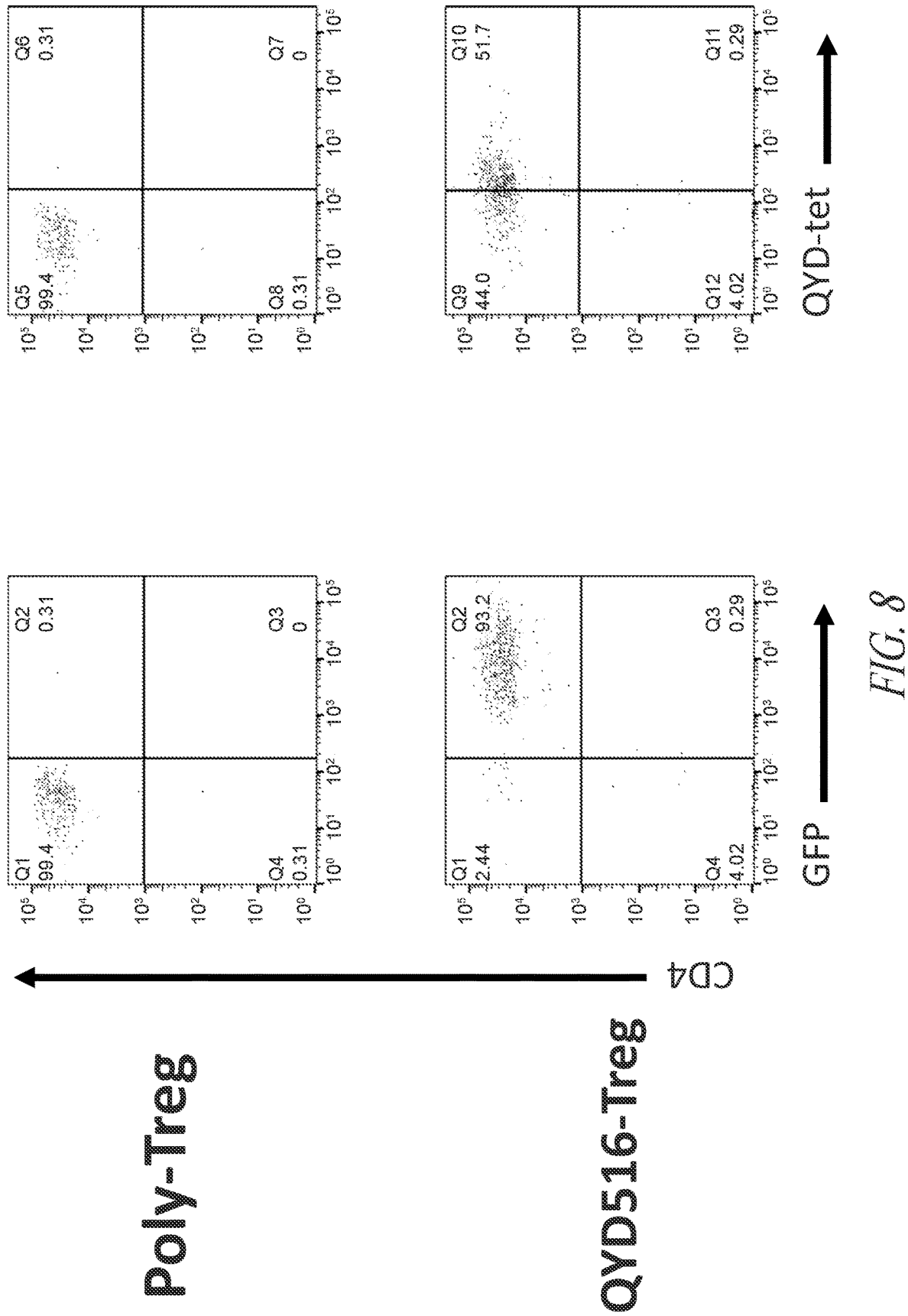
FIG. 8 is a diagram comparing the affinity of a polyclonal regulatory T cell (Poly-Treg) and regulatory T cell introduced with a TCR specific to a CMV antigen (QYD516) recognized by CD8+ T cells (QYD-Treg) to an antigen (QYD516). The left column shows GFP labels, and the right column shows QYD-tetramer labels. A functional subpopulation (CD4+) of each cell population was compared to polyclonal cells. It is understood that a group introduced with an antigen specific TCR has acquired affinity to an antigen.

The results of measuring the binding affinity to QYD are shown in FIG. 8. The binding affinity to QYD was increased in Treg introduced with a QYD specific TCR compared to polyclonal Treg.

Figure 9:
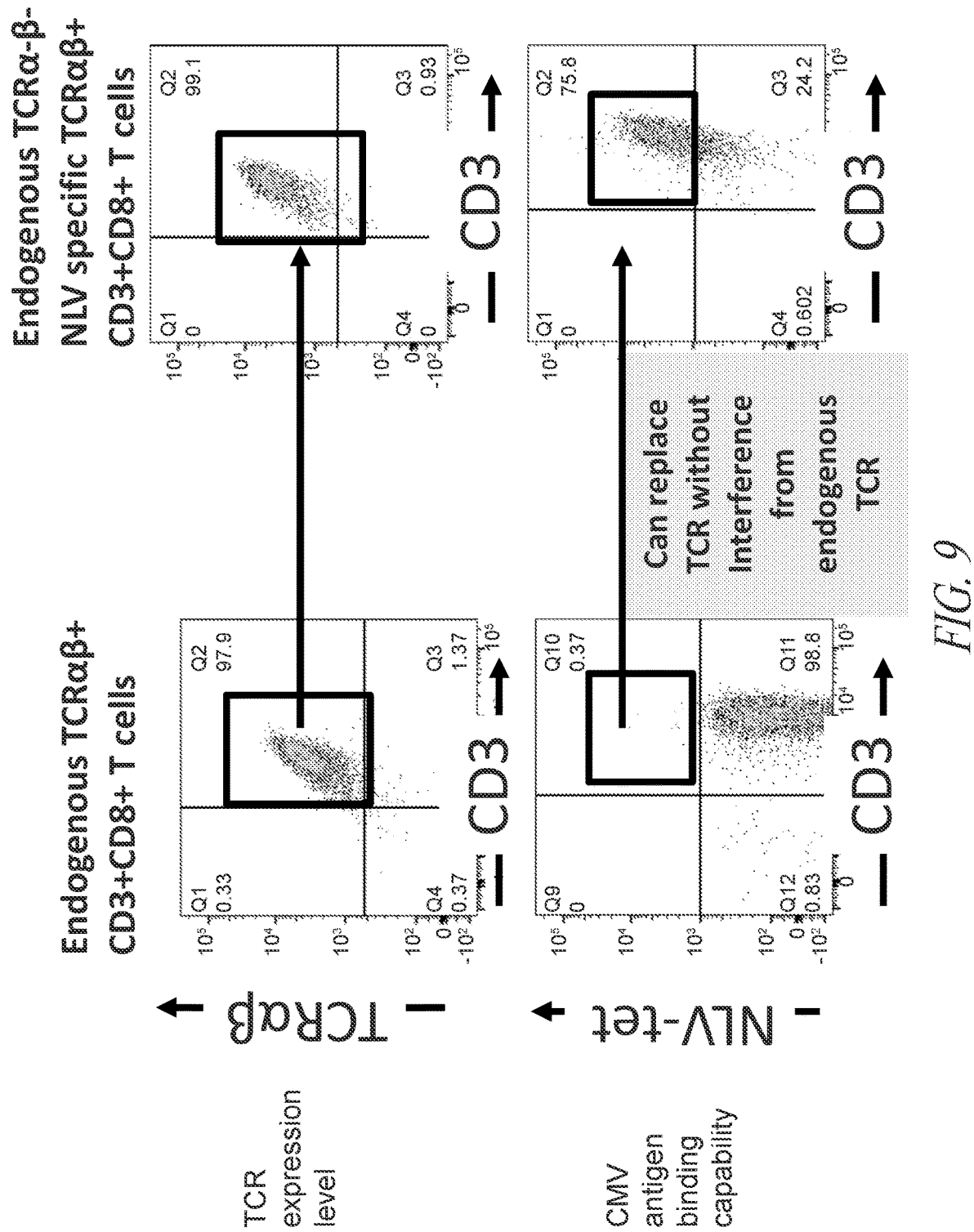
FIG. 9 shows the creation of cytomegalovirus specific cytotoxic T cells using the technology of the present disclosure (human peripheral blood T cells). The results of introducing a TCR into a cytotoxic T cell are shown. The top row shows results of analysis with the amount of expression of TCRαβ, and the bottom row shows results of analyzing the CMV antigen binding capability with an NLV-tetramer. The left column shows the analysis for a T cell having an endogenous TCR, and the right column shows analysis for a T cell with removal of an endogenous TCR and introduction of an NLV specific TCR. It is understood that a TCR was able to be replaced without interference from an endogenous TCR.

The results of similar TCR introduction to cytotoxic T cells are shown in FIG. 9. It is understood that TCR replacement was possible without interference from an endogenous TCR.

High affinity CMV pp65 NLV specific TCR expressing T cells were able to be established from knockdown of endogenous TCR by a TCR-specific TALEN and gene transfer by Cys-TCR.

Example 4: Properties of Manufactured Antigen Specific Regulatory T Cells (Summary)
The properties of antigen specific regulatory T cells manufactured in accordance with the approach in Example 3 were evaluated as follows.

[Confirmation of Retention of Treg Inherent Traits]
Antigen specific regulatory T cells manufactured in accordance with the approach in Example 3, polyclonal regulatory T cells, and TCR knockout regulatory T cells and control (CD25 negative CD4 positive T cell fraction) were stained with the following antibody, measured by FACS, and analyzed with respect to fluorescence intensity with FACS analysis software (flow jo) to investigate whether there is a difference in the properties of TCR replaced Treg and polyclonal Treg (before TCR replacement).

Figure 10:
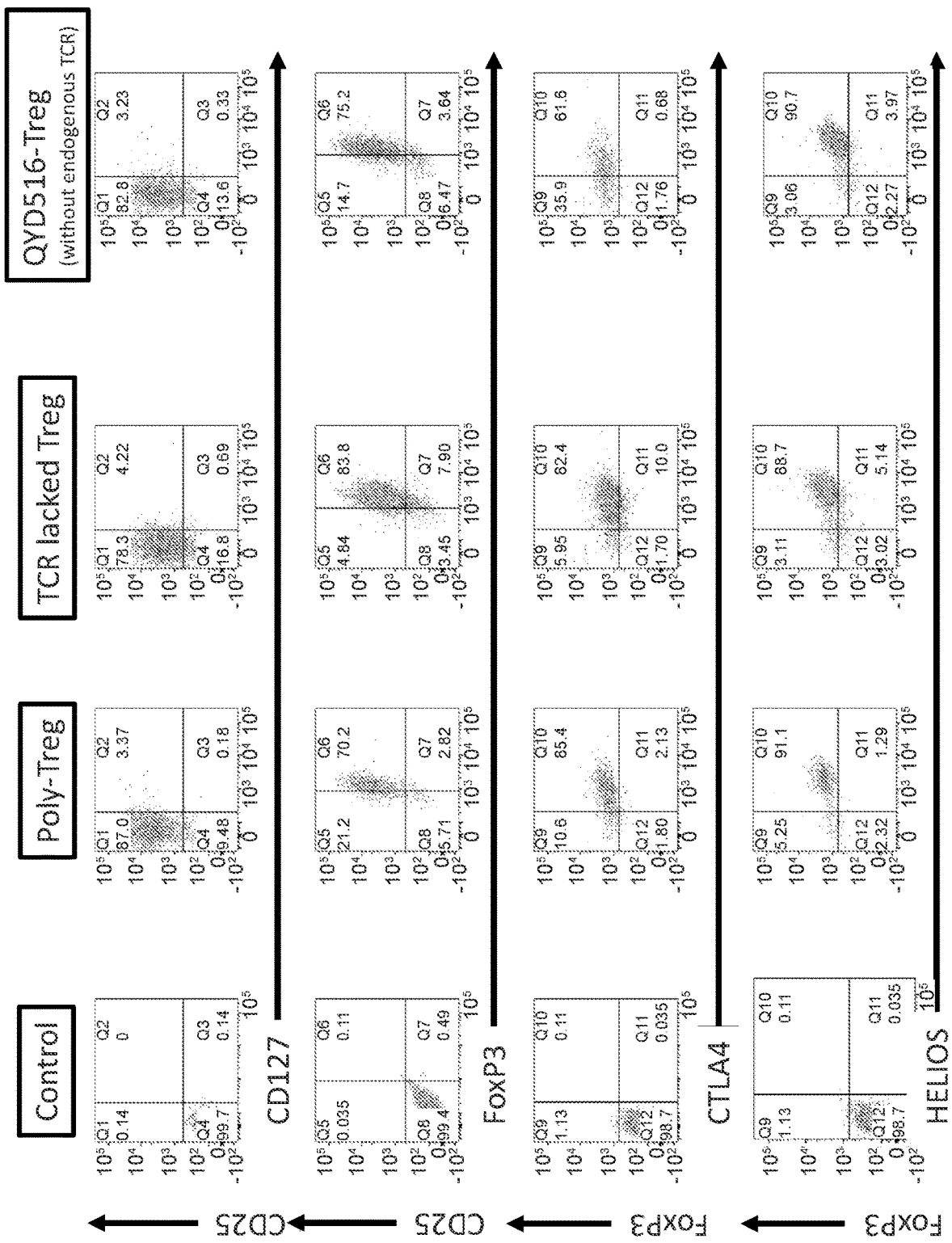
FIG. 10 is a dot plot showing the expression of a surface marker for an antigen specific regulatory T cell (rightmost column), polyclonal regulatory T cell (second column from left), TCR knockout regulatory T cell (second column from right), and control (CD25 negative CD4 positive T cell fraction; leftmost column). The top row shows analysis for CD127 and CD25, the second row from the top shows analysis for CD25 and FoxP3, the third row from the top shows analysis for FoxP3 and CTLA4, and the fourth row from the top shows analysis for FoxP3 and HELIOS.
Figure 11:
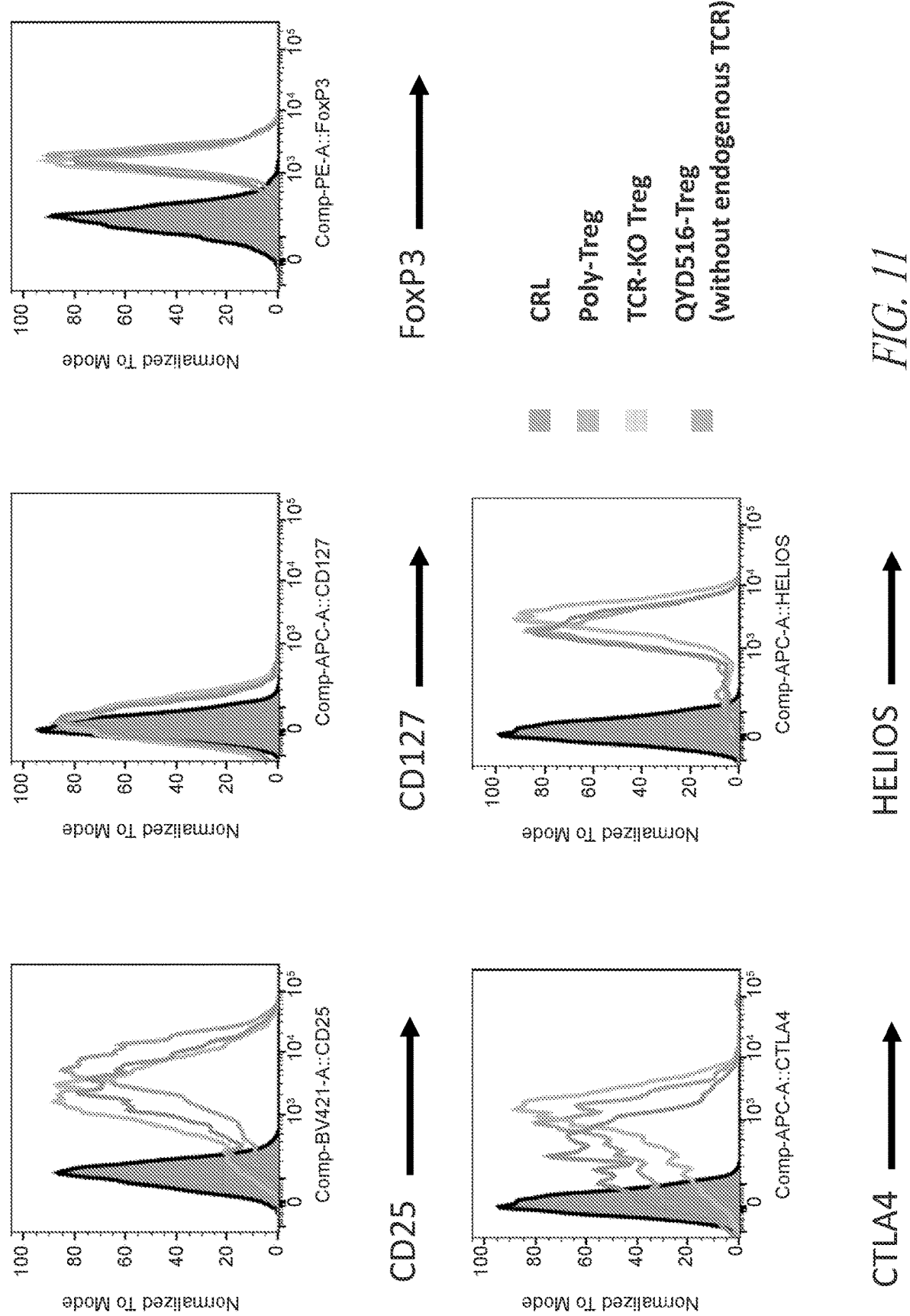
FIG. 11 is a histogram showing the expression of a surface marker for an antigen specific regulatory T cell, polyclonal regulatory T cell, TCR knockout regulatory T cell, and control (CD25 negative CD4 positive T cell fraction). The top row shows analysis for, from the left, CD25, CD127, and FoxP3, and the bottom row shows analysis for, from the left, CTLA4 and HELIOS.

Antibodies: Anti-human CD25 antibody, Anti-human CD127 antibody, Anti-human FoxP3 antibody, Anti-human CTLA-4 antibody, and Anti-human HELIOS antibody The results are shown in FIGS. 10 and 11. It was found that there is no significant difference in the surface marker expression of these cells, and traits inherent to regulatory T cells are retained after removal and introduction of TCR in the present invention.

[Growth in Response to Antigen Stimulation]
Tregs (QYD-Treg) obtained by TCR substitution in Example 3 were studied as to whether they recognize QYD peptide antigens and grow, and more specifically as follows.
(1) QYD-Tregs were pelleted by centrifugation and were suspended with 1 ml of PBS.
(2) 1 μL of Cell trace violet was added (Invitrogen, CellTrace Violet Cell Proliferation Kit, cat #C34557), and the Treg was shielded from light and incubated for 20 minutes at 37° C.
(3) The Treg was washed twice with PBS (300 G, 10 min, room temperature).
(4) Peptide pulsed antigen presenting cells and cell trace violet labeled QYD-Treg were mixed in a T cell culture (X-VIVO20+10% AB serum+2 mmol/l L-Glutamin+ 1% penicillin/streptomycin) so that the cell counts would be 1:1, and cultured for 5 days in a 96 well plate.
(5) FACS confirmed that the fluorescence intensity of Cell trace violet was attenuated, and QYD-Treg was divided.

Figure 12:
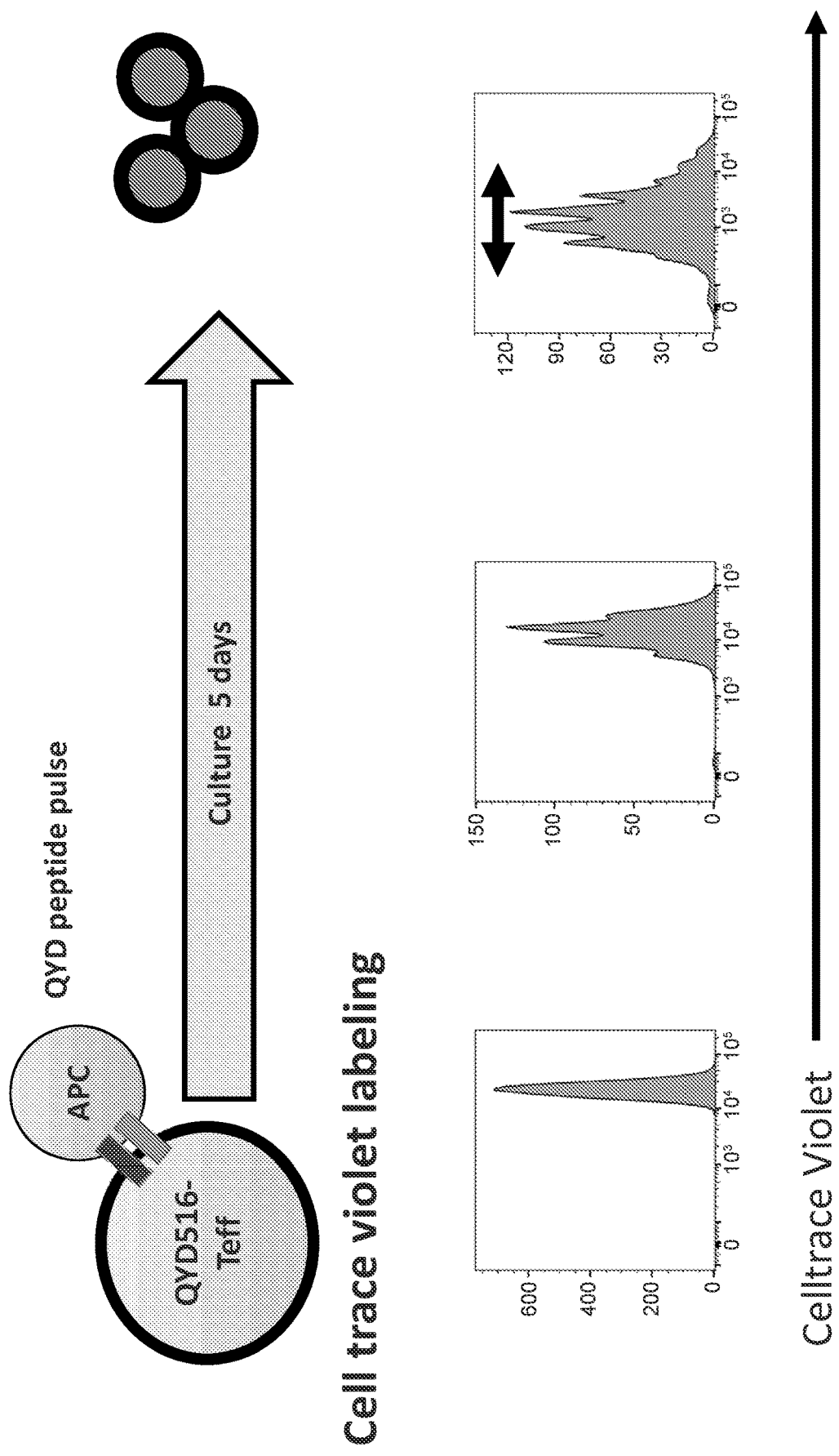
FIG. 12 is a diagram showing the growth of antigen specific effector T cells due to antigen stimulation. The growth is shown for, from the left, day 0, day 3, and day 5. It is understood that QYD-516 specific effector T cells grew in response to antigen stimulation.
Figure 13:
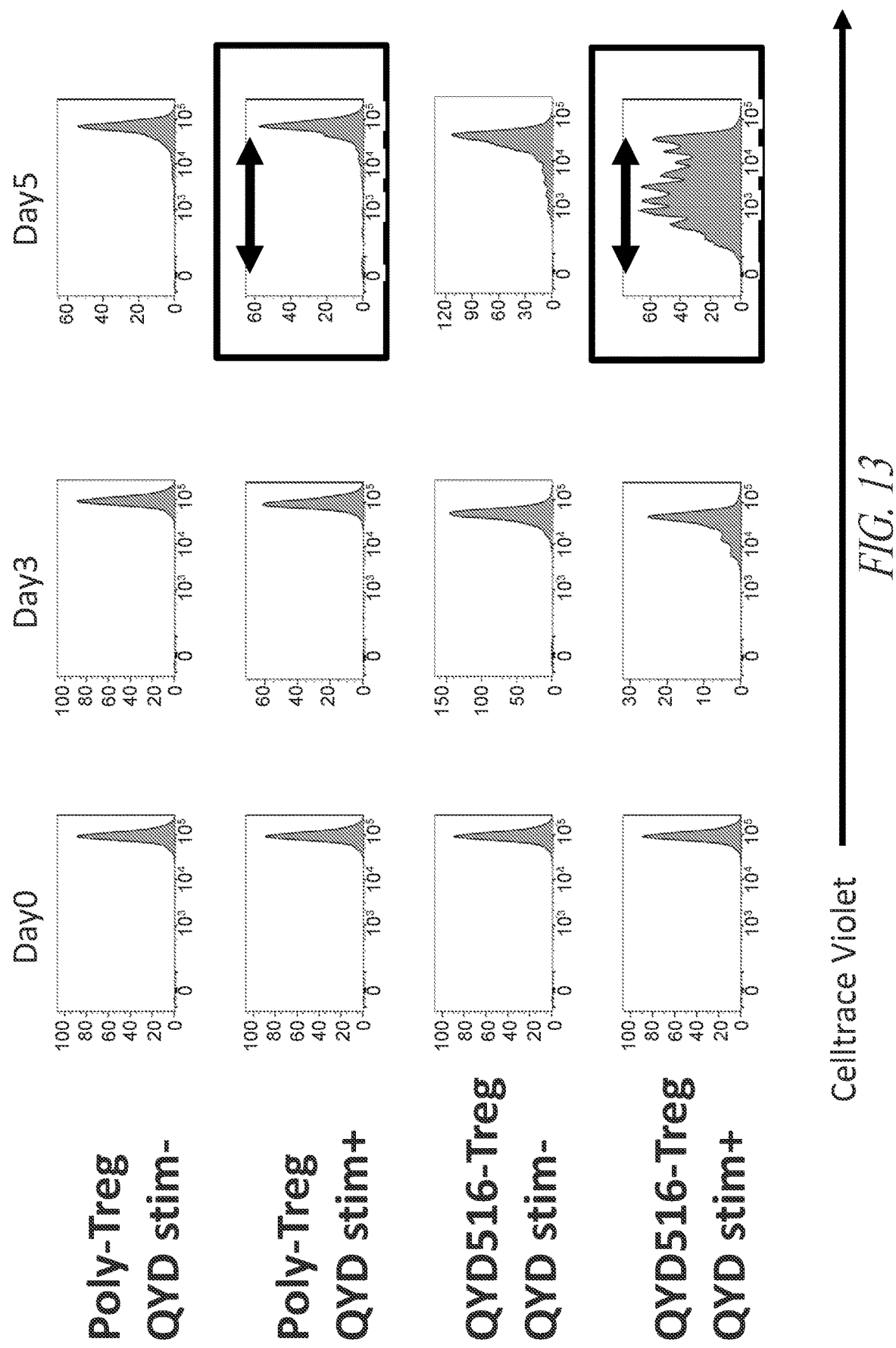
FIG. 13 shows growth of QYD-516 specific Treg that responded to antigen stimulation. The figure shows that the QYD-516 specific Treg grew in response to antigen stimulation by antigen presenting cells. While the growth of regulatory T cells was not observed for polyclonal regulatory T cells, growth was observed in an antigen specific regulatory T cell population.

The results are shown in FIGS. 12 and 13. After 5 days of culture, the fluorescence intensity of Cell trace violet was attenuated. It is understood that QYD-Treg grew in response to antigen stimulation by antigen presenting cells. The growth was not observed in a group without QYD stimulation or the group of polyclonal regulatory T cells, demonstrating the highly specific response to antigen of the manufactured regulatory T cells by the method of the invention.

[Suppression of Antigen Specific Effector T Cell by Antigen Specific Regulatory T Cell]
It was studied whether Treg (QYD-Treg) obtained by TCR substitution suppresses antigen specific growth of QYD-Teff, more specifically in the following manner.

A. Separation of Antigen Presenting Cells (Separation of CD4 Negative CD8 Negative Cells)

Miltenyi CD8 microbeads, human (130-045-201) were used, and a Miltenyi CD4+ T Cell isolation kit, human (130-096-533) was used:
  (1) PBMCs were separated from 50 mL of peripheral blood with Ficoll-Paque PREMIUM, and cell pellets were created by centrifugation (400 G, 10 min, room temperature).
  (2) The pellets were suspended in 80 µL of MACS Buffer, and 20 µL of CD8 MicroBeads were added.
  (3) The pellets were incubated for 15 minutes at 4° C.
  (4) The pellets were washed with MACS Buffer (300 G, 10 min, room temperature).
  (5) MACS Buffer was added so as to reach a total of 500 µL, and CD8− fractions were collected by magnetic separation and centrifuged (400 G, 10 min, room temperature) to create cell pellets.
  (6) The pellets were suspended in 40 µL of MACS Buffer, and 10 µL of T Cell Biotin-Antibody Cocktail was added.
  (7) The pellets were incubated for 5 minutes at 4° C.
  (8) 30 µL of MACS Buffer and 20 µL of CD4+ T Cell MicroBead Cocktail were added.
  (9) The pellets were incubated for 10 minutes at 4° C.
  (10) MACS Buffer was added so as to reach a total of 500 µL, and CD4− fractions were collected by magnetic separation (CD4−8− T cells are formed).

B. Peptide Pulsing of Antigen Presenting Cells
  (1) CD4− 8− cells collected in A were suspended in 1 ml of X-VIVO 20
  (2) A peptide (QYDPVAALF: QYD (SEQ ID NO: 92)) was added so as to reach 1 µM.
  (3) The cells were incubated for 2 hours at room temperature.
  (4) 35 Gy of γ ray was irradiated.

C. Treg Suppression Assay
  (1) CD8+ T cells that have undergone gene transfer of QYD-TCR (QYD-T eff) were pelleted by centrifugation and were suspended with 1 ml of PBS.
  (2) 1 µL of Cell trace violet was added (Invitrogen, CellTrace Violet Cell Proliferation Kit, cat #C34557), and the cells were shielded from light and incubated for 20 minutes at 37° C.
  (3) The cells were washed twice with PBS (300 G, 10 min, room temperature).
  (4) The antigen presenting cells that were peptide pulsed in a step of B and cell trace violet labeled QYD-Teff were mixed in a T cell culture (X-VIVO 20+10% AB serum+2 mmol/l L-Glutamin+1% penicillin/streptomycin) so that the cell counts would be 2:1, and seeded in a 96 well plate.
  (5) C. The Treg (Treg introduced with a desired TCR) cell count was adjusted and added to each well of (4) so that the ratio to cell counts with respect to CD8+ T cells would be 16:1, 8:1, 4:1, 2:1, or 1:1.
  (6) Fluorescence intensity of cell trace violet under conditions of each cell ratio was measured by FACS on days 5 and 7 to confirm suppression of growth of QYD-Teff.

Figure 14:
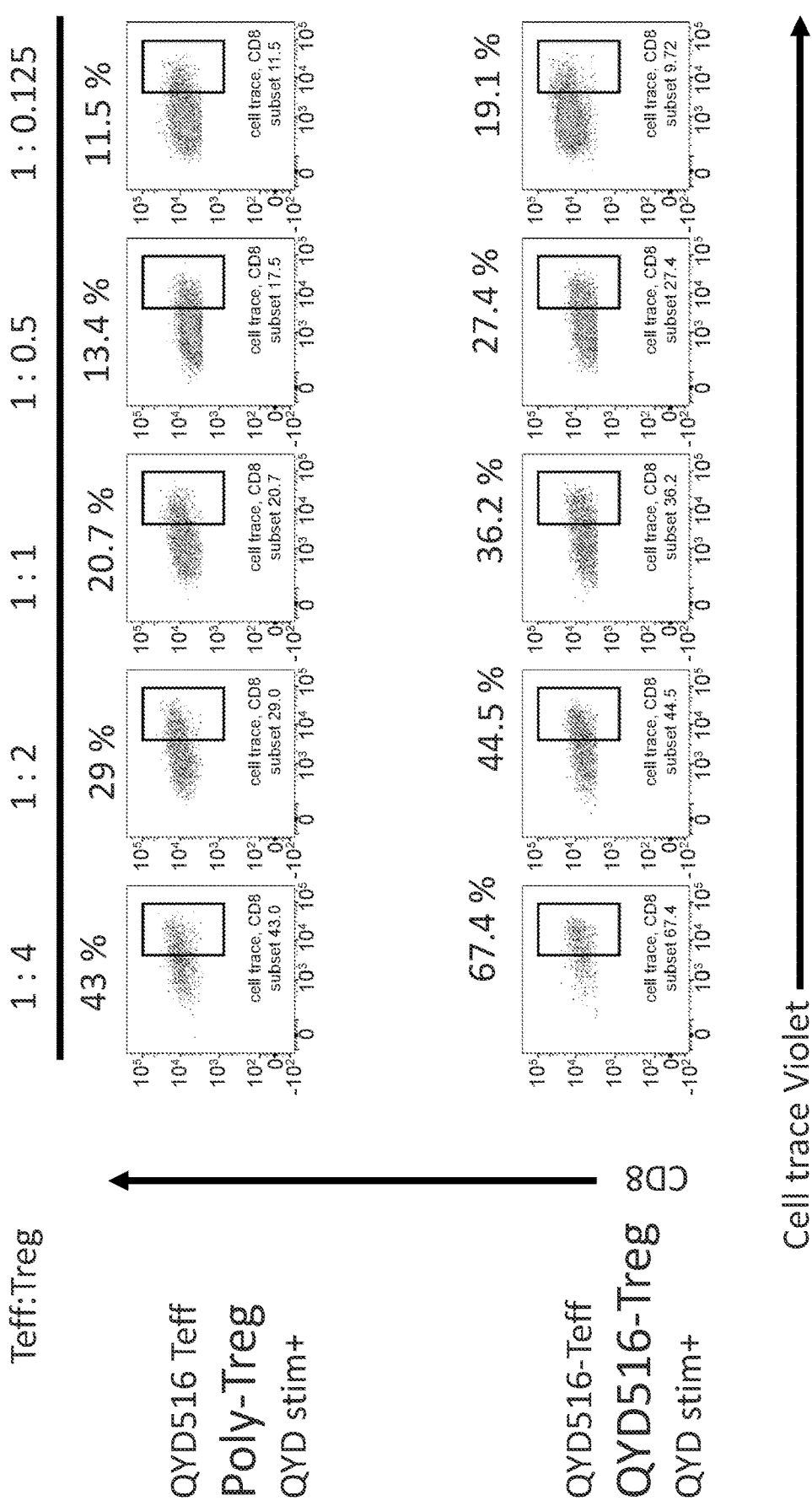
FIG. 14 is a diagram showing that the growth of antigen specific effector T cells due to antigen stimulation is suppressed by an antigen specific regulatory T cell. It is shown that QYD-Treg was better than Poly-Treg in suppression of QYD-Teff growth.
Figure 15:
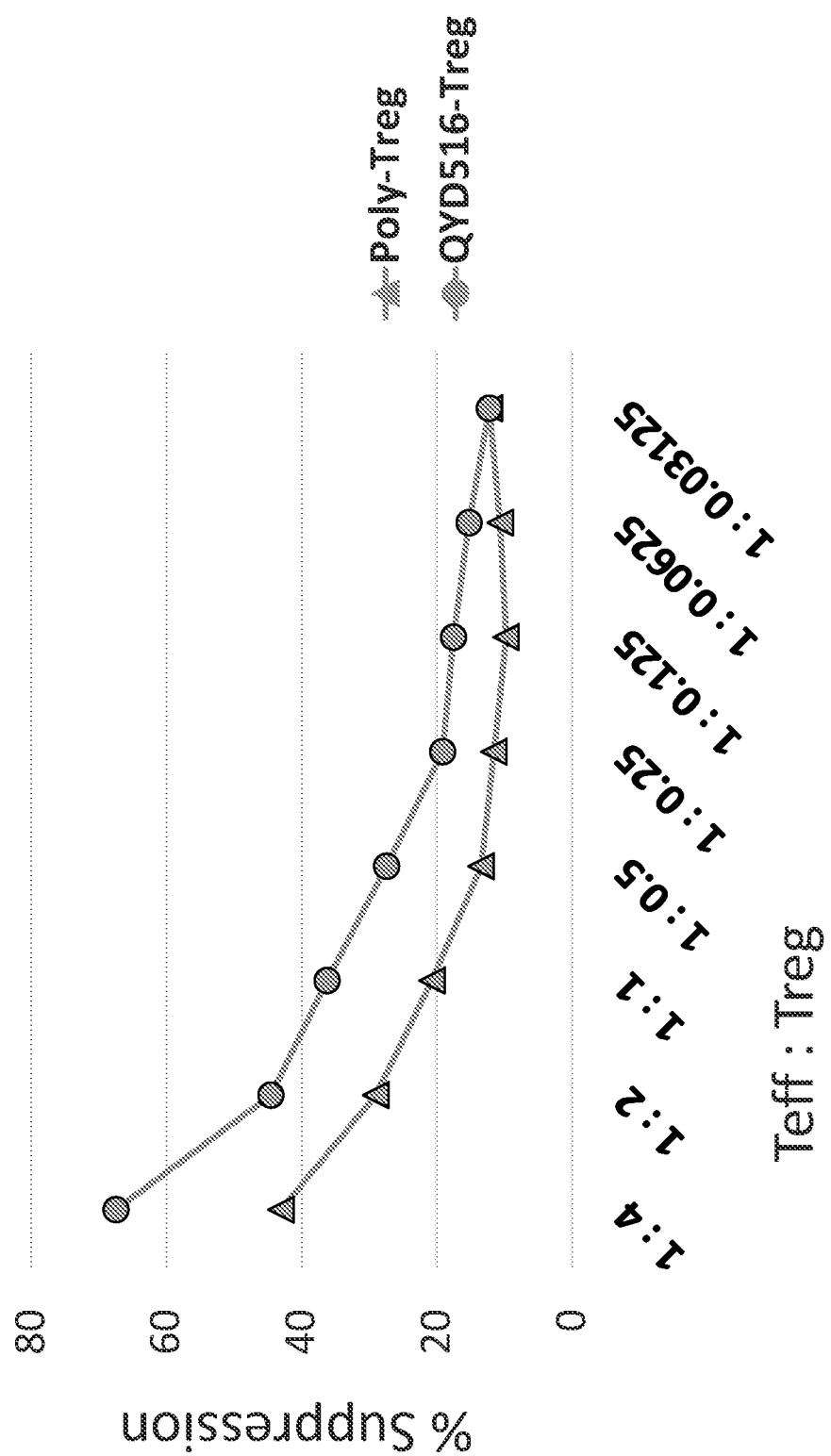
FIG. 15 is a diagram showing that the growth of antigen specific effector T cells due to antigen stimulation is suppressed by an antigen specific regulatory T cell. It is shown that QYD-Treg was better than Poly-Treg in suppression of QYD-Teff growth.

The results are shown in FIGS. 14 and 15. Antigen specific regulatory T cells exhibited significantly higher suppression of effector T cell growth compared to polyclonal regulatory T cells.

Example 5: In Vitro Immunosuppression by Antigen Specific Regulatory T Cells (Summary)

The objective of this Example is to demonstrate in vitro that antigen specific regulatory T cells manufactured in accordance with the method of the invention can be applied to autoimmune diseases.

MART-1 antigens, autoantigens of skin pigment cells, are target antigens that can be the cause of vitiligo, which is a refractory autoimmune disease in the field of dermatology. T cells that recognize this antigen are also present in the peripheral blood of healthy individuals.

(Materials and Methods)
  (1) Clone a MART-1 specific TCRαβ pair gene using hTEC10 from a specimen of a healthy individual.
  (2) Edit the TCR genome of regulatory T cells with Platinum TALEN to eliminate the expression of endogenous TCR.
  (3) Grow regulatory T cells after genome editing.
  (4) Introduce the cloned TCRαβ pair gene into the grown regulatory T cells.
  (5) Evaluate the change in responsiveness to a MART-1 antigen of MART-1 antigen specific effector T cells or the like by co-culture with regulatory T cells introduced with a TCR gene.

(Results)

18 or more types of MART-1 specific TCRαβ pair genes can be cloned using hTEC10 from specimens of two healthy individuals. The binding affinity to MART-1 of these MART-1 specific TCRs can be evaluated to select the most highly functional TCR and create MART-1 antigen specific Treg introduced with a gene of said TCR. Immune responses to a MART-1 antigen as a model antigen of autoimmune disease is suppressed by the TCR substituted Treg described above.

Example 6: Analysis of Efficacy of Teff→Treg on Autoimmune Disease Mouse Model (Summary)

Figure 16:
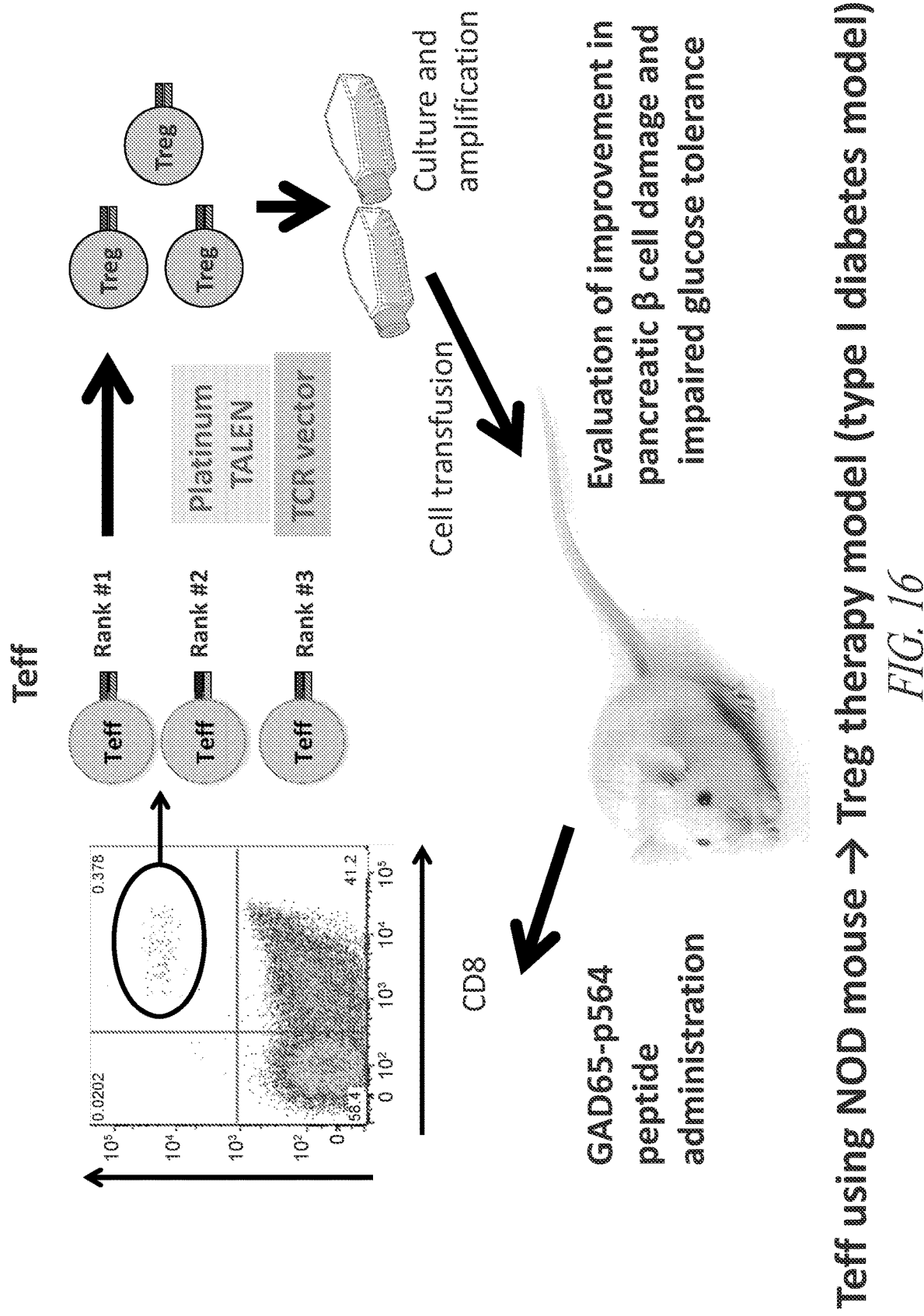
FIG. 16 is a diagram showing the summary of an experiment using an animal model in Example 6.

This Example shows immunosuppression by the manufactured antigen specific regulatory T cells in an animal model in order to demonstrate the in vivo applicability of antigen specific regulatory T cells to autoimmune diseases. The summary of this Example is shown in FIG. 16.

(Materials and Methods)

The following mouse and autoantigens are used to investigate the applicability to the following disease models.
Mouse model: NOD (non-obese diabetic) mouse
Autoantigen model: GAD65
Disease model: type I diabetes Animal experiments are conducted as follows.
  (1) Transnasally administer peptide antigen p546 (30 µg) from GAD65 to a 7-day old NOD mouse on days 7, 9, and 11 since birth.
  (2) Separate p546 responsive effector CD8+ T cells (p546-Teff) from a 4-week old female mouse immunized by the method of (1) by flow cytometry by using an H-2Kd/p546 tetramer.
  (3) Comprehensively identify TRAV and TRBV of p546-Teff with a next generation sequencer to confirm the presence of a high frequency clonotype, and then identify a pair by single cell cloning.
  (4) Introduce p546 antigen responsive TCR (p546-TCR-eff) identified by the processes of (1) to (3) described above into a mouse T cell strain lacking the expression of an endogenous TCR using a retroviral vector, and determine the functional hierarchy thereof.

(5) Separate CD4+CD25+ regulatory T cells by the bead column method from the spleen/lymph node/peripheral blood of a 4-week old male NOD mouse and knock out TCR using Platinum TALEN.

(6) Introduce a candidate of highly functional p546-Teff-TCR obtained in the process of (4) into TCR knockout CD4+CD25+ regulatory T cells (p546-Teff-TCR expressing Treg).

(7) Amplify Treg introduced with a Mock vector and Treg introduced with p546-TCReff in the presence of anti-CD3/CD28 antibodies and IL-2, and transfuse the Treg into a NOD mouse that has developed type I diabetes, and compare whether improvement in pancreatic β cell damage and impaired glucose tolerance is achieved.

(Results)

Improvement in pancreatic β cell damage and impaired glucose tolerance is not observed in the NOD mouse transfused with Mock vector-introduced Treg, but improvement in pancreatic β cell damage and impaired glucose tolerance is observed in the NOD mouse transfused with p546-TCReff-introduced Treg.

Example 6-2: Cleavage of Mouse TCR (Summary)

Platinum TALEN was created for cleaving mouse TCR to evaluate the cleavage activity by an assay (SSA assay) using a reporter plasmid.

(Materials and Methods)

Three types of Platinum TALEN (TRA2-TALEN, TRB1-TALEN, and TRB2-TALEN) were created for cleavage of mouse TCR.

Mouse TRA2-TALEN, mouse TRB1-TALEN, and mouse TRB2-TALEN were designed to include a cleavage site within the TRA gene Cα2 region, TRB gene Cβ1 region, and TRB gene Cβ2 region of the mouse, respectively. The respective target sequences were:
mouse TRA2-TALEN: left side TCTGCCTGTT-CACCGACT (SEQ ID NO: 130) and right side AATGTGCCGAAAACCATGGA (SEQ ID NO: 131),
mouse TRB1-TALEN: left side TGACTCCACC-CAAGGTCTCC (SEQ ID NO: 132) and right side AAAAGCAGAGATTGCAAACA (SEQ ID NO: 133),
mouse TRB2-TALEN: left side TGTGCTTGGCCAGGGGCTTC (SEQ ID NO: 134) and right side GGAGCTGAGCTGGTGGGTGA (SEQ ID NO: 135). The preparation procedure for Platinum TALEN was in accordance with [Manufacture of Platinum TALEN] in (Example 2: Removal of endogenous TCR).

An SSA assay using human embryonic kidney derived cell strain HEK293T was conducted by the method described in the following URL (Sakuma T, et al. Genes to Cells 2013).

(Results)

Figure 28:
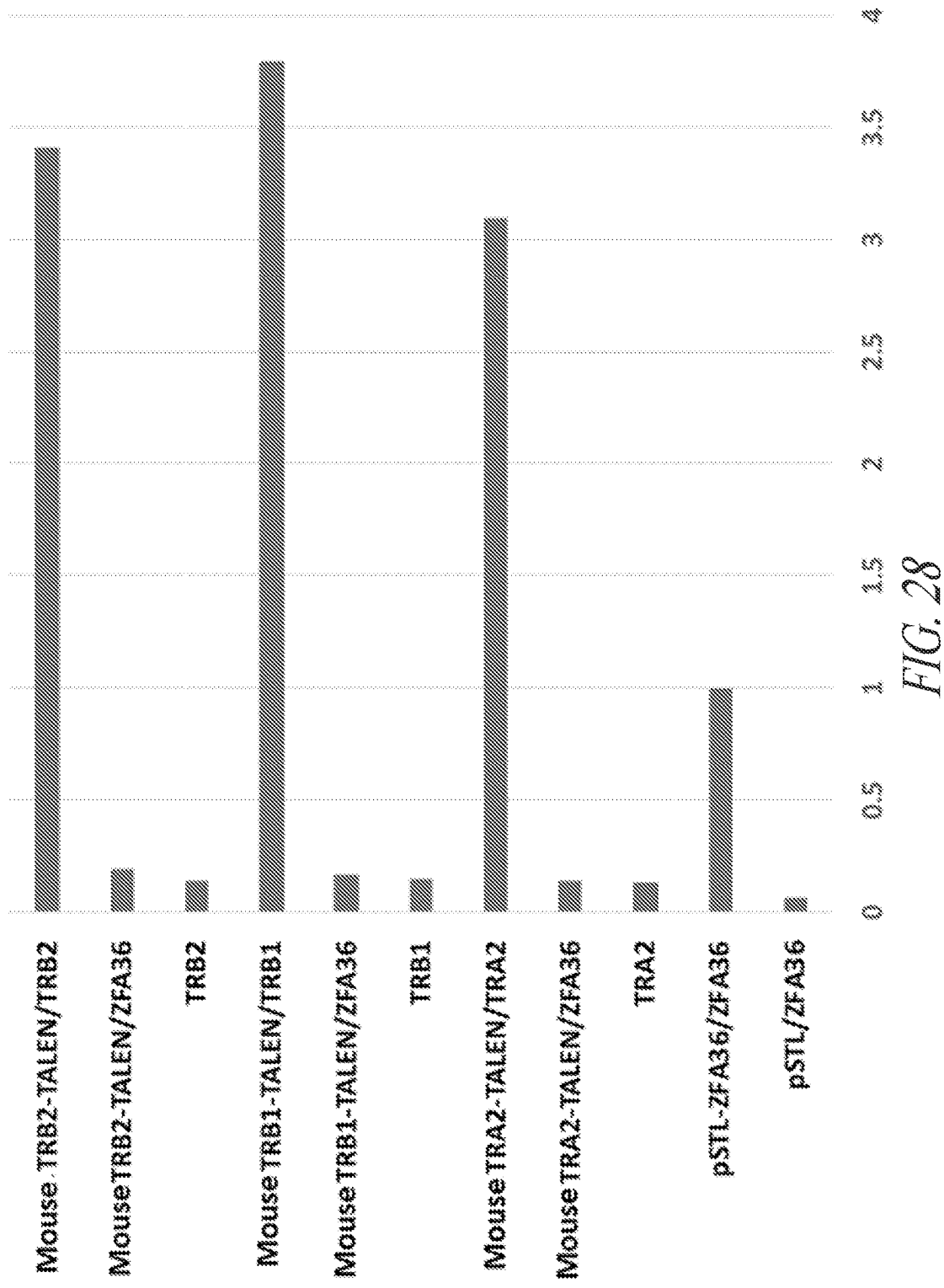
FIG. 28 is a diagram showing results of evaluating the cleavage activity of three types of platinum TALEN (TRA2-TALEN, TRB1-TALEN, and TRB2-TALEN) produced for cleaving a mouse TCR, by an assay method (SSA assay) using a reporter plasmid. It can be understood that if the cleavage activity of a zinc finger nuclease control (pSTL-ZFA36/ZFA36) is 1, the activities on a target cleavage site of mouse TRA2-TALEN, mouse TRB1-TALEN, and mouse TRB2-TALEN are 3.09-fold, 3.79-fold, and 3.41-fold, respectively. pSTL is a negative control for ZFA36. TRA2, TRB1, and TRB2 are each negative controls for only a reporter in the absence of TALEN, and TRA2-TALEN/ZFA36, TRB1-TALEN/ZFA36, and TRB2-TALEN/ZFA36 are each negative controls when a reporter gene is ZFA36.

The results are shown in FIG. 28. It can be understood that if the cleavage activity of a Zinc finger nuclease control (pSTL-ZFA36/ZFA36) is 1, the activity against the target cleavage site of mouse TRA2-TALEN, mouse TRB1-TALEN, and mouse TRB2-TALEN is 3.09-fold, 3.79-fold, and 3.41-fold, respectively. pSTL is a negative control of ZFA36. TRA2, TRB1, and TRB2 are negative controls of only a reporter in the absence of TALEN. TRA2-TALEN/ZFA36, TRB1-TALEN/ZFA36, and TRB2-TALEN/ZFA36 are each negative controls when the reporter gene is ZFA36.

Example 7: Example of Production

A product comprising one or more of the following components is provided for use in the method of the invention.

Means for editing a TCR gene: is provided in a form of a composition or the like for editing a TCR gene; and uses a genome editing enzyme (TALEN, CRISPR/Cas9, ZFN) that targets a TCR gene or the like. A targeting site and a functional domain are provided together, or they are provided separately. Alternatively, a genome editing enzyme is provided in a form of a polypeptide. A genome editing enzyme is provided in a form of an mRNA. A genome editing enzyme is provided with an introducing vector.

Means for checking for a mutation of an endogenous TCR gene: provides a PCR primer specific to an endogenous TCR gene. It is possible to check, before genome editing, that there is no mutation at a targeted site so that a specific editing can be performed.

Means for checking for the removal of an endogenous TCR gene: provides an antibody used in measurement of a change upon removal of endogenous TCR; provides an anti-CD3 antibody or anti-TCR antibody; and provides a labeled antibody.

Means for introducing an exogenous TCR: provides a vector or the like for introducing TCR; and uses a lentiviral vector incorporating a fluorescent pigment with low cytotoxicity such as Venus or a non-viral vector such as Sleeping Beauty utilizing transposon.

Means for detecting cells introduced with a gene: provides an antibody used in the measurement of a change upon introduction of an endogenous TCR; provides an anti-CD3 antibody or anti-TCR antibody; and provides a labeled antibody.

Example 8: Creation of T Cells that Express Cancer Antigen Specific TCR (Summary)

In this Example, T cells expressing cancer antigen specific TCR were created in accordance with the method described herein to investigate the cytocidal activity of the cells.

(Materials and Methods)

HLA-A*0201-restricted NY-ESO-$1_{157\text{-}165}$ (SLL-MWITQC) (SEQ ID NO: 115) was selected as the target epitope. 1G4 TCR with the following configuration in each segment of the variable region was used as TCR with specificity to said epitope.

TABLE 11

| TRAV | TRAJ | TCRA CDR3 (SEQ ID NO: 116) | TRBV | TRBJ | TCRB CDR3 (SEQ ID NO: 117) |
|---|---|---|---|---|---|
| TRAV21*01 | TRAJ6*01 | CAVRPTSGGSYIPTF | TRBV6-5*01 | TRBJ2-2*01 | CASSYVGNTGELFF |

[Creation of Vector for Introducing 1G4 TCR Using a pMXs Vector]

(1) A Vα cassette and Vβ, cassette of 1G4 TCR were prepared (each base sequence is described below).

[Chemical Formula 11]
Vα cassette
(SEQ ID NO: 118)
TGGAGGAGAACCCTGGACCTATGGAGACCCTCTTGGGCCTGCTGATCCTGT

GGCTGCAGCTGCAGTGGGTGAGCAGCAAGCAGGAGGTGACCCAGATTCCTG

CCGCCCTGAGCGTGCCTGAAGGCGAGAATCTGGTGCTGAACTGCAGCTTCA

CCGACAGCGCCATCTACAACCTGCAGTGGTTCAGACAGGACCCCGGCAAGG

GCCTGACCAGCCTGCTGCTGATCCAGAGCAGCCAGAGAGAGCAGACCAGCG

GCAGACTGAACGCCAGCCTGGACAAGAGCAGCGGCAGAAGCACCCTGTATA

TCGCCGCCAGCCAGCCAGGCGATAGCGCCACCTACCTGTGTGCCGTGAGAC

CAACCAGCGGCGGCAGCTATATCCCCACCTTTGGCAGAGGCACCAGCCTGA

TCGTGCACCCCTACATCCAGAACCCCGACCCCGCCGTGTACCAGCTGAGAG

ACTCTAAATCCAGTGACAAGTCTGTCTGCCTATTCACC

Vβ cassette
(SEQ ID NO: 119)
TGCCGGATCTAGCTAGTTAATTAAGGATCCGAATTCCTGCAGGATGAGCAT

CGGCCTGCTGTGTTGTGCCGCCCTGTCTCTGCTGTGGGCTGGACCAGTGAA

TGCCGGCGTGACACAGACCCCTAAGTTCCAGGTGCTGAAGACCGGCCAGAG

CATGACCCTGCAGTGCGCCCAGGACATGAACCACGAGTACATGAGCTGGTA

CAGACAGGACCCCGGCATGGGCCTGAGACTGATCCACTACAGCGTGGGCGC

CGGAATCACAGACCAGGGCGAGGTGCCAAACGGCTACAACGTGAGCAGAAG

CACCACCGAGGATTTCCCACTGAGACTGCTGTCTGCCGCCCCAAGCCAGAC

CAGCGTGTACTTTTGCGCCAGCAGCTACGTGGGCAACACCGGCGAGCTGTT

CTTCGGCGAGGGCAGCAGACTGACCGTGCTGGAGGACCTGAAGAACGTGTT

CCCTCCTGAGGTGGCCGTGTTTGAGCCAAGCGAGGCCGAGATCAGCCACAC

CCAAAAGGCCACACTGGTGTGCCTGGCCACAGGCTTCTTCCCCGACCACGT

GGAGCTGAGCTGGTGGGTGAA (2) A pMXs-IRES-GFP vector was cleaved with BamHI and NotI.
(3) A primer was designed so that an overlap sequence was formed at each binding section, specifically as follows:

[Chemical Formula 12]
Vα: 5'-TGGAGGAGAACCCTGGACCT-3'

5'-GGTGAATAGGCAGACAGACTT-3'

Cα: 5'-GAGACTCTAAATCCAGTGAC-3'

5'-GGGGGCGGAATTTACGTAGCGGCCGCTCAGCTGCT-3'

Vβ: 5'-TGCCGGATCTAGCTAGTTAATTAAGGATCCGAATTCCTGCAGG-3'

5'-TTCACCCACCAGCTCAGCTC-3'

Cβ: 5'-TTCACCCACCAGCTCAGCTC-3'

5'-AGGTCCAGGGTTCTCCTCCA-3'
(Corresponding to, from the top, SEQ ID NOs: 70 to 77)

(4) Each fragment was amplified by PCR using the primer in (3).
(5) The fragments obtained in (2) and (4) were purified. The fragment of (2) (vector) was purified to attain 25 ng/μl.
The fragments of (4) (Vα, Cα, Vβ, Cβ) were each purified to attain 10 ng/μl.
(6) Gibson assembly reaction (NEB, Gibson Assembly Master Mix, in accordance with the Manufacture's Instruction) was performed. To 5 μl of Gibson Assembly Master Mix, 1 μl of vector, 0.75 μl of Vα, 0.75 μl of Vβ, 0.75 μl of Cα, and 0.75 μl of Cβ, were added. 1 hour at 50° C.
(7) The reaction solution in (6) was diluted 4-fold, and the samples were transformed to competent cells (JM109).
(8) DNA was purified with Miniprep and studied by sequencing.

[Introduction of 1G4 TCR into TCR-Null Jurkat Cells and Primary T Cells]

Figure 21:
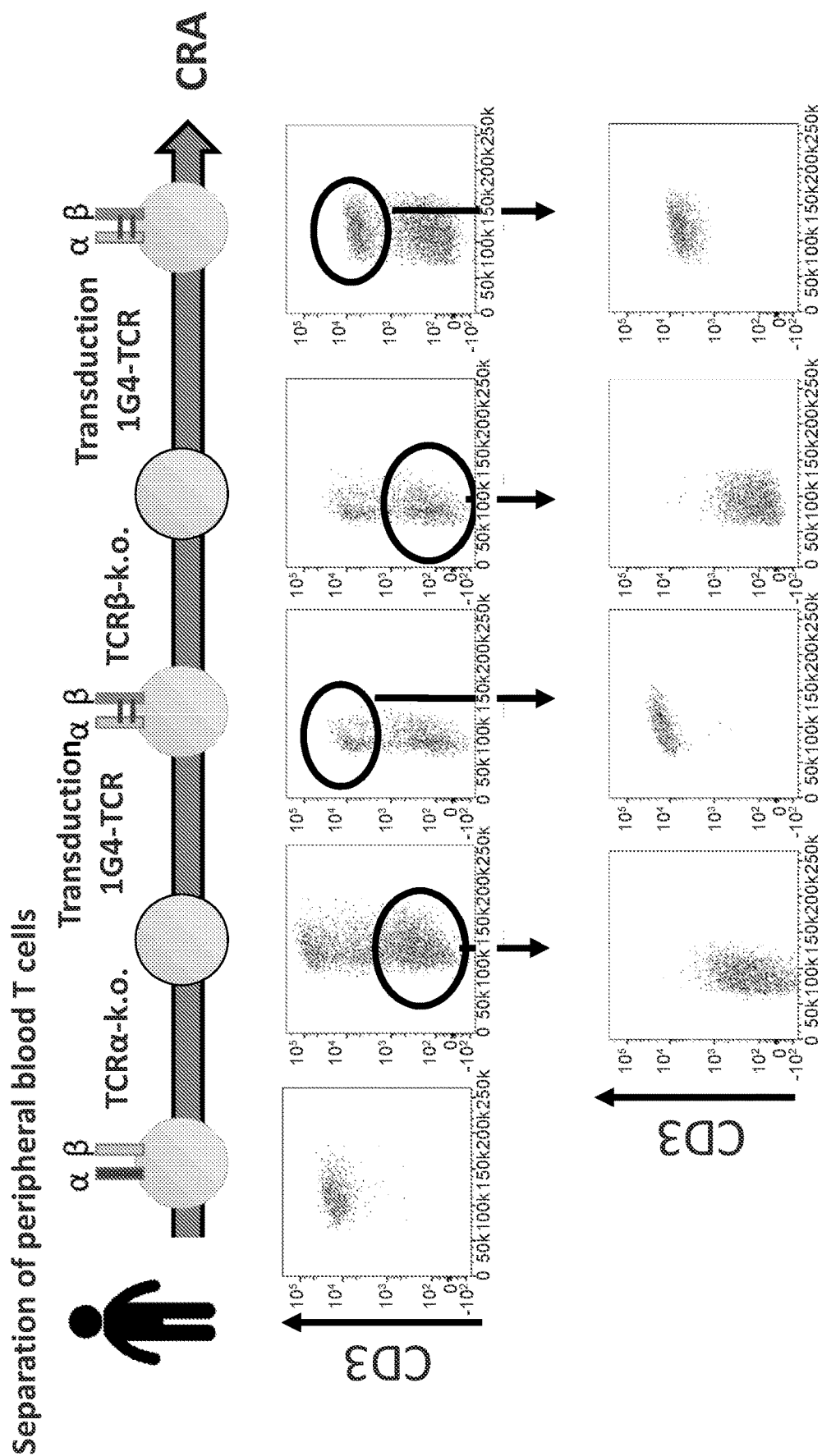
FIG. 21 is a schematic diagram showing the procedure for creating a 1G4 TCR expressing T cell by the Stepwise TCR genome editing method. The state of CD3 expression of cells in each step is shown. The middle row shows the distribution of CD3 expression of a cell population before sorting by CD3 expression. The bottom row shows the distribution of CD3 expression of a cell population after sorting by CD3 expression.

1G4 TCR was introduced into cells by the following procedure. TCR-null Jurkat cells were created using the CRISPR system based on the procedure described in Miyama et al. Sci Rep 2017. T cells separated from donor peripheral blood was used as primary T cells. FIG. 21 shows the change in CD3 expression in the process of manufacture of TCR-null Jurkat cells.

Day 1:
(1) PLAT-GP was seeded in a 10 cm dish and cultured to 70% confluence.
(2) 10 μg of pMXs-IRES-1G4 vector and 5 μg of VSV-G were added to 1.4 ml of OPTI-MEM I and incubated for 5 minutes at room temperature.
(3) 50 μl of Lipofectamine 2000 was added to 1.4 ml of OPTI-MEM I and incubated for 5 minutes at room temperature.
(4) (2) and (3) were mixed and incubated for 20 minutes at room temperature.
(5) The mixture of (4) was added to a culture of PLAT-GP and cultured for 48 hours.

Day 4-1:
(1) Supernatant was collected from PLAT-GP and centrifuged (1500 rpm×5 min, 4° C.)
(2) The supernatant was passed through a 0.45 μM filter and further centrifuged (6000 G×16 hr, 4° C.)

Day 4-2:
The TCR-null Jurkat cells or primary T cells in the culture were dispensed in a 24 well plate at 5×10$^5$/well.

Day 5:
(1) The supernatant in the centrifuge tube of Day 4-1-(2) was removed, and pellets were suspended in 500 μl of X-VIVO 20 to create a viral solution.
(2) After adding the viral solution to a medium of TCR-null Jurkat cells or primary T cells dispensed on the previous day and centrifuging (2000 rpm×30 min, 32° C.), the culture was continued for 24 hours. The next day, the infection rate was confirmed by the ratio of GFP positive cells (flow cytometry) among viable cells.

[NY-ESO-1 SLL specific TCR-T killing assay using B-LCL (B-lymphoblastoid cell lines)]

Cytocidal activity of the created T cells that express cancer antigen specific TCR was investigated by the following procedure.

Preparation of B-LCL (Target Cells):

$2\times10^6$ B-LCLs were prepared in a 24 well plate, and cultured for 1 hour after adding 50 µl of $^{51}$Cr and NY-ESO-1 epitope peptide (SLLMWITQC (SEQ ID NO: 115)) (final concentration 1 ng/µl).

The cells were washed twice with RPMI 1640 (300 G, 10 min, 4° C.)

SLL peptide added B-LCLs were adjusted to $1\times10^4$/100 µl RPMI 1640.

Similarly, B-LCL without the addition of an epitope peptide were adjusted to $1\times10^4$/100 µl RPMI 1640 as controls.

Preparation of NY-ESO-1 SLL Specific TCR-T (Effector Cells), and Positive and Negative Controls:

The cell count of NY-ESO-1 SLL specific TCR-T in the culture was adjusted so that the ratio of effector (NY-ESO-1 SLL specific TCR-T):target (B-LCL) was ultimately 30:1, 10:1, 3:1, or 1:1 ($3\times10^5$/100 µl RPMI 1640, $1\times10^5$/100 µl RPMI 1640, $3\times10^4$/100 µl RPMI 1640, $1\times10^4$/100 µl RPMI 1640) and dispensed into a 96 well plate.

100 µl of Triton X-100 was dispensed into a 96 well plate as a positive control.

100 µl of RPMI 1640 was dispensed into a 96 well plate as a negative control.

Chromium-51 Release Assay:

100 µl of B-LCL prepared in 1 was dispensed into each well of the 96 well plate prepared in 2 and cultured for 4 hours.

100 µl of supernatant was retrieved from each well and transferred into a microtube, and the gamma value of $^{51}$Cr released into the supernatant of each well was measured by a gamma counter.

The ratio (% lysis) of cytocidal effect with respect to the positive control of each well was calculated by the formula {(gamma value of each well)−(gamma value of negative control)}/(gamma value of positive control) and graphed.

(Results)

Figure 22:
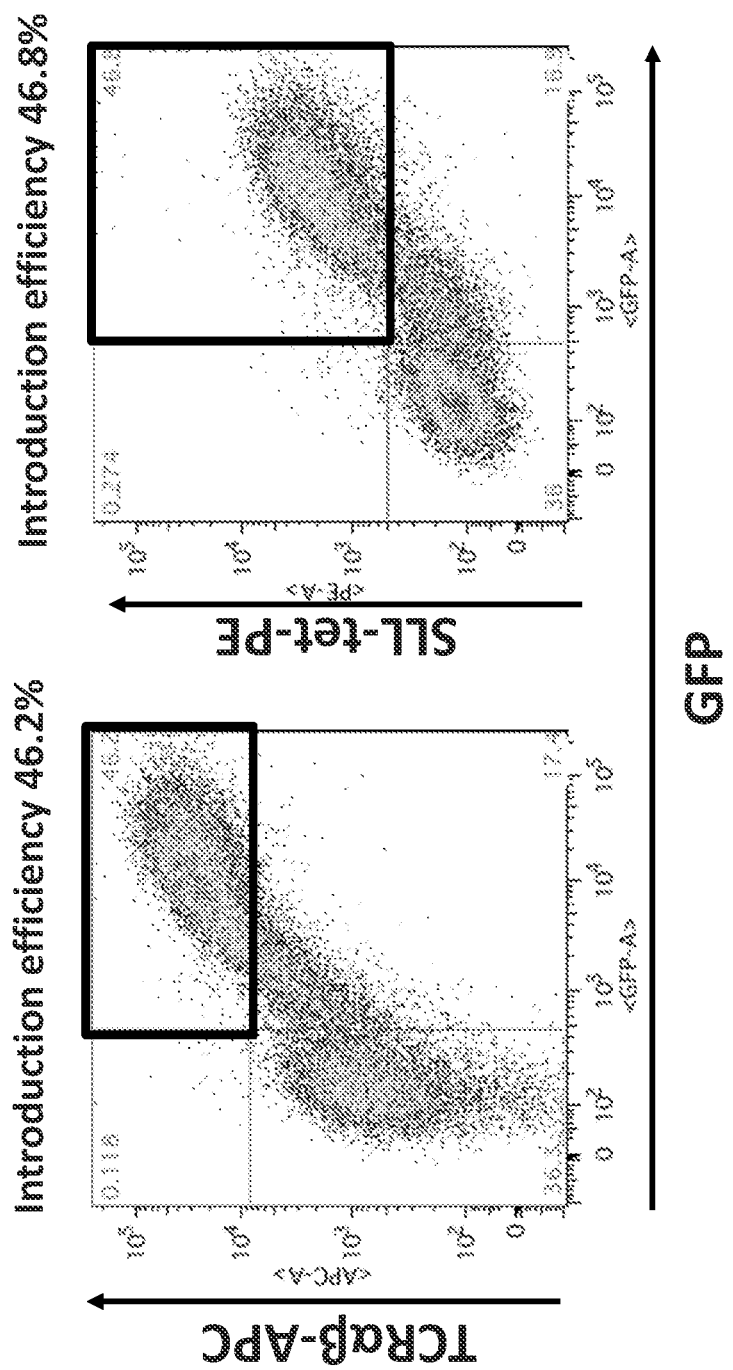
FIG. 22 is a diagram showing the results of introducing 1G4 TCR into a TCR non-expressing T cell strain (αβ null Jurkat cell). The left diagram shows the expression efficiency of an introduced TCR, and the right diagram shows the capability of a TCR introduced cell to bind to an SLL peptide tetramer. Similar efficiency is obtained in the left and right diagrams, indicating that almost all SLL peptides of expressed TCR are recognized. This shows the compatibility of a pMX vector to a genome edited T cell.
Figure 23:
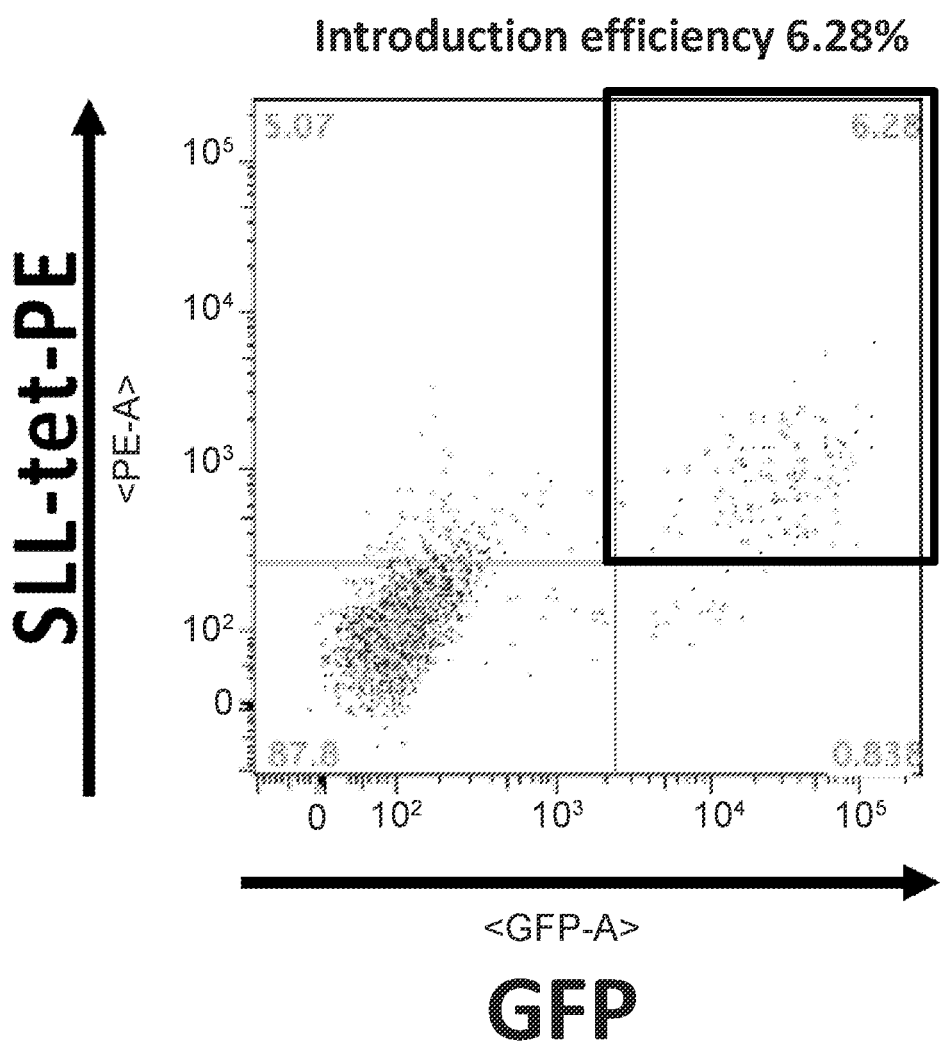
FIG. 23 is a diagram showing results of introducing 1G4 TCR into a human peripheral blood T cell.

Results of introducing 1G4 TCR into TCR-null Jurkat cells and primary T cells are shown in FIGS. 22 and 23, respectively. The efficiency of expression of the introduced TCR was 46.2% in the left diagram of FIG. 22, and the ratio of TCR introduced cells with binding affinity to SLL peptide tetramers was 46.8% in the right diagram of FIG. 22. Similar efficiencies are attained thereby, demonstrating that almost all TCR introduced into and expressed in TCR-null Jurkat cells recognize SLL peptides, i.e., expressed without mispairing. This shows that a pMX vector is compatible with genome edited T cells. The efficiency of introduction was 6.28% for primary T cells (FIG. 23).

Figure 26:
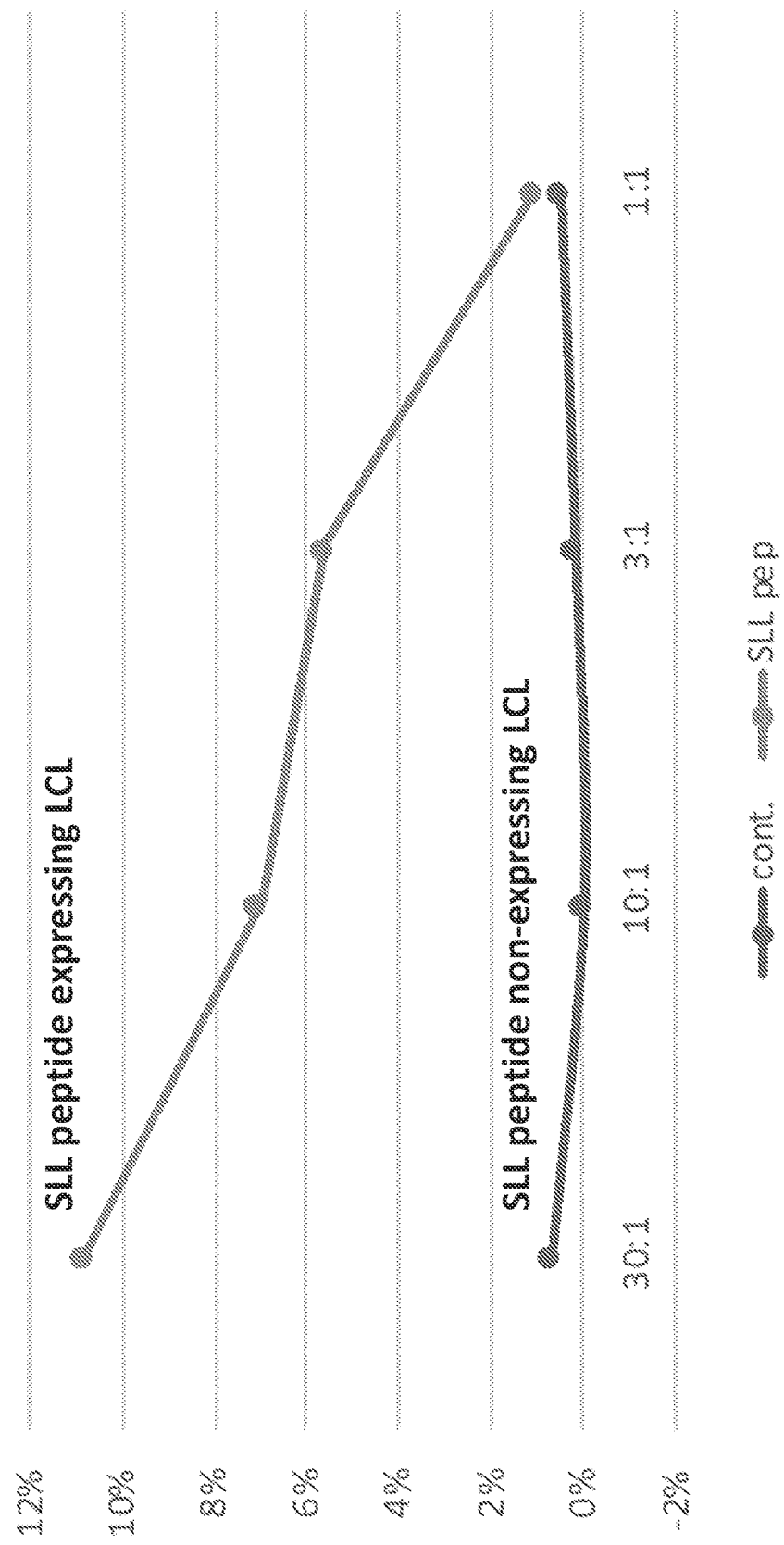
FIG. 26 is a diagram showing specific killer cell activity against SLL peptide expressing LCL of a 1G4 expressing genome edited T cell. The figure shows that a 1G4 expressing genome edited T cell exerts cytotoxic activity in a cell count dependent manner on NY-ESO-1 derived SLL peptide expressing LCL.

While cytocidal activity (release of $^{51}$Cr from the cells) was not observed at any concentration ratio for the negative controls, the created cancer antigen specific TCR expressing T cells exhibited concentration dependent cytocidal activity (FIG. 26).

Example 9: TCR Substitution by TAL-PITCh Method (Summary)

The modified T cells of the invention can be created by the TAL-PITCh method without using a viral vector.

(Materials and Methods)

Creation of endogenous TCR deficient NY-ESO-1 specific T cells using TAL-PITCh method Endogenous TCR deficient NY-ESO-1 specific T cells were created in accordance with the procedure described below.

1. mRNA Synthesis from Platinum TALEN:
  (1) Treat plasmids of Left (L)-TALEN and Right (R)-TALEN for cleaving a TRA or TRB gene for 2 hours at 30° C. with SmaI.
  (2) Treat with Proteinase K for 20 minutes at 50° C. and then purify with a QIAGEN PCR Purification Kit.
  (3) Synthesize mRNA with an mMESSAGE MACHINE T7 Kit (Life technologies), followed by poly(A) Tailing Kit (Life technologies) and purify the mRNA by LiCl precipitation method (in accordance with the Manufacturer's instruction).

Figure 24:
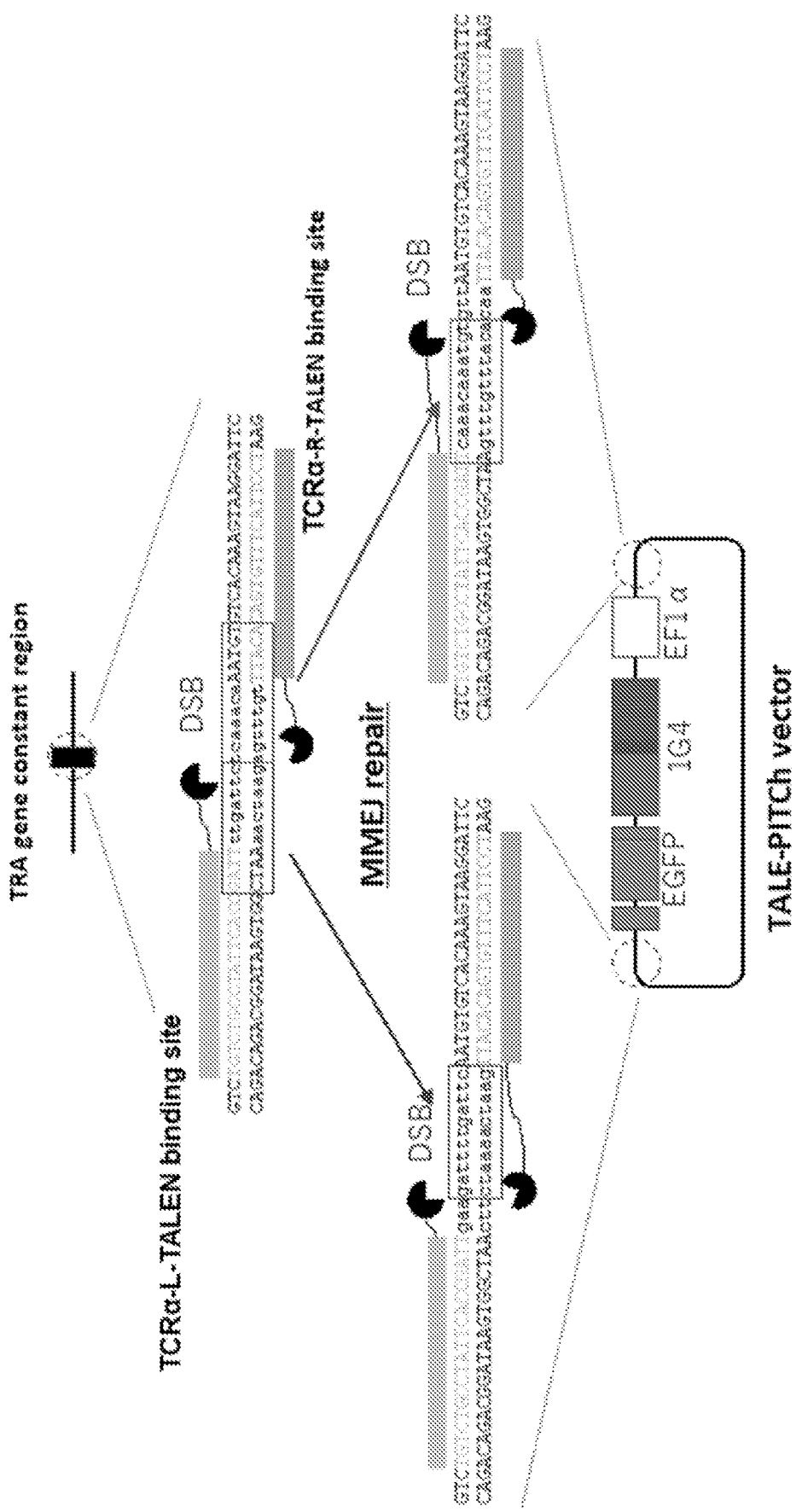
FIG. 24 is a schematic diagram showing the design of a TAL-PITCh vector. The sequences in the figure correspond to SEQ ID NOs: 120 and 121, respectively.
Figure 25:
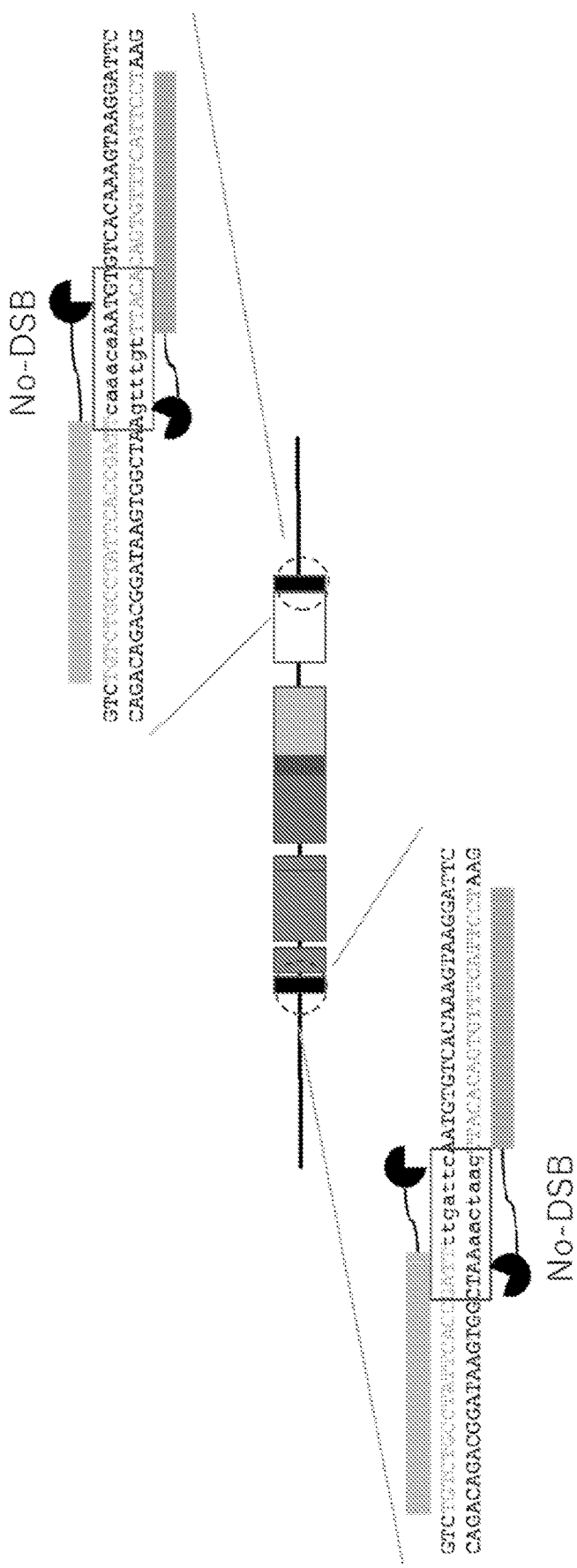
FIG. 25 is a schematic diagram showing the design of a TAL-PITCh vector. The sequences in the figure correspond to SEQ ID NOs: 120 and 121, respectively.

2. Design of TAL-PITCh Vector:

A TAL-PITCh vector is designed to be cleaved at both ends of an transgene with Left (L)-TALEN and Right (R)-TALEN for cleaving a TRA gene, such that a gene of interest is incorporated into the TRA gene cleavage site by microhomology mediated end joining (MMEJ) repair (FIG. 24; the portion surrounded by a square indicates a microhomology sequence). After the gene of interest is incorporated into the TRA gene cleavage site, there is a TALEN binding site at both ends, but not enough space to the cleavage site, so that a DNA double strand break (DSB) does not occur (FIG. 25). For a TAL-PITCh vector, a vector incorporating EGFP and a vector incorporating mKate2 are prepared to confirm by flow cytometry that both alleles of a TRA gene are cleaved (FIGS. 24 and 25 show a vector incorporating EGFP). For clinical applications, vectors with EGFP and mKate2 substituted with CD20 and CD34 as selection markers, respectively, are created.

3. Preparation of TRB Gene Cleaved T Cells Using Platinum TALEN mRNA:
  (1) Stimulate peripheral blood T cells with CD3/28 beads, and culture the cells for 3 days with X-VIVO 20+10% AB serum+2 mmol/l L-Glutamin+1% penicillin/streptomycin.
  (2) Introduce TCRβ-L-TALEN mRNA and TCRβ-R-TALEN mRNA into the cultured T cells using Amaxa 4D-Nucleofector (P3 Primary Cell 4D-Nucleofector™ X Kit S).
  1) Prepare cell pellets from $5\times10^5$ to $1\times10^6$ T cells by centrifugation (400 G, 10 minutes, room temperature).
  2) Suspend the cell pellets in a total of 20 µl of Nucleofector solution prepared by adding 3.6 µl of Supplement to 16.4 µl of Nucleofector P3 solution per reaction.
  3) Add TCRβ-L-TALEN mRNA and TCRβ-R-TALEN mRNA at 10 µg each.
  4) Perform Nucleofection (program: EO-115).
  5) Continue culture.
  6) Find the efficiency of cleavage of TCR gene after three days of Nucleofection by loss of expression of CD3 and TCRαβ by flow cytometry.
  (3) Collect CD3 negative fractions by magnetic sorting or FACS (Aria II).

4. Introduction of NY-ESO-1 Specific TCR (1G4) into TRA Gene Cleavage Site Using TAL-PITCh Method:
  (1) Stimulate TRB gene cleaved T cells obtained in 2 with CD3/28 beads and culture TRB gene cleaved T cells obtained in 2 for 3 days in X-VIVO 20+10% AB serum+2 mmol/l L-Glutamin+1% penicillin/streptomycin.
  (2) Introduce TCRα-L-TALEN mRNA and TCRα-R-TALEN mRNA and 2 types of TAL-PITCh vectors (1G4-EGFP and 1G4-mKate2) into the cultured T cells using Amaxa 4D-Nucleofector (P3 Primary Cell 4D-Nucleofector™ X Kit S).

1) Prepare cell pellets from 5×10⁵ to 1×10⁶ T cells by centrifugation (400 G, 10 minutes, room temperature).
2) Suspend the cell pellets in a total of 20 μl of Nucleofector solution prepared by adding 3.6 μl of Supplement to 16.4 μl of Nucleofector P3 solution per reaction.
3) Add TCRα-L-TALEN mRNA, TCRα-R-TALEN mRNA, 1G4-EGFP TAL-PITCh vector, and 1G4-mKate2 TAL-PITCh vector at 10 μg each.
4) Perform Nucleofection (program: EO-115).
5) Continue culture.
6) Find the efficiency of introducing 1G4-EGFP and 1G4-mKate2 after three days of Nucleofection by expression of EGFP and mKate2 by flow cytometry.
(3) Collect fractions where EGFP and mKate2 are both positive by FACS (Aria II).

(Results)

Figure 27:
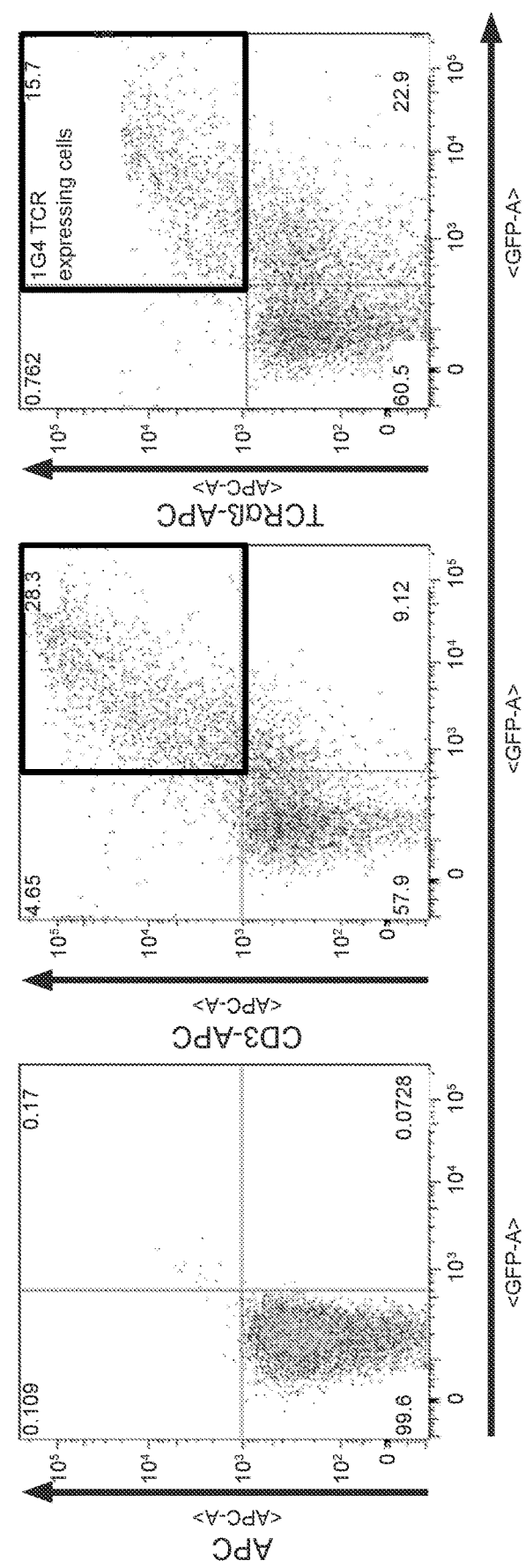
FIG. 27 is a diagram showing results of producing an endogenous TCR deficient NY-ESO-1 specific T cell using a TAL-PITCh vector. The figure shows that a 1G4 TCR incorporated into a TAL-PITCh vector is expressed in 15.7% of endogenous TCR deficient cells.

As shown in FIG. 27, a cell population expressing 1G4 TCR was able to be obtained. It is understood that endogenous TCR deficient NY-ESO-1 specific T cells can be created by the TAL-PITCh method without using a viral vector. Endogenous TCR deficient T cells expressing TCR having a desired antigen specificity can be created without using a viral vector by introducing desired exogenous TCR in place of NY-ESO-1 specific TCR.

Example 10: Full Genome Sequencing of Created Cells

After cloning the created cells by limiting dilution method or the like, the full genome sequencing can be performed to evaluate the properties of cells by the following method.

[DNA extraction using QIAamp DNA Mini Kit] (in accordance with the Manufacturer's instruction)
1. Pipette 20 μl of QIAGEN Protease at the bottom of a 1.5 ml microtube.
2. Add 1×10⁵ T cells suspended in 200 μl of PBS to the microtube.
3. Add 200 μl of Buffer AL to the sample.
4. Incubate for 10 minutes at 56° C.
5. Collect the solution adhering to the inside of a lid by spinning down the 1.5 ml microbe for several seconds.
6. After adding 200 μl of ethanol to the sample and vortexing the mixture for 15 seconds, collect the solution adhering to the inside of the lid by spinning down the 1.5 ml microbe for several seconds.
7. Apply the mixture from step 6 to a QIAamp Mini Spin Column. Close the lid and centrifuge for 1 minute at 6000×g. Transfer the QIAamp Mini Spin Column to a new 2 ml collection tube and discard collection tubes containing a filtrate.
8. Open the QIAamp Mini Spin Column and add 500 μl of Buffer AW1. Close the lid and centrifuge for 1 minute at 6000×g. Transfer the QIAamp Mini Spin Column to a new 2 ml collection tube and discard collection tubes containing a filtrate.
9. Open the QIAamp Mini Spin Column and add 500 μl of Buffer AW2. Close the lid and centrifuge for 3 minutes at 20000×g.
10. Transfer the QIAamp Mini Spin Column to a new 1.5 ml microtube and discard collection tubes containing a filtrate. Open the QIAamp Mini Spin Column and add 200 μl of purified water. After incubating for 1 minute at room temperature (20° C.), centrifuge for 1 minute at 6000×g to extract DNA.

[Creation of PCR Free Library and Full Genome Sequencing]
1. Fragment 1 μg a high molecular weight DNA into an average of about 300 bp with Bioruptor Pico (Diagenode, Belgium) and analyze the post-treatment state with an Agilent Bioanalyzer (Agilent Technologies, USA).
2. Perform end repair, A-tailing, and index adaptor-ligation on the fragmented DNA and purify with Agentcourt AMPure XP beads (Beckman Coulter, USA).
3. Analyze the quality of the size and concentration of the prepared DNA library with Agilent Bioanalyzer (Agilent Technologies, USA) and Bio-Rad real time PCR system.
4. Sequence the DNA library with HiSeq Xten (Illumina, USA) in accordance with the manufacturer's instruction, and determine the full genome sequence based on the sequence of unique reads obtained at Q30% or greater and coverage of 30×.

[Note]

As disclosed above, the present invention is exemplified by the use of its preferred embodiments. However, it is understood that the scope of the present invention should be interpreted based solely on the Claims. It is also understood that any patent, any patent application, and any other references cited herein should be incorporated herein by reference in the same manner as the contents are specifically described herein. The present application claims priority to Japanese Patent Application No. 2017-197010 filed on Oct. 10, 2017 and Japanese Patent Application No. 2018-167954 filed on Sep. 7, 2018 with the Japan Patent Office. The entire content thereof is incorporated herein by reference.

INDUSTRIAL APPLICABILITY

The present invention can be utilized in bioengineering of T cells and materialize highly functional TCR gene introduced T cell therapy without mispairing/off-target.

SEQUENCE LISTING FREE TEXT

SEQ ID NO 1: example of the amino acid sequence of a TALE DNA binding module
SEQ ID NO 2: HLA-A*02 restricted CMV pp65 peptide
SEQ ID NO 3: HLA-A2-HIV
SEQ ID NO 4: BSL-18E primer
SEQ ID NO 5: P20EA primer
SEQ ID NO 6: P10EA primer
SEQ ID NO 7: CA1 primer
SEQ ID NO 8: CA2 primer
SEQ ID NO 9: CB1 primer
SEQ ID NO 10: CB2 primer
SEQ ID NO 11: HuVaF primer
SEQ ID NO 12: HuVbF primer
SEQ ID NO 13: B-P20EA primer
SEQ ID NO 14: MID1
SEQ ID NO 15: MID2
SEQ ID NO 16: MID3
SEQ ID NO 17: MID4
SEQ ID NO 18: MID5
SEQ ID NO 19: MID6
SEQ ID NO 20: MID1
SEQ ID NO 21: MID8
SEQ ID NO 22: MID10
SEQ ID NO 23: MID11
SEQ ID NO 24: MID15
SEQ ID NO 25: MID16
SEQ ID NO 26: MID17
SEQ ID NO 27: MID18

SEQ ID NO 28: MID19
SEQ ID NO 29: MID20
SEQ ID NO 30: MID21
SEQ ID NO 31: MID22
SEQ ID NO 32: MID23
SEQ ID NO 33: MID24
SEQ ID NO 34: A adapter sequence
SEQ ID NO 35: P22EA-ST1-R primer
SEQ ID NO 36: Tag-1 primer
SEQ ID NO 37: Tag-2 primer
SEQ ID NO 38: CA-ST1-R
SEQ ID NO 39: CB-ST1-R
SEQ ID NO 40: TSO oligo
SEQ ID NO 41: TSO PCR primer
SEQ ID NO 42: SMART PCR primer
SEQ ID NO 43: TSO_TAG primer
SEQ ID NO 44: SMART_TAG primer
SEQ ID NO 45: SMART sequence in oligobeads
SEQ ID NO 46: full length TALEN-TCR-alpha2_L19 plasmid
SEQ ID NO 47: full length TALEN-TCR-alpha2_R19 plasmid
SEQ ID NO 48: full length TALEN-TCR-beta1_L19 plasmid
SEQ ID NO 49: full length TALEN-TCR-beta1_R19 plasmid
SEQ ID NO 50: full length TALEN-TCR-beta3_L19 plasmid
SEQ ID NO 51: full length TALEN-TCR-beta3_R19 plasmid
SEQ ID NO 52: TALEN-TCR-alpha2_L19 TALEN coding sequence
SEQ ID NO 53: TALEN-TCR-alpha2_L19 TALEN amino acid sequence
SEQ ID NO 54: TALEN-TCR-alpha2_R19 TALEN coding sequence
SEQ ID NO 55: TALEN-TCR-alpha2_R19 TALEN amino acid sequence
SEQ ID NO 56: TALEN-TCR-beta1_L19 TALEN coding sequence
SEQ ID NO 57: TALEN-TCR-beta1_L19 TALEN amino acid sequence
SEQ ID NO 58: TALEN-TCR-beta1_R19 TALEN coding sequence
SEQ ID NO 59: TALEN-TCR-beta1_R19 TALEN amino acid sequence
SEQ ID NO 60: TALEN-TCR-beta3_L19 TALEN coding sequence
SEQ ID NO 61: TALEN-TCR-beta3_L19 TALEN amino acid sequence
SEQ ID NO 62: TALEN-TCR-beta3_R19 TALEN coding sequence
SEQ ID NO 63: TALEN-TCR-beta3_R19 TALEN amino acid sequence
SEQ ID NO 64: TCR-alpha2-f primer
SEQ ID NO 65: TCR-alpha2-r primer
SEQ ID NO 66: TCR-beta1-c1-f primer
SEQ ID NO 67: TCR-beta1-c1-r primer
SEQ ID NO 68: TCR-beta1-c2-f primer
SEQ ID NO 69: TCR-beta1-c2-r primer
SEQ ID NO 70: Vα cloning forward primer
SEQ ID NO 71: Vα cloning reverse primer
SEQ ID NO 72: Cα cloning forward primer
SEQ ID NO 73: Cα cloning reverse primer
SEQ ID NO 74: Vβ, cloning forward primer
SEQ ID NO 75: Vβ cloning reverse primer
SEQ ID NO 76: Cβ cloning forward primer
SEQ ID NO 77: Cβ cloning reverse primer
SEQ ID NO 78: TCRα constant region for introduction
SEQ ID NO 79: TCRβ constant region for introduction
SEQ ID NO 80: target sequence of α2L
SEQ ID NO 81: target sequence of α2R
SEQ ID NO 82: target sequence of β1L
SEQ ID NO 83: target sequence of β1R
SEQ ID NO 84: target sequence of β3L
SEQ ID NO 85: target sequence of β3R
SEQ ID NO 86: TALEN_α2L binding domain
SEQ ID NO 87: TALEN_α2R binding domain
SEQ ID NO 88: TALEN_β1L binding domain
SEQ ID NO 89: TALEN_β1R binding domain
SEQ ID NO 90: TALEN_β3L binding domain
SEQ ID NO 91: TALEN_β3R binding domain
SEQ ID NO 92: QYD peptide
SEQ ID NO 93 to 110: example of CDR3 sequence of human TRA or TRB
SEQ ID NO 111 to 113: example of the amino acid sequence of DNA binding module of Platinum TALEN
SEQ ID NO 114: example of the amino acid sequence of DNA binding module of Zhang TALEN
SEQ ID NO 115: HLA-A*0201-restricted NY-ESO-1$_{157-165}$
SEQ ID NO 116: 1G4 TCRA CDR3
SEQ ID NO 117: 1G4 TCRB CDR3
SEQ ID NO 118: Vα cassette of 1G4 TCR
SEQ ID NO 119: Vβ, cassette of 1G4 TCR
SEQ ID NO 120 to 129: base sequences in FIGS. 24 and 25
SEQ ID NO 130: target sequence of mouse TRA2-TALEN on the left side
SEQ ID NO 131: target sequence of mouse TRA2-TALEN on the right side
SEQ ID NO 132: target sequence of mouse TRB1-TALEN on the left side
SEQ ID NO 133: target sequence of mouse TRB1-TALEN on the right side
SEQ ID NO 134: target sequence of mouse TRB2-TALEN on the left side
SEQ ID NO 135: target sequence of mouse TRB2-TALEN on the right side

The invention claimed is:

1. A method of editing a T cell receptor (TCR) gene, comprising introducing into a T cell a composition comprising a nucleic acid encoding a polypeptide comprising a DNA binding domain and a functional domain, wherein
the DNA binding domain and the functional domain are connected by a polypeptide consisting of 35 to 55 amino acids,
the DNA binding domain comprises a plurality of DNA binding modules consecutively from the N-terminal side of the DNA binding domain,
a combination of the xth amino acid and the yth amino acid in the 4n-3th DNA binding module from the N-terminus being identical for any n,
a combination of the xth amino acid and the yth amino acid in the 4n-2th DNA binding module from the N-terminus being identical for any n,
a combination of the xth amino acid and the yth amino acid in the 4n-1th DNA binding module from the N-terminus being identical for any n, and
a combination of the xth amino acid and the yth amino acid in the 4nth DNA binding module from the N-terminus being identical for any n,
the combination of the xth amino acid and the yth amino acid in the 4n-3th DNA binding module from the N-terminus, the combination of the xth amino acid and the yth amino acid in the 4n-2th DNA binding module from the N-terminus, the combination of the xth amino acid and the yth amino acid in the 4n-1th DNA binding module from the N-terminus, and the combination of the xth amino acid and the yth amino acid in the 4nth DNA binding module from the N-terminus are different from one another, and n is a natural number from 1 to 10, x is a natural number from 1 to 40, y is a natural number from 1 to 40, and x and y are different natural numbers, wherein the functional domain is a DNA cleaving domain, wherein the editing of a TCR gene is removal of an endogenous TCR gene, and wherein the DNA binding domain comprises the amino acid sequence of SEQ ID NO: 86, the amino acid sequence of SEQ ID NO: 87, the amino acid sequence of SEQ ID NO: 88, the amino acid sequence of SEQ ID NO: 89, the amino acid sequence of SEQ ID NO: 90, or the amino acid sequence of SEQ ID NO: 91.

2. The method of claim 1, comprising:

introducing into a T cell the composition wherein the DNA binding domain specifically binds to a gene encoding TCRα; and introducing into a T cell the composition wherein the DNA binding domain specifically binds to a gene encoding TCRβ.

3. The method of claim 1, further comprising introducing an exogenous TCR gene into the T cell, thereby producing a TCR modified T cell.

4. The method of claim 3, wherein the exogenous TCR has specificity to New York esophageal squamous cell carcinoma 1 (NY-ESO-1).

5. The method of claim 3, further comprising the step of preparing a T cell product comprising the TCR modified T cell.

\* \* \* \* \*

SEQUENCE LISTING

<160> NUMBER OF SEQ ID NOS: 135

<210> SEQ ID NO 1
<211> LENGTH: 34
<212> TYPE: PRT
<213> ORGANISM: artificial sequence
<220> FEATURE:
<223> OTHER INFORMATION: Exemplary amino acid sequence of TALE DNA binding module

<400> SEQUENCE: 1

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 2
<211> LENGTH: 9
<212> TYPE: PRT
<213> ORGANISM: artificial sequence
<220> FEATURE:
<223> OTHER INFORMATION: HLA-A*02-restricted CMV pp65 peptide

<400> SEQUENCE: 2

Asn Leu Val Pro Met Val Ala Thr Val
1               5

<210> SEQ ID NO 3
<211> LENGTH: 9
<212> TYPE: PRT
<213> ORGANISM: artificial sequence
<220> FEATURE:
<223> OTHER INFORMATION: HLA-A2-HIV

<400> SEQUENCE: 3

Lys Leu Thr Pro Leu Cys Val Thr Leu
1               5

<210> SEQ ID NO 4
<211> LENGTH: 35
<212> TYPE: DNA
<213> ORGANISM: artificial sequence
<220> FEATURE:
<223> OTHER INFORMATION: BSL-18E primer
<220> FEATURE:
<221> NAME/KEY: misc_feature
<222> LOCATION: (35)..(35)
<223> OTHER INFORMATION: n is a, c, g, t or u

<400> SEQUENCE: 4
aaagcggccg catgcttttt tttttttttt tttvn                          35

<210> SEQ ID NO 5
<211> LENGTH: 20
<212> TYPE: DNA
<213> ORGANISM: artificial sequence
<220> FEATURE:
<223> OTHER INFORMATION: P20EA primer

<400> SEQUENCE: 5
taatacgact ccgaattccc                                           20

<210> SEQ ID NO 6
<211> LENGTH: 10
<212> TYPE: DNA
<213> ORGANISM: artificial sequence
<220> FEATURE:
<223> OTHER INFORMATION: P10EA primer

<400> SEQUENCE: 6
gggaattcgg                                                      10

<210> SEQ ID NO 7

-continued

```
<211> LENGTH: 23
<212> TYPE: DNA
<213> ORGANISM: artificial sequence
<220> FEATURE:
<223> OTHER INFORMATION: CA1 primer

<400> SEQUENCE: 7
tgttgaaggc gtttgcacat gca                                              23

<210> SEQ ID NO 8
<211> LENGTH: 23
<212> TYPE: DNA
<213> ORGANISM: artificial sequence
<220> FEATURE:
<223> OTHER INFORMATION: CA2 primer

<400> SEQUENCE: 8
gtgcatagac ctcatgtcta gca                                              23

<210> SEQ ID NO 9
<211> LENGTH: 23
<212> TYPE: DNA
<213> ORGANISM: artificial sequence
<220> FEATURE:
<223> OTHER INFORMATION: CB1 primer

<400> SEQUENCE: 9
gaactggact tgacagcgga act                                              23

<210> SEQ ID NO 10
<211> LENGTH: 23
<212> TYPE: DNA
<213> ORGANISM: artificial sequence
<220> FEATURE:
<223> OTHER INFORMATION: CB2 primer

<400> SEQUENCE: 10
aggcagtatc tggagtcatt gag                                              23

<210> SEQ ID NO 11
<211> LENGTH: 63
<212> TYPE: DNA
<213> ORGANISM: artificial sequence
<220> FEATURE:
<223> OTHER INFORMATION: HuVbF primer
<220> FEATURE:
<221> NAME/KEY: misc_feature
<222> LOCATION: (31)..(40)
<223> OTHER INFORMATION: n = A, T, C or G

<400> SEQUENCE: 11
ccatctcatc cctgcgtgtc tccgactcag nnnnnnnnnn ataggcagac agacttgtca      60
ctg                                                                   63

<210> SEQ ID NO 12
<211> LENGTH: 63
<212> TYPE: DNA
<213> ORGANISM: artificial sequence
<220> FEATURE:
<223> OTHER INFORMATION: HuVbF primer
<220> FEATURE:
<221> NAME/KEY: misc_feature
<222> LOCATION: (31)..(40)
<223> OTHER INFORMATION: n = A, T, C or G

<400> SEQUENCE: 12
ccatctcatc cctgcgtgtc tccgactcag nnnnnnnnnn acaccagtgt ggccttttgg      60
```

```
gtg                                                                63

<210> SEQ ID NO 13
<211> LENGTH: 46
<212> TYPE: DNA
<213> ORGANISM: artificial sequence
<220> FEATURE:
<223> OTHER INFORMATION: B-P20EA primer

<400> SEQUENCE: 13
cctatcccct gtgtgccttg gcagtctaat acgactccga attccc                 46

<210> SEQ ID NO 14
<211> LENGTH: 10
<212> TYPE: DNA
<213> ORGANISM: artificial sequence
<220> FEATURE:
<223> OTHER INFORMATION: MID1

<400> SEQUENCE: 14
acgagtgcgt                                                         10

<210> SEQ ID NO 15
<211> LENGTH: 10
<212> TYPE: DNA
<213> ORGANISM: artificial sequence
<220> FEATURE:
<223> OTHER INFORMATION: MID2

<400> SEQUENCE: 15
acgctcgaca                                                         10

<210> SEQ ID NO 16
<211> LENGTH: 10
<212> TYPE: DNA
<213> ORGANISM: artificial sequence
<220> FEATURE:
<223> OTHER INFORMATION: MID3

<400> SEQUENCE: 16
agacgcactc                                                         10

<210> SEQ ID NO 17
<211> LENGTH: 10
<212> TYPE: DNA
<213> ORGANISM: artificial sequence
<220> FEATURE:
<223> OTHER INFORMATION: MID4

<400> SEQUENCE: 17
agcactgtag                                                         10

<210> SEQ ID NO 18
<211> LENGTH: 10
<212> TYPE: DNA
<213> ORGANISM: artificial sequence
<220> FEATURE:
<223> OTHER INFORMATION: MID5

<400> SEQUENCE: 18
atcagacacg                                                         10

<210> SEQ ID NO 19
<211> LENGTH: 10
<212> TYPE: DNA
```

```
<213> ORGANISM: artificial sequence
<220> FEATURE:
<223> OTHER INFORMATION: MID6

<400> SEQUENCE: 19
atatcgcgag                                                          10

<210> SEQ ID NO 20
<211> LENGTH: 10
<212> TYPE: DNA
<213> ORGANISM: artificial sequence
<220> FEATURE:
<223> OTHER INFORMATION: MID7

<400> SEQUENCE: 20
cgtgtctcta                                                          10

<210> SEQ ID NO 21
<211> LENGTH: 10
<212> TYPE: DNA
<213> ORGANISM: artificial sequence
<220> FEATURE:
<223> OTHER INFORMATION: MID8

<400> SEQUENCE: 21
ctcgcgtgtc                                                          10

<210> SEQ ID NO 22
<211> LENGTH: 10
<212> TYPE: DNA
<213> ORGANISM: artificial sequence
<220> FEATURE:
<223> OTHER INFORMATION: MID10

<400> SEQUENCE: 22
tctctatgcg                                                          10

<210> SEQ ID NO 23
<211> LENGTH: 10
<212> TYPE: DNA
<213> ORGANISM: artificial sequence
<220> FEATURE:
<223> OTHER INFORMATION: MID11

<400> SEQUENCE: 23
tgatacgtct                                                          10

<210> SEQ ID NO 24

<400> SEQUENCE: 24

000

<210> SEQ ID NO 25
<211> LENGTH: 10
<212> TYPE: DNA
<213> ORGANISM: artificial sequence
<220> FEATURE:
<223> OTHER INFORMATION: MID16

<400> SEQUENCE: 25
tcacgtacta                                                          10

<210> SEQ ID NO 26
<211> LENGTH: 10
<212> TYPE: DNA
```

```
<213> ORGANISM: artificial sequence
<220> FEATURE:
<223> OTHER INFORMATION: MID17

<400> SEQUENCE: 26
cgtctagtac                                                          10

<210> SEQ ID NO 27
<211> LENGTH: 10
<212> TYPE: DNA
<213> ORGANISM: artificial sequence
<220> FEATURE:
<223> OTHER INFORMATION: MID18

<400> SEQUENCE: 27
tctacgtagc                                                          10

<210> SEQ ID NO 28
<211> LENGTH: 10
<212> TYPE: DNA
<213> ORGANISM: artificial sequence
<220> FEATURE:
<223> OTHER INFORMATION: MID19

<400> SEQUENCE: 28
tgtactactc                                                          10

<210> SEQ ID NO 29
<211> LENGTH: 10
<212> TYPE: DNA
<213> ORGANISM: artificial sequence
<220> FEATURE:
<223> OTHER INFORMATION: MID20

<400> SEQUENCE: 29
acgactacag                                                          10

<210> SEQ ID NO 30
<211> LENGTH: 10
<212> TYPE: DNA
<213> ORGANISM: artificial sequence
<220> FEATURE:
<223> OTHER INFORMATION: MID21

<400> SEQUENCE: 30
cgtagactag                                                          10

<210> SEQ ID NO 31
<211> LENGTH: 10
<212> TYPE: DNA
<213> ORGANISM: artificial sequence
<220> FEATURE:
<223> OTHER INFORMATION: MID22

<400> SEQUENCE: 31
tacgagtatg                                                          10

<210> SEQ ID NO 32
<211> LENGTH: 10
<212> TYPE: DNA
<213> ORGANISM: artificial sequence
<220> FEATURE:
<223> OTHER INFORMATION: MID23

<400> SEQUENCE: 32
tactctcgtg                                                          10
```

<210> SEQ ID NO 33
<211> LENGTH: 10
<212> TYPE: DNA
<213> ORGANISM: artificial sequence
<220> FEATURE:
<223> OTHER INFORMATION: MID24

<400> SEQUENCE: 33
tagagacgag                                                            10

<210> SEQ ID NO 34
<211> LENGTH: 26
<212> TYPE: DNA
<213> ORGANISM: artificial sequence
<220> FEATURE:
<223> OTHER INFORMATION: A adaptor sequence

<400> SEQUENCE: 34
ccatctcatc cctgcgtgtc tccgac                                          26

<210> SEQ ID NO 35
<211> LENGTH: 55
<212> TYPE: DNA
<213> ORGANISM: artificial sequence
<220> FEATURE:
<223> OTHER INFORMATION: P22EA-ST1-R primer

<400> SEQUENCE: 35
gtctcgtggg ctcggagatg tgtataagag acagctaata cgactccgaa ttccc          55

<210> SEQ ID NO 36
<211> LENGTH: 33
<212> TYPE: DNA
<213> ORGANISM: artificial sequence
<220> FEATURE:
<223> OTHER INFORMATION: Tag-1 primer

<400> SEQUENCE: 36
gtctcgtggg ctcggagatg tgtataagag aca                                  33

<210> SEQ ID NO 37
<211> LENGTH: 33
<212> TYPE: DNA
<213> ORGANISM: artificial sequence
<220> FEATURE:
<223> OTHER INFORMATION: Tag-2 primer

<400> SEQUENCE: 37
tcgtcggcag cgtcagatgt gtataagaga cag                                  33

<210> SEQ ID NO 38
<211> LENGTH: 51
<212> TYPE: DNA
<213> ORGANISM: artificial sequence
<220> FEATURE:
<223> OTHER INFORMATION: CA-ST1-R

<400> SEQUENCE: 38
tcgtcggcag cgtcagatgt gtataagaga caggagggtc agggttctgg a              51

<210> SEQ ID NO 39
<211> LENGTH: 52
<212> TYPE: DNA
<213> ORGANISM: artificial sequence
<220> FEATURE:

-continued

<223> OTHER INFORMATION: CB-ST1-R

<400> SEQUENCE: 39
tcgtcggcag cgtcagatgt gtataagaga caggctcaaa cacagcgacc tc        52

<210> SEQ ID NO 40
<211> LENGTH: 29
<212> TYPE: DNA
<213> ORGANISM: artificial sequence
<220> FEATURE:
<223> OTHER INFORMATION: TSO oligo

<400> SEQUENCE: 40
gtcgcacggt ccatcgcagc agtcacagg                                   29

<210> SEQ ID NO 41
<211> LENGTH: 24
<212> TYPE: DNA
<213> ORGANISM: artificial sequence
<220> FEATURE:
<223> OTHER INFORMATION: TSO PCR primer

<400> SEQUENCE: 41
gtcgcacggt ccatcgcagc agtc                                        24

<210> SEQ ID NO 42
<211> LENGTH: 23
<212> TYPE: DNA
<213> ORGANISM: artificial sequence
<220> FEATURE:
<223> OTHER INFORMATION: SMART PCR primer

<400> SEQUENCE: 42
aagcagtggt atcaacgcag agt                                         23

<210> SEQ ID NO 43
<211> LENGTH: 59
<212> TYPE: DNA
<213> ORGANISM: artificial sequence
<220> FEATURE:
<223> OTHER INFORMATION: TSO_TAG primer

<400> SEQUENCE: 43
gtctcgtggg ctcggagatg tgtataagag acagcgtcgc acggtccatc gcagcagtc  59

<210> SEQ ID NO 44
<211> LENGTH: 56
<212> TYPE: DNA
<213> ORGANISM: artificial sequence
<220> FEATURE:
<223> OTHER INFORMATION: SMART_TAG primer

<400> SEQUENCE: 44
tcgtcggcag cgtcagatgt gtataagaga cagaagcagt ggtatcaacg cagagt     56

<210> SEQ ID NO 45
<211> LENGTH: 23
<212> TYPE: DNA
<213> ORGANISM: artificial sequence
<220> FEATURE:
<223> OTHER INFORMATION: SMART sequence in oligo bead

<400> SEQUENCE: 45
aagcagtggt atcaacgcag agt                                         23

<210> SEQ ID NO 46
<211> LENGTH: 8363
<212> TYPE: DNA
<213> ORGANISM: artificial sequence
<220> FEATURE:
<223> OTHER INFORMATION: TALEN-TCR-alpha2_L19 plasmid full length

<400> SEQUENCE: 46

| | | | | | |
|---|---|---|---|---|---|
| agccatctgt | tgtttgcccc | tccccgtgc | cttccttgac | cctggaaggt | gccactccca | 60 |
| ctgtcctttc | ctaataaaat | gaggaaattg | catcacaaca | ctcaaccta | tctcggtcta | 120 |
| ttcttttgat | ttataaggga | ttttgccgat | ttcggcctat | tggttaaaaa | atgagctgat | 180 |
| ttaacaaaaa | tttaacgcga | attaattctg | tggaatgtgt | gtcagttagg | gtgtggaaag | 240 |
| tccccaggct | ccccagcagg | cagaagtatg | caaagcatgc | atctcaatta | gtcagcaacc | 300 |
| aggtgtggaa | agtccccagg | ctccccagca | ggcagaagta | tgcaaagcat | gcatctcaat | 360 |
| tagtcagcaa | ccatagtccc | gcccctaact | ccgcccatcc | cgcccctaac | ccgcccagt | 420 |
| tccgcccatt | ctccgcccca | tggctgacta | atttttttta | tttatgcaga | ggccgaggcc | 480 |
| gcctctgcct | ctgagctatt | ccagaagtag | tgaggaggct | tttttggagg | cctaggcttt | 540 |
| tgcaaaaagc | tcccgggagc | ttgtatatcc | attttcggat | ctgatcagca | cgtgatgaaa | 600 |
| aagcctgaac | tcaccgcgac | gtctgtcgag | aagtttctga | tcgaaaagtt | cgacagcgtt | 660 |
| tccgacctga | tgcagctctc | ggagggcgaa | gaatctcgtg | ctttcagctt | cgatgtagga | 720 |
| gggcgtggat | atgtcctgcg | ggtaaatagc | tgcgccgatg | gtttctacaa | agatcgttat | 780 |
| gtttatcggc | actttgcatc | ggccgcgctc | ccgattccgg | aagtgcttga | cattggggaa | 840 |
| ttcagcgaga | gcctgaccta | ttgcatctcc | cgccgtgcac | agggtgtcac | gttgcaagac | 900 |
| ctgcctgaaa | ccgaactgcc | cgctgttctg | cagccggtcg | cggaggccat | ggatgcgatc | 960 |
| gctgcggccg | atcttagcca | gacgagcggg | ttcggcccat | tcggaccgca | aggaatcggt | 1020 |
| caatacacta | catggcgtga | tttcatatgc | gcgattgctg | atccccatgt | gtatcactgg | 1080 |
| caaactgtga | tggacgacac | cgtcagtgcg | tccgtcgcgc | aggctctcga | tgagctgatg | 1140 |
| ctttgggccg | aggactgccc | cgaagtccgg | cacctcgtgc | acgcggattt | cggctccaac | 1200 |
| aatgtcctga | cggacaatgg | ccgcataaca | gcggtcattg | actggagcga | ggcgatgttc | 1260 |
| ggggattccc | aatacgaggt | cgccaacatc | ttcttctgga | ggccgtggtt | ggcttgtatg | 1320 |
| gagcagcaga | cgcgctactt | cgagcggagg | catccggagc | ttgcaggatc | gccgcggctc | 1380 |
| cgggcgtata | tgctccgcat | tggtcttgac | caactctatc | agagcttggt | tgacggcaat | 1440 |
| ttcgatgatg | cagcttgggc | gcagggtcga | tgcgacgcaa | tcgtccgatc | cggagccggg | 1500 |
| actgtcgggc | gtacacaaat | cgcccgcaga | agcgcggccg | tctggaccga | tggctgtgta | 1560 |
| gaagtactcg | ccgatagtgg | aaaccgacgc | cccagcactc | gtccgagggc | aaaggaatag | 1620 |
| cacgtgctac | gagatttcga | ttccaccgcc | gccttctatg | aaaggttggg | cttcggaatc | 1680 |
| gttttccggg | acgccggctg | gatgatcctc | cagcgcgggg | atctcatgct | ggagttcttc | 1740 |
| gcccacccca | acttgtttat | tgcagcttat | aatggttaca | aataaagcaa | tagcatcaca | 1800 |
| aatttcacaa | ataaagcatt | ttttcactg | cattctagtt | gtggtttgtc | caaactcatc | 1860 |
| aatgtatctt | atcatgtctg | tataccgtcg | acctctagct | agagcttggc | gtaatcatgg | 1920 |
| tcattaccaa | tgcttaatca | gtgaggcacc | tatctcagcg | atctgtctat | ttcgttcatc | 1980 |
| catagttgcc | tgactccccg | tcgtgtagat | aactacgata | cgggagggct | taccatctgg | 2040 |
| ccccagcgct | gcgatgatac | cgcgagaacc | acgctcaccg | gctccggatt | tatcagcaat | 2100 |

```
aaaccagcca gccggaaggg ccgagcgcag aagtggtcct gcaactttat ccgcctccat    2160
ccagtctatt aattgttgcc gggaagctag agtaagtagt tcgccagtta atagtttgcg    2220
caacgttgtt gccatcgcta caggcatcgt ggtgtcacgc tcgtcgtttg gtatggcttc    2280
attcagctcc ggttcccaac gatcaaggcg agttacatga tcccccatgt tgtgcaaaaa    2340
agcggttagc tccttcggtc ctccgatcgt tgtcagaagt aagttggccg cagtgttatc    2400
actcatggtt atggcagcac tgcataattc tcttactgtc atgccatccg taagatgctt    2460
ttctgtgact ggtgagtact caaccaagtc attctgagaa tagtgtatgc ggcgaccgag    2520
ttgctcttgc ccggcgtcaa tacgggataa taccgcgcca catagcagaa ctttaaaagt    2580
gctcatcatt ggaaaacgtt cttcggggcg aaaactctca aggatcttac cgctgttgag    2640
atccagttcg atgtaaccca ctcgtgcacc caactgatct tcagcatctt ttactttcac    2700
cagcgtttct gggtgagcaa aaacaggaag gcaaaatgcc gcaaaaaagg gaataagggc    2760
gacacggaaa tgttgaatac tcatattctt ccttttttcaa tattattgaa gcatttatca    2820
gggttattgt ctcatgagcg gatacatatt tgaatgtatt tagaaaaata aacaaatagg    2880
ggtcagtgtt acaaccaatt aaccaattct gaacattatc gcgagcccat ttatacctga    2940
atatggctca taacacccct tgctcatgac caaaatccct taacgtgagt tacgcgcgcg    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactctttt ccgaaggtaa ctggcttcag cagagcgcag    3180
ataccaaata ctgttcttct agtgtagccg tagttagccc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggcctttttta   3660 cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaaggcg agagtaggga actgccaggc    3840
atcaaactaa gcagaaggcc cctgacggat ggcctttttg cgtttctaca aactcttttct    3900 gtgttgtaaa acgacggcca gtcttaagct cgggccccct gggcggttct gataacgagt    3960
aatcgttaat ccgcaaataa cgtaaaaacc cgcttcggcg ggttttttta tgggggagt    4020 ttagggaaag agcatttgtc agaatattta agggcgcctg tcactttgct tgatatatga    4080 gaattatttaa accttataaa tgagaaaaaa gcaacgcact ttaaataaga tacgttgctt    4140
tttcgattga tgaacaccta taattaaact attcatctat tatttatgat tttttgtata    4200
tacaatattt ctagtttgtt aaagagaatt aagaaaataa atctcgaaaa taataaaggg    4260
aaaatcagtt tttgatatca aaattataca tgtcaacgat aatacaaaat ataatacaaa    4320
ctataagatg ttatcagtat ttattatcat ttagaataaa ttttgtgtcg cccttaattg    4380
tgagcggata acaattacga gcttcatgca cagtggcgtt gacattgatt attgactagt    4440
tattaatagt aatcaattac ggggtcatta gttcatagcc catatatgga gttccgcgtt    4500
```

```
acataactta cggtaaatgg cccgcctggc tgaccgccca acgaccccg cccattgacg   4560 tcaataatga cgtatgttcc catagtaacg ccaataggga ctttccattg acgtcaatgg   4620
gtggagtatt tacggtaaac tgcccacttg gcagtacatc aagtgtatca tatgccaagt   4680
acgcccccta ttgacgtcaa tgacggtaaa tggcccgcct ggcattatgc ccagtacatg   4740
accttatggg actttcctac ttggcagtac atctacgtat tagtcatcgc tattaccatg   4800
gtgatgcggt tttggcagta catcaatggg cgtggatagc ggtttgactc acggggattt   4860
ccaagtctcc accccattga cgtcaatggg agtttgtttt ggcaccaaaa tcaacgggac   4920
tttccaaaat gtcgtaacaa ctccgcccca ttgacgcaaa tgggcggtag gcgtgtacgg   4980
tgggaggtct atataagcag agctctctgg ctaactagag aacccactgc ttactggctt   5040
atcgaaatta atacgactca ctatagggaa gcttcttgtt cttttttgcag aagctcagaa   5100 taaacgctca actttggcct cgaggccacc atggcttcct cccctccaaa gaaaaagaga   5160
aaggttgcgg ccgctgacta caaggatgac gacgataaaa gttggaagga cgcaagtggt   5220
tggtctagaa tgcatgcggc cccgcgacgg cgtgctgcgc aaccctccga cgcttcgccg   5280
gccgcgcagg tggatctacg cacgctcggc tacagtcagc agcagcaaga gaagatcaaa   5340
ccgaaggtgc gttcgacagt ggcgcagcac cacgaggcac tggtgggcca tgggtttaca   5400
cacgcgcaca tcgttgcgct cagccaacac ccggcagcgt tagggaccgt cgctgtcacg   5460
tatcagcaca taatcacggc gttgccagag gcgacacacg aagacatcgt tggcgtcggc   5520
aaacagtggt ccggcgcacg cgccctggag gccttgctca cggatgcggg ggagttgaga   5580
ggtccgccgt tacagttgga cacaggccaa cttgtgaaga ttgcaaaacg tggcggcgtg   5640
accgcaatgg aggcagtgca tgcatcgcgc aatgcgctca cgggagcacc cctcaacctg   5700
accccagacc aagttgtcgc gattgcaagc aacaacggag gcaaacaagc cttagaaaca   5760
gtccagagat tgttgccggt gctgtgccaa gaccacggcc tgaccccga acaggttgtc   5820 gctattgcta gtaacggcgg aggcaaacag gcgctggaaa cagttcagcg cctcttgccg   5880
gtcttgtgtc aggcccacgg cctgaccccg gaccaggtgg ttgcaatcgc gtcacacgat   5940
gggggaaagc aggccctaga aaccgttcag cgactcctgc ccgtcctgtg ccaggcccac   6000
ggcctgaccc ccgcccaggt tgtcgctatt gctagtaacg gcggaggcaa acaggcgctg   6060
gaaacagttc agcgcctctt gccggtcttg tgtcaggacc acggcctgac cccagaccaa   6120
gttgtcgcga ttgcaagcaa caacggaggc aaacaagcct tagaaacagt ccagagattg   6180
ttgccggtgc tgtgccaaga ccacggcctg accccgaaac aggtggttgc aatcgcgtca   6240
cacgatgggg gaaagcaggc cctagaaacc gttcagcgac tcctgcccgt cctgtgccag   6300
gcccacggcc tgaccccgga ccaggtggtt gcaatcgcgt cacacgatgg gggaaagcag   6360
gccctagaaa ccgttcagcg actcctgccc gtcctgtgcc aggcccacgg cctgaccccc   6420
gcccaggttg tcgctattgc tagtaacggc ggaggcaaac aggcgctgga aacagttcag   6480
cgcctcttgc cggtcttgtg tcaggaccac ggcctgaccc agaccaggt tgtggccatc   6540 gccagcaaca taggtggcaa gcaggccctc gaaaccgtcc agagactgtt accggttctc   6600
tgccaggacc acgcctgac ccccgaacag ttgtcgcta ttgctagtaa cggcggaggc   6660
aaacaggcgc tggaaacagt tcagcgcctc ttgccggtct tgtgtcaggc ccacggcctg   6720 accccgacc aggttgtcgc tattgctagt aacggcggag gcaaacaggc gctggaaaca   6780
gttcagcgcc tcttgccggt cttgtgtcag gcccacggcc tgaccccggc ccaggtggtt   6840
```

```
gcaatcgcgt cacacgatgg gggaaagcag gccctagaaa ccgttcagcg actcctgccc    6900
gtcctgtgcc aggaccacgg cctgacccca gaccaggttg tggccatcgc cagcaacata    6960
ggtggcaagc aggccctcga aaccgtccag agactgttac cggttctctg ccaggaccac    7020
ggcctgaccc cggaacaggt ggttgcaatc gcgtcacacg atgggggaaa gcaggcccta    7080
gaaaccgttc agcgactcct gcccgtcctg tgccaggccc acggcctgac cccggaccag    7140
gtggttgcaa tcgcgtcaca cgatggggga agcaggcccc tagaaaccgt tcagcgactc    7200
ctgcccgtcc tgtgccaggc ccacggcctg accccagccc aagttgtcgc gattgcaagc    7260
aacaacggag gcaaacaagc cttagaaaca gtccagagat tgttgccggt gctgtgccaa    7320
gaccacggcc tgaccccaga ccaggttgtg gccatcgcca gcaacatagg tggcaagcag    7380
gccctcgaaa ccgtccagag actgttaccg gttctctgcc aggaccacgg cctgaccccc    7440
gaacaggttg tcgctattgc tagtaacggc ggaggcaaac aggcgctgga aacagttcag    7500
cgcctcttgc cggtcttgtg tcaggcccac ggcctgacgc ctgagcaggt agtggctatt    7560
gcatccaacg gaggggcag acccgcactg gagtcaatcg tggcccagct tcgaggccg     7620
gaccccgcgc tggccgcact cactaatgat catcttgtag cgctggcctg cctcggcgga    7680
cgtcctgcca tggatgcagt gaaaaaggga ttgccgcacg cgccggaatt gatcagatcc    7740
cagctagtga atctgaatt ggaagagaag aaatctgaac ttagacataa attgaaatat     7800
gtgccacatg aatatattga attgattgaa atcgcaagaa attcaactca ggatagaatc    7860
cttgaaatga aggtgatgga gttctttatg aaggtttatg gttatcgtgg taaacatttg    7920
ggtggatcaa ggaaaccaga cggagcaatt tatactgtcg gatctcctat tgattacggt    7980
gtgatcgttg atactaaggc atattcagga ggttataatc ttccaattgg tcaagcagat    8040
gaaatgcaaa gatatgtcga agagaatcaa acaagaaaca agcatatcaa ccctaatgaa    8100
tggtggaaag tctatccatc ttcagtaaca gaatttaagt tcttgtttgt gagtggtcat    8160
ttcaaaggaa actacaaagc tcagcttaca agattgaatc atatcactaa ttgtaatgga    8220
gctgttctta gtgtagaaga gcttttgatt ggtggagaaa tgattaaagc tggtacattg    8280
acacttgagg aagtgagaag gaaatttaat aacggtgaga taaactttta aaaaatcagc    8340
ctcgactgtg ccttctagtt gcc                                             8363
```

<210> SEQ ID NO 47
<211> LENGTH: 8363
<212> TYPE: DNA
<213> ORGANISM: artificial sequence
<220> FEATURE:
<223> OTHER INFORMATION: TALEN-TCR-alpha2_R19 plasmid full length

<400> SEQUENCE: 47

```
agccatctgt tgtttgcccc tcccccgtgc cttccttgac cctggaaggt gccactccca      60
ctgtcctttc ctaataaaat gaggaaattg catcacaaca ctcaaccata tctcggtcta     120
ttcttttgat ttataaggga ttttgccgat ttcggcctat tggttaaaaa atgagctgat     180
ttaacaaaaa tttaacgcga attaattctg tggaatgtgt gtcagttagg gtgtggaaag    240
tccccaggct ccccagcagg cagaagtatg caaagcatgc atctcaatta gtcagcaacc    300
aggtgtggaa agtccccagg ctccccagca ggcagaagta tgcaaagcat gcatctcaat    360
tagtcagcaa ccatagtccc gcccctaact ccgcccatcc cgcccctaac tccgcccagt    420
tccgcccatt ctccgcccca tggctgacta attttttttta tttatgcaga ggccgaggcc    480
gcctctgcct ctgagctatt ccagaagtag tgaggaggct ttttttggagg cctaggcttt    540
```

```
tgcaaaaagc tcccgggagc ttgtatatcc attttcggat ctgatcagca cgtgatgaaa    600
aagcctgaac tcaccgcgac gtctgtcgag aagtttctga tcgaaaagtt cgacagcgtt    660
tccgacctga tgcagctctc ggagggcgaa gaatctcgtg ctttcagctt cgatgtagga    720
gggcgtggat atgtcctgcg ggtaaatagc tgcgccgatg gtttctacaa agatcgttat    780
gtttatcggc actttgcatc ggccgcgctc ccgattccgg aagtgcttga cattggggaa    840
ttcagcgaga gcctgaccta ttgcatctcc cgccgtgcac agggtgtcac gttgcaagac    900
ctgcctgaaa ccgaactgcc cgctgttctg cagccggtcg cggaggccat ggatgcgatc    960
gctgcggccg atcttagcca gacgagcggg ttcggcccat tcggaccgca aggaatcggt   1020
caatacacta catggcgtga tttcatatgc gcgattgctg atccccatgt gtatcactgg   1080
caaactgtga tggacgacac cgtcagtgcg tccgtcgcgc aggctctcga tgagctgatg   1140
ctttgggccg aggactgccc cgaagtccgg cacctcgtgc acgcggattt cggctccaac   1200
aatgtcctga cggacaatgg ccgcataaca gcggtcattg actggagcga ggcgatgttc   1260
ggggattccc aatacgaggt cgccaacatc ttcttctgga ggccgtggtt ggcttgtatg   1320
gagcagcaga cgcgctactt cgagcggagg catccggagc ttgcaggatc gccgcggctc   1380
cgggcgtata tgctccgcat tggtcttgac caactctatc agagcttggt tgacggcaat   1440
ttcgatgatg cagcttgggc gcagggtcga tgcgacgcaa tcgtccgatc cggagccggg   1500
actgtcgggc gtacacaaat cgcccgcaga agcgcggccg tctggaccga tggctgtgta   1560
gaagtactcg ccgatagtgg aaaccgacgc cccagcactc gtccgagggc aaaggaatag   1620
cacgtgctac gagatttcga ttccaccgcc gccttctatg aaaggttggg cttcggaatc   1680
gttttccggg acgccggctg gatgatcctc cagcgcgggg atctcatgct ggagttcttc   1740 gcccaccca acttgtttat tgcagcttat aatggttaca aataaagcaa tagcatcaca   1800
aatttcacaa ataaagcatt ttttcactg cattctagtt gtggtttgtc caaactcatc   1860
aatgtatctt atcatgtctg tataccgtcg acctctagct agagcttggc gtaatcatgg   1920
tcattaccaa tgcttaatca gtgaggcacc tatctcagcg atctgtctat ttcgttcatc   1980
catagttgcc tgactccccg tcgtgtagat aactacgata cgggagggct taccatctgg   2040
ccccagcgct gcgatgatac cgcgagaacc acgctcaccg gctccggatt tatcagcaat   2100
aaaccagcca gccggaaggg ccgagcgcag aagtggtcct gcaactttat ccgcctccat   2160
ccagtctatt aattgttgcc gggaagctag agtaagtagt tcgccagtta atagtttgcg   2220
caacgttgtt gccatcgcta caggcatcgt ggtgtcacgc tcgtcgtttg gtatggcttc   2280
attcagctcc ggttcccaac gatcaaggcg agttacatga tcccccatgt tgtgcaaaaa   2340
agcggttagc tccttcggtc ctccgatcgt tgtcagaagt aagttggccg cagtgttatc   2400
actcatggtt atggcagcac tgcataattc tcttactgtc atgccatccg taagatgctt   2460
ttctgtgact ggtgagtact caaccaagtc attctgagaa tagtgtatgc ggcgaccgag   2520
ttgctcttgc ccggcgtcaa tacgggataa taccgcgcca catagcagaa ctttaaaagt   2580
gctcatcatt ggaaaacgtt cttcggggcg aaaactctca aggatcttac cgctgttgag   2640
atccagttcg atgtaaccca ctcgtgcacc caactgatct tcagcatctt ttactttcac   2700
cagcgtttct gggtgagcaa aacaggaag gcaaaatgcc gcaaaaaagg gaataagggc   2760
gacacggaaa tgttgaatac tcatattctt ccttttttcaa tattattgaa gcatttatca   2820
gggttattgt ctcatgagcg gatacatatt tgaatgtatt tagaaaaata aacaaatagg   2880
```

| | |
|---|---|
| ggtcagtgtt acaaccaatt aaccaattct gaacattatc gcgagcccat ttatacctga | 2940 |
| atatggctca taacacccct tgctcatgac caaaatccct taacgtgagt tacgcgcgcg | 3000 |
| tcgttccact gagcgtcaga ccccgtagaa aagatcaaag gatcttcttg agatcctttt | 3060 |
| tttctgcgcg taatctgctg cttgcaaaca aaaaaaccac cgctaccagc ggtggtttgt | 3120 |
| ttgccggatc aagagctacc aactcttttt ccgaaggtaa ctggcttcag cagagcgcag | 3180 |
| ataccaaata ctgttcttct agtgtagccg tagttagccc caccttcaa gaactctgta | 3240 |
| gcaccgccta catacctcgc tctgctaatc ctgttaccag tggctgctgc cagtggcgat | 3300 |
| aagtcgtgtc ttaccgggtt ggactcaaga cgatagttac cggataaggc gcagcggtcg | 3360 |
| ggctgaacgg ggggttcgtg cacacagccc agcttggagc gaacgaccta caccgaactg | 3420 |
| agatacctac agcgtgagct atgagaaagc gccacgcttc ccgaagggag aaaggcggac | 3480 |
| aggtatccgg taagcggcag ggtcggaaca ggagagcgca cgagggagct tccagggggA | 3540 |
| aacgcctggt atctttatag tcctgtcggg tttcgccacc tctgacttga gcgtcgattt | 3600 |
| ttgtgatgct cgtcaggggg gcggagccta tggaaaaacg ccagcaacgc ggccttttta | 3660 |
| cggttcctgg ccttttgctg gccttttgct cacatgttct ttcctgcgtt atcccctgat | 3720 |
| tctgtggata accgtattac cgcctttgag tgagctgata ccgctcgccg cagccgaacg | 3780 |
| accgagcgca gcgagtcagt gagcgaggaa gcggaaggcg agagtaggga actgccaggc | 3840 |
| atcaaactaa gcagaaggcc cctgacggat ggccttttg cgtttctaca actcttttct | 3900 |
| gtgttgtaaa acgacggcca gtcttaagct cgggccccct gggcggttct gataacgagt | 3960 |
| aatcgttaat ccgcaaataa cgtaaaaacc cgcttcggcg gtttttttta tgggggggagt | 4020 |
| ttagggaaag agcatttgtc agaatattta agggcgcctg tcactttgct tgatatatga | 4080 |
| gaattattta accttataaa tgagaaaaaa gcaacgcact ttaaataaga tacgttgctt | 4140 |
| tttcgattga tgaacaccta taattaaact attcatctat tatttatgat ttttttgtata | 4200 |
| tacaatattt ctagtttgtt aaagagaatt aagaaaataa atctcgaaaa taataaaggg | 4260 |
| aaaatcagtt tttgatatca aaattataca tgtcaacgat aatacaaaat ataatacaaa | 4320 |
| ctataagatg ttatcagtat ttattatcat ttagaataaa ttttgtgtcg cccttaattg | 4380 |
| tgagcggata acaattacga gcttcatgca cagtggcgtt gacattgatt attgactagt | 4440 |
| tattaatagt aatcaattac ggggtcatta gttcatagcc catatatgga gttccgcgtt | 4500 |
| acataactta cggtaaatgg cccgcctggc tgaccgccca acgacccccg cccattgacg | 4560 |
| tcaataatga cgtatgttcc catagtaacg ccaatagggga cttccattg acgtcaatgg | 4620 |
| gtggagtatt tacggtaaac tgcccacttg gcagtacatc aagtgtatca tatgccaagt | 4680 |
| acgccccta ttgacgtcaa tgacggtaaa tggcccgcct ggcattatgc ccagtacatg | 4740 |
| accttatggg actttcctac ttggcagtac atctacgtat tagtcatcgc tattaccatg | 4800 |
| gtgatgcggt tttggcagta catcaatggg cgtggatagc ggtttgactc acggggattt | 4860 |
| ccaagtctcc accccattga cgtcaatggg agtttgtttt ggcaccaaaa tcaacgggac | 4920 |
| tttccaaaat gtcgtaacaa ctccgcccca ttgacgcaaa tgggcggtag cgtgtacgg | 4980 |
| tgggaggtct atataagcag agctctctgg ctaactagag aacccactgc ttactggctt | 5040 |
| atcgaaatta atacgactca ctatagggaa gcttcttgtt cttttgcag aagctcagaa | 5100 |
| taaacgctca actttggcct cgaggccacc atggcttcct cccctccaaa gaaaagaga | 5160 |
| aaggttgcgg ccgctgacta caaggatgac gacgataaag gttggaagga cgcaagtggt | 5220 |
| tggtctagaa tgcatgcggc cccgcgacgg cgtgctgcgc aaccctccga cgcttcgccg | 5280 |

```
gccgcgcagg tggatctacg cacgctcggc tacagtcagc agcagcaaga gaagatcaaa    5340
ccgaaggtgc gttcgacagt ggcgcagcac cacgaggcac tggtgggcca tgggtttaca    5400
cacgcgcaca tcgttgcgct cagccaacac ccggcagcgt tagggaccgt cgctgtcacg    5460
tatcagcaca taatcacggc gttgccagag gcgacacacg aagacatcgt tggcgtcggc    5520
aaacagtggt ccggcgcacg cgccctggag gccttgctca cggatgcggg ggagttgaga    5580
ggtccgccgt tacagttgga cacaggccaa cttgtgaaga ttgcaaaacg tggcggcgtg    5640
accgcaatgg aggcagtgca tgcatcgcgc aatgcgctca cgggagcacc cctcaacctg    5700
accccggacc aggtggttgc aatcgcgtca cacgatgggg aaagcaggc cctagaaacc     5760
gttcagcgac tcctgcccgt cctgtgccag gaccacggcc tgaccccgga acaggtggtt    5820
gcaatcgcgt cacacgatgg gggaaagcag gccctagaaa ccgttcagcg actcctgccc    5880
gtcctgtgcc aggcccacgg cctgaccccc gaccaggttg tcgctattgc tagtaacggc    5940
ggaggcaaac aggcgctgga acagttcag cgcctcttgc cggtcttgtg tcaggcccac     6000
ggcctgaccc ccgcccaggt tgtcgctatt gctagtaacg gcggaggcaa acaggcgctg    6060
gaaacagttc agcgcctctt gccggtcttg tgtcaggacc acggcctgac cccagaccag    6120
gttgtggcca tcgccagcaa cataggtggc aagcaggccc tcgaaaccgt ccagagactg    6180
ttaccggttc tctgccagga ccacggcctg accccgaac aggtggttgc aatcgcgtca     6240
cacgatgggg aaagcaggc cctagaaacc gttcagcgac tcctgcccgt cctgtgccag     6300
gcccacggcc tgaccccga ccaggttgtc gctattgcta gtaacggcgg aggcaaacag     6360
gcgctggaaa cagttcagcg cctcttgccg gtcttgtgtc aggcccacgg cctgaccccc    6420
gcccaggttg tcgctattgc tagtaacggc ggaggcaaac aggcgctgga aacagttcag    6480
cgcctcttgc cggtcttgtg tcaggaccac ggcctgaccc ccgaccaggt tgtcgctatt    6540
gctagtaacg gcggaggcaa acaggcgctg gaaacagttc agcgcctctt gccggtcttg    6600
tgtcaggacc acggcctgac cccagaacaa gttgtcgcga ttgcaagcaa caacggaggc    6660
aaacaagcct tagaaacagt ccagagattg ttgccggtgc tgtgccaagc ccacggcctg    6720
accccgacc aggttgtcgc tattgctagt aacggcggag gcaaacaggc gctggaaaca     6780
gttcagcgcc tcttgccggt cttgtgtcag gcccacggcc tgaccccagc ccaagttgtc    6840
gcgattgcaa gcaacaacgg aggcaaacaa gccttagaaa cagtccagag attgttgccg    6900
gtgctgtgcc aagaccacgg cctgaccccca gaccaggttg tggccatcgc cagcaacata    6960
ggtggcaagc aggccctcga aaccgtccag agactgttac cggttctctg ccaggaccac    7020
ggcctgaccc cggaacaggt ggttgcaatc gcgtcacacg atgggggaaa gcaggcccta    7080
gaaaccgttc agcgactcct gccgtcctg tgccaggccc acggcctgac cccagaccag     7140
gttgtggcca tcgccagcaa cataggtggc aagcaggccc tcgaaaccgt ccagagactg    7200
ttaccggttc tctgccaggc ccacggcctg accccgccc aggtggttgc aatcgcgtca     7260
cacgatgggg aaagcaggc cctagaaacc gttcagcgac tcctgcccgt cctgtgccag     7320
gaccacggcc tgaccccaga ccaggttgtg ccatcgcca gcaacatagg tggcaagcag     7380
gccctcgaaa ccgtccagag actgttaccg gttctctgcc aggaccacgg cctgaccccc    7440
gaacaggttg tcgctattgc tagtaacggc ggaggcaaac aggcgctgga aacagttcag    7500
cgcctcttgc cggtcttgtg tcaggcccac ggcctgacgc ctgagcaggt agtggctatt    7560
gcatccaacg gagggggcag accgcactg gagtcaatcg tggcccagct ttcgaggccg     7620
```

```
gaccccgcgc tggccgcact cactaatgat catcttgtag cgctggcctg cctcggcgga   7680
cgtcctgcca tggatgcagt gaaaaaggga ttgccgcacg cgccggaatt gatcagatcc   7740
cagctagtga atctgaatt ggaagagaag aaatctgaac ttagacataa attgaaatat    7800
gtgccacatg aatatattga attgattgaa atcgcaagaa attcaactca ggatagaatc   7860
cttgaaatga aggtgatgga gttctttatg aaggtttatg gttatcgtgg taaacatttg   7920
ggtggatcaa ggaaaccaga cggagcaatt tatactgtcg gatctcctat tgattacggt   7980
gtgatcgttg atactaaggc atattcagga ggttataatc ttccaattgg tcaagcagat   8040
gaaatgcaaa gatatgtcga agagaatcaa acaagaaaca agcatatcaa ccctaatgaa   8100
tggtggaaag tctatccatc ttcagtaaca gaatttaagt tcttgtttgt gagtggtcat   8160
ttcaaaggaa actacaaagc tcagcttaca agattgaatc atatcactaa ttgtaatgga   8220
gctgttctta gtgtagaaga cttttgatt ggtggagaaa tgattaaagc tggtacattg    8280
acacttgagg aagtgagaag gaaatttaat aacggtgaga taaactttta aaaaatcagc   8340
ctcgactgtg ccttctagtt gcc                                           8363

<210> SEQ ID NO 48
<211> LENGTH: 8363
<212> TYPE: DNA
<213> ORGANISM: artificial sequence
<220> FEATURE:
<223> OTHER INFORMATION: TALEN-TCR-beta1_L19 plasmid full length

<400> SEQUENCE: 48
agccatctgt tgtttgcccc tcccccgtgc cttccttgac cctggaaggt gccactccca     60
ctgtcctttc ctaataaaat gaggaaattg catcacaaca ctcaaccctat ctcggtcta    120 ttcttttgat ttataaggga ttttgccgat ttcggcctat tggttaaaaa atgagctgat    180
ttaacaaaaa tttaacgcga attaattctg tggaatgtgt gtcagttagg gtgtggaaag   240
tccccaggct ccccagcagg cagaagtatg caaagcatgc atctcaatta gtcagcaacc   300
aggtgtggaa agtccccagg ctccccagca ggcagaagta tgcaaagcat gcatctcaat   360
tagtcagcaa ccatagtccc gcccctaact ccgcccatcc cgcccctaac tccgcccagt   420
tccgcccatt ctccgcccca tggctgacta atttttttta tttatgcaga ggccgaggcc   480
gcctctgcct ctgagctatt ccagaagtag tgaggaggct ttttggagg cctaggcttt     540 tgcaaaaagc tcccgggagc ttgtatatcc attttcggat ctgatcagca cgtgatgaaa   600
aagcctgaac tcaccgcgac gtctgtcgag aagtttctga tcgaaaagtt cgacagcgtt    660
tccgacctga tgcagctctc ggagggcgaa gaatctcgtg ctttcagctt cgatgtagga   720
gggcgtggat atgtcctgcg ggtaaatagc tgcgccgatg gtttctacaa agatcgttat   780
gtttatcggc actttgcatc ggccgcgctc ccgattccgg aagtgcttga cattgggggaa   840 ttcagcgaga gcctgaccta ttgcatctcc cgccgtgcac agggtgtcac gttgcaagac    900
ctgcctgaaa ccgaactgcc cgctgttctg cagccggtcg cggaggccat ggatgcgatc   960
gctgcggccg atcttagcca gacgagcggg ttcggcccat tcggaccgca aggaatcggt   1020
caatacacta catggcgtga tttcatatgc gcgattgctg atccccatgt gtatcactgg   1080
caaactgtga tggacgacac cgtcagtgcg tccgtcgcgc aggctctcga tgagctgatg   1140
ctttgggccg aggactgccc cgaagtccgg cacctcgtgc acgcggattt cggctccaac   1200
aatgtcctga cggacaatgg ccgcataaca gcggtcattg actggagcga ggcgatgttc   1260
ggggattccc aatacgaggt cgccaacatc ttcttctgga ggccgtggtt ggcttgtatg   1320
```

```
gagcagcaga cgcgctactt cgagcggagg catccggagc ttgcaggatc gccgcggctc   1380
cgggcgtata tgctccgcat tggtcttgac caactctatc agagcttggt tgacggcaat   1440
ttcgatgatg cagcttgggc gcagggtcga tgcgacgcaa tcgtccgatc cggagccggg   1500
actgtcgggc gtacacaaat cgcccgcaga agcgcggccg tctggaccga tggctgtgta   1560
gaagtactcg ccgatagtgg aaaccgacgc cccagcactc gtccgagggc aaaggaatag   1620
cacgtgctac gagatttcga ttccaccgcc gccttctatg aaaggttggg cttcggaatc   1680
gttttccggg acgccggctg gatgatcctc cagcgcgggg atctcatgct ggagttcttc   1740
gcccacccca acttgtttat tgcagcttat aatggttaca aataaagcaa tagcatcaca   1800
aatttcacaa ataaagcatt tttttcactg cattctagtt gtggtttgtc caaactcatc   1860
aatgtatctt atcatgtctg tataccgtcg acctctagct agagcttggc gtaatcatgg   1920
tcattaccaa tgcttaatca gtgaggcacc tatctcagcg atctgtctat ttcgttcatc   1980
catagttgcc tgactcccg tcgtgtagat aactacgata cgggagggct taccatctgg   2040
ccccagcgct gcgatgatac cgcgagaacc acgctcaccg gctccggatt tatcagcaat   2100
aaaccagcca gccggaaggg ccgagcgcag aagtggtcct gcaactttat ccgcctccat   2160
ccagtctatt aattgttgcc gggaagctag agtaagtagt tcgccagtta atagtttgcg   2220
caacgttgtt gccatcgcta caggcatcgt ggtgtcacgc tcgtcgtttg gtatggcttc   2280
attcagctcc ggttcccaac gatcaaggcg agttacatga tcccccatgt tgtgcaaaaa   2340
agcggttagc tccttcggtc ctccgatcgt tgtcagaagt aagttggccg cagtgttatc   2400
actcatggtt atggcagcac tgcataattc tcttactgtc atgccatccg taagatgctt   2460
ttctgtgact ggtgagtact caaccaagtc attctgagaa tagtgtatgc ggcgaccgag   2520
ttgctcttgc ccggcgtcaa tacgggataa taccgcgcca catagcagaa ctttaaaagt   2580
gctcatcatt ggaaaacgtt cttcggggcg aaaactctca aggatcttac cgctgttgag   2640
atccagttcg atgtaaccca ctcgtgcacc caactgatct tcagcatctt ttactttcac   2700
cagcgtttct gggtgagcaa aaacaggaag gcaaaatgcc gcaaaaaagg gaataagggc   2760
gacacggaaa tgttgaatac tcatattctt ccttttttcaa tattattgaa gcatttatca   2820
gggttattgt ctcatgagcg gatacatatt tgaatgtatt tagaaaaata aacaaatagg   2880
ggtcagtgtt acaaccaatt aaccaattct gaacattatc gcgagcccat ttatacctga   2940
atatggctca taacacccct tgctcatgac caaaatccct taacgtgagt tacgcgcgcg   3000
tcgttccact gagcgtcaga ccccgtagaa aagatcaaag gatcttcttg agatcctttt   3060
tttctgcgcg taatctgctg cttgcaaaca aaaaaaccac cgctaccagc ggtggtttgt   3120
ttgccggatc aagagctacc aactcttttt ccgaaggtaa ctggcttcag cagagcgcag   3180
ataccaaata ctgttcttct agtgtagccg tagttagccc accacttcaa gaactctgta   3240
gcaccgccta catacctcgc tctgctaatc ctgttaccag tggctgctgc cagtggcgat   3300
aagtcgtgtc ttaccgggtt ggactcaaga cgatagttac cggataaggc gcagcggtcg   3360
ggctgaacgg ggggttcgtg cacacagccc agcttggagc gaacgaccta caccgaactg   3420
agatacctac agcgtgagct atgagaaagc gccacgcttc ccgaagggag aaaggcggac   3480
aggtatccgg taagcggcag ggtcggaaca ggagagcgca cgagggagct tccaggggga   3540
aacgcctggt atctttatag tcctgtcggg tttcgccacc tctgacttga gcgtcgattt   3600
ttgtgatgct cgtcaggggg gcggagccta tggaaaaacg ccagcaacgc ggcctttta   3660
```

| | |
|---|---|
| cggttcctgg cctttgctg gccttttgct cacatgttct ttcctgcgtt atccctgat | 3720 |
| tctgtggata accgtattac cgcctttgag tgagctgata ccgctcgccg cagccgaacg | 3780 |
| accgagcgca gcgagtcagt gagcgaggaa gcggaaggcg agagtaggga actgccaggc | 3840 |
| atcaaactaa gcagaaggcc cctgacggat ggccttttg cgtttctaca aactcttct | 3900 |
| gtgttgtaaa acgacggcca gtcttaagct cgggcccct gggcggttct gataacgagt | 3960 |
| aatcgttaat ccgcaaataa cgtaaaaacc cgcttcggcg gttttttta tgggggagt | 4020 |
| ttagggaaag agcatttgtc agaatattta agggcgcctg tcactttgct tgatatatga | 4080 |
| gaattattta accttataaa tgagaaaaaa gcaacgcact ttaaataaga tacgttgctt | 4140 |
| tttcgattga tgaacaccta taattaaact attcatctat tatttatgat ttttgtata | 4200 |
| tacaatattt ctagttttgtt aaagagaatt aagaaaataa atctcgaaaa taataaaggg | 4260 |
| aaaatcagtt tttgatatca aaattataca tgtcaacgat aatacaaat ataatacaaa | 4320 |
| ctataagatg ttatcagtat ttattatcat ttagaataaa ttttgtgtcg cccttaattg | 4380 |
| tgagcggata acaattacga gcttcatgca cagtggcgtt gacattgatt attgactagt | 4440 |
| tattaatagt aatcaattac ggggtcatta gttcatagcc catatatgga gttccgcgtt | 4500 |
| acataactta cggtaaatgg cccgcctggc tgaccgccca acgaccccg cccattgacg | 4560 |
| tcaataatga cgtatgttcc catagtaacg ccaataggga ctttccattg acgtcaatgg | 4620 |
| gtggagtatt tacggtaaac tgcccacttg gcagtacatc aagtgtatca tatgccaagt | 4680 |
| acgcccccta ttgacgtcaa tgacggtaaa tggcccgcct ggcattatgc ccagtacatg | 4740 |
| accttatggg actttcctac ttggcagtac atctacgtat tagtcatcgc tattaccatg | 4800 |
| gtgatgcggt tttggcagta catcaatggg cgtggatagc ggtttgactc acggggattt | 4860 |
| ccaagtctcc accccattga cgtcaatggg agtttgtttt ggcaccaaaa tcaacgggac | 4920 |
| tttccaaaat gtcgtaacaa ctccgcccca ttgacgcaaa tgggcggtag cgtgtacgg | 4980 |
| tgggaggtct atataagcag agctctctgg ctaactagag aacccactgc ttactggctt | 5040 |
| atcgaaatta atacgactca ctatagggaa gcttcttgtt cttttttgcag aagctcagaa | 5100 |
| taaacgctca actttggcct cgaggccacc atggcttcct cccctccaaa gaaaagaga | 5160 |
| aaggttgcgg ccgctgacta caaggatgac gacgataaaa gttggaagga cgcaagtggt | 5220 |
| tggtctagaa tgcatgcggc cccgcgacgg cgtgctgcgc aaccctccga cgcttcgccg | 5280 |
| gccgcgcagg tggatctacg cacgctcggc tacagtcagc agcagcaaga gaagatcaaa | 5340 |
| ccgaaggtgc gttcgacagt ggcgcagcac cacgaggcac tggtgggcca tgggtttaca | 5400 |
| cacgcgcaca tcgttgcgct cagccaacac ccggcagcgt tagggaccgt cgctgtcacg | 5460 |
| tatcagcaca taatcacggc gttgccagag gcgacacacg aagacatcgt tggcgtcggc | 5520 |
| aaacagtggt ccggcgcacg cgccctggag gccttgctca cggatgcggg ggagttgaga | 5580 |
| ggtccgccgt tacagttgga cacaggccaa cttgtgaaga ttgcaaaacg tggcggcgtg | 5640 |
| accgcaatgg aggcagtgca tgcatcgcgc aatgcgctca cggagcacc cctcaacctg | 5700 |
| accccagacc aagttgtcgc gattgcaagc aacaacggag gcaaacaagc cttagaaaca | 5760 |
| gtccagagat tgttgccggt gctgtgccaa gaccacggcc tgaccccga acaggttgtc | 5820 |
| gctattgcta gtaacggcgg aggcaaacag gcgctggaaa cagttcagcg cctcttgccg | 5880 |
| gtcttgtgtc aggcccacgg cctgaccccc gaccaggttg tcgctattgc tagtaacggc | 5940 |
| ggaggcaaac aggcgctgga aacagttcag cgcctcttgc cggtcttgtg tcaggccac | 6000 |
| ggcctgaccc cggcccaggt ggttgcaatc gcgtcacacg atgggggaaa gcaggcccta | 6060 |

```
gaaaccgttc agcgactcct gcccgtcctg tgccaggacc acggcctgac cccggaccag    6120
gtggttgcaa tcgcgtcaca cgatggggga aagcaggccc tagaaaccgt tcagcgactc    6180
ctgcccgtcc tgtgccagga ccacggcctg accccggaac aggtggttgc aatcgcgtca    6240
cacgatgggg aaagcaggcc ctagaaaccg ttcagcgact cctgcccgt  cctgtgccag    6300 gcccacggcc tgaccccaga ccaggttgtg ccatcgcca gcaacatagg tggcaagcag    6360
gccctcgaaa ccgtcagag actgttaccg gttctctgcc aggcccacgg cctgaccccg    6420
gcccaggtgg ttgcaatcgc gtcacacgat ggggaaagc aggccctaga accgttcag    6480 cgactcctgc ccgtcctgtg ccaggaccac ggcctgaccc cggaccaggt ggttgcaatc    6540
gcgtcacacg atgggggaaa gcaggccta gaaaccgttc agcgactcct gcccgtcctg    6600
tgccaggacc acggcctgac cccggaacag gtggttgcaa tcgcgtcaca cgatggggga    6660
aagcaggccc tagaaaccgt tcagcgactc ctgcccgtcc tgtgccaggc ccacggcctg    6720
accccagacc aagttgtcgc gattgcaagc aacaacggag gcaaacaagc cttagaaaca    6780
gtccagagat tgttgcctgt gctgtgccaa gcccacggcc tgaccccagc caggttgtg    6840 gccatcgcca gcaacatagg tggcaagcag gccctcgaaa ccgtccagag actgttaccg    6900
gttctctgcc aggaccacgg cctgacccca gaccaagttg tcgcgattgc aagcaacaac    6960
ggaggcaaac aagccttaga aacagtccag agattgttgc cggtgctgtg ccaagaccac    7020
ggcctgaccc cagaacaagt tgtcgcgatt gcaagcaaca acggaggcaa acaagcctta    7080
gaaacagtcc agagattgtt gccggtgctg tgccaagccc acggcctgac cccgaccag    7140 gttgtcgcta ttgctagtaa cggcggaggc aaacaggcgc tggaaacagt tcagcgcctc    7200
ttgccggtct tgtgtcaggc ccacggcctg accccggccc aggtggttgc aatcgcgtca    7260
cacgatgggg aaagcaggcc ctagaaaccg ttcagcgac  tcctgcccgt cctgtgccag    7320
gaccacggcc tgaccccaga ccaagttgtc gcgattgcaa gcaacaacgg aggcaaacaa    7380
gccttagaaa cagtccagag attgttgccg gtgctgtgcc aagaccacgg cctgaccccg    7440
gaacaggtgg ttgcaatcgc gtcacacgat ggggaaagc aggccctaga accgttcag    7500 cgactcctgc ccgtcctgtg ccaggccac ggcctgacgc tgagcaggt agtggctatt    7560 gcatccaacg gaggggcag acccgcactg gagtcaatcg tggcccagct ttcgaggccg    7620
gaccccgcgc tggccgcact cactaatgat catcttgtag cgctggcctg cctcggcgga    7680
cgtcctgcca tggatgcagt gaaaaggga ttgccgcacg cgccggaatt gatcagatcc    7740
cagctagtga atctgaatt ggaagagaag aaatctgaac ttagacataa attgaaatat    7800
gtgccacatg aatatattga attgattgaa atcgcaagaa attcaactca ggatagaatc    7860
cttgaaatga aggtgatgga gttctttatg aaggtttatg gttatcgtgg taaacatttg    7920
ggtggatcaa ggaaaccaga cggagcaatt tatactgtcg gatctcctat tgattacggt    7980
gtgatcgttg atactaaggc atattcagga ggttataatc ttccaattgg tcaagcagat    8040
gaaatgcaaa gatatgtcga agagaatcaa acaagaaaca agcatatcaa ccctaatgaa    8100
tggtggaaag tctatccatc ttcagtaaca gaatttaagt tcttgtttgt gagtggtcat    8160
ttcaaaggaa actacaaagc tcagcttaca agattgaatc atatcactaa ttgtaatgga    8220
gctgttctta gtgtagaaga gcttttgatt ggtggagaaa tgattaaagc tggtacattg    8280
acacttgagg aagtgagaag gaaatttaat aacggtgaga taaacttta aaaaatcagc    8340 ctcgactgtg ccttctagtt gcc                                            8363
```

<210> SEQ ID NO 49
<211> LENGTH: 8363
<212> TYPE: DNA
<213> ORGANISM: artificial sequence
<220> FEATURE:
<223> OTHER INFORMATION: TALEN-TCR-beta1_R19 plasmid full length

<400> SEQUENCE: 49

| | | | | | |
|---|---|---|---|---|---|
| agccatctgt | tgtttgcccc | tcccccgtgc | cttccttgac | cctggaaggt | gccactccca | 60 |
| ctgtcctttc | ctaataaaat | gaggaaattg | catcacaaca | ctcaaccta | tctcggtcta | 120 |
| ttcttttgat | ttataaggga | ttttgccgat | ttcggcctat | tggttaaaaa | atgagctgat | 180 |
| ttaacaaaaa | tttaacgcga | attaattctg | tggaatgtgt | gtcagttagg | gtgtggaaag | 240 |
| tccccaggct | ccccagcagg | cagaagtatg | caaagcatgc | atctcaatta | gtcagcaacc | 300 |
| aggtgtggaa | agtccccagg | ctccccagca | ggcagaagta | tgcaaagcat | gcatctcaat | 360 |
| tagtcagcaa | ccatagtccc | gcccctaact | ccgcccatcc | cgcccctaac | tccgcccagt | 420 |
| tccgcccatt | ctccgcccca | tggctgacta | atttttttta | tttatgcaga | ggccgaggcc | 480 |
| gcctctgcct | ctgagctatt | ccagaagtag | tgaggaggct | tttttggagg | cctaggcttt | 540 |
| tgcaaaaagc | tcccgggagc | ttgtatatcc | attttcggat | ctgatcagca | cgtgatgaaa | 600 |
| aagcctgaac | tcaccgcgac | gtctgtcgag | aagtttctga | tcgaaaagtt | cgacagcgtt | 660 |
| tccgacctga | tgcagctctc | ggagggcgaa | gaatctcgtg | ctttcagctt | cgatgtagga | 720 |
| gggcgtggat | atgtcctgcg | ggtaaatagc | tgcgccgatg | gtttctacaa | agatcgttat | 780 |
| gtttatcggc | actttgcatc | ggccgcgctc | ccgattccgg | aagtgcttga | cattgggga | 840 |
| ttcagcgaga | gcctgaccta | ttgcatctcc | cgccgtgcac | agggtgtcac | gttgcaagac | 900 |
| ctgcctgaaa | ccgaactgcc | cgctgttctg | cagccggtcg | cggaggccat | ggatgcgatc | 960 |
| gctgcggccg | atcttagcca | cgagcgggg | ttcggcccat | tcggaccgca | aggaatcggt | 1020 |
| caatacacta | catggcgtga | tttcatatgc | gcgattgctg | atccccatgt | gtatcactgg | 1080 |
| caaactgtga | tggacgacac | cgtcagtgcg | tccgtcgcgc | aggctctcga | tgagctgatg | 1140 |
| ctttgggccg | aggactgccc | cgaagtccgg | cacctcgtgc | acgcggattt | cggctccaac | 1200 |
| aatgtcctga | cggacaatgg | ccgcataaca | gcggtcattg | actggagcga | ggcgatgttc | 1260 |
| ggggattccc | aatacgaggt | cgccaacatc | ttcttctgga | ggccgtggtt | ggcttgtatg | 1320 |
| gagcagcaga | cgcgctactt | cgagcggagg | catccggagc | ttgcaggatc | gccgcggctc | 1380 |
| cgggcgtata | tgctccgcat | tggtcttgac | caactctatc | agagcttggt | tgacggcaat | 1440 |
| ttcgatgatg | cagcttgggc | gcagggtcga | tgcgacgcaa | tcgtccgatc | cggagccggg | 1500 |
| actgtcgggc | gtacacaaat | cgcccgcaga | agcgcggccg | tctggaccga | tggctgtgta | 1560 |
| gaagtactcg | ccgatagtgg | aaaccgacgc | cccagcactc | gtccgagggc | aaaggaatag | 1620 |
| cacgtgctac | gagatttcga | ttccaccgcc | gccttctatg | aaaggttggg | cttcggaatc | 1680 |
| gttttccggg | acgccggctg | gatgatcctc | cagcgcgggg | atctcatgct | ggagttcttc | 1740 |
| gcccacccca | acttgtttat | tgcagcttat | aatggttaca | aataaagcaa | tagcatcaca | 1800 |
| aatttcacaa | ataaagcatt | tttttcactg | cattctagtt | gtggtttgtc | caaactcatc | 1860 |
| aatgtatctt | atcatgtctg | tataccgtcg | acctctagct | agagcttggc | gtaatcatgg | 1920 |
| tcattaccaa | tgcttaatca | gtgaggcacc | tatctcagcg | atctgtctat | ttcgttcatc | 1980 |
| catagttgcc | tgactccccg | tcgtgtagat | aactacgata | cgggagggct | taccatctgg | 2040 |
| ccccagcgct | gcgatgatac | cgcgagaacc | acgctcaccg | gctccggatt | tatcagcaat | 2100 |

```
aaaccagcca gccggaaggg ccgagcgcag aagtggtcct gcaactttat ccgcctccat    2160
ccagtctatt aattgttgcc gggaagctag agtaagtagt tcgccagtta atagtttgcg    2220
caacgttgtt gccatcgcta caggcatcgt ggtgtcacgc tcgtcgtttg gtatggcttc    2280
attcagctcc ggttcccaac gatcaaggcg agttacatga tccccatgt tgtgcaaaaa    2340 agcggttagc tccttcggtc ctccgatcgt tgtcagaagt aagttggccg cagtgttatc    2400
actcatggtt atggcagcac tgcataattc tcttactgtc atgccatccg taagatgctt    2460
ttctgtgact ggtgagtact caaccaagtc attctgagaa tagtgtatgc ggcgaccgag    2520
ttgctcttgc ccggcgtcaa tacgggataa taccgcgcca catagcagaa ctttaaaagt    2580
gctcatcatt ggaaaacgtt cttcggggcg aaaactctca aggatcttac cgctgttgag    2640
atccagttcg atgtaaccca ctcgtgcacc caactgatct tcagcatctt ttactttcac    2700
cagcgtttct gggtgagcaa aacaggaag gcaaaatgcc gcaaaaaagg gaataagggc    2760
gacacggaaa tgttgaatac tcatattctt ccttttcaa tattattgaa gcatttatca    2820
gggttattgt ctcatgagcg gatacatatt tgaatgtatt tagaaaaata aacaaatagg    2880
ggtcagtgtt acaaccaatt aaccaattct gaacattatc gcgagcccat ttatacctga    2940
atatggctca taacaccccct tgctcatgac caaaatccct taacgtgagt tacgcgcgcg    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactctttt ccgaaggtaa ctggcttcag cagagcgcag    3180
ataccaaata ctgttcttct agtgtagccg tagttagccc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggcctttta    3660 cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaaggcg agagtaggga actgccaggc    3840
atcaaactaa gcagaaggcc cctgacggat ggcctttttg cgtttctaca aactctttct    3900
gtgttgtaaa acgacggcca gtcttaagct cgggcccct gggcggttct gataacgagt    3960
aatcgttaat ccgcaaataa cgtaaaaacc cgcttcggcg gttttttta tgggggagt    4020 ttagggaaag agcatttgtc agaatattta agggcgcctg tcactttgct tgatatatga    4080 gaattatttta accttataaa tgagaaaaaa gcaacgcact ttaaataaga tacgttgctt    4140
tttcgattga tgaacaccta taattaaact attcatctat tatttatgat tttttgtata    4200
tacaatattt ctagtttgtt aaagagaatt aagaaaataa atctcgaaaa taataaaggg    4260
aaaatcagtt tttgatatca aaattataca tgtcaacgat aatacaaaat ataatacaaa    4320
ctataagatg ttatcagtat ttattatcat ttagaataaa ttttgtgtcg cccttaattg    4380
tgagcggata acaattacga gcttcatgca cagtggcgtt gacattgatt attgactagt    4440
```

| | |
|---|---|
| tattaatagt aatcaattac ggggtcatta gttcatagcc catatatgga gttccgcgtt | 4500 |
| acataactta cggtaaatgg cccgcctggc tgaccgccca acgaccccg cccattgacg | 4560 |
| tcaataatga cgtatgttcc catagtaacg ccaataggga cttccattg acgtcaatgg | 4620 |
| gtggagtatt tacggtaaac tgcccacttg gcagtacatc aagtgtatca tatgccaagt | 4680 |
| acgcccccta ttgacgtcaa tgacggtaaa tggcccgcct ggcattatgc ccagtacatg | 4740 |
| accttatggg actttcctac ttggcagtac atctacgtat tagtcatcgc tattaccatg | 4800 |
| gtgatgcggt tttggcagta catcaatggg cgtggatagc ggtttgactc acggggattt | 4860 |
| ccaagtctcc accccattga cgtcaatggg agtttgtttt ggcaccaaaa tcaacgggac | 4920 |
| tttccaaaat gtcgtaacaa ctccgcccca ttgacgcaaa tgggcggtag gcgtgtacgg | 4980 |
| tgggaggtct atataagcag agctctctgg ctaactagag aacccactgc ttactggctt | 5040 |
| atcgaaatta atacgactca ctatagggaa gcttcttgtt cttttgcag aagctcagaa | 5100 |
| taaacgctca actttggcct cgaggccacc atggcttcct ccctccaaa gaaaagaga | 5160 |
| aaggttgcgg ccgctgacta caaggatgac gacgataaaa gttggaagga cgcaagtggt | 5220 |
| tggtctagaa tgcatgcggc cccgcgacgg cgtgctgcgc aaccctccga cgcttcgccg | 5280 |
| gccgcgcagg tggatctacg cacgctcggc tacagtcagc agcagcaaga gaagatcaaa | 5340 |
| ccgaaggtgc gttcgacagt ggcgcagcac cacgaggcac tggtgggcca tgggtttaca | 5400 |
| cacgcgcaca tcgttgcgct cagccaacac ccggcagcgt tagggaccgt cgctgtcacg | 5460 |
| tatcagcaca taatcacggc gttgccagag gcgacacacg aagacatcgt tggcgtcggc | 5520 |
| aaacagtggt ccgcgcacg cgccctggag gccttgctca cggatgcggg ggagttgaga | 5580 |
| ggtccgccgt tacagttgga cacaggccaa cttgtgaaga ttgcaaaacg tggcggcgtg | 5640 |
| accgcaatgg aggcagtgca tgcatcgcgc aatgcgctca cggagcacc cctcaacctg | 5700 |
| accccagacc aagttgtcgc gattgcaagc aacaacggag gcaaacaagc cttagaaaca | 5760 |
| gtccagagat tgttgccggt gctgtgccaa gaccacggcc tgaccccga acaggttgtc | 5820 |
| gctattgcta gtaacggcgg aggcaaacag gcgctggaaa cagttcagcg cctcttgccg | 5880 |
| gtcttgtgtc aggcccacgg cctgacccca gaccaagttg tcgcgattgc aagcaacaac | 5940 |
| ggaggcaaac aagccttaga aacagtccag agattgttgc ctgtgctgtg ccaagcccac | 6000 |
| ggcctgaccc cagcccaagt tgtcgcgatt gcaagcaaca acggaggcaa acaagcctta | 6060 |
| gaaacagtcc agagattgtt gccggtgctg tgccaagacc acggcctgac cccagaccaa | 6120 |
| gttgtcgcga ttgcaagcaa caacggaggc aaacaagcct tagaaacagt ccagagattg | 6180 |
| ttgccggtgc tgtgccaaga ccacggcctg accccagaac aggttgtggc catcgccagc | 6240 |
| aacataggtg gcaagcaggc cctcgaaacc gtccagagac tgttaccggt tctctgccag | 6300 |
| gcccacggcc tgaccccaga ccaagttgtc gcgattgcaa gcaacaacgg aggcaaacaa | 6360 |
| gccttagaaa cagtccagag attgttgcct gtgctgtgcc aagcccacgg cctgacccca | 6420 |
| gcccaggttg tggccatcgc cagcaacata ggtggcaagc aggccctcga aaccgtccag | 6480 |
| agactgttac cggttctctg ccaggaccac ggcctgaccc ccgaccaggt tgtcgctatt | 6540 |
| gctagtaacg gcgaggcaa acaggcgctg aaacagttc agcgcctctt gccggtcttg | 6600 |
| tgtcaggacc acggcctgac cccggaacag gtggttgcaa tcgcgtcaca cgatggggga | 6660 |
| aagcaggccc tagaaaccgt tcagcgactc ctgcccgtcc tgtgccaggc ccacggcctg | 6720 |
| accccgacc aggttgtcgc tattgctagt aacggcggag gcaaacaggc gctgaaaaca | 6780 |
| gttcagcgcc tcttgccggt cttgtgtcag gcccacggcc tgaccccggc ccaggtggtt | 6840 |

```
gcaatcgcgt cacacgatgg gggaaagcag gccctagaaa ccgttcagcg actcctgccc    6900
gtcctgtgcc aggaccacgg cctgacccccc gaccaggttg tcgctattgc tagtaacggc   6960
ggaggcaaac aggcgctgga aacagttcag cgcctcttgc cggtcttgtg tcaggaccac    7020
ggcctgaccc cagaacaagt tgtcgcgatt gcaagcaaca acggaggcaa acaagcctta    7080
gaaacagtcc agagattgtt gccggtgctg tgccaagccc acggcctgac cccggaccag    7140
gtggttgcaa tcgcgtcaca cgatggggga agcaggccc tagaaaccgt tcagcgactc     7200
ctgcccgtcc tgtgccaggc ccacggcctg accccgccc aggttgtcgc tattgctagt    7260
aacggcggag gcaaacaggc gctggaaaca gttcagcgcc tcttgccggt cttgtgtcag   7320
gaccacggcc tgaccccga ccaggttgtc gctattgcta gtaacggcgg aggcaaacag    7380
gcgctggaaa cagttcagcg cctcttgccg gtcttgtgtc aggaccacgg cctgaccccg    7440
gaacaggtgg ttgcaatcgc gtcacacgat gggggaaagc aggccctaga aaccgttcag    7500
cgactcctgc ccgtcctgtg ccaggccac ggcctgacgc ctgagcaggt agtggctatt    7560
gcatccaacg agggggcag acccgcactg gagtcaatcg tggcccagct ttcgaggccg    7620
gaccccgcgc tggccgcact cactaatgat catcttgtag cgctggcctg cctcggcgga    7680
cgtcctgcca tggatgcagt gaaaaaggga ttgccgcacg cgccggaatt gatcagatcc    7740
cagctagtga atctgaatt ggaagagaag aaatctgaac ttagacataa attgaaatat    7800
gtgccacatg aatatattga attgattgaa atcgcaagaa attcaactca ggatagaatc    7860
cttgaaatga aggtgatgga gttctttatg aaggtttatg gttatcgtgg taaacatttg    7920
ggtggatcaa ggaaaccaga cggagcaatt tatactgtcg gatctcctat tgattacggt    7980
gtgatcgttg atactaaggc atattcagga ggttataatc ttccaattgg tcaagcagat    8040
gaaatgcaaa gatatgtcga agagaatcaa acaagaaaca agcatatcaa ccctaatgaa    8100
tggtggaaag tctatccatc ttcagtaaca gaatttaagt tcttgtttgt gagtggtcat    8160
ttcaaaggaa actacaaagc tcagcttaca agattgaatc atatcactaa ttgtaatgga    8220
gctgttctta gtgtagaaga cttttgatt ggtggagaaa tgattaaagc tggtacattg    8280
acacttgagg aagtgagaag gaaatttaat aacggtgaga taaacttta aaaaatcagc    8340
ctcgactgtg ccttctagtt gcc                                          8363
```

<210> SEQ ID NO 50
<211> LENGTH: 8363
<212> TYPE: DNA
<213> ORGANISM: artificial sequence
<220> FEATURE:
<223> OTHER INFORMATION: TALEN-TCR-beta3_L19 plasmid full length

<400> SEQUENCE: 50

```
agccatctgt tgtttgcccc tcccccgtgc cttccttgac cctggaaggt gccactccca      60
ctgtcctttc ctaataaaat gaggaaattg catcacaaca ctcaaccta tctcggtcta     120
ttcttttgat ttataaggga ttttgccgat ttcggcctat tggttaaaaa atgagctgat    180
ttaacaaaaa tttaacgcga attaattctg tggaatgtgt gtcagttagg gtgtggaaag    240
tccccaggct ccccagcagg cagaagtatg caaagcatgc atctcaatta gtcagcaacc   300
aggtgtggaa agtccccagg ctccccagca gcagaagta tgcaaagcat gcatctcaat    360
tagtcagcaa ccatagtccc gcccctaact ccgcccatcc cgcccctaac tccgcccagt    420
tccgcccatt ctccgcccca tggctgacta atttttttta tttatgcaga ggccgaggcc    480
```

```
gcctctgcct ctgagctatt ccagaagtag tgaggaggct ttttggagg cctaggcttt    540 tgcaaaaagc tcccgggagc ttgtatatcc attttcggat ctgatcagca cgtgatgaaa    600
aagcctgaac tcaccgcgac gtctgtcgag aagtttctga tcgaaaagtt cgacagcgtt    660
tccgacctga tgcagctctc ggagggcgaa gaatctcgtg ctttcagctt cgatgtagga    720
gggcgtggat atgtcctgcg ggtaaatagc tgcgccgatg gtttctacaa agatcgttat    780
gtttatcggc actttgcatc ggccgcgctc ccgattccgg aagtgcttga cattggggaa    840
ttcagcgaga gcctgaccta ttgcatctcc cgccgtgcac agggtgtcac gttgcaagac    900
ctgcctgaaa ccgaactgcc cgctgttctg cagccggtcg cggaggccat ggatgcgatc    960
gctgcggccg atcttagcca gacgagcggg ttcggcccat tcggaccgca aggaatcggt   1020
caatacacta catggcgtga tttcatatgc gcgattgctg atccccatgt gtatcactgg   1080
caaactgtga tggacgacac cgtcagtgcg tccgtcgcgc aggctctcga tgagctgatg   1140
cttggggccg aggactgccc cgaagtccgg cacctcgtgc acgcggattt cggctccaac   1200
aatgtcctga cggacaatgg ccgcataaca gcggtcattg actggagcga ggcgatgttc   1260
ggggattccc aatacgaggt cgccaacatc ttcttctgga ggccgtggtt ggcttgtatg   1320
gagcagcaga cgcgctactt cgagcggagg catccggagc ttgcaggatc gccgcggctc   1380
cgggcgtata tgctccgcat tggtcttgac caactctatc agagcttggt tgacggcaat   1440
ttcgatgatg cagcttgggc gcagggtcga tgcgacgcaa tcgtccgatc cggagccggg   1500
actgtcgggc gtacacaaat cgcccgcaga agcgcggccg tctggaccga tggctgtgta   1560
gaagtactcg ccgatagtgg aaaccgacgc cccagcactc gtccgagggc aaaggaatag   1620
cacgtgctac gagatttcga ttccaccgcc gccttctatg aaaggttggg cttcggaatc   1680
gttttccggg acgccggctg gatgatcctc cagcgcgggg atctcatgct ggagttcttc   1740
gcccacccca acttgtttat tgcagcttat aatggttaca aataaagcaa tagcatcaca   1800
aatttcacaa ataaagcatt ttttttcactg cattctagtt gtggtttgtc caaactcatc   1860
aatgtatctt atcatgtctg tataccgtcg acctctagct agagcttggc gtaatcatgg   1920
tcattaccaa tgcttaatca gtgaggcacc tatctcagcg atctgtctat ttcgttcatc   1980
catagttgcc tgactccccg tcgtgtagat aactacgata cgggagggct taccatctgg   2040
ccccagcgct gcgatgatac cgcgagaacc acgctcaccg gctccggatt tatcagcaat   2100
aaaccagcca gccggaaggg ccgagcgcag aagtggtcct gcaactttat ccgcctccat   2160
ccagtctatt aattgttgcc gggaagctag agtaagtagt tcgccagtta atagtttgcg   2220
caacgttgtt gccatcgcta caggcatcgt ggtgtcacgc tcgtcgtttg gtatggcttc   2280
attcagctcc ggttcccaac gatcaaggcg agttacatga tcccccatgt tgtgcaaaaa   2340
agcggttagc tccttcggtc ctccgatcgt tgtcagaagt aagttggccg cagtgttatc   2400
actcatggtt atggcagcac tgcataattc tcttactgtc atgccatccg taagatgctt   2460
ttctgtgact ggtgagtact caaccaagtc attctgagaa tagtgtatgc ggcgaccgag   2520
ttgctcttgc ccggcgtcaa tacgggataa taccgcgcca catagcagaa ctttaaaagt   2580
gctcatcatt ggaaaacgtt cttcggggcg aaaactctca aggatcttac cgctgttgag   2640
atccagttcg atgtaaccca ctcgtgcacc caactgatct tcagcatctt ttactttcac   2700
cagcgtttct gggtgagcaa aaacaggaag gcaaaatgcc gcaaaaaagg gaataagggc   2760
gacacggaaa tgttgaatac tcatattctt ccttttcaa tattattgaa gcattttatc    2820
gggttattgt ctcatgagcg gatacatatt tgaatgtatt tagaaaaata aacaaatagg   2880
```

```
ggtcagtgtt acaaccaatt aaccaattct gaacattatc gcgagcccat ttatacctga    2940
atatggctca taacacccct tgctcatgac caaaatccct taacgtgagt tacgcgcgcg    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactcttttt ccgaaggtaa ctggcttcag cagagcgcag    3180
ataccaaata ctgttcttct agtgtagccg tagttagccc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggccttttta    3660
cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaaggcg agagtaggga actgccaggc    3840
atcaaactaa gcagaaggcc cctgacggat ggcctttttg cgtttctaca aactctttct    3900
gtgttgtaaa acgacggcca gtcttaagct cgggccccct gggcggttct gataacgagt    3960
aatcgttaat ccgcaaataa cgtaaaaacc cgcttcggcg gttttttta tgggggagt    4020 ttagggaaag agcatttgtc agaatattta agggcgcctg tcactttgct tgatatatga    4080
gaattattta accttataaa tgagaaaaaa gcaacgcact ttaaataaga tacgttgctt    4140
tttcgattga tgaacaccta taattaaact attcatctat tatttatgat tttttgtata    4200
tacaatattt ctagtttgtt aaagagaatt aagaaaataa atctcgaaaa taataaaggg    4260
aaaatcagtt tttgatatca aaattataca tgtcaacgat aatacaaaat ataatacaaa    4320
ctataagatg ttatcagtat ttattatcat ttagaataaa ttttgtgtcg cccttaattg    4380
tgagcggata acaattacga gcttcatgca cagtggcgtt gacattgatt attgactagt    4440
tattaatagt aatcaattac ggggtcatta gttcatagcc catatatgga gttccgcgtt    4500
acataactta cggtaaatgg cccgcctggc tgaccgccca acgacccccg cccattgacg    4560
tcaataatga cgtatgttcc catagtaacg ccaataggga cttt ccattg acgtcaatgg    4620 gtggagtatt tacggtaaac tgcccacttg gcagtacatc aagtgtatca tatgccaagt    4680 acgccccta ttgacgtcaa tgacggtaaa tggcccgcct ggcattatgc ccagtacatg    4740
accttatggg actttcctac ttggcagtac atctacgtat tagtcatcgc tattaccatg    4800
gtgatgcggt tttggcagta catcaatggg cgtggatagc ggtttgactc acggggattt    4860
ccaagtctcc accccattga cgtcaatggg agtttgtttt ggcaccaaaa tcaacgggac    4920
tttccaaaat gtcgtaacaa ctccgcccca ttgacgcaaa tgggcggtag gcgtgtacgg    4980
tgggaggtct atataagcag agctctctgg ctaactagag aacccactgc ttactggctt    5040
atcgaaatta atacgactca ctatagggaa gcttcttgtt cttttgcag aagctcagaa    5100 taaacgctca actttggcct cgaggccacc atggcttcct cccctccaaa gaaaagaga    5160 aaggttgcgg ccgctgacta caaggatgac gacgataaaa gttggaagga cgcaagtggt    5220
```

-continued

| | | |
|---|---|---|
| tggtctagaa tgcatgcggc cccgcgacgg cgtgctgcgc aaccctccga cgcttcgccg | 5280 |
| gccgcgcagg tggatctacg cacgctcggc tacagtcagc agcagcaaga gaagatcaaa | 5340 |
| ccgaaggtgc gttcgacagt ggcgcagcac cacgaggcac tggtgggcca tgggtttaca | 5400 |
| cacgcgcaca tcgttgcgct cagccaacac ccggcagcgt tagggaccgt cgctgtcacg | 5460 |
| tatcagcaca taatcacggc gttgccagag gcgacacacg aagacatcgt tggcgtcggc | 5520 |
| aaacagtggt ccgcgcacg cgccctggag gccttgctca cggatgcggg ggagttgaga | 5580 |
| ggtccgccgt tacagttgga cacaggccaa cttgtgaaga ttgcaaaacg tggcggcgtg | 5640 |
| accgcaatgg aggcagtgca tgcatcgcgc aatgcgctca cggagcaccc cctcaacctg | 5700 |
| accccagacc aagttgtcgc gattgcaagc aacaacggag gcaaacaagc cttagaaaca | 5760 |
| gtccagagat tgttgccggt gctgtgccaa gaccacggcc tgaccccga acaggttgtc | 5820 |
| gctattgcta gtaacggcgg aggcaaacag gcgctggaaa cagttcagcg cctcttgccg | 5880 |
| gtcttgtgtc aggcccacgg cctgacccca gaccaagttg tcgcgattgc aagcaacaac | 5940 |
| ggaggcaaac aagccttaga aacagtccag agattgttgc ctgtgctgtg ccaagcccac | 6000 |
| ggcctgaccc cggcccaggt ggttgcaatc gcgtcacacg atgggggaaa gcaggcccta | 6060 |
| gaaaccgttc agcgactcct gcccgtcctg tgccaggacc acggcctgac cccggaccag | 6120 |
| gtggttgcaa tcgcgtcaca cgatggggga agcaggccc tagaaaccgt tcagcgactc | 6180 |
| ctgcccgtcc tgtgccagga ccacggcctg accccgaac aggttgtcgc tattgctagt | 6240 |
| aacggcggag gcaaacaggc gctggaaaca gttcagcgcc tcttgccggt cttgtgtcag | 6300 |
| gcccacggc tgaccccaga ccaagttgtc gcgattgcaa gcaacaacgg aggcaaacaa | 6360 |
| gccttagaaa cagtccagag attgttgcct gtgctgtgcc aagcccacgg cctgacccca | 6420 |
| gcccaagttg tcgcgattgc aagcaacaac ggaggcaaac aagccttaga aacagtccag | 6480 |
| agattgttgc cggtgctgtg ccaagaccac ggcctgaccc cggaccaggt ggttgcaatc | 6540 |
| gcgtcacacg atgggggaaa gcaggcccta gaaaccgttc agcgactcct gcccgtcctg | 6600 |
| tgccaggacc acggcctgac cccggaacag gtggttgcaa tcgcgtcaca cgatggggga | 6660 |
| aagcaggccc tagaaaccgt tcagcgactc ctgcccgtcc tgtgccaggc ccacggcctg | 6720 |
| accccagacc aggttgtggc catcgccagc aacataggtg gcaagcaggc cctcgaaacc | 6780 |
| gtccagagac tgttaccggt tctctgccag gcccacggcc tgaccccggc caggtggtt | 6840 |
| gcaatcgcgt cacacgatgg gggaaagcag gccctagaaa ccgttcagcg actcctgccc | 6900 |
| gtcctgtgcc aggaccacgg cctgacccca gaccaggttg tggccatcgc cagcaacata | 6960 |
| ggtggcaagc aggccctcga aaccgtccag agactgttac cggttctctg ccaggaccac | 7020 |
| ggcctgaccc cagaacaagt tgtcgcgatt gcaagcaaca acggaggcaa acaagcctta | 7080 |
| gaaacagtcc agagattgtt gccggtgctg tgccaagccc acggcctgac cccagaccaa | 7140 |
| gttgtcgcga ttgcaagcaa caacggaggc aaacaagcct tagaaacagt ccagagattg | 7200 |
| ttgcctgtgc tgtgccaagc ccacggcctg accccgccc aggtggttgc aatcgcgtca | 7260 |
| cacgatgggg gaaagcaggc cctagaaacc gttcagcgac tcctgcccgt cctgtgccag | 7320 |
| gaccacggcc tgaccccga ccaggttgtc gctattgcta gtaacggcgg aggcaaacag | 7380 |
| gcgctggaaa cagttcagcg cctcttgccg gtcttgtgtc aggaccacgg cctgaccccc | 7440 |
| gaacaggttg tcgctattgc tagtaacggc ggaggcaaac aggcgctgga aacagttcag | 7500 |
| cgcctcttgc cggtcttgtg tcaggcccac ggcctgacgc tgagcaggt agtggctatt | 7560 |
| gcatcccacg acggggggcag acccgcactg gagtcaatcg tggcccagct ttcgaggccg | 7620 |

-continued

| | |
|---|---|
| gaccccgcgc tggccgcact cactaatgat catcttgtag cgctggcctg cctcggcgga | 7680 |
| cgtcctgcca tggatgcagt gaaaaaggga ttgccgcacg cgccggaatt gatcagatcc | 7740 |
| cagctagtga atctgaatt ggaagagaag aaatctgaac ttagacataa attgaaatat | 7800 |
| gtgccacatg aatatattga attgattgaa atcgcaagaa attcaactca ggatagaatc | 7860 |
| cttgaaatga aggtgatgga gttctttatg aaggtttatg gttatcgtgg taaacatttg | 7920 |
| ggtggatcaa ggaaaccaga cggagcaatt tatactgtcg gatctcctat tgattacggt | 7980 |
| gtgatcgttg atactaaggc atattcagga ggttataatc ttccaattgg tcaagcagat | 8040 |
| gaaatgcaaa gatatgtcga agagaatcaa acaagaaaca agcatatcaa ccctaatgaa | 8100 |
| tggtggaaag tctatccatc ttcagtaaca gaatttaagt tcttgtttgt gagtggtcat | 8160 |
| ttcaaaggaa actacaaagc tcagcttaca agattgaatc atatcactaa ttgtaatgga | 8220 |
| gctgttctta gtgtagaaga gcttttgatt ggtggagaaa tgattaaagc tggtacattg | 8280 |
| acacttgagg aagtgagaag gaaatttaat aacggtgaga taaacttta aaaaatcagc | 8340 |
| ctcgactgtg ccttctagtt gcc | 8363 |

<210> SEQ ID NO 51
<211> LENGTH: 8363
<212> TYPE: DNA
<213> ORGANISM: artificial sequence
<220> FEATURE:
<223> OTHER INFORMATION: TALEN-TCR-beta3_R19 plasmid full length

<400> SEQUENCE: 51

| | |
|---|---|
| agccatctgt tgtttgcccc tcccccgtgc cttccttgac cctggaaggt gccactccca | 60 |
| ctgtcctttc ctaataaaat gaggaaattg catcacaaca ctcaaccccta tctcggtcta | 120 |
| ttcttttgat ttataaggga ttttgccgat ttcggcctat tggttaaaaa atgagctgat | 180 |
| ttaacaaaaa tttaacgcga attaattctg tggaatgtgt gtcagttagg gtgtggaaag | 240 |
| tccccaggct ccccagcagg cagaagtatg caaagcatgc atctcaatta gtcagcaacc | 300 |
| aggtgtggaa agtccccagg ctccccagca ggcagaagta tgcaaagcat gcatctcaat | 360 |
| tagtcagcaa ccatagtccc gcccctaact ccgcccatcc cgcccctaac tccgcccagt | 420 |
| tccgcccatt ctccgcccca tggctgacta attttttta tttatgcaga ggccgaggcc | 480 |
| gcctctgcct ctgagctatt ccagaagtag tgaggaggct tttttggagg cctaggcttt | 540 |
| tgcaaaaagc tcccgggagc ttgtatatcc attttcggat ctgatcagca cgtgatgaaa | 600 |
| aagcctgaac tcaccgcgac gtctgtcgag aagtttctga tcgaaaagtt cgacagcgtt | 660 |
| tccgacctga tgcagctctc ggagggcgaa gaatctcgtg ctttcagctt cgatgtagga | 720 |
| gggcgtggat atgtcctgcg ggtaaatagc tgcgccgatg gtttctacaa agatcgttat | 780 |
| gtttatcggc actttgcatc ggccgcgctc ccgattccgg aagtgcttga cattggggaa | 840 |
| ttcagcgaga gcctgaccta ttgcatctcc cgccgtgcac agggtgtcac gttgcaagac | 900 |
| ctgcctgaaa ccgaactgcc cgctgttctg cagccggtcg cggaggccat ggatgcgatc | 960 |
| gctgcggccg atcttagcca gacgagcggg ttcggcccat tcggaccgca aggaatcggt | 1020 |
| caatacacta catggcgtga tttcatatgc gcgattgctg atccccatgt gtatcactgg | 1080 |
| caaactgtga tggacgacac cgtcagtgcg tccgtcgcgc aggctctcga tgagctgatg | 1140 |
| ctttgggccg aggactgccc cgaagtccgg cacctcgtgc acgcggattt cggctccaac | 1200 |
| aatgtcctga cggacaatgg ccgcataaca gcggtcattg actggagcga ggcgatgttc | 1260 |

```
gggggattccc aatacgaggt cgccaacatc ttcttctgga ggccgtggtt ggcttgtatg    1320
gagcagcaga cgcgctactt cgagcggagg catccggagc ttgcaggatc gccgcggctc    1380
cgggcgtata tgctccgcat tggtcttgac caactctatc agagcttggt tgacggcaat    1440
ttcgatgatg cagcttgggc gcagggtcga tgcgacgcaa tcgtccgatc cggagccggg    1500
actgtcgggc gtacacaaat cgcccgcaga agcgcggccg tctggaccga tggctgtgta    1560
gaagtactcg ccgatagtgg aaaccgacgc cccagcactc gtccgagggc aaaggaatag    1620
cacgtgctac gagatttcga ttccaccgcc gccttctatg aaaggttggg cttcggaatc    1680
gttttccggg acgccggctg gatgatcctc cagcgcgggg atctcatgct ggagttcttc    1740
gcccacccca acttgtttat tgcagcttat aatggttaca aataaagcaa tagcatcaca    1800
aatttcacaa ataaagcatt tttttcactg cattctagtt gtggtttgtc caaactcatc    1860
aatgtatctt atcatgtctg tataccgtcg acctctagct agagcttggc gtaatcatgg    1920
tcattaccaa tgcttaatca gtgaggcacc tatctcagcg atctgtctat ttcgttcatc    1980
catagttgcc tgactccccg tcgtgtagat aactacgata cgggagggct taccatctgg    2040
ccccagcgct gcgatgatac cgcgagaacc acgctcaccg gctccggatt tatcagcaat    2100
aaaccagcca gccggaaggg ccgagcgcag aagtggtcct gcaactttat ccgcctccat    2160
ccagtctatt aattgttgcc gggaagctag agtaagtagt tcgccagtta atagtttgcg    2220
caacgttgtt gccatcgcta caggcatcgt ggtgtcacgc tcgtcgtttg gtatggcttc    2280
attcagctcc ggttcccaac gatcaaggcg agttacatga tcccccatgt tgtgcaaaaa    2340
agcggttagc tccttcggtc ctccgatcgt tgtcagaagt aagttggccg cagtgttatc    2400
actcatggtt atggcagcac tgcataattc tcttactgtc atgccatccg taagatgctt    2460
ttctgtgact ggtgagtact caaccaagtc attctgagaa tagtgtatgc ggcgaccgag    2520
ttgctcttgc ccggcgtcaa tacgggataa taccgcgcca catagcagaa ctttaaaagt    2580
gctcatcatt ggaaaacgtt cttcggggcg aaaactctca aggatcttac cgctgttgag    2640
atccagttcg atgtaaccca ctcgtgcacc caactgatct tcagcatctt tactttcac     2700 cagcgttct gggtgagcaa aaacaggaag gcaaaatgcc gcaaaaaagg gaataagggc    2760
gacacggaaa tgttgaatac tcatattctt cctttttcaa tattattgaa gcatttatca    2820
gggttattgt ctcatgagcg gatacatatt tgaatgtatt tagaaaaata aacaaatagg    2880
ggtcagtgtt acaaccaatt aaccaattct gaacattatc gcgagcccat ttatacctga    2940
atatggctca taacacccct tgctcatgac caaaatccct taacgtgagt acgcgcgcg     3000 tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactcttttt ccgaaggtaa ctggcttcag cagagcgcag    3180
ataccaaata ctgttcttct agtgtagccg tagttagccc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggccttttta    3660
```

```
cggttcctgg cctttttgctg gccttttgct cacatgttct ttcctgcgtt atcccctgat  3720
tctgtggata accgtattac cgcctttgag tgagctgata ccgctcgccg cagccgaacg  3780
accgagcgca gcgagtcagt gagcgaggaa gcggaaggcg agagtaggga actgccaggc  3840
atcaaactaa gcagaaggcc cctgacggat ggccttttg cgtttctaca aactctttct  3900
gtgttgtaaa acgacggcca gtcttaagct cgggccccct gggcggttct gataacgagt  3960
aatcgttaat ccgcaaataa cgtaaaaacc cgcttcggcg gtttttttta tgggggggagt  4020
ttagggaaag agcatttgtc agaatattta agggcgcctg tcactttgct tgatatatga  4080
gaattattta accttataaa tgagaaaaaa gcaacgcact ttaaataaga tacgttgctt  4140
tttcgattga tgaacaccta taattaaact attcatctat tatttatgat tttttgtata  4200
tacaatattt ctagtttgtt aaagagaatt aagaaaataa atctcgaaaa taataaaggg  4260
aaaatcagtt tttgatatca aaattataca tgtcaacgat aatacaaaat ataatacaaa  4320
ctataagatg ttatcagtat ttattatcat ttagaataaa ttttgtgtcg cccttaattg  4380
tgagcggata acaattacga gcttcatgca cagtggcgtt gacattgatt attgactagt  4440
tattaatagt aatcaattac ggggtcatta gttcatagcc catatatgga gttccgcgtt  4500
acataactta cggtaaatgg cccgcctggc tgaccgccca acgacccccg cccattgacg  4560
tcaataatga cgtatgttcc catagtaacg ccaataggga ctttccattg acgtcaatgg  4620
gtggagtatt tacggtaaac tgcccacttg gcagtacatc aagtgtatca tatgccaagt  4680
acgccccta ttgacgtcaa tgacggtaaa tggcccgcct ggcattatgc ccagtacatg  4740
accttatggg actttcctac ttggcagtac atctacgtat tagtcatcgc tattaccatg  4800
gtgatgcggt tttggcagta catcaatggg cgtggatagc ggtttgactc acggggattt  4860
ccaagtctcc accccattga cgtcaatggg agtttgtttt ggcaccaaaa tcaacgggac  4920
tttccaaaat gtcgtaacaa ctccgcccca ttgacgcaaa tgggcggtag gcgtgtacgg  4980
tgggaggtct atataagcag agctctctgg ctaactagag aacccactgc ttactggctt  5040
atcgaaatta atacgactca ctatagggaa gcttcttgtt cttttttgcag aagctcagaa  5100
taaacgctca actttggcct cgaggccacc atggcttcct cccctccaaa gaaaagaga  5160
aaggttgcgg ccgctgacta caaggatgac gacgataaaa gttggaagga cgcaagtggt  5220
tggtctagaa tgcatgcggc cccgcgacgg cgtgctgcgc aaccctccga cgcttcgccg  5280
gccgcgcagg tggatctacg cacgctcggc tacagtcagc agcagcaaga gaagatcaaa  5340
ccgaaggtgc gttcgacagt ggcgcagcac cacgaggcac tggtgggcca tgggtttaca  5400
cacgcgcaca tcgttgcgct cagccaacac ccggcagcgt tagggaccgt cgctgtcacg  5460
tatcagcaca taatcacggc gttgccagag gcgacacacg aagacatcgt tggcgtcggc  5520
aaacagtggt ccggcgcacg cgccctggag gccttgctca cggatgcggg ggagttgaga  5580
ggtccgccgt tacagttgga cacaggccaa cttgtgaaga ttgcaaaacg tggcggcgtg  5640
accgcaatgg aggcagtgca tgcatcgcgc aatgcgctca cgggagcacc cctcaacctg  5700
accccgacc aggtggttgc aatcgcgtca cacgatgggg gaaagcaggc cctagaaacc  5760
gttcagcgac tcctgcccgt cctgtgccag gaccacggcc tgacccccaga acaggttgtg  5820
gccatcgcca gcaacatagg tggcaagcag gccctcgaaa ccgtccagag actgttaccg  5880
gttctctgcc aggcccacgg cctgacccg gaccaggtgg ttgcaatcgc gtcacacgat  5940
gggggaaagc aggccctaga aaccgttcag cgactcctgc ccgtcctgtg ccaggcccac  6000
```

-continued

```
ggcctgaccc cggcccaggt ggttgcaatc gcgtcacacg atgggggaaa gcaggcccta      6060
gaaaccgttc agcgactcct gcccgtcctg tgccaggacc acggcctgac cccggaccag      6120
gtggttgcaa tcgcgtcaca cgatggggga aagcaggccc tagaaaccgt tcagcgactc      6180
ctgcccgtcc tgtgccagga ccacggcctg accccagaac aggttgtggc catcgccagc      6240
aacataggtg gcaagcaggc cctcgaaacc gtccagagac tgttaccggt tctctgccag      6300
gcccacggcc tgaccccgga ccaggtggtt gcaatcgcgt cacacgatgg gggaaagcag      6360
gccctagaaa ccgttcagcg actcctgccc gtcctgtgcc aggcccacgg cctgaccccg      6420
gcccaggtgg ttgcaatcgc gtcacacgat gggggaaagc aggccctaga aaccgttcag      6480
cgactcctgc ccgtcctgtg ccaggaccac ggcctgaccc cagaccaggt tgtggccatc      6540
gccagcaaca taggtggcaa gcaggccctc gaaaccgtcc agagactgtt accggttctc      6600
tgccaggacc acggcctgac cccagaacaa gttgtcgcga ttgcaagcaa caacggaggc      6660
aaacaagcct tagaaacagt ccagagattg ttgccggtgc tgtgccaagc ccacggcctg      6720
accccggacc aggtggttgc aatcgcgtca cacgatgggg aaagcaggc cctagaaacc      6780 gttcagcgac tcctgcccgt cctgtgccag gcccacggcc tgaccccgc ccaggttgtc      6840 gctattgcta gtaacggcgg aggcaaacag gcgctggaaa cagttcagcg cctcttgccg      6900
gtcttgtgtc aggaccacgg cctgaccccg gaccaggtgg ttgcaatcgc gtcacacgat      6960
gggggaaagc aggccctaga aaccgttcag cgactcctgc ccgtcctgtg ccaggaccac      7020
ggcctgaccc cagaacaggt tgtggccatc gccagcaaca taggtggcaa gcaggccctc      7080
gaaaccgtcc agagactgtt accggttctc tgccaggccc acggcctgac cccagaccaa      7140
gttgtcgcga ttgcaagcaa caacggaggc aaacaagcct tagaaacagt ccagagattg      7200
ttgcctgtgc tgtgccaagc ccacggcctg accccgccc aggtggttgc aatcgcgtca      7260
cacgatgggg aaagcaggc cctagaaacc gttcagcgac tcctgcccgt cctgtgccag      7320
gaccacggcc tgaccccga ccaggttgtc gctattgcta gtaacggcgg aggcaaacag      7380
gcgctggaaa cagttcagcg cctcttgccg gtcttgtgtc aggaccacgg cctgaccccg      7440
gaacaggtgg ttgcaatcgc gtcacacgat ggggaaagc aggccctaga aaccgttcag      7500
cgactcctgc ccgtcctgtg ccaggcccac ggcctgacgc ctgagcaggt agtggctatt      7560
gcatcccacg acgggggcag acccgcactg gagtcaatcg tggcccagct ttcgaggccg      7620
gaccccgcgc tggccgcact cactaatgat catcttgtag cgctggcctg cctcggcgga      7680
cgtcctgcca tggatgcagt gaaaaaggga ttgccgcacg cgccggaatt gatcagatcc      7740
cagctagtga atctgaatt ggaagagaag aaatctgaac ttagacataa attgaaatat      7800
gtgccacatg aatatattga attgattgaa atcgcaagaa attcaactca ggatagaatc      7860
cttgaaatga aggtgatgga gttctttatg aaggtttatg ttatcgtgg taaacatttg      7920 ggtggatcaa ggaaaccaga cggagcaatt tatactgtcg gatctcctat tgattacggt      7980
gtgatcgttg atactaaggc atattcagga ggttataatc ttccaattgg tcaagcagat      8040
gaaatgcaaa gatatgtcga agagaatcaa acaagaaaca agcatatcaa ccctaatgaa      8100
tggtggaaag tctatccatc ttcagtaaca gaatttaagt tcttgtttgt gagtggtcat      8160
ttcaaaggaa actacaaagc tcagcttaca agattgaatc atatcactaa ttgtaatgga      8220
gctgttctta gtgtagaaga cttttgattt ggtggagaaa tgattaaagc tggtacattg      8280
acacttgagg aagtgagaag gaaatttaat aacggtgaga taaacttta aaaaatcagc      8340 ctcgactgtg ccttctagtt gcc                                              8363
```

<210> SEQ ID NO 52
<211> LENGTH: 3201
<212> TYPE: DNA
<213> ORGANISM: artificial sequence
<220> FEATURE:
<223> OTHER INFORMATION: TALEN-TCR-alpha2_L19 TALEN coding sequence
<220> FEATURE:
<221> NAME/KEY: CDS
<222> LOCATION: (1)..(3201)

<400> SEQUENCE: 52

```
atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
            20                  25                  30 aga atg cat gcg gcc ccg cga cgg cgt gct gcg caa ccc tcc gac gct     144
Arg Met His Ala Ala Pro Arg Arg Arg Ala Ala Gln Pro Ser Asp Ala
        35                  40                  45 tcg ccg gcc gcg cag gtg gat cta cgc acg ctc ggc tac agt cag cag     192
Ser Pro Ala Ala Gln Val Asp Leu Arg Thr Leu Gly Tyr Ser Gln Gln
    50                  55                  60 cag caa gag aag atc aaa ccg aag gtg cgt tcg aca gtg gcg cag cac     240
Gln Gln Glu Lys Ile Lys Pro Lys Val Arg Ser Thr Val Ala Gln His
65                  70                  75                  80 cac gag gca ctg gtg ggc cat ggg ttt aca cac gcg cac atc gtt gcg     288
His Glu Ala Leu Val Gly His Gly Phe Thr His Ala His Ile Val Ala
                85                  90                  95 ctc agc caa cac ccg gca gcg tta ggg acc gtc gct gtc acg tat cag     336
Leu Ser Gln His Pro Ala Ala Leu Gly Thr Val Ala Val Thr Tyr Gln
            100                 105                 110 cac ata atc acg gcg ttg cca gag gcg aca cac gaa gac atc gtt ggc     384
His Ile Ile Thr Ala Leu Pro Glu Ala Thr His Glu Asp Ile Val Gly
        115                 120                 125 gtc ggc aaa cag tgg tcc ggc gca cgc gcc ctg gag gcc ttg ctc acg     432
Val Gly Lys Gln Trp Ser Gly Ala Arg Ala Leu Glu Ala Leu Leu Thr
    130                 135                 140 gat gcg ggg gag ttg aga ggt ccg ccg tta cag ttg gac aca ggc caa     480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg     528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc cca     576
His Ala Ser Arg Asn Ala Leu Thr Gly Ala Pro Leu Asn Leu Thr Pro
            180                 185                 190 gac caa gtt gtc gcg att gca agc aac aac gga ggc aaa caa gcc tta     624
Asp Gln Val Val Ala Ile Ala Ser Asn Asn Gly Gly Lys Gln Ala Leu
        195                 200                 205 gaa aca gtc cag aga ttg ttg ccg gtg ctg tgc caa gac cac ggc ctg     672
Glu Thr Val Gln Arg Leu Leu Pro Val Leu Cys Gln Asp His Gly Leu
    210                 215                 220 acc ccc gaa cag gtt gtc gct att gct agt aac ggc gga ggc aaa cag     720
Thr Pro Glu Gln Val Val Ala Ile Ala Ser Asn Gly Gly Gly Lys Gln
225                 230                 235                 240 gcg ctg gaa aca gtt cag cgc ctc ttg ccg gtc ttg tgt cag gcc cac     768
Ala Leu Glu Thr Val Gln Arg Leu Leu Pro Val Leu Cys Gln Ala His
                245                 250                 255 ggc ctg acc ccg gac cag gtg gtt gca atc gcg tca cac gat ggg gga     816
Gly Leu Thr Pro Asp Gln Val Val Ala Ile Ala Ser His Asp Gly Gly
```

```
                Gly Leu Thr Pro Asp Gln Val Val Ala Ile Ala Ser His Asp Gly Gly
                            260                 265                 270 aag cag gcc cta gaa acc gtt cag cga ctc ctg ccc gtc ctg tgc cag             864
Lys Gln Ala Leu Glu Thr Val Gln Arg Leu Leu Pro Val Leu Cys Gln
            275                 280                 285 gcc cac ggc ctg acc ccc gcc cag gtt gtc gct att gct agt aac ggc             912
Ala His Gly Leu Thr Pro Ala Gln Val Val Ala Ile Ala Ser Asn Gly
            290                 295                 300 gga ggc aaa cag gcg ctg gaa aca gtt cag cgc ctc ttg ccg gtc ttg             960
Gly Gly Lys Gln Ala Leu Glu Thr Val Gln Arg Leu Leu Pro Val Leu
305                 310                 315                 320 tgt cag gac cac ggc ctg acc cca gac caa gtt gtc gcg att gca agc            1008
Cys Gln Asp His Gly Leu Thr Pro Asp Gln Val Val Ala Ile Ala Ser
                325                 330                 335 aac aac gga ggc aaa caa gcc tta gaa aca gtc cag aga ttg ttg ccg            1056
Asn Asn Gly Gly Lys Gln Ala Leu Glu Thr Val Gln Arg Leu Leu Pro
            340                 345                 350 gtg ctg tgc caa gac cac ggc ctg acc ccg gaa cag gtg gtt gca atc            1104
Val Leu Cys Gln Asp His Gly Leu Thr Pro Glu Gln Val Val Ala Ile
            355                 360                 365 gcg tca cac gat ggg gga aag cag gcc cta gaa acc gtt cag cga ctc            1152
Ala Ser His Asp Gly Gly Lys Gln Ala Leu Glu Thr Val Gln Arg Leu
        370                 375                 380 ctg ccc gtc ctg tgc cag gcc cac ggc ctg acc ccg gac cag gtg gtt            1200
Leu Pro Val Leu Cys Gln Ala His Gly Leu Thr Pro Asp Gln Val Val
385                 390                 395                 400 gca atc gcg tca cac gat ggg gga aag cag gcc cta gaa acc gtt cag            1248
Ala Ile Ala Ser His Asp Gly Gly Lys Gln Ala Leu Glu Thr Val Gln
                405                 410                 415 cga ctc ctg ccc gtc ctg tgc cag gcc cac ggc ctg acc ccc gcc cag            1296
Arg Leu Leu Pro Val Leu Cys Gln Ala His Gly Leu Thr Pro Ala Gln
            420                 425                 430 gtt gtc gct att gct agt aac ggc gga ggc aaa cag gcg ctg gaa aca            1344
Val Val Ala Ile Ala Ser Asn Gly Gly Gly Lys Gln Ala Leu Glu Thr
            435                 440                 445 gtt cag cgc ctc ttg ccg gtc ttg tgt cag gac cac ggc ctg acc cca            1392
Val Gln Arg Leu Leu Pro Val Leu Cys Gln Asp His Gly Leu Thr Pro
450                 455                 460 gac cag gtt gtg gcc atc gcc agc aac ata ggt ggc aag cag gcc ctc            1440
Asp Gln Val Val Ala Ile Ala Ser Asn Ile Gly Gly Lys Gln Ala Leu
465                 470                 475                 480 gaa acc gtc cag aga ctg tta ccg gtt ctc tgc cag gac cac ggc ctg            1488
Glu Thr Val Gln Arg Leu Leu Pro Val Leu Cys Gln Asp His Gly Leu
                485                 490                 495 acc ccc gaa cag gtt gtc gct att gct agt aac ggc gga ggc aaa cag            1536
Thr Pro Glu Gln Val Val Ala Ile Ala Ser Asn Gly Gly Gly Lys Gln
            500                 505                 510 gcg ctg gaa aca gtt cag cgc ctc ttg ccg gtc ttg tgt cag gcc cac            1584
Ala Leu Glu Thr Val Gln Arg Leu Leu Pro Val Leu Cys Gln Ala His
            515                 520                 525 ggc ctg acc ccc gac cag gtt gtc gct att gct agt aac ggc gga ggc            1632
Gly Leu Thr Pro Asp Gln Val Val Ala Ile Ala Ser Asn Gly Gly Gly
            530                 535                 540 aaa cag gcg ctg gaa aca gtt cag cgc ctc ttg ccg gtc ttg tgt cag            1680
Lys Gln Ala Leu Glu Thr Val Gln Arg Leu Leu Pro Val Leu Cys Gln
545                 550                 555                 560 gcc cac ggc ctg acc ccg gcc cag gtg gtt gca atc gcg tca cac gat            1728
Ala His Gly Leu Thr Pro Ala Gln Val Val Ala Ile Ala Ser His Asp
                565                 570                 575
```

-continued

| | |
|---|---|
| ggg gga aag cag gcc cta gaa acc gtt cag cga ctc ctg ccc gtc ctg<br>Gly Gly Lys Gln Ala Leu Glu Thr Val Gln Arg Leu Leu Pro Val Leu<br>    580                 585                 590 | 1776 |
| tgc cag gac cac ggc ctg acc cca gac cag gtt gtg gcc atc gcc agc<br>Cys Gln Asp His Gly Leu Thr Pro Asp Gln Val Val Ala Ile Ala Ser<br>        595                 600                 605 | 1824 |
| aac ata ggt ggc aag cag gcc ctc gaa acc gtc cag aga ctg tta ccg<br>Asn Ile Gly Gly Lys Gln Ala Leu Glu Thr Val Gln Arg Leu Leu Pro<br>    610                 615                 620 | 1872 |
| gtt ctc tgc cag gac cac ggc ctg acc ccg gaa cag gtg gtt gca atc<br>Val Leu Cys Gln Asp His Gly Leu Thr Pro Glu Gln Val Val Ala Ile<br>625                 630                 635                 640 | 1920 |
| gcg tca cac gat ggg gga aag cag gcc cta gaa acc gtt cag cga ctc<br>Ala Ser His Asp Gly Gly Lys Gln Ala Leu Glu Thr Val Gln Arg Leu<br>                645                 650                 655 | 1968 |
| ctg ccc gtc ctg tgc cag gcc cac ggc ctg acc ccg gac cag gtg gtt<br>Leu Pro Val Leu Cys Gln Ala His Gly Leu Thr Pro Asp Gln Val Val<br>            660                 665                 670 | 2016 |
| gca atc gcg tca cac gat ggg gga aag cag gcc cta gaa acc gtt cag<br>Ala Ile Ala Ser His Asp Gly Gly Lys Gln Ala Leu Glu Thr Val Gln<br>        675                 680                 685 | 2064 |
| cga ctc ctg ccc gtc ctg tgc cag gcc cac ggc ctg acc cca gcc caa<br>Arg Leu Leu Pro Val Leu Cys Gln Ala His Gly Leu Thr Pro Ala Gln<br>    690                 695                 700 | 2112 |
| gtt gtc gcg att gca agc aac aac gga ggc aaa caa gcc tta gaa aca<br>Val Val Ala Ile Ala Ser Asn Asn Gly Gly Lys Gln Ala Leu Glu Thr<br>705                 710                 715                 720 | 2160 |
| gtc cag aga ttg ttg ccg gtg ctg tgc caa gac cac ggc ctg acc cca<br>Val Gln Arg Leu Leu Pro Val Leu Cys Gln Asp His Gly Leu Thr Pro<br>                725                 730                 735 | 2208 |
| gac cag gtt gtg gcc atc gcc agc aac ata ggt ggc aag cag gcc ctc<br>Asp Gln Val Val Ala Ile Ala Ser Asn Ile Gly Gly Lys Gln Ala Leu<br>            740                 745                 750 | 2256 |
| gaa acc gtc cag aga ctg tta ccg gtt ctc tgc cag gac cac ggc ctg<br>Glu Thr Val Gln Arg Leu Leu Pro Val Leu Cys Gln Asp His Gly Leu<br>        755                 760                 765 | 2304 |
| acc ccc gaa cag gtt gtc gct att gct agt aac ggc gga ggc aaa cag<br>Thr Pro Glu Gln Val Val Ala Ile Ala Ser Asn Gly Gly Gly Lys Gln<br>    770                 775                 780 | 2352 |
| gcg ctg gaa aca gtt cag cgc ctc ttg ccg gtc ttg tgt cag gcc cac<br>Ala Leu Glu Thr Val Gln Arg Leu Leu Pro Val Leu Cys Gln Ala His<br>785                 790                 795                 800 | 2400 |
| ggc ctg acg cct gag cag gta gtg gct att gca tcc aac gga ggg ggc<br>Gly Leu Thr Pro Glu Gln Val Val Ala Ile Ala Ser Asn Gly Gly Gly<br>                805                 810                 815 | 2448 |
| aga ccc gca ctg gag tca atc gtg gcc cag ctt tcg agg ccg gac ccc<br>Arg Pro Ala Leu Glu Ser Ile Val Ala Gln Leu Ser Arg Pro Asp Pro<br>            820                 825                 830 | 2496 |
| gcg ctg gcc gca ctc act aat gat cat ctt gta gcg ctg gcc tgc ctc<br>Ala Leu Ala Ala Leu Thr Asn Asp His Leu Val Ala Leu Ala Cys Leu<br>        835                 840                 845 | 2544 |
| ggc gga cgt cct gcc atg gat gca gtg aaa aag gga ttg ccg cac gcg<br>Gly Gly Arg Pro Ala Met Asp Ala Val Lys Lys Gly Leu Pro His Ala<br>    850                 855                 860 | 2592 |
| ccg gaa ttg atc aga tcc cag cta gtg aaa tct gaa ttg gaa gag aag<br>Pro Glu Leu Ile Arg Ser Gln Leu Val Lys Ser Glu Leu Glu Glu Lys<br>865                 870                 875                 880 | 2640 |
| aaa tct gaa ctt aga cat aaa ttg aaa tat gtg cca cat gaa tat att<br>Lys Ser Glu Leu Arg His Lys Leu Lys Tyr Val Pro His Glu Tyr Ile<br>                885                 890                 895 | 2688 |

-continued

```
gaa ttg att gaa atc gca aga aat tca act cag gat aga atc ctt gaa        2736
Glu Leu Ile Glu Ile Ala Arg Asn Ser Thr Gln Asp Arg Ile Leu Glu
            900                 905                 910 atg aag gtg atg gag ttc ttt atg aag gtt tat ggt tat cgt ggt aaa        2784
Met Lys Val Met Glu Phe Phe Met Lys Val Tyr Gly Tyr Arg Gly Lys
915                 920                 925 cat ttg ggt gga tca agg aaa cca gac gga gca att tat act gtc gga       2832
His Leu Gly Gly Ser Arg Lys Pro Asp Gly Ala Ile Tyr Thr Val Gly
        930                 935                 940 tct cct att gat tac ggt gtg atc gtt gat act aag gca tat tca gga       2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc       2928
Gly Tyr Asn Leu Pro Ile Gly Gln Ala Asp Glu Met Gln Arg Tyr Val
                965                 970                 975 gaa gag aat caa aca aga aac aag cat atc aac cct aat gaa tgg tgg       2976
Glu Glu Asn Gln Thr Arg Asn Lys His Ile Asn Pro Asn Glu Trp Trp
            980                 985                 990 aaa gtc tat cca tct tca gta aca gaa ttt aag ttc ttg ttt gtg agt       3024
Lys Val Tyr Pro Ser Ser Val Thr Glu Phe Lys Phe Leu Phe Val Ser
                995                 1000                1005 ggt cat ttc aaa gga aac tac aaa gct cag ctt aca aga ttg aat           3069
Gly His Phe Lys Gly Asn Tyr Lys Ala Gln Leu Thr Arg Leu Asn
        1010                1015                1020 cat atc act aat tgt aat gga gct gtt ctt agt gta gaa gag ctt           3114
His Ile Thr Asn Cys Asn Gly Ala Val Leu Ser Val Glu Glu Leu
    1025                1030                1035 ttg att ggt gga gaa atg att aaa gct ggt aca ttg aca ctt gag           3159
Leu Ile Gly Gly Glu Met Ile Lys Ala Gly Thr Leu Thr Leu Glu
1040                1045                1050 gaa gtg aga agg aaa ttt aat aac ggt gag ata aac ttt taa               3201
Glu Val Arg Arg Lys Phe Asn Asn Gly Glu Ile Asn Phe
        1055                1060                1065
```

<210> SEQ ID NO 53
<211> LENGTH: 1066
<212> TYPE: PRT
<213> ORGANISM: artificial sequence
<220> FEATURE:
<223> OTHER INFORMATION: Synthetic Construct

<400> SEQUENCE: 53

```
Met Ala Ser Ser Pro Lys Lys Arg Lys Val Ala Ala Asp
1               5                   10                  15

Tyr Lys Asp Asp Asp Lys Ser Trp Lys Asp Ala Ser Gly Trp Ser
                20                  25                  30

Arg Met His Ala Ala Pro Arg Arg Ala Ala Gln Pro Ser Asp Ala
            35                  40                  45

Ser Pro Ala Ala Gln Val Asp Leu Arg Thr Leu Gly Tyr Ser Gln Gln
50                  55                  60

Gln Gln Glu Lys Ile Lys Pro Lys Val Arg Ser Thr Val Ala Gln His
65                  70                  75                  80

His Glu Ala Leu Val Gly His Gly Phe Thr His Ala His Ile Val Ala
                85                  90                  95

Leu Ser Gln His Pro Ala Ala Leu Gly Thr Val Ala Val Thr Tyr Gln
            100                 105                 110

His Ile Ile Thr Ala Leu Pro Glu Ala Thr His Glu Asp Ile Val Gly
        115                 120                 125
```

```
Val Gly Lys Gln Trp Ser Gly Ala Arg Ala Leu Glu Ala Leu Leu Thr
130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
                165                 170                 175

His Ala Ser Arg Asn Ala Leu Thr Gly Ala Pro Leu Asn Leu Thr Pro
                180                 185                 190

Asp Gln Val Val Ala Ile Ala Ser Asn Asn Gly Gly Lys Gln Ala Leu
                195                 200                 205

Glu Thr Val Gln Arg Leu Leu Pro Val Leu Cys Gln Asp His Gly Leu
210                 215                 220

Thr Pro Glu Gln Val Val Ala Ile Ala Ser Asn Gly Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser His Asp Gly Gly
                260                 265                 270

Lys Gln Ala Leu Glu Thr Val Gln Arg Leu Leu Pro Val Leu Cys Gln
                275                 280                 285

Ala His Gly Leu Thr Pro Ala Gln Val Val Ala Ile Ala Ser Asn Gly
                290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

Asn Asn Gly Gly Lys Gln Ala Leu Glu Thr Val Gln Arg Leu Leu Pro
                340                 345                 350

Val Leu Cys Gln Asp His Gly Leu Thr Pro Glu Gln Val Val Ala Ile
                355                 360                 365

Ala Ser His Asp Gly Gly Lys Gln Ala Leu Glu Thr Val Gln Arg Leu
                370                 375                 380

Leu Pro Val Leu Cys Gln Ala His Gly Leu Thr Pro Asp Gln Val Val
385                 390                 395                 400

Ala Ile Ala Ser His Asp Gly Gly Lys Gln Ala Leu Glu Thr Val Gln
                405                 410                 415

Arg Leu Leu Pro Val Leu Cys Gln Ala His Gly Leu Thr Pro Ala Gln
                420                 425                 430

Val Val Ala Ile Ala Ser Asn Gly Gly Gly Lys Gln Ala Leu Glu Thr
                435                 440                 445

Val Gln Arg Leu Leu Pro Val Leu Cys Gln Asp His Gly Leu Thr Pro
450                 455                 460

Asp Gln Val Val Ala Ile Ala Ser Asn Ile Gly Gly Lys Gln Ala Leu
465                 470                 475                 480

Glu Thr Val Gln Arg Leu Leu Pro Val Leu Cys Gln Asp His Gly Leu
                485                 490                 495

Thr Pro Glu Gln Val Val Ala Ile Ala Ser Asn Gly Gly Gly Lys Gln
                500                 505                 510

Ala Leu Glu Thr Val Gln Arg Leu Leu Pro Val Leu Cys Gln Ala His
                515                 520                 525

Gly Leu Thr Pro Asp Gln Val Val Ala Ile Ala Ser Asn Gly Gly Gly
                530                 535                 540

Lys Gln Ala Leu Glu Thr Val Gln Arg Leu Leu Pro Val Leu Cys Gln
```

```
              545                 550                 555                 560
         Ala His Gly Leu Thr Pro Ala Gln Val Val Ala Ile Ala Ser His Asp
                         565                 570                 575

Gly Gly Lys Gln Ala Leu Glu Thr Val Gln Arg Leu Leu Pro Val Leu
                         580                 585                 590

Cys Gln Asp His Gly Leu Thr Pro Asp Gln Val Val Ala Ile Ala Ser
                         595                 600                 605

Asn Ile Gly Gly Lys Gln Ala Leu Glu Thr Val Gln Arg Leu Leu Pro
                         610                 615                 620

Val Leu Cys Gln Asp His Gly Leu Thr Pro Glu Gln Val Val Ala Ile
         625                 630                 635                 640

Ala Ser His Asp Gly Gly Lys Gln Ala Leu Glu Thr Val Gln Arg Leu
                         645                 650                 655

Leu Pro Val Leu Cys Gln Ala His Gly Leu Thr Pro Asp Gln Val Val
                         660                 665                 670

Ala Ile Ala Ser His Asp Gly Gly Lys Gln Ala Leu Glu Thr Val Gln
                         675                 680                 685

Arg Leu Leu Pro Val Leu Cys Gln Ala His Gly Leu Thr Pro Ala Gln
                         690                 695                 700

Val Val Ala Ile Ala Ser Asn Asn Gly Gly Lys Gln Ala Leu Glu Thr
         705                 710                 715                 720

Val Gln Arg Leu Leu Pro Val Leu Cys Gln Asp His Gly Leu Thr Pro
                         725                 730                 735

Asp Gln Val Val Ala Ile Ala Ser Asn Ile Gly Gly Lys Gln Ala Leu
                         740                 745                 750

Glu Thr Val Gln Arg Leu Leu Pro Val Leu Cys Gln Asp His Gly Leu
                         755                 760                 765

Thr Pro Glu Gln Val Val Ala Ile Ala Ser Asn Gly Gly Gly Lys Gln
                         770                 775                 780

Ala Leu Glu Thr Val Gln Arg Leu Leu Pro Val Leu Cys Gln Ala His
         785                 790                 795                 800

Gly Leu Thr Pro Glu Gln Val Val Ala Ile Ala Ser Asn Gly Gly Gly
                         805                 810                 815

Arg Pro Ala Leu Glu Ser Ile Val Ala Gln Leu Ser Arg Pro Asp Pro
                         820                 825                 830

Ala Leu Ala Ala Leu Thr Asn Asp His Leu Val Ala Leu Ala Cys Leu
                         835                 840                 845

Gly Gly Arg Pro Ala Met Asp Ala Val Lys Lys Gly Leu Pro His Ala
         850                 855                 860

Pro Glu Leu Ile Arg Ser Gln Leu Val Lys Ser Glu Leu Glu Glu Lys
         865                 870                 875                 880

Lys Ser Glu Leu Arg His Lys Leu Lys Tyr Val Pro His Glu Tyr Ile
                         885                 890                 895

Glu Leu Ile Glu Ile Ala Arg Asn Ser Thr Gln Asp Arg Ile Leu Glu
                         900                 905                 910

Met Lys Val Met Glu Phe Phe Met Lys Val Tyr Gly Tyr Arg Gly Lys
                         915                 920                 925

His Leu Gly Gly Ser Arg Lys Pro Asp Gly Ala Ile Tyr Thr Val Gly
                         930                 935                 940

Ser Pro Ile Asp Tyr Gly Val Ile Val Asp Thr Lys Ala Tyr Ser Gly
         945                 950                 955                 960

Gly Tyr Asn Leu Pro Ile Gly Gln Ala Asp Glu Met Gln Arg Tyr Val
                         965                 970                 975
```

```
Glu Glu Asn Gln Thr Arg Asn Lys His Ile Asn Pro Asn Glu Trp Trp
            980                 985                 990

Lys Val Tyr Pro Ser Ser Val Thr Glu Phe Lys Phe Leu Phe Val Ser
            995                1000                1005

Gly His Phe Lys Gly Asn Tyr Lys Ala Gln Leu Thr Arg Leu Asn
           1010                1015                1020

His Ile Thr Asn Cys Asn Gly Ala Val Leu Ser Val Glu Glu Leu
  1025                1030                1035

Leu Ile Gly Gly Glu Met Ile Lys Ala Gly Thr Leu Thr Leu Glu
  1040                1045                1050

Glu Val Arg Arg Lys Phe Asn Asn Gly Glu Ile Asn Phe
  1055                1060                1065

<210> SEQ ID NO 54
<211> LENGTH: 3201
<212> TYPE: DNA
<213> ORGANISM: artificial sequence
<220> FEATURE:
<223> OTHER INFORMATION: TALEN-TCR-alpha2_R19 TALEN coding sequence
<220> FEATURE:
<221> NAME/KEY: CDS
<222> LOCATION: (1)..(3201)

<400> SEQUENCE: 54 atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                  10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
            20                  25                  30 aga atg cat gcg gcc ccg cga cgg cgt gct gcg caa ccc tcc gac gct     144
Arg Met His Ala Ala Pro Arg Arg Arg Ala Ala Gln Pro Ser Asp Ala
        35                  40                  45 tcg ccg gcc gcg cag gtg gat cta cgc acg ctc ggc tac agt cag cag     192
Ser Pro Ala Ala Gln Val Asp Leu Arg Thr Leu Gly Tyr Ser Gln Gln
    50                  55                  60 cag caa gag aag atc aaa ccg aag gtg cgt tcg aca gtg gcg cag cac     240
Gln Gln Glu Lys Ile Lys Pro Lys Val Arg Ser Thr Val Ala Gln His
65                  70                  75                  80 cac gag gca ctg gtg ggc cat ggg ttt aca cac gcg cac atc gtt gcg     288
His Glu Ala Leu Val Gly His Gly Phe Thr His Ala His Ile Val Ala
                85                  90                  95 ctc agc caa cac ccg gca gcg tta ggg acc gtc gct gtc acg tat cag     336
Leu Ser Gln His Pro Ala Ala Leu Gly Thr Val Ala Val Thr Tyr Gln
            100                 105                 110 cac ata atc acg gcg ttg cca gag gcg aca cac gaa gac atc gtt ggc     384
His Ile Ile Thr Ala Leu Pro Glu Ala Thr His Glu Asp Ile Val Gly
        115                 120                 125 gtc ggc aaa cag tgg tcc ggc gca cgc gcc ctg gag gcc ttg ctc acg     432
Val Gly Lys Gln Trp Ser Gly Ala Arg Ala Leu Glu Ala Leu Leu Thr
    130                 135                 140 gat gcg ggg gag ttg aga ggt ccg ccg tta cag ttg gac aca ggc caa     480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg     528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc ccg     576
His Ala Ser Arg Asn Ala Leu Thr Gly Ala Pro Leu Asn Leu Thr Pro
            180                 185                 190
```

-continued

```
gac cag gtg gtt gca atc gcg tca cac gat ggg gga aag cag gcc cta      624
Asp Gln Val Val Ala Ile Ala Ser His Asp Gly Gly Lys Gln Ala Leu
            195                 200                 205 gaa acc gtt cag cga ctc ctg ccc gtc ctg tgc cag gac cac ggc ctg      672
Glu Thr Val Gln Arg Leu Leu Pro Val Leu Cys Gln Asp His Gly Leu
    210                 215                 220 acc ccg gaa cag gtg gtt gca atc gcg tca cac gat ggg gga aag cag      720
Thr Pro Glu Gln Val Val Ala Ile Ala Ser His Asp Gly Gly Lys Gln
225                 230                 235                 240 gcc cta gaa acc gtt cag cga ctc ctg ccc gtc ctg tgc cag gcc cac      768
Ala Leu Glu Thr Val Gln Arg Leu Leu Pro Val Leu Cys Gln Ala His
                245                 250                 255 ggc ctg acc ccc gac cag gtt gtc gct att gct agt aac ggc gga ggc      816
Gly Leu Thr Pro Asp Gln Val Val Ala Ile Ala Ser Asn Gly Gly Gly
        260                 265                 270 aaa cag gcg ctg gaa aca gtt cag cgc ctc ttg ccg gtc ttg tgt cag      864
Lys Gln Ala Leu Glu Thr Val Gln Arg Leu Leu Pro Val Leu Cys Gln
            275                 280                 285 gcc cac ggc ctg acc ccc gcc cag gtt gtc gct att gct agt aac ggc      912
Ala His Gly Leu Thr Pro Ala Gln Val Val Ala Ile Ala Ser Asn Gly
    290                 295                 300 gga ggc aaa cag gcg ctg gaa aca gtt cag cgc ctc ttg ccg gtc ttg      960
Gly Gly Lys Gln Ala Leu Glu Thr Val Gln Arg Leu Leu Pro Val Leu
305                 310                 315                 320 tgt cag gac cac ggc ctg acc cca gac cag gtt gtg gcc atc gcc agc     1008
Cys Gln Asp His Gly Leu Thr Pro Asp Gln Val Val Ala Ile Ala Ser
                325                 330                 335 aac ata ggt ggc aag cag gcc ctc gaa acc gtc cag aga ctg tta ccg     1056
Asn Ile Gly Gly Lys Gln Ala Leu Glu Thr Val Gln Arg Leu Leu Pro
        340                 345                 350 gtt ctc tgc cag gac cac ggc ctg acc ccg gaa cag gtg gtt gca atc     1104
Val Leu Cys Gln Asp His Gly Leu Thr Pro Glu Gln Val Val Ala Ile
            355                 360                 365 gcg tca cac gat ggg gga aag cag gcc cta gaa acc gtt cag cga ctc     1152
Ala Ser His Asp Gly Gly Lys Gln Ala Leu Glu Thr Val Gln Arg Leu
    370                 375                 380 ctg ccc gtc ctg tgc cag gcc cac ggc ctg acc ccc gac cag gtt gtc    1200
Leu Pro Val Leu Cys Gln Ala His Gly Leu Thr Pro Asp Gln Val Val
385                 390                 395                 400 gct att gct agt aac ggc gga ggc aaa cag gcg ctg gaa aca gtt cag    1248
Ala Ile Ala Ser Asn Gly Gly Gly Lys Gln Ala Leu Glu Thr Val Gln
                405                 410                 415 cgc ctc ttg ccg gtc ttg tgt cag gcc cac ggc ctg acc ccc gcc cag    1296
Arg Leu Leu Pro Val Leu Cys Gln Ala His Gly Leu Thr Pro Ala Gln
        420                 425                 430 gtt gtc gct att gct agt aac ggc gga ggc aaa cag gcg ctg gaa aca    1344
Val Val Ala Ile Ala Ser Asn Gly Gly Gly Lys Gln Ala Leu Glu Thr
            435                 440                 445 gtt cag cgc ctc ttg ccg gtc ttg tgt cag gac cac ggc ctg acc ccc    1392
Val Gln Arg Leu Leu Pro Val Leu Cys Gln Asp His Gly Leu Thr Pro
    450                 455                 460 gac cag gtt gtc gct att gct agt aac ggc gga ggc aaa cag gcg ctg    1440
Asp Gln Val Val Ala Ile Ala Ser Asn Gly Gly Gly Lys Gln Ala Leu
465                 470                 475                 480 gaa aca gtt cag cgc ctc ttg ccg gtc ttg tgt cag gac cac ggc ctg    1488
Glu Thr Val Gln Arg Leu Leu Pro Val Leu Cys Gln Asp His Gly Leu
                485                 490                 495 acc cca gaa caa gtt gtc gcg att gca agc aac aac gga ggc aaa caa    1536
Thr Pro Glu Gln Val Val Ala Ile Ala Ser Asn Asn Gly Gly Lys Gln
```

```
                500                 505                 510
gcc tta gaa aca gtc cag aga ttg ttg ccg gtg ctg tgc caa gcc cac    1584
Ala Leu Glu Thr Val Gln Arg Leu Leu Pro Val Leu Cys Gln Ala His
        515                 520                 525 ggc ctg acc ccc gac cag gtt gtc gct att gct agt aac ggc gga ggc    1632
Gly Leu Thr Pro Asp Gln Val Val Ala Ile Ala Ser Asn Gly Gly Gly
530                 535                 540 aaa cag gcg ctg gaa aca gtt cag cgc ctc ttg ccg gtc ttg tgt cag    1680
Lys Gln Ala Leu Glu Thr Val Gln Arg Leu Leu Pro Val Leu Cys Gln
545                 550                 555                 560 gcc cac ggc ctg acc cca gcc caa gtt gtc gcg att gca agc aac aac    1728
Ala His Gly Leu Thr Pro Ala Gln Val Val Ala Ile Ala Ser Asn Asn
                565                 570                 575 gga ggc aaa caa gcc tta gaa aca gtc cag aga ttg ttg ccg gtg ctg    1776
Gly Gly Lys Gln Ala Leu Glu Thr Val Gln Arg Leu Leu Pro Val Leu
        580                 585                 590 tgc caa gac cac ggc ctg acc cca gac cag gtt gtg gcc atc gcc agc    1824
Cys Gln Asp His Gly Leu Thr Pro Asp Gln Val Val Ala Ile Ala Ser
595                 600                 605 aac ata ggt ggc aag cag gcc ctc gaa acc gtc cag aga ctg tta ccg    1872
Asn Ile Gly Gly Lys Gln Ala Leu Glu Thr Val Gln Arg Leu Leu Pro
610                 615                 620 gtt ctc tgc cag gac cac ggc ctg acc ccg gaa cag gtg gtt gca atc    1920
Val Leu Cys Gln Asp His Gly Leu Thr Pro Glu Gln Val Val Ala Ile
625                 630                 635                 640 gcg tca cac gat ggg gga aag cag gcc cta gaa acc gtt cag cga ctc    1968
Ala Ser His Asp Gly Gly Lys Gln Ala Leu Glu Thr Val Gln Arg Leu
                645                 650                 655 ctg ccc gtc ctg tgc cag gcc cac ggc ctg acc cca gac cag gtt gtg    2016
Leu Pro Val Leu Cys Gln Ala His Gly Leu Thr Pro Asp Gln Val Val
        660                 665                 670 gcc atc gcc agc aac ata ggt ggc aag cag gcc ctc gaa acc gtc cag    2064
Ala Ile Ala Ser Asn Ile Gly Gly Lys Gln Ala Leu Glu Thr Val Gln
675                 680                 685 aga ctg tta ccg gtt ctc tgc cag gcc cac ggc ctg acc ccg gcc cag    2112
Arg Leu Leu Pro Val Leu Cys Gln Ala His Gly Leu Thr Pro Ala Gln
690                 695                 700 gtg gtt gca atc gcg tca cac gat ggg gga aag cag gcc cta gaa acc    2160
Val Val Ala Ile Ala Ser His Asp Gly Gly Lys Gln Ala Leu Glu Thr
705                 710                 715                 720 gtt cag cga ctc ctg ccc gtc ctg tgc cag gac cac ggc ctg acc cca    2208
Val Gln Arg Leu Leu Pro Val Leu Cys Gln Asp His Gly Leu Thr Pro
                725                 730                 735 gac cag gtt gtg gcc atc gcc agc aac ata ggt ggc aag cag gcc ctc    2256
Asp Gln Val Val Ala Ile Ala Ser Asn Ile Gly Gly Lys Gln Ala Leu
        740                 745                 750 gaa acc gtc cag aga ctg tta ccg gtt ctc tgc cag gac cac ggc ctg    2304
Glu Thr Val Gln Arg Leu Leu Pro Val Leu Cys Gln Asp His Gly Leu
755                 760                 765 acc ccc gaa cag gtt gtc gct att gct agt aac ggc gga ggc aaa cag    2352
Thr Pro Glu Gln Val Val Ala Ile Ala Ser Asn Gly Gly Gly Lys Gln
770                 775                 780 gcg ctg gaa aca gtt cag cgc ctc ttg ccg gtc ttg tgt cag gcc cac    2400
Ala Leu Glu Thr Val Gln Arg Leu Leu Pro Val Leu Cys Gln Ala His
785                 790                 795                 800 ggc ctg acg cct gag cag gta gtg gct att gca tcc aac gga ggg ggc    2448
Gly Leu Thr Pro Glu Gln Val Val Ala Ile Ala Ser Asn Gly Gly Gly
                805                 810                 815 aga ccc gca ctg gag tca atc gtg gcc cag ctt tcg agg ccg gac ccc    2496
```

-continued

```
                Arg Pro Ala Leu Glu Ser Ile Val Ala Gln Leu Ser Arg Pro Asp Pro
                                820                 825                 830 gcg ctg gcc gca ctc act aat gat cat ctt gta gcg ctg gcc tgc ctc         2544
Ala Leu Ala Ala Leu Thr Asn Asp His Leu Val Ala Leu Ala Cys Leu
            835                 840                 845 ggc gga cgt cct gcc atg gat gca gtg aaa aag gga ttg ccg cac gcg         2592
Gly Gly Arg Pro Ala Met Asp Ala Val Lys Lys Gly Leu Pro His Ala
850                 855                 860 ccg gaa ttg atc aga tcc cag cta gtg aaa tct gaa ttg gaa gag aag         2640
Pro Glu Leu Ile Arg Ser Gln Leu Val Lys Ser Glu Leu Glu Glu Lys
865                 870                 875                 880 aaa tct gaa ctt aga cat aaa ttg aaa tat gtg cca cat gaa tat att         2688
Lys Ser Glu Leu Arg His Lys Leu Lys Tyr Val Pro His Glu Tyr Ile
                885                 890                 895 gaa ttg att gaa atc gca aga aat tca act cag gat aga atc ctt gaa         2736
Glu Leu Ile Glu Ile Ala Arg Asn Ser Thr Gln Asp Arg Ile Leu Glu
                900                 905                 910 atg aag gtg atg gag ttc ttt atg aag gtt tat ggt tat cgt ggt aaa         2784
Met Lys Val Met Glu Phe Phe Met Lys Val Tyr Gly Tyr Arg Gly Lys
                915                 920                 925 cat ttg ggt gga tca agg aaa cca gac gga gca att tat act gtc gga         2832
His Leu Gly Gly Ser Arg Lys Pro Asp Gly Ala Ile Tyr Thr Val Gly
930                 935                 940 tct cct att gat tac ggt gtg atc gtt gat act aag gca tat tca gga         2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc         2928
Gly Tyr Asn Leu Pro Ile Gly Gln Ala Asp Glu Met Gln Arg Tyr Val
                965                 970                 975 gaa gag aat caa aca aga aac aag cat atc aac cct aat gaa tgg tgg         2976
Glu Glu Asn Gln Thr Arg Asn Lys His Ile Asn Pro Asn Glu Trp Trp
                980                 985                 990 aaa gtc tat cca tct tca gta aca gaa ttt aag ttc ttg ttt gtg agt        3024
Lys Val Tyr Pro Ser Ser Val Thr Glu Phe Lys Phe Leu Phe Val Ser
                995                 1000                1005 ggt cat ttc aaa gga aac tac aaa gct cag ctt aca aga ttg aat           3069
Gly His Phe Lys Gly Asn Tyr Lys Ala Gln Leu Thr Arg Leu Asn
    1010                1015                1020 cat atc act aat tgt aat gga gct gtt ctt agt gta gaa gag ctt           3114
His Ile Thr Asn Cys Asn Gly Ala Val Leu Ser Val Glu Glu Leu
    1025                1030                1035 ttg att ggt gga gaa atg att aaa gct ggt aca ttg aca ctt gag           3159
Leu Ile Gly Gly Glu Met Ile Lys Ala Gly Thr Leu Thr Leu Glu
    1040                1045                1050 gaa gtg aga agg aaa ttt aat aac ggt gag ata aac ttt taa               3201
Glu Val Arg Arg Lys Phe Asn Asn Gly Glu Ile Asn Phe
    1055                1060                1065
```

<210> SEQ ID NO 55
<211> LENGTH: 1066
<212> TYPE: PRT
<213> ORGANISM: artificial sequence
<220> FEATURE:
<223> OTHER INFORMATION: Synthetic Construct

<400> SEQUENCE: 55

```
Met Ala Ser Ser Pro Lys Lys Arg Lys Val Ala Ala Asp
1               5                   10                  15

Tyr Lys Asp Asp Asp Asp Lys Ser Trp Lys Asp Ala Ser Gly Trp Ser
                20                  25                  30
```

Arg Met His Ala Ala Pro Arg Arg Ala Ala Gln Pro Ser Asp Ala
            35                  40                  45

Ser Pro Ala Ala Gln Val Asp Leu Arg Thr Leu Gly Tyr Ser Gln Gln
 50                  55                  60

Gln Gln Glu Lys Ile Lys Pro Lys Val Arg Ser Thr Val Ala Gln His
 65                  70                  75                  80

His Glu Ala Leu Val Gly His Gly Phe Thr His Ala His Ile Val Ala
                 85                  90                  95

Leu Ser Gln His Pro Ala Ala Leu Gly Thr Val Ala Val Thr Tyr Gln
             100                 105                 110

His Ile Ile Thr Ala Leu Pro Glu Ala Thr His Glu Asp Ile Val Gly
             115                 120                 125

Val Gly Lys Gln Trp Ser Gly Ala Arg Ala Leu Glu Ala Leu Leu Thr
130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
                165                 170                 175

His Ala Ser Arg Asn Ala Leu Thr Gly Ala Pro Leu Asn Leu Thr Pro
            180                 185                 190

Asp Gln Val Val Ala Ile Ala Ser His Asp Gly Gly Lys Gln Ala Leu
            195                 200                 205

Glu Thr Val Gln Arg Leu Leu Pro Val Leu Cys Gln Asp His Gly Leu
            210                 215                 220

Thr Pro Glu Gln Val Val Ala Ile Ala Ser His Asp Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser Asn Gly Gly Gly
            260                 265                 270

Lys Gln Ala Leu Glu Thr Val Gln Arg Leu Leu Pro Val Leu Cys Gln
            275                 280                 285

Ala His Gly Leu Thr Pro Ala Gln Val Val Ala Ile Ala Ser Asn Gly
290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

Asn Ile Gly Gly Lys Gln Ala Leu Glu Thr Val Gln Arg Leu Leu Pro
            340                 345                 350

Val Leu Cys Gln Asp His Gly Leu Thr Pro Glu Gln Val Val Ala Ile
            355                 360                 365

Ala Ser His Asp Gly Gly Lys Gln Ala Leu Glu Thr Val Gln Arg Leu
370                 375                 380

Leu Pro Val Leu Cys Gln Ala His Gly Leu Thr Pro Asp Gln Val Val
385                 390                 395                 400

Ala Ile Ala Ser Asn Gly Gly Gly Lys Gln Ala Leu Glu Thr Val Gln
                405                 410                 415

Arg Leu Leu Pro Val Leu Cys Gln Ala His Gly Leu Thr Pro Ala Gln
            420                 425                 430

Val Val Ala Ile Ala Ser Asn Gly Gly Gly Lys Gln Ala Leu Glu Thr
            435                 440                 445

Val Gln Arg Leu Leu Pro Val Leu Cys Gln Asp His Gly Leu Thr Pro

```
            450                 455                 460
Asp Gln Val Val Ala Ile Ala Ser Asn Gly Gly Lys Gln Ala Leu
465                 470                 475                 480

Glu Thr Val Gln Arg Leu Leu Pro Val Leu Cys Gln Asp His Gly Leu
                485                 490                 495

Thr Pro Glu Gln Val Val Ala Ile Ala Ser Asn Asn Gly Gly Lys Gln
                500                 505                 510

Ala Leu Glu Thr Val Gln Arg Leu Leu Pro Val Leu Cys Gln Ala His
            515                 520                 525

Gly Leu Thr Pro Asp Gln Val Val Ala Ile Ala Ser Asn Gly Gly Gly
            530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser Asn Asn
                565                 570                 575

Gly Gly Lys Gln Ala Leu Glu Thr Val Gln Arg Leu Leu Pro Val Leu
            580                 585                 590

Cys Gln Asp His Gly Leu Thr Pro Asp Gln Val Val Ala Ile Ala Ser
            595                 600                 605

Asn Ile Gly Gly Lys Gln Ala Leu Glu Thr Val Gln Arg Leu Leu Pro
610                 615                 620

Val Leu Cys Gln Asp His Gly Leu Thr Pro Glu Gln Val Val Ala Ile
625                 630                 635                 640

Ala Ser His Asp Gly Gly Lys Gln Ala Leu Glu Thr Val Gln Arg Leu
                645                 650                 655

Leu Pro Val Leu Cys Gln Ala His Gly Leu Thr Pro Asp Gln Val Val
                660                 665                 670

Ala Ile Ala Ser Asn Ile Gly Gly Lys Gln Ala Leu Glu Thr Val Gln
            675                 680                 685

Arg Leu Leu Pro Val Leu Cys Gln Ala His Gly Leu Thr Pro Ala Gln
            690                 695                 700

Val Val Ala Ile Ala Ser His Asp Gly Gly Lys Gln Ala Leu Glu Thr
705                 710                 715                 720

Val Gln Arg Leu Leu Pro Val Leu Cys Gln Asp His Gly Leu Thr Pro
                725                 730                 735

Asp Gln Val Val Ala Ile Ala Ser Asn Ile Gly Gly Lys Gln Ala Leu
                740                 745                 750

Glu Thr Val Gln Arg Leu Leu Pro Val Leu Cys Gln Asp His Gly Leu
            755                 760                 765

Thr Pro Glu Gln Val Val Ala Ile Ala Ser Asn Gly Gly Gly Lys Gln
            770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser Asn Gly Gly Gly
                805                 810                 815

Arg Pro Ala Leu Glu Ser Ile Val Ala Gln Leu Ser Arg Pro Asp Pro
                820                 825                 830

Ala Leu Ala Ala Leu Thr Asn Asp His Leu Val Ala Leu Ala Cys Leu
            835                 840                 845

Gly Gly Arg Pro Ala Met Asp Ala Val Lys Lys Gly Leu Pro His Ala
            850                 855                 860

Pro Glu Leu Ile Arg Ser Gln Leu Val Lys Ser Glu Leu Glu Glu Lys
865                 870                 875                 880
```

```
Lys Ser Glu Leu Arg His Lys Leu Lys Tyr Val Pro His Glu Tyr Ile
                885                 890                 895

Glu Leu Ile Glu Ile Ala Arg Asn Ser Thr Gln Asp Arg Ile Leu Glu
            900                 905                 910

Met Lys Val Met Glu Phe Phe Met Lys Val Tyr Gly Tyr Arg Gly Lys
        915                 920                 925

His Leu Gly Gly Ser Arg Lys Pro Asp Gly Ala Ile Tyr Thr Val Gly
    930                 935                 940

Ser Pro Ile Asp Tyr Gly Val Ile Val Asp Thr Lys Ala Tyr Ser Gly
945                 950                 955                 960

Gly Tyr Asn Leu Pro Ile Gly Gln Ala Asp Glu Met Gln Arg Tyr Val
                965                 970                 975

Glu Glu Asn Gln Thr Arg Asn Lys His Ile Asn Pro Asn Glu Trp Trp
            980                 985                 990

Lys Val Tyr Pro Ser Ser Val Thr Glu Phe Lys Phe Leu Phe Val Ser
        995                 1000                1005

Gly His Phe Lys Gly Asn Tyr Lys Ala Gln Leu Thr Arg Leu Asn
    1010                1015                1020

His Ile Thr Asn Cys Asn Gly Ala Val Leu Ser Val Glu Glu Leu
    1025                1030                1035

Leu Ile Gly Gly Glu Met Ile Lys Ala Gly Thr Leu Thr Leu Glu
    1040                1045                1050

Glu Val Arg Arg Lys Phe Asn Asn Gly Glu Ile Asn Phe
    1055                1060                1065

<210> SEQ ID NO 56
<211> LENGTH: 3201
<212> TYPE: DNA
<213> ORGANISM: artificial sequence
<220> FEATURE:
<223> OTHER INFORMATION: TALEN-TCR-beta1_L19 TALEN coding sequence
<220> FEATURE:
<221> NAME/KEY: CDS
<222> LOCATION: (1)..(3201)

<400> SEQUENCE: 56 atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
            20                  25                  30 aga atg cat gcg gcc ccg cga cgg cgt gct gcg caa ccc tcc gac gct      144
Arg Met His Ala Ala Pro Arg Arg Arg Ala Ala Gln Pro Ser Asp Ala
        35                  40                  45 tcg ccg gcc gcg cag gtg gat cta cgc acg ctc ggc tac agt cag cag      192
Ser Pro Ala Ala Gln Val Asp Leu Arg Thr Leu Gly Tyr Ser Gln Gln
    50                  55                  60 cag caa gag aag atc aaa ccg aag gtg cgt tcg aca gtg gcg cag cac      240
Gln Gln Glu Lys Ile Lys Pro Lys Val Arg Ser Thr Val Ala Gln His
65                  70                  75                  80 cac gag gca ctg gtg ggc cat ggg ttt aca cac gcg cac atc gtt gcg      288
His Glu Ala Leu Val Gly His Gly Phe Thr His Ala His Ile Val Ala
                85                  90                  95 ctc agc caa cac ccg gca gcg tta ggg acc gtc gct gtc acg tat cag      336
Leu Ser Gln His Pro Ala Ala Leu Gly Thr Val Ala Val Thr Tyr Gln
            100                 105                 110 cac ata atc acg gcg ttg cca gag gcg aca cac gaa gac atc gtt ggc      384
```

```
                His Ile Ile Thr Ala Leu Pro Glu Ala Thr His Glu Asp Ile Val Gly
                                115                 120                 125 gtc ggc aaa cag tgg tcc ggc gca cgc gcc ctg gag gcc ttg ctc acg              432
Val Gly Lys Gln Trp Ser Gly Ala Arg Ala Leu Glu Ala Leu Leu Thr
    130                 135                 140 gat gcg ggg gag ttg aga ggt ccg ccg tta cag ttg gac aca ggc caa              480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg              528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc cca              576
His Ala Ser Arg Asn Ala Leu Thr Gly Ala Pro Leu Asn Leu Thr Pro
            180                 185                 190 gac caa gtt gtc gcg att gca agc aac aac gga ggc aaa caa gcc tta              624
Asp Gln Val Val Ala Ile Ala Ser Asn Asn Gly Gly Lys Gln Ala Leu
        195                 200                 205 gaa aca gtc cag aga ttg ttg ccg gtg ctg tgc caa gac cac ggc ctg              672
Glu Thr Val Gln Arg Leu Leu Pro Val Leu Cys Gln Asp His Gly Leu
    210                 215                 220 acc ccc gaa cag gtt gtc gct att gct agt aac ggc gga ggc aaa cag              720
Thr Pro Glu Gln Val Val Ala Ile Ala Ser Asn Gly Gly Gly Lys Gln
225                 230                 235                 240 gcg ctg gaa aca gtt cag cgc ctc ttg ccg gtc ttg tgt cag gcc cac              768
Ala Leu Glu Thr Val Gln Arg Leu Leu Pro Val Leu Cys Gln Ala His
                245                 250                 255 ggc ctg acc ccc gac cag gtt gtc gct att gct agt aac ggc gga ggc              816
Gly Leu Thr Pro Asp Gln Val Val Ala Ile Ala Ser Asn Gly Gly Gly
            260                 265                 270 aaa cag gcg ctg gaa aca gtt cag cgc ctc ttg ccg gtc ttg tgt cag              864
Lys Gln Ala Leu Glu Thr Val Gln Arg Leu Leu Pro Val Leu Cys Gln
        275                 280                 285 gcc cac ggc ctg acc ccg gcg cag gtg gtt gca atc gcg tca cac gat              912
Ala His Gly Leu Thr Pro Ala Gln Val Val Ala Ile Ala Ser His Asp
    290                 295                 300 ggg gga aag cag gcc cta gaa acc gtt cag cga ctc ctg ccc gtc ctg              960
Gly Gly Lys Gln Ala Leu Glu Thr Val Gln Arg Leu Leu Pro Val Leu
305                 310                 315                 320 tgc cag gac cac ggc ctg acc ccg gac cag gtg gtt gca atc gcg tca             1008
Cys Gln Asp His Gly Leu Thr Pro Asp Gln Val Val Ala Ile Ala Ser
                325                 330                 335 cac gat ggg gga aag cag gcc cta gaa acc gtt cag cga ctc ctg ccc             1056
His Asp Gly Gly Lys Gln Ala Leu Glu Thr Val Gln Arg Leu Leu Pro
            340                 345                 350 gtc ctg tgc cag gac cac ggc ctg acc ccg gaa cag gtg gtt gca atc             1104
Val Leu Cys Gln Asp His Gly Leu Thr Pro Glu Gln Val Val Ala Ile
        355                 360                 365 gcg tca cac gat ggg gga aag cag gcc cta gaa acc gtt cag cga ctc             1152
Ala Ser His Asp Gly Gly Lys Gln Ala Leu Glu Thr Val Gln Arg Leu
    370                 375                 380 ctg ccc gtc ctg tgc cag gcc cac ggc ctg acc cca gac cag gtt gtg             1200
Leu Pro Val Leu Cys Gln Ala His Gly Leu Thr Pro Asp Gln Val Val
385                 390                 395                 400 gcc atc gcc agc aac ata ggt ggc aag cag gcc ctc gaa acc gtc cag             1248
Ala Ile Ala Ser Asn Ile Gly Gly Lys Gln Ala Leu Glu Thr Val Gln
                405                 410                 415 aga ctg tta ccg gtt ctc tgc cag gcc cac ggc ctg acc ccg gcc cag             1296
Arg Leu Leu Pro Val Leu Cys Gln Ala His Gly Leu Thr Pro Ala Gln
            420                 425                 430
```

| | |
|---|---|
| gtg gtt gca atc gcg tca cac gat ggg gga aag cag gcc cta gaa acc<br>Val Val Ala Ile Ala Ser His Asp Gly Gly Lys Gln Ala Leu Glu Thr<br>            435                          440                          445 | 1344 |
| gtt cag cga ctc ctg ccc gtc ctg tgc cag gac cac ggc ctg acc ccg<br>Val Gln Arg Leu Leu Pro Val Leu Cys Gln Asp His Gly Leu Thr Pro<br>450                          455                          460 | 1392 |
| gac cag gtg gtt gca atc gcg tca cac gat ggg gga aag cag gcc cta<br>Asp Gln Val Val Ala Ile Ala Ser His Asp Gly Gly Lys Gln Ala Leu<br>465                          470                          475                          480 | 1440 |
| gaa acc gtt cag cga ctc ctg ccc gtc ctg tgc cag gac cac ggc ctg<br>Glu Thr Val Gln Arg Leu Leu Pro Val Leu Cys Gln Asp His Gly Leu<br>                          485                          490                          495 | 1488 |
| acc ccg gaa cag gtg gtt gca atc gcg tca cac gat ggg gga aag cag<br>Thr Pro Glu Gln Val Val Ala Ile Ala Ser His Asp Gly Gly Lys Gln<br>                     500                          505                          510 | 1536 |
| gcc cta gaa acc gtt cag cga ctc ctg ccc gtc ctg tgc cag gcc cac<br>Ala Leu Glu Thr Val Gln Arg Leu Leu Pro Val Leu Cys Gln Ala His<br>               515                          520                          525 | 1584 |
| ggc ctg acc cca gac caa gtt gtc gcg att gca agc aac aac gga ggc<br>Gly Leu Thr Pro Asp Gln Val Val Ala Ile Ala Ser Asn Asn Gly Gly<br>530                          535                          540 | 1632 |
| aaa caa gcc tta gaa aca gtc cag aga ttg ttg cct gtg ctg tgc caa<br>Lys Gln Ala Leu Glu Thr Val Gln Arg Leu Leu Pro Val Leu Cys Gln<br>545                          550                          555                          560 | 1680 |
| gcc cac ggc ctg acc cca gcc cag gtt gtg gcc atc gcc agc aac ata<br>Ala His Gly Leu Thr Pro Ala Gln Val Val Ala Ile Ala Ser Asn Ile<br>                          565                          570                          575 | 1728 |
| ggt ggc aag cag gcc ctc gaa acc gtc cag aga ctg tta ccg gtt ctc<br>Gly Gly Lys Gln Ala Leu Glu Thr Val Gln Arg Leu Leu Pro Val Leu<br>                   580                          585                          590 | 1776 |
| tgc cag gac cac ggc ctg acc cca gac caa gtt gtc gcg att gca agc<br>Cys Gln Asp His Gly Leu Thr Pro Asp Gln Val Val Ala Ile Ala Ser<br>                595                          600                          605 | 1824 |
| aac aac gga ggc aaa caa gcc tta gaa aca gtc cag aga ttg ttg ccg<br>Asn Asn Gly Gly Lys Gln Ala Leu Glu Thr Val Gln Arg Leu Leu Pro<br>610                          615                          620 | 1872 |
| gtg ctg tgc caa gac cac ggc ctg acc cca gaa caa gtt gtc gcg att<br>Val Leu Cys Gln Asp His Gly Leu Thr Pro Glu Gln Val Val Ala Ile<br>625                          630                          635                          640 | 1920 |
| gca agc aac aac gga ggc aaa caa gcc tta gaa aca gtc cag aga ttg<br>Ala Ser Asn Asn Gly Gly Lys Gln Ala Leu Glu Thr Val Gln Arg Leu<br>                          645                          650                          655 | 1968 |
| ttg ccg gtg ctg tgc caa gcc cac ggc ctg acc ccc gac cag gtt gtc<br>Leu Pro Val Leu Cys Gln Ala His Gly Leu Thr Pro Asp Gln Val Val<br>               660                          665                          670 | 2016 |
| gct att gct agt aac ggc gga ggc aaa cag gcg ctg gaa aca gtt cag<br>Ala Ile Ala Ser Asn Gly Gly Gly Lys Gln Ala Leu Glu Thr Val Gln<br>               675                          680                          685 | 2064 |
| cgc ctc ttg ccg gtc ttg tgt cag gcc cac ggc ctg acc ccg gcc cag<br>Arg Leu Leu Pro Val Leu Cys Gln Ala His Gly Leu Thr Pro Ala Gln<br>               690                          695                          700 | 2112 |
| gtg gtt gca atc gcg tca cac gat ggg gga aag cag gcc cta gaa acc<br>Val Val Ala Ile Ala Ser His Asp Gly Gly Lys Gln Ala Leu Glu Thr<br>705                          710                          715                          720 | 2160 |
| gtt cag cga ctc ctg ccc gtc ctg tgc cag gac cac ggc ctg acc cca<br>Val Gln Arg Leu Leu Pro Val Leu Cys Gln Asp His Gly Leu Thr Pro<br>                          725                          730                          735 | 2208 |
| gac caa gtt gtc gcg att gca agc aac aac gga ggc aaa caa gcc tta<br>Asp Gln Val Val Ala Ile Ala Ser Asn Asn Gly Gly Lys Gln Ala Leu<br>                          740                          745                          750 | 2256 |

```
gaa aca gtc cag aga ttg ttg ccg gtg ctg tgc caa gac cac ggc ctg      2304
Glu Thr Val Gln Arg Leu Leu Pro Val Leu Cys Gln Asp His Gly Leu
        755                 760                 765 acc ccg gaa cag gtg gtt gca atc gcg tca cac gat ggg gga aag cag      2352
Thr Pro Glu Gln Val Val Ala Ile Ala Ser His Asp Gly Gly Lys Gln
    770                 775                 780 gcc cta gaa acc gtt cag cga ctc ctg ccc gtc ctg tgc cag gcc cac      2400
Ala Leu Glu Thr Val Gln Arg Leu Leu Pro Val Leu Cys Gln Ala His
785                 790                 795                 800 ggc ctg acg cct gag cag gta gtg gct att gca tcc aac gga ggg ggc      2448
Gly Leu Thr Pro Glu Gln Val Val Ala Ile Ala Ser Asn Gly Gly Gly
                805                 810                 815 aga ccc gca ctg gag tca atc gtg gcc cag ctt tcg agg ccg gac ccc      2496
Arg Pro Ala Leu Glu Ser Ile Val Ala Gln Leu Ser Arg Pro Asp Pro
            820                 825                 830 gcg ctg gcc gca ctc act aat gat cat ctt gta gcg ctg gcc tgc ctc      2544
Ala Leu Ala Ala Leu Thr Asn Asp His Leu Val Ala Leu Ala Cys Leu
        835                 840                 845 ggc gga cgt cct gcc atg gat gca gtg aaa aag gga ttg ccg cac gcg      2592
Gly Gly Arg Pro Ala Met Asp Ala Val Lys Lys Gly Leu Pro His Ala
    850                 855                 860 ccg gaa ttg atc aga tcc cag cta gtg aaa tct gaa ttg gaa gag aag      2640
Pro Glu Leu Ile Arg Ser Gln Leu Val Lys Ser Glu Leu Glu Glu Lys
865                 870                 875                 880 aaa tct gaa ctt aga cat aaa ttg aaa tat gtg cca cat gaa tat att      2688
Lys Ser Glu Leu Arg His Lys Leu Lys Tyr Val Pro His Glu Tyr Ile
                885                 890                 895 gaa ttg att gaa atc gca aga aat tca act cag gat aga atc ctt gaa      2736
Glu Leu Ile Glu Ile Ala Arg Asn Ser Thr Gln Asp Arg Ile Leu Glu
            900                 905                 910 atg aag gtg atg gag ttc ttt atg aag gtt tat ggt tat cgt ggt aaa      2784
Met Lys Val Met Glu Phe Phe Met Lys Val Tyr Gly Tyr Arg Gly Lys
        915                 920                 925 cat ttg ggt gga tca agg aaa cca gac gga gca att tat act gtc gga      2832
His Leu Gly Gly Ser Arg Lys Pro Asp Gly Ala Ile Tyr Thr Val Gly
    930                 935                 940 tct cct att gat tac ggt gtg atc gtt gat act aag gca tat tca gga      2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc      2928
Gly Tyr Asn Leu Pro Ile Gly Gln Ala Asp Glu Met Gln Arg Tyr Val
                965                 970                 975 gaa gag aat caa aca aga aac aag cat atc aac cct aat gaa tgg tgg      2976
Glu Glu Asn Gln Thr Arg Asn Lys His Ile Asn Pro Asn Glu Trp Trp
            980                 985                 990 aaa gtc tat cca tct tca gta aca gaa ttt aag ttc ttg ttt gtg agt     3024
Lys Val Tyr Pro Ser Ser Val Thr Glu Phe Lys Phe Leu Phe Val Ser
        995                 1000                1005 ggt cat ttc aaa gga aac tac aaa gct cag ctt aca aga ttg aat         3069
Gly His Phe Lys Gly Asn Tyr Lys Ala Gln Leu Thr Arg Leu Asn
    1010                1015                1020 cat atc act aat tgt aat gga gct gtt ctt agt gta gaa gag ctt         3114
His Ile Thr Asn Cys Asn Gly Ala Val Leu Ser Val Glu Glu Leu
1025                1030                1035 ttg att ggt gga gaa atg att aaa gct ggt aca ttg aca ctt gag         3159
Leu Ile Gly Gly Glu Met Ile Lys Ala Gly Thr Leu Thr Leu Glu
        1040                1045                1050 gaa gtg aga agg aaa ttt aat aac ggt gag ata aac ttt taa             3201
Glu Val Arg Arg Lys Phe Asn Asn Gly Glu Ile Asn Phe
```

1055                1060                1065

<210> SEQ ID NO 57
<211> LENGTH: 1066
<212> TYPE: PRT
<213> ORGANISM: artificial sequence
<220> FEATURE:
<223> OTHER INFORMATION: Synthetic Construct

<400> SEQUENCE: 57

Met Ala Ser Ser Pro Lys Lys Arg Lys Val Ala Ala Ala Asp
1               5                   10                  15

Tyr Lys Asp Asp Asp Asp Lys Ser Trp Lys Asp Ala Ser Gly Trp Ser
            20                  25                  30

Arg Met His Ala Ala Pro Arg Arg Ala Ala Gln Pro Ser Asp Ala
        35                  40                  45

Ser Pro Ala Ala Gln Val Asp Leu Arg Thr Leu Gly Tyr Ser Gln Gln
    50                  55                  60

Gln Gln Glu Lys Ile Lys Pro Lys Val Arg Ser Thr Val Ala Gln His
65                  70                  75                  80

His Glu Ala Leu Val Gly His Gly Phe Thr His Ala His Ile Val Ala
                85                  90                  95

Leu Ser Gln His Pro Ala Ala Leu Gly Thr Val Ala Val Thr Tyr Gln
            100                 105                 110

His Ile Ile Thr Ala Leu Pro Glu Ala Thr His Glu Asp Ile Val Gly
        115                 120                 125

Val Gly Lys Gln Trp Ser Gly Ala Arg Ala Leu Glu Ala Leu Leu Thr
130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
                165                 170                 175

His Ala Ser Arg Asn Ala Leu Thr Gly Ala Pro Leu Asn Leu Thr Pro
            180                 185                 190

Asp Gln Val Val Ala Ile Ala Ser Asn Asn Gly Gly Lys Gln Ala Leu
        195                 200                 205

Glu Thr Val Gln Arg Leu Leu Pro Val Leu Cys Gln Asp His Gly Leu
210                 215                 220

Thr Pro Glu Gln Val Val Ala Ile Ala Ser Asn Gly Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser Asn Gly Gly Gly
            260                 265                 270

Lys Gln Ala Leu Glu Thr Val Gln Arg Leu Leu Pro Val Leu Cys Gln
        275                 280                 285

Ala His Gly Leu Thr Pro Ala Gln Val Val Ala Ile Ala Ser His Asp
290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

His Asp Gly Gly Lys Gln Ala Leu Glu Thr Val Gln Arg Leu Leu Pro
            340                 345                 350

Val Leu Cys Gln Asp His Gly Leu Thr Pro Glu Gln Val Val Ala Ile

-continued

```
              355                 360                 365
Ala Ser His Asp Gly Lys Gln Ala Leu Glu Thr Val Gln Arg Leu
370                 375                 380

Leu Pro Val Leu Cys Gln Ala His Gly Leu Thr Pro Asp Gln Val Val
385                 390                 395                 400

Ala Ile Ala Ser Asn Ile Gly Gly Lys Gln Ala Leu Glu Thr Val Gln
                405                 410                 415

Arg Leu Leu Pro Val Leu Cys Gln Ala His Gly Leu Thr Pro Ala Gln
            420                 425                 430

Val Val Ala Ile Ala Ser His Asp Gly Gly Lys Gln Ala Leu Glu Thr
        435                 440                 445

Val Gln Arg Leu Leu Pro Val Leu Cys Gln Asp His Gly Leu Thr Pro
    450                 455                 460

Asp Gln Val Val Ala Ile Ala Ser His Asp Gly Gly Lys Gln Ala Leu
465                 470                 475                 480

Glu Thr Val Gln Arg Leu Leu Pro Val Leu Cys Gln Asp His Gly Leu
                485                 490                 495

Thr Pro Glu Gln Val Val Ala Ile Ala Ser His Asp Gly Gly Lys Gln
            500                 505                 510

Ala Leu Glu Thr Val Gln Arg Leu Leu Pro Val Leu Cys Gln Ala His
        515                 520                 525

Gly Leu Thr Pro Asp Gln Val Val Ala Ile Ala Ser Asn Asn Gly Gly
    530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser Asn Ile
                565                 570                 575

Gly Gly Lys Gln Ala Leu Glu Thr Val Gln Arg Leu Leu Pro Val Leu
            580                 585                 590

Cys Gln Asp His Gly Leu Thr Pro Asp Gln Val Val Ala Ile Ala Ser
        595                 600                 605

Asn Asn Gly Gly Lys Gln Ala Leu Glu Thr Val Gln Arg Leu Leu Pro
    610                 615                 620

Val Leu Cys Gln Asp His Gly Leu Thr Pro Glu Gln Val Val Ala Ile
625                 630                 635                 640

Ala Ser Asn Asn Gly Gly Lys Gln Ala Leu Glu Thr Val Gln Arg Leu
                645                 650                 655

Leu Pro Val Leu Cys Gln Ala His Gly Leu Thr Pro Asp Gln Val Val
            660                 665                 670

Ala Ile Ala Ser Asn Gly Gly Gly Lys Gln Ala Leu Glu Thr Val Gln
        675                 680                 685

Arg Leu Leu Pro Val Leu Cys Gln Ala His Gly Leu Thr Pro Ala Gln
    690                 695                 700

Val Val Ala Ile Ala Ser His Asp Gly Gly Lys Gln Ala Leu Glu Thr
705                 710                 715                 720

Val Gln Arg Leu Leu Pro Val Leu Cys Gln Asp His Gly Leu Thr Pro
                725                 730                 735

Asp Gln Val Val Ala Ile Ala Ser Asn Asn Gly Gly Lys Gln Ala Leu
            740                 745                 750

Glu Thr Val Gln Arg Leu Leu Pro Val Leu Cys Gln Asp His Gly Leu
        755                 760                 765

Thr Pro Glu Gln Val Val Ala Ile Ala Ser His Asp Gly Gly Lys Gln
    770                 775                 780
```

-continued

```
Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser Asn Gly Gly Gly
            805                 810                 815

Arg Pro Ala Leu Glu Ser Ile Val Ala Gln Leu Ser Arg Pro Asp Pro
        820                 825                 830

Ala Leu Ala Ala Leu Thr Asn Asp His Leu Val Ala Leu Ala Cys Leu
    835                 840                 845

Gly Gly Arg Pro Ala Met Asp Ala Val Lys Lys Gly Leu Pro His Ala
850                 855                 860

Pro Glu Leu Ile Arg Ser Gln Leu Val Lys Ser Glu Leu Glu Glu Lys
865                 870                 875                 880

Lys Ser Glu Leu Arg His Lys Leu Lys Tyr Val Pro His Glu Tyr Ile
                885                 890                 895

Glu Leu Ile Glu Ile Ala Arg Asn Ser Thr Gln Asp Arg Ile Leu Glu
            900                 905                 910

Met Lys Val Met Glu Phe Phe Met Lys Val Tyr Gly Tyr Arg Gly Lys
        915                 920                 925

His Leu Gly Gly Ser Arg Lys Pro Asp Gly Ala Ile Tyr Thr Val Gly
    930                 935                 940

Ser Pro Ile Asp Tyr Gly Val Ile Val Asp Thr Lys Ala Tyr Ser Gly
945                 950                 955                 960

Gly Tyr Asn Leu Pro Ile Gly Gln Ala Asp Glu Met Gln Arg Tyr Val
                965                 970                 975

Glu Glu Asn Gln Thr Arg Asn Lys His Ile Asn Pro Asn Glu Trp Trp
            980                 985                 990

Lys Val Tyr Pro Ser Ser Val Thr Glu Phe Lys Phe Leu Phe Val Ser
        995                 1000                1005

Gly His Phe Lys Gly Asn Tyr Lys Ala Gln Leu Thr Arg Leu Asn
    1010                1015                1020

His Ile Thr Asn Cys Asn Gly Ala Val Leu Ser Val Glu Glu Leu
    1025                1030                1035

Leu Ile Gly Gly Glu Met Ile Lys Ala Gly Thr Leu Thr Leu Glu
    1040                1045                1050

Glu Val Arg Arg Lys Phe Asn Asn Gly Glu Ile Asn Phe
    1055                1060                1065

<210> SEQ ID NO 58
<211> LENGTH: 3201
<212> TYPE: DNA
<213> ORGANISM: artificial sequence
<220> FEATURE:
<223> OTHER INFORMATION: TALEN-TCR-beta1_R19 TALEN coding sequence
<220> FEATURE:
<221> NAME/KEY: CDS
<222> LOCATION: (1)..(3201)

<400> SEQUENCE: 58 atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
            20                  25                  30 aga atg cat gcg gcc ccg cga cgg cgt gct gcg caa ccc tcc gac gct     144
Arg Met His Ala Ala Pro Arg Arg Arg Ala Ala Gln Pro Ser Asp Ala
        35                  40                  45
```

| | | |
|---|---|---|
| tcg ccg gcc gcg cag gtg gat cta cgc acg ctc ggc tac agt cag cag<br>Ser Pro Ala Ala Gln Val Asp Leu Arg Thr Leu Gly Tyr Ser Gln Gln<br>50                  55                  60 | | 192 |
| cag caa gag aag atc aaa ccg aag gtg cgt tcg aca gtg gcg cag cac<br>Gln Gln Glu Lys Ile Lys Pro Lys Val Arg Ser Thr Val Ala Gln His<br>65                    70                  75                  80 | | 240 |
| cac gag gca ctg gtg ggc cat ggg ttt aca cac gcg cac atc gtt gcg<br>His Glu Ala Leu Val Gly His Gly Phe Thr His Ala His Ile Val Ala<br>                          85                          90                          95 | | 288 |
| ctc agc caa cac ccg gca gcg tta ggg acc gtc gct gtc acg tat cag<br>Leu Ser Gln His Pro Ala Ala Leu Gly Thr Val Ala Val Thr Tyr Gln<br>                    100                        105                        110 | | 336 |
| cac ata atc acg gcg ttg cca gag gcg aca cac gaa gac atc gtt ggc<br>His Ile Ile Thr Ala Leu Pro Glu Ala Thr His Glu Asp Ile Val Gly<br>                  115                        120                        125 | | 384 |
| gtc ggc aaa cag tgg tcc ggc gca cgc gcc ctg gag gcc ttg ctc acg<br>Val Gly Lys Gln Trp Ser Gly Ala Arg Ala Leu Glu Ala Leu Leu Thr<br>130                  135                        140 | | 432 |
| gat gcg ggg gag ttg aga ggt ccg ccg tta cag ttg gac aca ggc caa<br>Asp Ala Gly Glu Leu Arg Gly Pro Pro Leu Gln Leu Asp Thr Gly Gln<br>145                  150                  155                  160 | | 480 |
| ctt gtg aag att gca aaa cgt ggc ggc gtg acc gca atg gag gca gtg<br>Leu Val Lys Ile Ala Lys Arg Gly Gly Val Thr Ala Met Glu Ala Val<br>                  165                        170                        175 | | 528 |
| cat gca tcg cgc aat gcg ctc acg gga gca ccc ctc aac ctg acc cca<br>His Ala Ser Arg Asn Ala Leu Thr Gly Ala Pro Leu Asn Leu Thr Pro<br>                  180                        185                        190 | | 576 |
| gac caa gtt gtc gcg att gca agc aac aac gga ggc aaa caa gcc tta<br>Asp Gln Val Val Ala Ile Ala Ser Asn Asn Gly Gly Lys Gln Ala Leu<br>195                  200                        205 | | 624 |
| gaa aca gtc cag aga ttg ttg ccg gtg ctg tgc caa gac cac ggc ctg<br>Glu Thr Val Gln Arg Leu Leu Pro Val Leu Cys Gln Asp His Gly Leu<br>                  210                        215                        220 | | 672 |
| acc ccc gaa cag gtt gtc gct att gct agt aac ggc gga ggc aaa cag<br>Thr Pro Glu Gln Val Val Ala Ile Ala Ser Asn Gly Gly Gly Lys Gln<br>225                  230                  235                  240 | | 720 |
| gcg ctg gaa aca gtt cag cgc ctc ttg ccg gtc ttg tgt cag gcc cac<br>Ala Leu Glu Thr Val Gln Arg Leu Leu Pro Val Leu Cys Gln Ala His<br>                          245                        250                        255 | | 768 |
| ggc ctg acc cca gac caa gtt gtc gcg att gca agc aac aac gga ggc<br>Gly Leu Thr Pro Asp Gln Val Val Ala Ile Ala Ser Asn Asn Gly Gly<br>                  260                        265                        270 | | 816 |
| aaa caa gcc tta gaa aca gtc cag aga ttg ttg cct gtg ctg tgc caa<br>Lys Gln Ala Leu Glu Thr Val Gln Arg Leu Leu Pro Val Leu Cys Gln<br>                  275                        280                        285 | | 864 |
| gcc cac ggc ctg acc cca gcc caa gtt gtc gcg att gca agc aac aac<br>Ala His Gly Leu Thr Pro Ala Gln Val Val Ala Ile Ala Ser Asn Asn<br>290                  295                  300 | | 912 |
| gga ggc aaa caa gcc tta gaa aca gtc cag aga ttg ttg ccg gtg ctg<br>Gly Gly Lys Gln Ala Leu Glu Thr Val Gln Arg Leu Leu Pro Val Leu<br>305                  310                  315                  320 | | 960 |
| tgc caa gac cac ggc ctg acc cca gac caa gtt gtc gcg att gca agc<br>Cys Gln Asp His Gly Leu Thr Pro Asp Gln Val Val Ala Ile Ala Ser<br>                  325                        330                        335 | | 1008 |
| aac aac gga ggc aaa caa gcc tta gaa aca gtc cag aga ttg ttg ccg<br>Asn Asn Gly Gly Lys Gln Ala Leu Glu Thr Val Gln Arg Leu Leu Pro<br>                  340                        345                        350 | | 1056 |
| gtg ctg tgc caa gac cac ggc ctg acc cca gaa cag gtt gtg gcc atc<br>Val Leu Cys Gln Asp His Gly Leu Thr Pro Glu Gln Val Val Ala Ile | | 1104 |

```
                355                 360                 365
gcc agc aac ata ggt ggc aag cag gcc ctc gaa acc gtc cag aga ctg    1152
Ala Ser Asn Ile Gly Gly Lys Gln Ala Leu Glu Thr Val Gln Arg Leu
370                 375                 380 tta ccg gtt ctc tgc cag gcc cac ggc ctg acc cca gac caa gtt gtc    1200
Leu Pro Val Leu Cys Gln Ala His Gly Leu Thr Pro Asp Gln Val Val
385                 390                 395                 400 gcg att gca agc aac aac gga ggc aaa caa gcc tta gaa aca gtc cag    1248
Ala Ile Ala Ser Asn Asn Gly Gly Lys Gln Ala Leu Glu Thr Val Gln
            405                 410                 415 aga ttg ttg cct gtg ctg tgc caa gcc cac ggc ctg acc cca gcc cag    1296
Arg Leu Leu Pro Val Leu Cys Gln Ala His Gly Leu Thr Pro Ala Gln
        420                 425                 430 gtt gtg gcc atc gcc agc aac ata ggt ggc aag cag gcc ctc gaa acc    1344
Val Val Ala Ile Ala Ser Asn Ile Gly Gly Lys Gln Ala Leu Glu Thr
    435                 440                 445 gtc cag aga ctg tta ccg gtt ctc tgc cag gac cac ggc ctg acc ccc    1392
Val Gln Arg Leu Leu Pro Val Leu Cys Gln Asp His Gly Leu Thr Pro
450                 455                 460 gac cag gtt gtc gct att gct agt aac ggc gga ggc aaa cag gcg ctg    1440
Asp Gln Val Val Ala Ile Ala Ser Asn Gly Gly Gly Lys Gln Ala Leu
465                 470                 475                 480 gaa aca gtt cag cgc ctc ttg ccg gtc ttg tgt cag gac cac ggc ctg    1488
Glu Thr Val Gln Arg Leu Leu Pro Val Leu Cys Gln Asp His Gly Leu
            485                 490                 495 acc ccg gaa cag gtg gtt gca atc gcg tca cac gat ggg gga aag cag    1536
Thr Pro Glu Gln Val Val Ala Ile Ala Ser His Asp Gly Gly Lys Gln
        500                 505                 510 gcc cta gaa acc gtt cag cga ctc ctg ccc gtc ctg tgc cag gcc cac    1584
Ala Leu Glu Thr Val Gln Arg Leu Leu Pro Val Leu Cys Gln Ala His
    515                 520                 525 ggc ctg acc ccc gac cag gtt gtc gct att gct agt aac ggc gga ggc    1632
Gly Leu Thr Pro Asp Gln Val Val Ala Ile Ala Ser Asn Gly Gly Gly
530                 535                 540 aaa cag gcg ctg gaa aca gtt cag cgc ctc ttg ccg gtc ttg tgt cag    1680
Lys Gln Ala Leu Glu Thr Val Gln Arg Leu Leu Pro Val Leu Cys Gln
545                 550                 555                 560 gcc cac ggc ctg acc ccg gcc cag gtg gtt gca atc gcg tca cac gat    1728
Ala His Gly Leu Thr Pro Ala Gln Val Val Ala Ile Ala Ser His Asp
            565                 570                 575 ggg gga aag cag gcc cta gaa acc gtt cag cga ctc ctg ccc gtc ctg    1776
Gly Gly Lys Gln Ala Leu Glu Thr Val Gln Arg Leu Leu Pro Val Leu
        580                 585                 590 tgc cag gac cac ggc ctg acc ccc gac cag gtt gtc gct att gct agt    1824
Cys Gln Asp His Gly Leu Thr Pro Asp Gln Val Val Ala Ile Ala Ser
    595                 600                 605 aac ggc gga ggc aaa cag gcg ctg gaa aca gtt cag cgc ctc ttg ccg    1872
Asn Gly Gly Gly Lys Gln Ala Leu Glu Thr Val Gln Arg Leu Leu Pro
610                 615                 620 gtc ttg tgt cag gac cac ggc ctg acc cca gaa caa gtt gtc gcg att    1920
Val Leu Cys Gln Asp His Gly Leu Thr Pro Glu Gln Val Val Ala Ile
625                 630                 635                 640 gca agc aac aac gga ggc aaa caa gcc tta gaa aca gtc cag aga ttg    1968
Ala Ser Asn Asn Gly Gly Lys Gln Ala Leu Glu Thr Val Gln Arg Leu
            645                 650                 655 ttg ccg gtg ctg tgc caa gcc cac ggc ctg acc ccg gac cag gtg gtt    2016
Leu Pro Val Leu Cys Gln Ala His Gly Leu Thr Pro Asp Gln Val Val
        660                 665                 670 gca atc gcg tca cac gat ggg gga aag cag gcc cta gaa acc gtt cag    2064
Ala Ile Ala Ser His Asp Gly Gly Lys Gln Ala Leu Glu Thr Val Gln
```

```
                Ala Ile Ala Ser His Asp Gly Gly Lys Gln Ala Leu Glu Thr Val Gln
                        675                 680                 685 cga ctc ctg ccc gtc ctg tgc cag gcc cac ggc ctg acc ccc gcc cag              2112
Arg Leu Leu Pro Val Leu Cys Gln Ala His Gly Leu Thr Pro Ala Gln
        690                 695                 700 gtt gtc gct att gct agt aac ggc gga ggc aaa cag gcg ctg gaa aca              2160
Val Val Ala Ile Ala Ser Asn Gly Gly Gly Lys Gln Ala Leu Glu Thr
705                 710                 715                 720 gtt cag cgc ctc ttg ccg gtc ttg tgt cag gac cac ggc ctg acc ccc              2208
Val Gln Arg Leu Leu Pro Val Leu Cys Gln Asp His Gly Leu Thr Pro
                725                 730                 735 gac cag gtt gtc gct att gct agt aac ggc gga ggc aaa cag gcg ctg              2256
Asp Gln Val Val Ala Ile Ala Ser Asn Gly Gly Gly Lys Gln Ala Leu
            740                 745                 750 gaa aca gtt cag cgc ctc ttg ccg gtc ttg tgt cag gac cac ggc ctg              2304
Glu Thr Val Gln Arg Leu Leu Pro Val Leu Cys Gln Asp His Gly Leu
        755                 760                 765 acc ccg gaa cag gtg gtt gca atc gcg tca cac gat ggg gga aag cag              2352
Thr Pro Glu Gln Val Val Ala Ile Ala Ser His Asp Gly Gly Lys Gln
770                 775                 780 gcc cta gaa acc gtt cag cga ctc ctg ccc gtc ctg tgc cag gcc cac              2400
Ala Leu Glu Thr Val Gln Arg Leu Leu Pro Val Leu Cys Gln Ala His
785                 790                 795                 800 ggc ctg acg cct gag cag gta gtg gct att gca tcc aac gga ggg ggc              2448
Gly Leu Thr Pro Glu Gln Val Val Ala Ile Ala Ser Asn Gly Gly Gly
                805                 810                 815 aga ccc gca ctg gag tca atc gtg gcc cag ctt tcg agg ccg gac ccc              2496
Arg Pro Ala Leu Glu Ser Ile Val Ala Gln Leu Ser Arg Pro Asp Pro
            820                 825                 830 gcg ctg gcc gca ctc act aat gat cat ctt gta gcg ctg gcc tgc ctc              2544
Ala Leu Ala Ala Leu Thr Asn Asp His Leu Val Ala Leu Ala Cys Leu
        835                 840                 845 ggc gga cgt cct gcc atg gat gca gtg aaa aag gga ttg ccg cac gcg              2592
Gly Gly Arg Pro Ala Met Asp Ala Val Lys Lys Gly Leu Pro His Ala
850                 855                 860 ccg gaa ttg atc aga tcc cag cta gtg aaa tct gaa ttg gaa gag aag              2640
Pro Glu Leu Ile Arg Ser Gln Leu Val Lys Ser Glu Leu Glu Glu Lys
865                 870                 875                 880 aaa tct gaa ctt aga cat aaa ttg aaa tat gtg cca cat gaa tat att              2688
Lys Ser Glu Leu Arg His Lys Leu Lys Tyr Val Pro His Glu Tyr Ile
                885                 890                 895 gaa ttg att gaa atc gca aga aat tca act cag gat aga atc ctt gaa              2736
Glu Leu Ile Glu Ile Ala Arg Asn Ser Thr Gln Asp Arg Ile Leu Glu
            900                 905                 910 atg aag gtg atg gag ttc ttt atg aag gtt tat ggt tat cgt ggt aaa              2784
Met Lys Val Met Glu Phe Phe Met Lys Val Tyr Gly Tyr Arg Gly Lys
        915                 920                 925 cat ttg ggt gga tca agg aaa cca gac gga gca att tat act gtc gga              2832
His Leu Gly Gly Ser Arg Lys Pro Asp Gly Ala Ile Tyr Thr Val Gly
930                 935                 940 tct cct att gat tac ggt gtg atc gtt gat act aag gca tat tca gga              2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc              2928
Gly Tyr Asn Leu Pro Ile Gly Gln Ala Asp Glu Met Gln Arg Tyr Val
                965                 970                 975 gaa gag aat caa aca aga aac aag cat atc aac cct aat gaa tgg tgg              2976
Glu Glu Asn Gln Thr Arg Asn Lys His Ile Asn Pro Asn Glu Trp Trp
            980                 985                 990
```

| | | | | | | | | | | | | | | | |
|---|---|---|---|---|---|---|---|---|---|---|---|---|---|---|---|
|aaa|gtc|tat|cca|tct|tca|gta|aca|gaa|ttt|aag|ttc|ttg|ttt|gtg|agt|
|Lys|Val|Tyr|Pro|Ser|Ser|Val|Thr|Glu|Phe|Lys|Phe|Leu|Phe|Val|Ser|
| |  |995| | | |1000| | | |1005| | | | | |

3024

| | | | | | | | | | | | | | | |
|---|---|---|---|---|---|---|---|---|---|---|---|---|---|---|
|ggt|cat|ttc|aaa|gga|aac|tac|aaa|gct|cag|ctt|aca|aga|ttg|aat|
|Gly|His|Phe|Lys|Gly|Asn|Tyr|Lys|Ala|Gln|Leu|Thr|Arg|Leu|Asn|
| |1010| | | | |1015| | | | |1020| | | |

3069

| | | | | | | | | | | | | | | |
|---|---|---|---|---|---|---|---|---|---|---|---|---|---|---|
|cat|atc|act|aat|tgt|aat|gga|gct|gtt|ctt|agt|gta|gaa|gag|ctt|
|His|Ile|Thr|Asn|Cys|Asn|Gly|Ala|Val|Leu|Ser|Val|Glu|Glu|Leu|
| | |1025| | | | |1030| | | | |1035| | |

3114

| | | | | | | | | | | | | | | |
|---|---|---|---|---|---|---|---|---|---|---|---|---|---|---|
|ttg|att|ggt|gga|gaa|atg|att|aaa|gct|ggt|aca|ttg|aca|ctt|gag|
|Leu|Ile|Gly|Gly|Glu|Met|Ile|Lys|Ala|Gly|Thr|Leu|Thr|Leu|Glu|
| |1040| | | | |1045| | | | |1050| | | |

3159

| | | | | | | | | | | | | |
|---|---|---|---|---|---|---|---|---|---|---|---|---|
|gaa|gtg|aga|agg|aaa|ttt|aat|aac|ggt|gag|ata|aac|ttt|taa|
|Glu|Val|Arg|Arg|Lys|Phe|Asn|Asn|Gly|Glu|Ile|Asn|Phe| |
| |1055| | | | |1060| | | | |1065| | |

3201

<210> SEQ ID NO 59
<211> LENGTH: 1066
<212> TYPE: PRT
<213> ORGANISM: artificial sequence
<220> FEATURE:
<223> OTHER INFORMATION: Synthetic Construct

<400> SEQUENCE: 59

Met Ala Ser Ser Pro Lys Lys Arg Lys Val Ala Ala Asp
1               5                   10                  15

Tyr Lys Asp Asp Asp Lys Ser Trp Lys Asp Ala Ser Gly Trp Ser
            20                  25                  30

Arg Met His Ala Ala Pro Arg Arg Ala Ala Gln Pro Ser Asp Ala
        35                  40                  45

Ser Pro Ala Ala Gln Val Asp Leu Arg Thr Leu Gly Tyr Ser Gln Gln
    50                  55                  60

Gln Gln Glu Lys Ile Lys Pro Lys Val Arg Ser Thr Val Ala Gln His
65                  70                  75                  80

His Glu Ala Leu Val Gly His Gly Phe Thr Ala His Ile Val Ala
                85                  90                  95

Leu Ser Gln His Pro Ala Ala Leu Gly Thr Val Ala Val Thr Tyr Gln
            100                 105                 110

His Ile Ile Thr Ala Leu Pro Glu Ala Thr His Glu Asp Ile Val Gly
        115                 120                 125

Val Gly Lys Gln Trp Ser Gly Ala Arg Ala Leu Glu Ala Leu Leu Thr
    130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
                165                 170                 175

His Ala Ser Arg Asn Ala Leu Thr Gly Ala Pro Leu Asn Leu Thr Pro
            180                 185                 190

Asp Gln Val Val Ala Ile Ala Ser Asn Asn Gly Gly Lys Gln Ala Leu
        195                 200                 205

Glu Thr Val Gln Arg Leu Leu Pro Val Leu Cys Gln Asp His Gly Leu
    210                 215                 220

Thr Pro Glu Gln Val Val Ala Ile Ala Ser Asn Gly Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser Asn Asn Gly Gly

```
                260                 265                 270
Lys Gln Ala Leu Glu Thr Val Gln Arg Leu Leu Pro Val Leu Cys Gln
            275                 280                 285

Ala His Gly Leu Thr Pro Ala Gln Val Val Ala Ile Ala Ser Asn Asn
            290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

Asn Asn Gly Gly Lys Gln Ala Leu Glu Thr Val Gln Arg Leu Leu Pro
            340                 345                 350

Val Leu Cys Gln Asp His Gly Leu Thr Pro Glu Gln Val Val Ala Ile
            355                 360                 365

Ala Ser Asn Ile Gly Gly Lys Gln Ala Leu Glu Thr Val Gln Arg Leu
            370                 375                 380

Leu Pro Val Leu Cys Gln Ala His Gly Leu Thr Pro Asp Gln Val Val
385                 390                 395                 400

Ala Ile Ala Ser Asn Asn Gly Gly Lys Gln Ala Leu Glu Thr Val Gln
                405                 410                 415

Arg Leu Leu Pro Val Leu Cys Gln Ala His Gly Leu Thr Pro Ala Gln
            420                 425                 430

Val Val Ala Ile Ala Ser Asn Ile Gly Gly Lys Gln Ala Leu Glu Thr
            435                 440                 445

Val Gln Arg Leu Leu Pro Val Leu Cys Gln Asp His Gly Leu Thr Pro
            450                 455                 460

Asp Gln Val Val Ala Ile Ala Ser Asn Gly Gly Gly Lys Gln Ala Leu
465                 470                 475                 480

Glu Thr Val Gln Arg Leu Leu Pro Val Leu Cys Gln Asp His Gly Leu
                485                 490                 495

Thr Pro Glu Gln Val Val Ala Ile Ala Ser His Asp Gly Gly Lys Gln
            500                 505                 510

Ala Leu Glu Thr Val Gln Arg Leu Leu Pro Val Leu Cys Gln Ala His
            515                 520                 525

Gly Leu Thr Pro Asp Gln Val Val Ala Ile Ala Ser Asn Gly Gly Gly
            530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser His Asp
                565                 570                 575

Gly Gly Lys Gln Ala Leu Glu Thr Val Gln Arg Leu Leu Pro Val Leu
            580                 585                 590

Cys Gln Asp His Gly Leu Thr Pro Asp Gln Val Val Ala Ile Ala Ser
            595                 600                 605

Asn Gly Gly Gly Lys Gln Ala Leu Glu Thr Val Gln Arg Leu Leu Pro
610                 615                 620

Val Leu Cys Gln Asp His Gly Leu Thr Pro Glu Gln Val Val Ala Ile
625                 630                 635                 640

Ala Ser Asn Asn Gly Gly Lys Gln Ala Leu Glu Thr Val Gln Arg Leu
                645                 650                 655

Leu Pro Val Leu Cys Gln Ala His Gly Leu Thr Pro Asp Gln Val Val
            660                 665                 670

Ala Ile Ala Ser His Asp Gly Gly Lys Gln Ala Leu Glu Thr Val Gln
            675                 680                 685
```

Arg Leu Leu Pro Val Leu Cys Gln Ala His Gly Leu Thr Pro Ala Gln
690                 695                 700

Val Val Ala Ile Ala Ser Asn Gly Gly Gly Lys Gln Ala Leu Glu Thr
705                 710                 715                 720

Val Gln Arg Leu Leu Pro Val Leu Cys Gln Asp His Gly Leu Thr Pro
            725                 730                 735

Asp Gln Val Val Ala Ile Ala Ser Asn Gly Gly Gly Lys Gln Ala Leu
        740                 745                 750

Glu Thr Val Gln Arg Leu Leu Pro Val Leu Cys Gln Asp His Gly Leu
    755                 760                 765

Thr Pro Glu Gln Val Val Ala Ile Ala Ser His Asp Gly Gly Lys Gln
770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser Asn Gly Gly Gly
            805                 810                 815

Arg Pro Ala Leu Glu Ser Ile Val Ala Gln Leu Ser Arg Pro Asp Pro
            820                 825                 830

Ala Leu Ala Ala Leu Thr Asn Asp His Leu Val Ala Leu Ala Cys Leu
        835                 840                 845

Gly Gly Arg Pro Ala Met Asp Ala Val Lys Lys Gly Leu Pro His Ala
850                 855                 860

Pro Glu Leu Ile Arg Ser Gln Leu Val Lys Ser Glu Leu Glu Glu Lys
865                 870                 875                 880

Lys Ser Glu Leu Arg His Lys Leu Lys Tyr Val Pro His Glu Tyr Ile
            885                 890                 895

Glu Leu Ile Glu Ile Ala Arg Asn Ser Thr Gln Asp Arg Ile Leu Glu
            900                 905                 910

Met Lys Val Met Glu Phe Phe Met Lys Val Tyr Gly Tyr Arg Gly Lys
            915                 920                 925

His Leu Gly Gly Ser Arg Lys Pro Asp Gly Ala Ile Tyr Thr Val Gly
930                 935                 940

Ser Pro Ile Asp Tyr Gly Val Ile Val Asp Thr Lys Ala Tyr Ser Gly
945                 950                 955                 960

Gly Tyr Asn Leu Pro Ile Gly Gln Ala Asp Glu Met Gln Arg Tyr Val
            965                 970                 975

Glu Glu Asn Gln Thr Arg Asn Lys His Ile Asn Pro Asn Glu Trp Trp
        980                 985                 990

Lys Val Tyr Pro Ser Ser Val Thr Glu Phe Lys Phe Leu Phe Val Ser
            995                 1000                1005

Gly His Phe Lys Gly Asn Tyr Lys Ala Gln Leu Thr Arg Leu Asn
    1010                1015                1020

His Ile Thr Asn Cys Asn Gly Ala Val Leu Ser Val Glu Glu Leu
    1025                1030                1035

Leu Ile Gly Gly Glu Met Ile Lys Ala Gly Thr Leu Thr Leu Glu
    1040                1045                1050

Glu Val Arg Arg Lys Phe Asn Asn Gly Glu Ile Asn Phe
    1055                1060                1065

<210> SEQ ID NO 60
<211> LENGTH: 3201
<212> TYPE: DNA
<213> ORGANISM: artificial sequence
<220> FEATURE:

<223> OTHER INFORMATION: TALEN-TCR-beta3_L19 TALEN coding sequence
<220> FEATURE:
<221> NAME/KEY: CDS
<222> LOCATION: (1)..(3201)

<400> SEQUENCE: 60

```
atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
                20                  25                  30 aga atg cat gcg gcc ccg cga cgg cgt gct gcg caa ccc tcc gac gct     144
Arg Met His Ala Ala Pro Arg Arg Arg Ala Ala Gln Pro Ser Asp Ala
            35                  40                  45 tcg ccg gcc gcg cag gtg gat cta cgc acg ctc ggc tac agt cag cag     192
Ser Pro Ala Ala Gln Val Asp Leu Arg Thr Leu Gly Tyr Ser Gln Gln
        50                  55                  60 cag caa gag aag atc aaa ccg aag gtg cgt tcg aca gtg gcg cag cac     240
Gln Gln Glu Lys Ile Lys Pro Lys Val Arg Ser Thr Val Ala Gln His
65                  70                  75                  80 cac gag gca ctg gtg ggc cat ggg ttt aca cac gcg cac atc gtt gcg     288
His Glu Ala Leu Val Gly His Gly Phe Thr His Ala His Ile Val Ala
                85                  90                  95 ctc agc caa cac ccg gca gcg tta ggg acc gtc gct gtc acg tat cag     336
Leu Ser Gln His Pro Ala Ala Leu Gly Thr Val Ala Val Thr Tyr Gln
            100                 105                 110 cac ata atc acg gcg ttg cca gag gcg aca cac gaa gac atc gtt ggc     384
His Ile Ile Thr Ala Leu Pro Glu Ala Thr His Glu Asp Ile Val Gly
        115                 120                 125 gtc ggc aaa cag tgg tcc ggc gca cgc gcc ctg gag gcc ttg ctc acg     432
Val Gly Lys Gln Trp Ser Gly Ala Arg Ala Leu Glu Ala Leu Leu Thr
130                 135                 140 gat gcg ggg gag ttg aga ggt ccg ccg tta cag ttg gac aca ggc caa     480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg     528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc cca     576
His Ala Ser Arg Asn Ala Leu Thr Gly Ala Pro Leu Asn Leu Thr Pro
            180                 185                 190 gac caa gtt gtc gcg att gca agc aac aac gga ggc aaa caa gcc tta     624
Asp Gln Val Val Ala Ile Ala Ser Asn Asn Gly Gly Lys Gln Ala Leu
        195                 200                 205 gaa aca gtc cag aga ttg ttg ccg gtg ctg tgc caa gac cac ggc ctg     672
Glu Thr Val Gln Arg Leu Leu Pro Val Leu Cys Gln Asp His Gly Leu
210                 215                 220 acc ccc gaa cag gtt gtc gct att gct agt aac gga gga aaa cag         720
Thr Pro Glu Gln Val Val Ala Ile Ala Ser Asn Gly Gly Lys Gln
225                 230                 235                 240 gcg ctg gaa aca gtt cag cgc ctc ttg ccg gtc ttg tgt cag gcc cac     768
Ala Leu Glu Thr Val Gln Arg Leu Leu Pro Val Leu Cys Gln Ala His
                245                 250                 255 ggc ctg acc cca gac caa gtt gtc gcg att gca agc aac aac gga ggc     816
Gly Leu Thr Pro Asp Gln Val Val Ala Ile Ala Ser Asn Asn Gly Gly
            260                 265                 270 aaa caa gcc tta gaa aca gtc cag aga ttg ttg cct gtg ctg tgc caa     864
Lys Gln Ala Leu Glu Thr Val Gln Arg Leu Leu Pro Val Leu Cys Gln
        275                 280                 285
```

-continued

| | | |
|---|---|---|
| gcc cac ggc ctg acc ccg gcc cag gtg gtt gca atc gcg tca cac gat<br>Ala His Gly Leu Thr Pro Ala Gln Val Val Ala Ile Ala Ser His Asp<br>290                                      295                        300 | | 912 |
| ggg gga aag cag gcc cta gaa acc gtt cag cga ctc ctg ccc gtc ctg<br>Gly Gly Lys Gln Ala Leu Glu Thr Val Gln Arg Leu Leu Pro Val Leu<br>305                                310                        315                    320 | | 960 |
| tgc cag gac cac ggc ctg acc ccg gac cag gtg gtt gca atc gcg tca<br>Cys Gln Asp His Gly Leu Thr Pro Asp Gln Val Val Ala Ile Ala Ser<br>                        325                        330                    335 | | 1008 |
| cac gat ggg gga aag cag gcc cta gaa acc gtt cag cga ctc ctg ccc<br>His Asp Gly Gly Lys Gln Ala Leu Glu Thr Val Gln Arg Leu Leu Pro<br>          340                        345                        350 | | 1056 |
| gtc ctg tgc cag gac cac ggc ctg acc ccc gaa cag gtt gtc gct att<br>Val Leu Cys Gln Asp His Gly Leu Thr Pro Glu Gln Val Val Ala Ile<br>               355                        360                    365 | | 1104 |
| gct agt aac ggc gga ggc aaa cag gcg ctg gaa aca gtt cag cgc ctc<br>Ala Ser Asn Gly Gly Gly Lys Gln Ala Leu Glu Thr Val Gln Arg Leu<br>          370                        375                        380 | | 1152 |
| ttg ccg gtc ttg tgt cag gcc cac ggc ctg acc cca gac caa gtt gtc<br>Leu Pro Val Leu Cys Gln Ala His Gly Leu Thr Pro Asp Gln Val Val<br>385                                390                        395                    400 | | 1200 |
| gcg att gca agc aac aac gga ggc aaa caa gcc tta gaa aca gtc cag<br>Ala Ile Ala Ser Asn Asn Gly Gly Lys Gln Ala Leu Glu Thr Val Gln<br>                            405                        410                    415 | | 1248 |
| aga ttg ttg cct gtg ctg tgc caa gcc cac ggc ctg acc cca gcc caa<br>Arg Leu Leu Pro Val Leu Cys Gln Ala His Gly Leu Thr Pro Ala Gln<br>                    420                        425                    430 | | 1296 |
| gtt gtc gcg att gca agc aac aac gga ggc aaa caa gcc tta gaa aca<br>Val Val Ala Ile Ala Ser Asn Asn Gly Gly Lys Gln Ala Leu Glu Thr<br>               435                        440                    445 | | 1344 |
| gtc cag aga ttg ttg ccg gtg ctg tgc caa gac cac ggc ctg acc ccg<br>Val Gln Arg Leu Leu Pro Val Leu Cys Gln Asp His Gly Leu Thr Pro<br>          450                        455                        460 | | 1392 |
| gac cag gtg gtt gca atc gcg tca cac gat ggg gga aag cag gcc cta<br>Asp Gln Val Val Ala Ile Ala Ser His Asp Gly Gly Lys Gln Ala Leu<br>465                                470                        475                    480 | | 1440 |
| gaa acc gtt cag cga ctc ctg ccc gtc ctg tgc cag gac cac ggc ctg<br>Glu Thr Val Gln Arg Leu Leu Pro Val Leu Cys Gln Asp His Gly Leu<br>                        485                        490                    495 | | 1488 |
| acc ccg gaa cag gtg gtt gca atc gcg tca cac gat ggg gga aag cag<br>Thr Pro Glu Gln Val Val Ala Ile Ala Ser His Asp Gly Gly Lys Gln<br>          500                        505                        510 | | 1536 |
| gcc cta gaa acc gtt cag cga ctc ctg ccc gtc ctg tgc cag gcc cac<br>Ala Leu Glu Thr Val Gln Arg Leu Leu Pro Val Leu Cys Gln Ala His<br>               515                        520                    525 | | 1584 |
| ggc ctg acc cca gac cag gtt gtg gcc atc gcc agc aac ata ggt ggc<br>Gly Leu Thr Pro Asp Gln Val Val Ala Ile Ala Ser Asn Ile Gly Gly<br>          530                        535                        540 | | 1632 |
| aag cag gcc ctc gaa acc gtc cag aga ctg tta ccg gtt ctc tgc cag<br>Lys Gln Ala Leu Glu Thr Val Gln Arg Leu Leu Pro Val Leu Cys Gln<br>545                                550                        555                    560 | | 1680 |
| gcc cac ggc ctg acc ccg gcc cag gtg gtt gca atc gcg tca cac gat<br>Ala His Gly Leu Thr Pro Ala Gln Val Val Ala Ile Ala Ser His Asp<br>                        565                        570                    575 | | 1728 |
| ggg gga aag cag gcc cta gaa acc gtt cag cga ctc ctg ccc gtc ctg<br>Gly Gly Lys Gln Ala Leu Glu Thr Val Gln Arg Leu Leu Pro Val Leu<br>          580                        585                        590 | | 1776 |
| tgc cag gac cac ggc ctg acc cca gac cag gtt gtg gcc atc gcc agc<br>Cys Gln Asp His Gly Leu Thr Pro Asp Gln Val Val Ala Ile Ala Ser<br>               595                        600                    605 | | 1824 |

-continued

```
aac ata ggt ggc aag cag gcc ctc gaa acc gtc cag aga ctg tta ccg    1872
Asn Ile Gly Gly Lys Gln Ala Leu Glu Thr Val Gln Arg Leu Leu Pro
    610             615                 620 gtt ctc tgc cag gac cac ggc ctg acc cca gaa caa gtt gtc gcg att    1920
Val Leu Cys Gln Asp His Gly Leu Thr Pro Glu Gln Val Val Ala Ile
625                 630                 635                 640 gca agc aac aac gga ggc aaa caa gcc tta gaa aca gtc cag aga ttg    1968
Ala Ser Asn Asn Gly Gly Lys Gln Ala Leu Glu Thr Val Gln Arg Leu
                645                 650                 655 ttg ccg gtg ctg tgc caa gcc cac ggc ctg acc cca gac caa gtt gtc    2016
Leu Pro Val Leu Cys Gln Ala His Gly Leu Thr Pro Asp Gln Val Val
            660                 665                 670 gcg att gca agc aac aac gga ggc aaa caa gcc tta gaa aca gtc cag    2064
Ala Ile Ala Ser Asn Asn Gly Gly Lys Gln Ala Leu Glu Thr Val Gln
        675                 680                 685 aga ttg ttg cct gtg ctg tgc caa gcc cac ggc ctg acc ccg gcc cag    2112
Arg Leu Leu Pro Val Leu Cys Gln Ala His Gly Leu Thr Pro Ala Gln
    690                 695                 700 gtg gtt gca atc gcg tca cac gat ggg gga aag cag gcc cta gaa acc    2160
Val Val Ala Ile Ala Ser His Asp Gly Gly Lys Gln Ala Leu Glu Thr
705                 710                 715                 720 gtt cag cga ctc ctg ccc gtc ctg tgc cag gac cac ggc ctg acc ccc    2208
Val Gln Arg Leu Leu Pro Val Leu Cys Gln Asp His Gly Leu Thr Pro
                725                 730                 735 gac cag gtt gtc gct att gct agt aac ggc gga ggc aaa cag gcg ctg    2256
Asp Gln Val Val Ala Ile Ala Ser Asn Gly Gly Gly Lys Gln Ala Leu
            740                 745                 750 gaa aca gtt cag cgc ctc ttg ccg gtc ttg tgt cag gac cac ggc ctg    2304
Glu Thr Val Gln Arg Leu Leu Pro Val Leu Cys Gln Asp His Gly Leu
        755                 760                 765 acc ccc gaa cag gtt gtc gct att gct agt aac ggc gga ggc aaa cag    2352
Thr Pro Glu Gln Val Val Ala Ile Ala Ser Asn Gly Gly Gly Lys Gln
    770                 775                 780 gcg ctg gaa aca gtt cag cgc ctc ttg ccg gtc ttg tgt cag gcc cac    2400
Ala Leu Glu Thr Val Gln Arg Leu Leu Pro Val Leu Cys Gln Ala His
785                 790                 795                 800 ggc ctg acg cct gag cag gta gtg gct att gca tcc cac gac ggg ggc    2448
Gly Leu Thr Pro Glu Gln Val Val Ala Ile Ala Ser His Asp Gly Gly
                805                 810                 815 aga ccc gca ctg gag tca atc gtg gcc cag ctt tcg agg ccg gac ccc    2496
Arg Pro Ala Leu Glu Ser Ile Val Ala Gln Leu Ser Arg Pro Asp Pro
            820                 825                 830 gcg ctg gcc gca ctc act aat gat cat ctt gta gcg ctg gcc tgc ctc    2544
Ala Leu Ala Ala Leu Thr Asn Asp His Leu Val Ala Leu Ala Cys Leu
        835                 840                 845 ggc gga cgt cct gcc atg gat gca gtg aaa aag gga ttg ccg cac gcg    2592
Gly Gly Arg Pro Ala Met Asp Ala Val Lys Lys Gly Leu Pro His Ala
    850                 855                 860 ccg gaa ttg atc aga tcc cag cta gtg aaa tct gaa ttg gaa gag aag    2640
Pro Glu Leu Ile Arg Ser Gln Leu Val Lys Ser Glu Leu Glu Glu Lys
865                 870                 875                 880 aaa tct gaa ctt aga cat aaa ttg aaa tat gtg cca cat gaa tat att    2688
Lys Ser Glu Leu Arg His Lys Leu Lys Tyr Val Pro His Glu Tyr Ile
                885                 890                 895 gaa ttg att gaa atc gca aga aat tca act cag gat aga atc ctt gaa    2736
Glu Leu Ile Glu Ile Ala Arg Asn Ser Thr Gln Asp Arg Ile Leu Glu
            900                 905                 910 atg aag gtg atg gag ttc ttt atg aag gtt tat ggt tat cgt ggt aaa    2784
Met Lys Val Met Glu Phe Phe Met Lys Val Tyr Gly Tyr Arg Gly Lys
```

```
                915                 920                 925
cat ttg ggt gga tca agg aaa cca gac gga gca att tat act gtc gga     2832
His Leu Gly Gly Ser Arg Lys Pro Asp Gly Ala Ile Tyr Thr Val Gly
    930                 935                 940 tct cct att gat tac ggt gtg atc gtt gat act aag gca tat tca gga     2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc     2928
Gly Tyr Asn Leu Pro Ile Gly Gln Ala Asp Glu Met Gln Arg Tyr Val
                965                 970                 975 gaa gag aat caa aca aga aac aag cat atc aac cct aat gaa tgg tgg     2976
Glu Glu Asn Gln Thr Arg Asn Lys His Ile Asn Pro Asn Glu Trp Trp
            980                 985                 990 aaa gtc tat cca tct tca gta aca gaa ttt aag ttc ttg ttt gtg agt     3024
Lys Val Tyr Pro Ser Ser Val Thr Glu Phe Lys Phe Leu Phe Val Ser
        995                 1000                1005 ggt cat ttc aaa gga aac tac aaa gct cag ctt aca aga ttg aat         3069
Gly His Phe Lys Gly Asn Tyr Lys Ala Gln Leu Thr Arg Leu Asn
    1010                1015                1020 cat atc act aat tgt aat gga gct gtt ctt agt gta gaa gag ctt         3114
His Ile Thr Asn Cys Asn Gly Ala Val Leu Ser Val Glu Glu Leu
    1025                1030                1035 ttg att ggt gga gaa atg att aaa gct ggt aca ttg aca ctt gag         3159
Leu Ile Gly Gly Glu Met Ile Lys Ala Gly Thr Leu Thr Leu Glu
    1040                1045                1050 gaa gtg aga agg aaa ttt aat aac ggt gag ata aac ttt taa             3201
Glu Val Arg Arg Lys Phe Asn Asn Gly Glu Ile Asn Phe
    1055                1060                1065
```

<210> SEQ ID NO 61
<211> LENGTH: 1066
<212> TYPE: PRT
<213> ORGANISM: artificial sequence
<220> FEATURE:
<223> OTHER INFORMATION: Synthetic Construct

<400> SEQUENCE: 61

```
Met Ala Ser Ser Pro Lys Lys Lys Arg Lys Val Ala Ala Ala Asp
1               5                   10                  15

Tyr Lys Asp Asp Asp Lys Ser Trp Lys Asp Ala Ser Gly Trp Ser
                20                  25                  30

Arg Met His Ala Ala Pro Arg Arg Ala Ala Gln Pro Ser Asp Ala
            35                  40                  45

Ser Pro Ala Ala Gln Val Asp Leu Arg Thr Leu Gly Tyr Ser Gln Gln
    50                  55                  60

Gln Gln Glu Lys Ile Lys Pro Lys Val Arg Ser Thr Val Ala Gln His
65                  70                  75                  80

His Glu Ala Leu Val Gly His Gly Phe Thr His Ala His Ile Val Ala
                85                  90                  95

Leu Ser Gln His Pro Ala Ala Leu Gly Thr Val Ala Val Thr Tyr Gln
            100                 105                 110

His Ile Ile Thr Ala Leu Pro Glu Ala Thr His Glu Asp Ile Val Gly
        115                 120                 125

Val Gly Lys Gln Trp Ser Gly Ala Arg Ala Leu Glu Ala Leu Leu Thr
    130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
```

```
                 165                 170                 175
His Ala Ser Arg Asn Ala Leu Thr Gly Ala Pro Leu Asn Leu Thr Pro
            180                 185                 190

Asp Gln Val Val Ala Ile Ala Ser Asn Asn Gly Gly Lys Gln Ala Leu
            195                 200                 205

Glu Thr Val Gln Arg Leu Leu Pro Val Leu Cys Gln Asp His Gly Leu
            210                 215                 220

Thr Pro Glu Gln Val Val Ala Ile Ala Ser Asn Gly Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Asp Gln Val Val Ala Ile Ala Ser Asn Asn Gly Gly
            260                 265                 270

Lys Gln Ala Leu Glu Thr Val Gln Arg Leu Leu Pro Val Leu Cys Gln
            275                 280                 285

Ala His Gly Leu Thr Pro Ala Gln Val Val Ala Ile Ala Ser His Asp
            290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

His Asp Gly Gly Lys Gln Ala Leu Glu Thr Val Gln Arg Leu Leu Pro
            340                 345                 350

Val Leu Cys Gln Asp His Gly Leu Thr Pro Glu Gln Val Val Ala Ile
            355                 360                 365

Ala Ser Asn Gly Gly Gly Lys Gln Ala Leu Glu Thr Val Gln Arg Leu
            370                 375                 380

Leu Pro Val Leu Cys Gln Ala His Gly Leu Thr Pro Asp Gln Val Val
385                 390                 395                 400

Ala Ile Ala Ser Asn Asn Gly Gly Lys Gln Ala Leu Glu Thr Val Gln
                405                 410                 415

Arg Leu Leu Pro Val Leu Cys Gln Ala His Gly Leu Thr Pro Ala Gln
            420                 425                 430

Val Val Ala Ile Ala Ser Asn Asn Gly Gly Lys Gln Ala Leu Glu Thr
            435                 440                 445

Val Gln Arg Leu Leu Pro Val Leu Cys Gln Asp His Gly Leu Thr Pro
            450                 455                 460

Asp Gln Val Val Ala Ile Ala Ser His Asp Gly Gly Lys Gln Ala Leu
465                 470                 475                 480

Glu Thr Val Gln Arg Leu Leu Pro Val Leu Cys Gln Asp His Gly Leu
                485                 490                 495

Thr Pro Glu Gln Val Val Ala Ile Ala Ser His Asp Gly Gly Lys Gln
            500                 505                 510

Ala Leu Glu Thr Val Gln Arg Leu Leu Pro Val Leu Cys Gln Ala His
            515                 520                 525

Gly Leu Thr Pro Asp Gln Val Val Ala Ile Ala Ser Asn Ile Gly Gly
            530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser His Asp
                565                 570                 575

Gly Gly Lys Gln Ala Leu Glu Thr Val Gln Arg Leu Leu Pro Val Leu
            580                 585                 590
```

-continued

```
Cys Gln Asp His Gly Leu Thr Pro Asp Gln Val Val Ala Ile Ala Ser
        595                 600                 605

Asn Ile Gly Gly Lys Gln Ala Leu Glu Thr Val Gln Arg Leu Leu Pro
    610                 615                 620

Val Leu Cys Gln Asp His Gly Leu Thr Pro Glu Gln Val Val Ala Ile
625                 630                 635                 640

Ala Ser Asn Asn Gly Gly Lys Gln Ala Leu Glu Thr Val Gln Arg Leu
            645                 650                 655

Leu Pro Val Leu Cys Gln Ala His Gly Leu Thr Pro Asp Gln Val Val
                660                 665                 670

Ala Ile Ala Ser Asn Asn Gly Gly Lys Gln Ala Leu Glu Thr Val Gln
            675                 680                 685

Arg Leu Leu Pro Val Leu Cys Gln Ala His Gly Leu Thr Pro Ala Gln
    690                 695                 700

Val Val Ala Ile Ala Ser His Asp Gly Gly Lys Gln Ala Leu Glu Thr
705                 710                 715                 720

Val Gln Arg Leu Leu Pro Val Leu Cys Gln Asp His Gly Leu Thr Pro
            725                 730                 735

Asp Gln Val Val Ala Ile Ala Ser Asn Gly Gly Lys Gln Ala Leu
        740                 745                 750

Glu Thr Val Gln Arg Leu Leu Pro Val Leu Cys Gln Asp His Gly Leu
    755                 760                 765

Thr Pro Glu Gln Val Val Ala Ile Ala Ser Asn Gly Gly Lys Gln
770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser His Asp Gly Gly
            805                 810                 815

Arg Pro Ala Leu Glu Ser Ile Val Ala Gln Leu Ser Arg Pro Asp Pro
        820                 825                 830

Ala Leu Ala Ala Leu Thr Asn Asp His Leu Val Ala Leu Ala Cys Leu
        835                 840                 845

Gly Gly Arg Pro Ala Met Asp Ala Val Lys Lys Gly Leu Pro His Ala
    850                 855                 860

Pro Glu Leu Ile Arg Ser Gln Leu Val Lys Ser Glu Leu Glu Glu Lys
865                 870                 875                 880

Lys Ser Glu Leu Arg His Lys Leu Lys Tyr Val Pro His Glu Tyr Ile
            885                 890                 895

Glu Leu Ile Glu Ile Ala Arg Asn Ser Thr Gln Asp Arg Ile Leu Glu
        900                 905                 910

Met Lys Val Met Glu Phe Phe Met Lys Val Tyr Gly Tyr Arg Gly Lys
    915                 920                 925

His Leu Gly Gly Ser Arg Lys Pro Asp Gly Ala Ile Tyr Thr Val Gly
    930                 935                 940

Ser Pro Ile Asp Tyr Gly Val Ile Val Asp Thr Lys Ala Tyr Ser Gly
945                 950                 955                 960

Gly Tyr Asn Leu Pro Ile Gly Gln Ala Asp Glu Met Gln Arg Tyr Val
            965                 970                 975

Glu Glu Asn Gln Thr Arg Asn Lys His Ile Asn Pro Asn Glu Trp Trp
        980                 985                 990

Lys Val Tyr Pro Ser Ser Val Thr Glu Phe Lys Phe Leu Phe Val Ser
            995                 1000                1005
```

-continued

```
Gly His Phe Lys Gly Asn Tyr Lys Ala Gln Leu Thr Arg Leu Asn
    1010                1015                1020

His Ile Thr Asn Cys Asn Gly Ala Val Leu Ser Val Glu Glu Leu
    1025                1030                1035

Leu Ile Gly Gly Glu Met Ile Lys Ala Gly Thr Leu Thr Leu Glu
    1040                1045                1050

Glu Val Arg Arg Lys Phe Asn Asn Gly Glu Ile Asn Phe
    1055                1060                1065

<210> SEQ ID NO 62
<211> LENGTH: 3201
<212> TYPE: DNA
<213> ORGANISM: artificial sequence
<220> FEATURE:
<223> OTHER INFORMATION: TALEN-TCR-beta3_R19 TALEN coding sequence
<220> FEATURE:
<221> NAME/KEY: CDS
<222> LOCATION: (1)..(3201)

<400> SEQUENCE: 62 atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
                20                  25                  30 aga atg cat gcg gcc ccg cga cgg cgt gct gcg caa ccc tcc gac gct     144
Arg Met His Ala Ala Pro Arg Arg Arg Ala Ala Gln Pro Ser Asp Ala
            35                  40                  45 tcg ccg gcc gcg cag gtg gat cta cgc acg ctc ggc tac agt cag cag     192
Ser Pro Ala Ala Gln Val Asp Leu Arg Thr Leu Gly Tyr Ser Gln Gln
        50                  55                  60 cag caa gag aag atc aaa ccg aag gtg cgt tcg aca gtg gcg cag cac     240
Gln Gln Glu Lys Ile Lys Pro Lys Val Arg Ser Thr Val Ala Gln His
65                  70                  75                  80 cac gag gca ctg gtg ggc cat ggg ttt aca cac gcg cac atc gtt gcg     288
His Glu Ala Leu Val Gly His Gly Phe Thr His Ala His Ile Val Ala
                85                  90                  95 ctc agc caa cac ccg gca gcg tta ggg acc gtc gct gtc acg tat cag     336
Leu Ser Gln His Pro Ala Ala Leu Gly Thr Val Ala Val Thr Tyr Gln
            100                 105                 110 cac ata atc acg gcg ttg cca gag gca aca cac gaa gac atc gtt ggc     384
His Ile Ile Thr Ala Leu Pro Glu Ala Thr His Glu Asp Ile Val Gly
        115                 120                 125 gtc ggc aaa cag tgg tcc ggc gca cgc gcc ctg gag gcc ttg ctc acg     432
Val Gly Lys Gln Trp Ser Gly Ala Arg Ala Leu Glu Ala Leu Leu Thr
    130                 135                 140 gat gcg ggg gag ttg aga ggt ccg ccg tta cag ttg gac aca ggc caa     480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg     528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc ccg     576
His Ala Ser Arg Asn Ala Leu Thr Gly Ala Pro Leu Asn Leu Thr Pro
            180                 185                 190 gac cag gtg gtt gca atc gcg tca cac gat ggg gga aag cag gcc cta     624
Asp Gln Val Val Ala Ile Ala Ser His Asp Gly Gly Lys Gln Ala Leu
        195                 200                 205 gaa acc gtt cag cga ctc ctg ccc gtc ctg tgc cag gac cac ggc ctg     672
Glu Thr Val Gln Arg Leu Leu Pro Val Leu Cys Gln Asp His Gly Leu
```

-continued

```
                210                 215                 220
acc cca gaa cag gtt gtg gcc atc gcc agc aac ata ggt ggc aag cag        720
Thr Pro Glu Gln Val Val Ala Ile Ala Ser Asn Ile Gly Gly Lys Gln
225                 230                 235                 240 gcc ctc gaa acc gtc cag aga ctg tta ccg gtt ctc tgc cag gcc cac        768
Ala Leu Glu Thr Val Gln Arg Leu Leu Pro Val Leu Cys Gln Ala His
                245                 250                 255 ggc ctg acc ccg gac cag gtg gtt gca atc gcg tca cac gat ggg gga        816
Gly Leu Thr Pro Asp Gln Val Val Ala Ile Ala Ser His Asp Gly Gly
                260                 265                 270 aag cag gcc cta gaa acc gtt cag cga ctc ctg ccc gtc ctg tgc cag        864
Lys Gln Ala Leu Glu Thr Val Gln Arg Leu Leu Pro Val Leu Cys Gln
                275                 280                 285 gcc cac ggc ctg acc ccg gcc cag gtg gtt gca atc gcg tca cac gat        912
Ala His Gly Leu Thr Pro Ala Gln Val Val Ala Ile Ala Ser His Asp
                290                 295                 300 ggg gga aag cag gcc cta gaa acc gtt cag cga ctc ctg ccc gtc ctg        960
Gly Gly Lys Gln Ala Leu Glu Thr Val Gln Arg Leu Leu Pro Val Leu
305                 310                 315                 320 tgc cag gac cac ggc ctg acc ccg gac cag gtg gtt gca atc gcg tca       1008
Cys Gln Asp His Gly Leu Thr Pro Asp Gln Val Val Ala Ile Ala Ser
                325                 330                 335 cac gat ggg gga aag cag gcc cta gaa acc gtt cag cga ctc ctg ccc       1056
His Asp Gly Gly Lys Gln Ala Leu Glu Thr Val Gln Arg Leu Leu Pro
                340                 345                 350 gtc ctg tgc cag gac cac ggc ctg acc cca gaa cag gtt gtg gcc atc       1104
Val Leu Cys Gln Asp His Gly Leu Thr Pro Glu Gln Val Val Ala Ile
                355                 360                 365 gcc agc aac ata ggt ggc aag cag gcc ctc gaa acc gtc cag aga ctg       1152
Ala Ser Asn Ile Gly Gly Lys Gln Ala Leu Glu Thr Val Gln Arg Leu
                370                 375                 380 tta ccg gtt ctc tgc cag gcc cac ggc ctg acc ccg gac cag gtg gtt       1200
Leu Pro Val Leu Cys Gln Ala His Gly Leu Thr Pro Asp Gln Val Val
385                 390                 395                 400 gca atc gcg tca cac gat ggg gga aag cag gcc cta gaa acc gtt cag       1248
Ala Ile Ala Ser His Asp Gly Gly Lys Gln Ala Leu Glu Thr Val Gln
                405                 410                 415 cga ctc ctg ccc gtc ctg tgc cag gcc cac ggc ctg acc ccg gcc cag       1296
Arg Leu Leu Pro Val Leu Cys Gln Ala His Gly Leu Thr Pro Ala Gln
                420                 425                 430 gtg gtt gca atc gcg tca cac gat ggg gga aag cag gcc cta gaa acc       1344
Val Val Ala Ile Ala Ser His Asp Gly Gly Lys Gln Ala Leu Glu Thr
                435                 440                 445 gtt cag cga ctc ctg ccc gtc ctg tgc cag gac cac ggc ctg acc cca       1392
Val Gln Arg Leu Leu Pro Val Leu Cys Gln Asp His Gly Leu Thr Pro
450                 455                 460 gac cag gtt gtg gcc atc gcc agc aac ata ggt ggc aag cag gcc ctc       1440
Asp Gln Val Val Ala Ile Ala Ser Asn Ile Gly Gly Lys Gln Ala Leu
465                 470                 475                 480 gaa acc gtc cag aga ctg tta ccg gtt ctc tgc cag gac cac ggc ctg       1488
Glu Thr Val Gln Arg Leu Leu Pro Val Leu Cys Gln Asp His Gly Leu
                485                 490                 495 acc cca gaa caa gtt gtc gcg att gca agc aac aac gga ggc aaa caa       1536
Thr Pro Glu Gln Val Val Ala Ile Ala Ser Asn Asn Gly Gly Lys Gln
                500                 505                 510 gcc tta gaa aca gtc cag aga ttg ttg ccg gtg ctg tgc caa gcc cac       1584
Ala Leu Glu Thr Val Gln Arg Leu Leu Pro Val Leu Cys Gln Ala His
                515                 520                 525 ggc ctg acc ccg gac cag gtg gtt gca atc gcg tca cac gat ggg gga       1632
```

```
Gly Leu Thr Pro Asp Gln Val Val Ala Ile Ala Ser His Asp Gly Gly
            530                 535                 540 aag cag gcc cta gaa acc gtt cag cga ctc ctg ccc gtc ctg tgc cag      1680
Lys Gln Ala Leu Glu Thr Val Gln Arg Leu Leu Pro Val Leu Cys Gln
545                 550                 555                 560 gcc cac ggc ctg acc ccc gcc cag gtt gtc gct att gct agt aac ggc      1728
Ala His Gly Leu Thr Pro Ala Gln Val Val Ala Ile Ala Ser Asn Gly
                565                 570                 575 gga ggc aaa cag gcg ctg gaa aca gtt cag cgc ctc ttg ccg gtc ttg      1776
Gly Gly Lys Gln Ala Leu Glu Thr Val Gln Arg Leu Leu Pro Val Leu
            580                 585                 590 tgt cag gac cac ggc ctg acc ccg gac cag gtg gtt gca atc gcg tca      1824
Cys Gln Asp His Gly Leu Thr Pro Asp Gln Val Val Ala Ile Ala Ser
595                 600                 605 cac gat ggg gga aag cag gcc cta gaa acc gtt cag cga ctc ctg ccc      1872
His Asp Gly Gly Lys Gln Ala Leu Glu Thr Val Gln Arg Leu Leu Pro
                610                 615                 620 gtc ctg tgc cag gac cac ggc ctg acc cca gaa cag gtt gtg gcc atc      1920
Val Leu Cys Gln Asp His Gly Leu Thr Pro Glu Gln Val Val Ala Ile
625                 630                 635                 640 gcc agc aac ata ggt ggc aag cag gcc ctc gaa acc gtc cag aga ctg      1968
Ala Ser Asn Ile Gly Gly Lys Gln Ala Leu Glu Thr Val Gln Arg Leu
                645                 650                 655 tta ccg gtt ctc tgc cag gcc cac ggc ctg acc cca gac caa gtt gtc      2016
Leu Pro Val Leu Cys Gln Ala His Gly Leu Thr Pro Asp Gln Val Val
            660                 665                 670 gcg att gca agc aac aac gga ggc aaa caa gcc tta gaa aca gtc cag      2064
Ala Ile Ala Ser Asn Asn Gly Gly Lys Gln Ala Leu Glu Thr Val Gln
                675                 680                 685 aga ttg ttg cct gtg ctg tgc caa gcc cac ggc ctg acc ccg gcc cag      2112
Arg Leu Leu Pro Val Leu Cys Gln Ala His Gly Leu Thr Pro Ala Gln
690                 695                 700 gtg gtt gca atc gcg tca cac gat ggg gga aag cag gcc cta gaa acc      2160
Val Val Ala Ile Ala Ser His Asp Gly Gly Lys Gln Ala Leu Glu Thr
705                 710                 715                 720 gtt cag cga ctc ctg ccc gtc ctg tgc cag gac cac ggc ctg acc ccc      2208
Val Gln Arg Leu Leu Pro Val Leu Cys Gln Asp His Gly Leu Thr Pro
                725                 730                 735 gac cag gtt gtc gct att gct agt aac ggc gga ggc aaa cag gcg ctg      2256
Asp Gln Val Val Ala Ile Ala Ser Asn Gly Gly Gly Lys Gln Ala Leu
            740                 745                 750 gaa aca gtt cag cgc ctc ttg ccg gtc ttg tgt cag gac cac ggc ctg      2304
Glu Thr Val Gln Arg Leu Leu Pro Val Leu Cys Gln Asp His Gly Leu
                755                 760                 765 acc ccg gaa cag gtg gtt gca atc gcg tca cac gat ggg gga aag cag      2352
Thr Pro Glu Gln Val Val Ala Ile Ala Ser His Asp Gly Gly Lys Gln
770                 775                 780 gcc cta gaa acc gtt cag cga ctc ctg ccc gtc ctg tgc cag gcc cac      2400
Ala Leu Glu Thr Val Gln Arg Leu Leu Pro Val Leu Cys Gln Ala His
785                 790                 795                 800 ggc ctg acg cct gag cag gta gtg gct att gca tcc cac gac ggg ggc      2448
Gly Leu Thr Pro Glu Gln Val Val Ala Ile Ala Ser His Asp Gly Gly
                805                 810                 815 aga ccc gca ctg gag tca atc gtg gcc cag ctt tcg agg ccg gac ccc      2496
Arg Pro Ala Leu Glu Ser Ile Val Ala Gln Leu Ser Arg Pro Asp Pro
            820                 825                 830 gcg ctg gcc gca ctc act aat gat cat ctt gta gcg ctg gcc tgc ctc      2544
Ala Leu Ala Ala Leu Thr Asn Asp His Leu Val Ala Leu Ala Cys Leu
                835                 840                 845
```

```
ggc gga cgt cct gcc atg gat gca gtg aaa aag gga ttg ccg cac gcg       2592
Gly Gly Arg Pro Ala Met Asp Ala Val Lys Lys Gly Leu Pro His Ala
850                 855                 860 ccg gaa ttg atc aga tcc cag cta gtg aaa tct gaa ttg gaa gag aag       2640
Pro Glu Leu Ile Arg Ser Gln Leu Val Lys Ser Glu Leu Glu Glu Lys
865                 870                 875                 880 aaa tct gaa ctt aga cat aaa ttg aaa tat gtg cca cat gaa tat att       2688
Lys Ser Glu Leu Arg His Lys Leu Lys Tyr Val Pro His Glu Tyr Ile
                885                 890                 895 gaa ttg att gaa atc gca aga aat tca act cag gat aga atc ctt gaa       2736
Glu Leu Ile Glu Ile Ala Arg Asn Ser Thr Gln Asp Arg Ile Leu Glu
            900                 905                 910 atg aag gtg atg gag ttc ttt atg aag gtt tat ggt tat cgt ggt aaa       2784
Met Lys Val Met Glu Phe Phe Met Lys Val Tyr Gly Tyr Arg Gly Lys
        915                 920                 925 cat ttg ggt gga tca agg aaa cca gac gga gca att tat act gtc gga       2832
His Leu Gly Gly Ser Arg Lys Pro Asp Gly Ala Ile Tyr Thr Val Gly
    930                 935                 940 tct cct att gat tac ggt gtg atc gtt gat act aag gca tat tca gga       2880
Ser Pro Ile Asp Tyr Gly Val Ile Val Asp Thr Lys Ala Tyr Ser Gly
945                 950                 955                 960 ggt tat aat ctt cca att ggt caa gca gat gaa atg caa aga tat gtc       2928
Gly Tyr Asn Leu Pro Ile Gly Gln Ala Asp Glu Met Gln Arg Tyr Val
                965                 970                 975 gaa gag aat caa aca aga aac aag cat atc aac cct aat gaa tgg tgg       2976
Glu Glu Asn Gln Thr Arg Asn Lys His Ile Asn Pro Asn Glu Trp Trp
            980                 985                 990 aaa gtc tat cca tct tca gta aca gaa ttt aag ttc ttg ttt gtg agt       3024
Lys Val Tyr Pro Ser Ser Val Thr Glu Phe Lys Phe Leu Phe Val Ser
        995                 1000                1005 ggt cat ttc aaa gga aac tac aaa gct cag ctt aca aga ttg aat          3069
Gly His Phe Lys Gly Asn Tyr Lys Ala Gln Leu Thr Arg Leu Asn
    1010                1015                1020 cat atc act aat tgt aat gga gct gtt ctt agt gta gaa gag ctt          3114
His Ile Thr Asn Cys Asn Gly Ala Val Leu Ser Val Glu Glu Leu
    1025                1030                1035 ttg att ggt gga gaa atg att aaa gct ggt aca ttg aca ctt gag          3159
Leu Ile Gly Gly Glu Met Ile Lys Ala Gly Thr Leu Thr Leu Glu
    1040                1045                1050 gaa gtg aga agg aaa ttt aat aac ggt gag ata aac ttt taa              3201
Glu Val Arg Arg Lys Phe Asn Asn Gly Glu Ile Asn Phe
    1055                1060                1065

<210> SEQ ID NO 63
<211> LENGTH: 1066
<212> TYPE: PRT
<213> ORGANISM: artificial sequence
<220> FEATURE:
<223> OTHER INFORMATION: Synthetic Construct

<400> SEQUENCE: 63

Met Ala Ser Ser Pro Lys Lys Lys Arg Lys Val Ala Ala Asp
1               5                   10                  15

Tyr Lys Asp Asp Asp Asp Lys Ser Trp Lys Asp Ala Ser Gly Trp Ser
                20                  25                  30

Arg Met His Ala Ala Pro Arg Arg Ala Ala Gln Pro Ser Asp Ala
            35                  40                  45

Ser Pro Ala Ala Gln Val Asp Leu Arg Thr Leu Gly Tyr Ser Gln Gln
        50                  55                  60

Gln Gln Glu Lys Ile Lys Pro Lys Val Arg Ser Thr Val Ala Gln His
```

```
            65                  70                  75                  80
His Glu Ala Leu Val Gly His Gly Phe Thr His Ala His Ile Val Ala
                    85                  90                  95
Leu Ser Gln His Pro Ala Ala Leu Gly Thr Val Ala Val Thr Tyr Gln
                    100                 105                 110
His Ile Ile Thr Ala Leu Pro Glu Ala Thr His Glu Asp Ile Val Gly
                    115                 120                 125
Val Gly Lys Gln Trp Ser Gly Ala Arg Ala Leu Glu Ala Leu Leu Thr
                    130                 135                 140
Asp Ala Gly Glu Leu Arg Gly Pro Leu Gln Leu Asp Thr Gly Gln
145                 150                 155                 160
Leu Val Lys Ile Ala Lys Arg Gly Gly Val Thr Ala Met Glu Ala Val
                    165                 170                 175
His Ala Ser Arg Asn Ala Leu Thr Gly Ala Pro Leu Asn Leu Thr Pro
                    180                 185                 190
Asp Gln Val Val Ala Ile Ala Ser His Asp Gly Gly Lys Gln Ala Leu
                    195                 200                 205
Glu Thr Val Gln Arg Leu Leu Pro Val Leu Cys Gln Asp His Gly Leu
                    210                 215                 220
Thr Pro Glu Gln Val Val Ala Ile Ala Ser Asn Ile Gly Gly Lys Gln
225                 230                 235                 240
Ala Leu Glu Thr Val Gln Arg Leu Leu Pro Val Leu Cys Gln Ala His
                    245                 250                 255
Gly Leu Thr Pro Asp Gln Val Val Ala Ile Ala Ser His Asp Gly Gly
                    260                 265                 270
Lys Gln Ala Leu Glu Thr Val Gln Arg Leu Leu Pro Val Leu Cys Gln
                    275                 280                 285
Ala His Gly Leu Thr Pro Ala Gln Val Val Ala Ile Ala Ser His Asp
                    290                 295                 300
Gly Gly Lys Gln Ala Leu Glu Thr Val Gln Arg Leu Leu Pro Val Leu
305                 310                 315                 320
Cys Gln Asp His Gly Leu Thr Pro Asp Gln Val Val Ala Ile Ala Ser
                    325                 330                 335
His Asp Gly Gly Lys Gln Ala Leu Glu Thr Val Gln Arg Leu Leu Pro
                    340                 345                 350
Val Leu Cys Gln Asp His Gly Leu Thr Pro Glu Gln Val Val Ala Ile
                    355                 360                 365
Ala Ser Asn Ile Gly Gly Lys Gln Ala Leu Glu Thr Val Gln Arg Leu
                    370                 375                 380
Leu Pro Val Leu Cys Gln Ala His Gly Leu Thr Pro Asp Gln Val Val
385                 390                 395                 400
Ala Ile Ala Ser His Asp Gly Gly Lys Gln Ala Leu Glu Thr Val Gln
                    405                 410                 415
Arg Leu Leu Pro Val Leu Cys Gln Ala His Gly Leu Thr Pro Ala Gln
                    420                 425                 430
Val Val Ala Ile Ala Ser His Asp Gly Gly Lys Gln Ala Leu Glu Thr
                    435                 440                 445
Val Gln Arg Leu Leu Pro Val Leu Cys Gln Asp His Gly Leu Thr Pro
                    450                 455                 460
Asp Gln Val Val Ala Ile Ala Ser Asn Ile Gly Gly Lys Gln Ala Leu
465                 470                 475                 480
Glu Thr Val Gln Arg Leu Leu Pro Val Leu Cys Gln Asp His Gly Leu
                    485                 490                 495
```

```
Thr Pro Glu Gln Val Val Ala Ile Ala Ser Asn Asn Gly Gly Lys Gln
            500                 505                 510

Ala Leu Glu Thr Val Gln Arg Leu Leu Pro Val Leu Cys Gln Ala His
        515                 520                 525

Gly Leu Thr Pro Asp Gln Val Val Ala Ile Ala Ser His Asp Gly Gly
    530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser Asn Gly
                565                 570                 575

Gly Gly Lys Gln Ala Leu Glu Thr Val Gln Arg Leu Leu Pro Val Leu
            580                 585                 590

Cys Gln Asp His Gly Leu Thr Pro Asp Gln Val Val Ala Ile Ala Ser
        595                 600                 605

His Asp Gly Gly Lys Gln Ala Leu Glu Thr Val Gln Arg Leu Leu Pro
    610                 615                 620

Val Leu Cys Gln Asp His Gly Leu Thr Pro Glu Gln Val Val Ala Ile
625                 630                 635                 640

Ala Ser Asn Ile Gly Gly Lys Gln Ala Leu Glu Thr Val Gln Arg Leu
                645                 650                 655

Leu Pro Val Leu Cys Gln Ala His Gly Leu Thr Pro Asp Gln Val Val
            660                 665                 670

Ala Ile Ala Ser Asn Asn Gly Gly Lys Gln Ala Leu Glu Thr Val Gln
        675                 680                 685

Arg Leu Leu Pro Val Leu Cys Gln Ala His Gly Leu Thr Pro Ala Gln
    690                 695                 700

Val Val Ala Ile Ala Ser His Asp Gly Gly Lys Gln Ala Leu Glu Thr
705                 710                 715                 720

Val Gln Arg Leu Leu Pro Val Leu Cys Gln Asp His Gly Leu Thr Pro
                725                 730                 735

Asp Gln Val Val Ala Ile Ala Ser Asn Gly Gly Lys Gln Ala Leu
            740                 745                 750

Glu Thr Val Gln Arg Leu Leu Pro Val Leu Cys Gln Asp His Gly Leu
        755                 760                 765

Thr Pro Glu Gln Val Val Ala Ile Ala Ser His Asp Gly Gly Lys Gln
    770                 775                 780

Ala Leu Glu Thr Val Gln Arg Leu Leu Pro Val Leu Cys Gln Ala His
785                 790                 795                 800

Gly Leu Thr Pro Glu Gln Val Val Ala Ile Ala Ser His Asp Gly Gly
                805                 810                 815

Arg Pro Ala Leu Glu Ser Ile Val Ala Gln Leu Ser Arg Pro Asp Pro
            820                 825                 830

Ala Leu Ala Ala Leu Thr Asn Asp His Leu Val Ala Leu Ala Cys Leu
        835                 840                 845

Gly Gly Arg Pro Ala Met Asp Ala Val Lys Lys Gly Leu Pro His Ala
    850                 855                 860

Pro Glu Leu Ile Arg Ser Gln Leu Val Lys Ser Glu Leu Glu Glu Lys
865                 870                 875                 880

Lys Ser Glu Leu Arg His Lys Leu Lys Tyr Val Pro His Glu Tyr Ile
                885                 890                 895

Glu Leu Ile Glu Ile Ala Arg Asn Ser Thr Gln Asp Arg Ile Leu Glu
            900                 905                 910
```

-continued

```
Met Lys Val Met Glu Phe Phe Met Lys Val Tyr Gly Tyr Arg Gly Lys
            915                 920                 925

His Leu Gly Gly Ser Arg Lys Pro Asp Gly Ala Ile Tyr Thr Val Gly
        930                 935                 940

Ser Pro Ile Asp Tyr Gly Val Ile Val Asp Thr Lys Ala Tyr Ser Gly
945                 950                 955                 960

Gly Tyr Asn Leu Pro Ile Gly Gln Ala Asp Glu Met Gln Arg Tyr Val
                965                 970                 975

Glu Glu Asn Gln Thr Arg Asn Lys His Ile Asn Pro Asn Glu Trp Trp
            980                 985                 990

Lys Val Tyr Pro Ser Ser Val Thr Glu Phe Lys Phe Leu Phe Val Ser
            995                 1000                1005

Gly His Phe Lys Gly Asn Tyr Lys Ala Gln Leu Thr Arg Leu Asn
    1010                1015                1020

His Ile Thr Asn Cys Asn Gly Ala Val Leu Ser Val Glu Glu Leu
    1025                1030                1035

Leu Ile Gly Gly Glu Met Ile Lys Ala Gly Thr Leu Thr Leu Glu
    1040                1045                1050

Glu Val Arg Arg Lys Phe Asn Asn Gly Glu Ile Asn Phe
    1055                1060                1065

<210> SEQ ID NO 64
<211> LENGTH: 26
<212> TYPE: DNA
<213> ORGANISM: artificial sequence
<220> FEATURE:
<223> OTHER INFORMATION: TCR-alpha2-f primer

<400> SEQUENCE: 64
ctctgcatga ctcactagca ctctat                                        26

<210> SEQ ID NO 65
<211> LENGTH: 26
<212> TYPE: DNA
<213> ORGANISM: artificial sequence
<220> FEATURE:
<223> OTHER INFORMATION: TCR-alpha2-r primer

<400> SEQUENCE: 65
gactgactta gtgagctggg aaagat                                        26

<210> SEQ ID NO 66
<211> LENGTH: 25
<212> TYPE: DNA
<213> ORGANISM: artificial sequence
<220> FEATURE:
<223> OTHER INFORMATION: TCR-beta1-c1-f primer

<400> SEQUENCE: 66
ctaatatgtg tcactacccc acgag                                         25

<210> SEQ ID NO 67
<211> LENGTH: 26
<212> TYPE: DNA
<213> ORGANISM: artificial sequence
<220> FEATURE:
<223> OTHER INFORMATION: TCR-beta1-c1-r primer

<400> SEQUENCE: 67
gagagttaca caggccacat agaaag                                        26
```

```
<210> SEQ ID NO 68
<211> LENGTH: 25
<212> TYPE: DNA
<213> ORGANISM: artificial sequence
<220> FEATURE:
<223> OTHER INFORMATION: TCR-beta1-c2-f primer

<400> SEQUENCE: 68
gaggagacat cacctggaat gttag                                            25

<210> SEQ ID NO 69
<211> LENGTH: 26
<212> TYPE: DNA
<213> ORGANISM: artificial sequence
<220> FEATURE:
<223> OTHER INFORMATION: TCR-beta1-c2-r primer

<400> SEQUENCE: 69
gatatattag gctgtgctct ggctct                                           26

<210> SEQ ID NO 70
<211> LENGTH: 20
<212> TYPE: DNA
<213> ORGANISM: artificial sequence
<220> FEATURE:
<223> OTHER INFORMATION: Forward primer for Va cloning

<400> SEQUENCE: 70
tggaggagaa ccctggacct                                                  20

<210> SEQ ID NO 71
<211> LENGTH: 21
<212> TYPE: DNA
<213> ORGANISM: artificial sequence
<220> FEATURE:
<223> OTHER INFORMATION: Reverse primer for Va cloning

<400> SEQUENCE: 71
ggtgaatagg cagacagact t                                                21

<210> SEQ ID NO 72
<211> LENGTH: 20
<212> TYPE: DNA
<213> ORGANISM: artificial sequence
<220> FEATURE:
<223> OTHER INFORMATION: Forward primer for Ca cloning

<400> SEQUENCE: 72
gagactctaa atccagtgac                                                  20

<210> SEQ ID NO 73
<211> LENGTH: 35
<212> TYPE: DNA
<213> ORGANISM: artificial sequence
<220> FEATURE:
<223> OTHER INFORMATION: Reverse primer for Ca cloning

<400> SEQUENCE: 73
gggggcggaa tttacgtagc ggccgctcag ctgct                                 35

<210> SEQ ID NO 74
<211> LENGTH: 43
<212> TYPE: DNA
<213> ORGANISM: artificial sequence
<220> FEATURE:
<223> OTHER INFORMATION: Forward primer for Vb cloning
```

```
<400> SEQUENCE: 74
tgccggatct agctagttaa ttaaggatcc gaattcctgc agg                43

<210> SEQ ID NO 75
<211> LENGTH: 20
<212> TYPE: DNA
<213> ORGANISM: artificial sequence
<220> FEATURE:
<223> OTHER INFORMATION: Reverse primer for Vb cloning

<400> SEQUENCE: 75
ttcacccacc agctcagctc                                          20

<210> SEQ ID NO 76
<211> LENGTH: 20
<212> TYPE: DNA
<213> ORGANISM: artificial sequence
<220> FEATURE:
<223> OTHER INFORMATION: Forward primer for Cb cloning

<400> SEQUENCE: 76
ttcacccacc agctcagctc                                          20

<210> SEQ ID NO 77
<211> LENGTH: 20
<212> TYPE: DNA
<213> ORGANISM: artificial sequence
<220> FEATURE:
<223> OTHER INFORMATION: Reverse primer for Cb cloning

<400> SEQUENCE: 77
aggtccaggg ttctcctcca                                          20

<210> SEQ ID NO 78
<211> LENGTH: 141
<212> TYPE: PRT
<213> ORGANISM: artificial sequence
<220> FEATURE:
<223> OTHER INFORMATION: TCRalpha constant region for introduction
<220> FEATURE:
<221> NAME/KEY: misc_feature
<222> LOCATION: (1)..(1)
<223> OTHER INFORMATION: Xaa can be any naturally occurring amino acid

<400> SEQUENCE: 78

Xaa Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140
```

130                 135                 140

<210> SEQ ID NO 79
<211> LENGTH: 177
<212> TYPE: PRT
<213> ORGANISM: artificial sequence
<220> FEATURE:
<223> OTHER INFORMATION: TCRbeta constant region for introduction

<400> SEQUENCE: 79

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 80
<211> LENGTH: 20
<212> TYPE: DNA
<213> ORGANISM: artificial sequence
<220> FEATURE:
<223> OTHER INFORMATION: Target sequence of alpha 2 L

<400> SEQUENCE: 80
tgtctgccta ttcaccgatt                                                    20

<210> SEQ ID NO 81
<211> LENGTH: 20
<212> TYPE: DNA
<213> ORGANISM: artificial sequence
<220> FEATURE:
<223> OTHER INFORMATION: Target sequence of alpha 2 R

<400> SEQUENCE: 81
tccttacttt gtgacacatt                                                    20

<210> SEQ ID NO 82
<211> LENGTH: 20
<212> TYPE: DNA
<213> ORGANISM: artificial sequence
<220> FEATURE:
<223> OTHER INFORMATION: Target sequence of beta 1 L

```
<400> SEQUENCE: 82
tgttcccacc cgaggtcgct                                              20

<210> SEQ ID NO 83
<211> LENGTH: 20
<212> TYPE: DNA
<213> ORGANISM: artificial sequence
<220> FEATURE:
<223> OTHER INFORMATION: Target sequence of beta 1 R

<400> SEQUENCE: 83
tgtgggagat ctctgcttct                                              20

<210> SEQ ID NO 84
<211> LENGTH: 20
<212> TYPE: DNA
<213> ORGANISM: artificial sequence
<220> FEATURE:
<223> OTHER INFORMATION: Target sequence of beta 3 L

<400> SEQUENCE: 84
tgtgcctggc cacaggcttc                                              20

<210> SEQ ID NO 85
<211> LENGTH: 20
<212> TYPE: DNA
<213> ORGANISM: artificial sequence
<220> FEATURE:
<223> OTHER INFORMATION: Target sequence of beta 3 R

<400> SEQUENCE: 85
tcacccacca gctcagctcc                                              20

<210> SEQ ID NO 86
<211> LENGTH: 633
<212> TYPE: PRT
<213> ORGANISM: artificial sequence
<220> FEATURE:
<223> OTHER INFORMATION: TALEN alpha 2 L binding domain

<400> SEQUENCE: 86
```

Leu Thr Pro Asp Gln Val Val Ala Ile Ala Ser Asn Asn Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Glu Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Asp Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Ala Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser Asn Asn Gly Gly Lys Gln Ala Leu Glu Thr Val Gln Arg
145                 150                 155                 160

```
Leu Leu Pro Val Leu Cys Gln Asp His Gly Leu Thr Pro Glu Gln Val
            165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Asp
            195                 200                 205

Gln Val Val Ala Ile Ala Ser His Asp Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Ala Gln Val Val Ala Ile Ala Ser Asn Gly Gly Lys Gln Ala
            245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser Asn Ile Gly Gly Lys
            275                 280                 285

Gln Ala Leu Glu Thr Val Gln Arg Leu Leu Pro Val Leu Cys Gln Asp
            290                 295                 300

His Gly Leu Thr Pro Glu Gln Val Val Ala Ile Ala Ser Asn Gly Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Asp Gln Val Val Ala Ile Ala Ser Asn
            340                 345                 350

Gly Gly Lys Gln Ala Leu Glu Thr Val Gln Arg Leu Leu Pro Val
            355                 360                 365

Leu Cys Gln Ala His Gly Leu Thr Pro Ala Gln Val Val Ala Ile Ala
            370                 375                 380

Ser His Asp Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
            405                 410                 415

Ile Ala Ser Asn Ile Gly Gly Lys Gln Ala Leu Glu Thr Val Gln Arg
            420                 425                 430

Leu Leu Pro Val Leu Cys Gln Asp His Gly Leu Thr Pro Glu Gln Val
            435                 440                 445

Val Ala Ile Ala Ser His Asp Gly Gly Lys Gln Ala Leu Glu Thr Val
            450                 455                 460

Gln Arg Leu Leu Pro Val Leu Cys Gln Ala His Gly Leu Thr Pro Asp
465                 470                 475                 480

Gln Val Val Ala Ile Ala Ser His Asp Gly Gly Lys Gln Ala Leu Glu
            485                 490                 495

Thr Val Gln Arg Leu Leu Pro Val Leu Cys Gln Ala His Gly Leu Thr
            500                 505                 510

Pro Ala Gln Val Val Ala Ile Ala Ser Asn Asn Gly Gly Lys Gln Ala
            515                 520                 525

Leu Glu Thr Val Gln Arg Leu Leu Pro Val Leu Cys Gln Asp His Gly
            530                 535                 540

Leu Thr Pro Asp Gln Val Val Ala Ile Ala Ser Asn Ile Gly Gly Lys
545                 550                 555                 560

Gln Ala Leu Glu Thr Val Gln Arg Leu Leu Pro Val Leu Cys Gln Asp
            565                 570                 575
```

```
His Gly Leu Thr Pro Glu Gln Val Val Ala Ile Ala Ser Asn Gly Gly
                580                 585                 590

Gly Lys Gln Ala Leu Glu Thr Val Gln Arg Leu Leu Pro Val Leu Cys
        595                 600                 605

Gln Ala His Gly Leu Thr Pro Glu Gln Val Val Ala Ile Ala Ser Asn
    610                 615                 620

Gly Gly Gly Arg Pro Ala Leu Glu Ser
625                 630

<210> SEQ ID NO 87
<211> LENGTH: 633
<212> TYPE: PRT
<213> ORGANISM: artificial sequence
<220> FEATURE:
<223> OTHER INFORMATION: TALEN alpha 2 R binding domain

<400> SEQUENCE: 87

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Asp Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Ala Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser Asn Ile Gly Gly Lys Gln Ala Leu Glu Thr Val Gln Arg
145                 150                 155                 160

Leu Leu Pro Val Leu Cys Gln Asp His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Asp
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Ala Gln Val Val Ala Ile Ala Ser Asn Gly Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser Asn Gly Gly Gly Lys
        275                 280                 285

Gln Ala Leu Glu Thr Val Gln Arg Leu Leu Pro Val Leu Cys Gln Asp
    290                 295                 300
```

His Gly Leu Thr Pro Glu Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Asp Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Ala Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Ser Asn Ile Gly Gly Lys Gln Ala Leu Glu Thr Val Gln Arg
            420                 425                 430

Leu Leu Pro Val Leu Cys Gln Asp His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Asp
465                 470                 475                 480

Gln Val Val Ala Ile Ala Ser Asn Ile Gly Gly Lys Gln Ala Leu Glu
                485                 490                 495

Thr Val Gln Arg Leu Leu Pro Val Leu Cys Gln Ala His Gly Leu Thr
            500                 505                 510

Pro Ala Gln Val Val Ala Ile Ala Ser His Asp Gly Gly Lys Gln Ala
        515                 520                 525

Leu Glu Thr Val Gln Arg Leu Leu Pro Val Leu Cys Gln Asp His Gly
    530                 535                 540

Leu Thr Pro Asp Gln Val Val Ala Ile Ala Ser Asn Ile Gly Gly Lys
545                 550                 555                 560

Gln Ala Leu Glu Thr Val Gln Arg Leu Leu Pro Val Leu Cys Gln Asp
                565                 570                 575

His Gly Leu Thr Pro Glu Gln Val Val Ala Ile Ala Ser Asn Gly Gly
            580                 585                 590

Gly Lys Gln Ala Leu Glu Thr Val Gln Arg Leu Leu Pro Val Leu Cys
        595                 600                 605

Gln Ala His Gly Leu Thr Pro Glu Gln Val Val Ala Ile Ala Ser Asn
    610                 615                 620

Gly Gly Gly Arg Pro Ala Leu Glu Ser
625                 630

<210> SEQ ID NO 88
<211> LENGTH: 633
<212> TYPE: PRT
<213> ORGANISM: artificial sequence
<220> FEATURE:
<223> OTHER INFORMATION: TALEN beta 1 L binding domain

<400> SEQUENCE: 88

Leu Thr Pro Asp Gln Val Val Ala Ile Ala Ser Asn Asn Gly Gly Lys
1               5                   10                  15

Gln Ala Leu Glu Thr Val Gln Arg Leu Leu Pro Val Leu Cys Gln Asp
                20                  25                  30

-continued

```
His Gly Leu Thr Pro Glu Gln Val Ala Ile Ala Ser Asn Gly Gly
         35                  40                  45

Gly Lys Gln Ala Leu Glu Thr Val Gln Arg Leu Leu Pro Val Leu Cys
 50                  55                  60

Gln Ala His Gly Leu Thr Pro Asp Gln Val Val Ala Ile Ala Ser Asn
 65                  70                  75                  80

Gly Gly Gly Lys Gln Ala Leu Glu Thr Val Gln Arg Leu Leu Pro Val
                 85                  90                  95

Leu Cys Gln Ala His Gly Leu Thr Pro Ala Gln Val Val Ala Ile Ala
                100                 105                 110

Ser His Asp Gly Gly Lys Gln Ala Leu Glu Thr Val Gln Arg Leu Leu
            115                 120                 125

Pro Val Leu Cys Gln Asp His Gly Leu Thr Pro Asp Gln Val Val Ala
            130                 135                 140

Ile Ala Ser His Asp Gly Gly Lys Gln Ala Leu Glu Thr Val Gln Arg
145                 150                 155                 160

Leu Leu Pro Val Leu Cys Gln Asp His Gly Leu Thr Pro Glu Gln Val
                165                 170                 175

Val Ala Ile Ala Ser His Asp Gly Gly Lys Gln Ala Leu Glu Thr Val
                180                 185                 190

Gln Arg Leu Leu Pro Val Leu Cys Gln Ala His Gly Leu Thr Pro Asp
            195                 200                 205

Gln Val Val Ala Ile Ala Ser Asn Ile Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Ala Gln Val Val Ala Ile Ala Ser His Asp Gly Gly Lys Gln Ala
                245                 250                 255

Leu Glu Thr Val Gln Arg Leu Leu Pro Val Leu Cys Gln Asp His Gly
                260                 265                 270

Leu Thr Pro Asp Gln Val Val Ala Ile Ala Ser His Asp Gly Gly Lys
            275                 280                 285

Gln Ala Leu Glu Thr Val Gln Arg Leu Leu Pro Val Leu Cys Gln Asp
290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Asp Gln Val Val Ala Ile Ala Ser Asn
            340                 345                 350

Asn Gly Gly Lys Gln Ala Leu Glu Thr Val Gln Arg Leu Leu Pro Val
            355                 360                 365

Leu Cys Gln Ala His Gly Leu Thr Pro Ala Gln Val Val Ala Ile Ala
370                 375                 380

Ser Asn Ile Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Asp His Gly Leu Thr Pro Glu Gln Val
            435                 440                 445

Val Ala Ile Ala Ser Asn Asn Gly Gly Lys Gln Ala Leu Glu Thr Val
```

```
                  450              455              460
Gln Arg Leu Leu Pro Val Leu Cys Gln Ala His Gly Leu Thr Pro Asp
465                 470                 475                 480

Gln Val Val Ala Ile Ala Ser Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Ala Gln Val Val Ala Ile Ala Ser His Asp Gly Gly Lys Gln Ala
        515                 520                 525

Leu Glu Thr Val Gln Arg Leu Leu Pro Val Leu Cys Gln Asp His Gly
    530                 535                 540

Leu Thr Pro Asp Gln Val Val Ala Ile Ala Ser Asn Asn Gly Gly Lys
545                 550                 555                 560

Gln Ala Leu Glu Thr Val Gln Arg Leu Leu Pro Val Leu Cys Gln Asp
                565                 570                 575

His Gly Leu Thr Pro Glu Gln Val Val Ala Ile Ala Ser His Asp Gly
            580                 585                 590

Gly Lys Gln Ala Leu Glu Thr Val Gln Arg Leu Leu Pro Val Leu Cys
        595                 600                 605

Gln Ala His Gly Leu Thr Pro Glu Gln Val Val Ala Ile Ala Ser Asn
    610                 615                 620

Gly Gly Gly Arg Pro Ala Leu Glu Ser
625                 630

<210> SEQ ID NO 89
<211> LENGTH: 633
<212> TYPE: PRT
<213> ORGANISM: artificial sequence
<220> FEATURE:
<223> OTHER INFORMATION: TALEN beta 1 R binding domain

<400> SEQUENCE: 89

Leu Thr Pro Asp Gln Val Val Ala Ile Ala Ser Asn Asn Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Glu Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Asp Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Ala Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Asp His Gly Leu Thr Pro Glu Gln Val
                165                 170                 175

Val Ala Ile Ala Ser Asn Ile Gly Gly Lys Gln Ala Leu Glu Thr Val
```

```
              180              185              190
Gln Arg Leu Leu Pro Val Leu Cys Gln Ala His Gly Leu Thr Pro Asp
        195                 200                 205

Gln Val Val Ala Ile Ala Ser Asn Asn Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Ala Gln Val Val Ala Ile Ala Ser Asn Ile Gly Gly Lys Gln Ala
                    245                 250                 255

Leu Glu Thr Val Gln Arg Leu Leu Pro Val Leu Cys Gln Asp His Gly
                260                 265                 270

Leu Thr Pro Asp Gln Val Val Ala Ile Ala Ser Asn Gly Gly Gly Lys
            275                 280                 285

Gln Ala Leu Glu Thr Val Gln Arg Leu Leu Pro Val Leu Cys Gln Asp
        290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                    325                 330                 335

Gln Ala His Gly Leu Thr Pro Asp Gln Val Val Ala Ile Ala Ser Asn
                340                 345                 350

Gly Gly Gly Lys Gln Ala Leu Glu Thr Val Gln Arg Leu Leu Pro Val
            355                 360                 365

Leu Cys Gln Ala His Gly Leu Thr Pro Ala Gln Val Val Ala Ile Ala
        370                 375                 380

Ser His Asp Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                    405                 410                 415

Ile Ala Ser Asn Gly Gly Gly Lys Gln Ala Leu Glu Thr Val Gln Arg
                420                 425                 430

Leu Leu Pro Val Leu Cys Gln Asp His Gly Leu Thr Pro Glu Gln Val
            435                 440                 445

Val Ala Ile Ala Ser Asn Asn Gly Gly Lys Gln Ala Leu Glu Thr Val
        450                 455                 460

Gln Arg Leu Leu Pro Val Leu Cys Gln Ala His Gly Leu Thr Pro Asp
465                 470                 475                 480

Gln Val Val Ala Ile Ala Ser His Asp Gly Gly Lys Gln Ala Leu Glu
                    485                 490                 495

Thr Val Gln Arg Leu Leu Pro Val Leu Cys Gln Ala His Gly Leu Thr
                500                 505                 510

Pro Ala Gln Val Val Ala Ile Ala Ser Asn Gly Gly Lys Gln Ala
            515                 520                 525

Leu Glu Thr Val Gln Arg Leu Leu Pro Val Leu Cys Gln Asp His Gly
        530                 535                 540

Leu Thr Pro Asp Gln Val Val Ala Ile Ala Ser Asn Gly Gly Gly Lys
545                 550                 555                 560

Gln Ala Leu Glu Thr Val Gln Arg Leu Leu Pro Val Leu Cys Gln Asp
                    565                 570                 575

His Gly Leu Thr Pro Glu Gln Val Val Ala Ile Ala Ser His Asp Gly
                580                 585                 590

Gly Lys Gln Ala Leu Glu Thr Val Gln Arg Leu Leu Pro Val Leu Cys
            595                 600                 605
```

```
Gln Ala His Gly Leu Thr Pro Glu Gln Val Val Ala Ile Ala Ser Asn
    610                 615                 620

Gly Gly Gly Arg Pro Ala Leu Glu Ser
625                 630

<210> SEQ ID NO 90
<211> LENGTH: 633
<212> TYPE: PRT
<213> ORGANISM: artificial sequence
<220> FEATURE:
<223> OTHER INFORMATION: TALEN beta 3 L binding domain

<400> SEQUENCE: 90

Leu Thr Pro Asp Gln Val Val Ala Ile Ala Ser Asn Asn Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Glu Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Asp Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Ala Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Asp His Gly Leu Thr Pro Glu Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Asp
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Ala Gln Val Val Ala Ile Ala Ser Asn Asn Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser His Asp Gly Gly Lys
        275                 280                 285

Gln Ala Leu Glu Thr Val Gln Arg Leu Leu Pro Val Leu Cys Gln Asp
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335
```

Gln Ala His Gly Leu Thr Pro Asp Gln Val Val Ala Ile Ala Ser Asn
                        340                 345                 350

Ile Gly Gly Lys Gln Ala Leu Glu Thr Val Gln Arg Leu Leu Pro Val
                355                 360                 365

Leu Cys Gln Ala His Gly Leu Thr Pro Ala Gln Val Val Ala Ile Ala
        370                 375                 380

Ser His Asp Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Ser Asn Ile Gly Gly Lys Gln Ala Leu Glu Thr Val Gln Arg
                420                 425                 430

Leu Leu Pro Val Leu Cys Gln Asp His Gly Leu Thr Pro Glu Gln Val
                435                 440                 445

Val Ala Ile Ala Ser Asn Asn Gly Gly Lys Gln Ala Leu Glu Thr Val
            450                 455                 460

Gln Arg Leu Leu Pro Val Leu Cys Gln Ala His Gly Leu Thr Pro Asp
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
                500                 505                 510

Pro Ala Gln Val Val Ala Ile Ala Ser His Asp Gly Gly Lys Gln Ala
                515                 520                 525

Leu Glu Thr Val Gln Arg Leu Leu Pro Val Leu Cys Gln Asp His Gly
        530                 535                 540

Leu Thr Pro Asp Gln Val Val Ala Ile Ala Ser Asn Gly Gly Gly Lys
545                 550                 555                 560

Gln Ala Leu Glu Thr Val Gln Arg Leu Leu Pro Val Leu Cys Gln Asp
                565                 570                 575

His Gly Leu Thr Pro Glu Gln Val Val Ala Ile Ala Ser Asn Gly Gly
                580                 585                 590

Gly Lys Gln Ala Leu Glu Thr Val Gln Arg Leu Leu Pro Val Leu Cys
                595                 600                 605

Gln Ala His Gly Leu Thr Pro Glu Gln Val Val Ala Ile Ala Ser His
                610                 615                 620

Asp Gly Gly Arg Pro Ala Leu Glu Ser
625                 630

<210> SEQ ID NO 91
<211> LENGTH: 633
<212> TYPE: PRT
<213> ORGANISM: artificial sequence
<220> FEATURE:
<223> OTHER INFORMATION: TALEN beta 3 R binding domain

<400> SEQUENCE: 91

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
                20                  25                  30

His Gly Leu Thr Pro Glu Gln Val Val Ala Ile Ala Ser Asn Ile Gly
            35                  40                  45

Gly Lys Gln Ala Leu Glu Thr Val Gln Arg Leu Leu Pro Val Leu Cys
        50                  55                  60

```
Gln Ala His Gly Leu Thr Pro Asp Gln Val Val Ala Ile Ala Ser His
 65                  70                  75                  80

Asp Gly Gly Lys Gln Ala Leu Glu Thr Val Gln Arg Leu Leu Pro Val
                 85                  90                  95

Leu Cys Gln Ala His Gly Leu Thr Pro Ala Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Asp His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Arg Leu Leu Pro Val Leu Cys Gln Ala His Gly Leu Thr Pro Asp
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Ala Gln Val Val Ala Ile Ala Ser His Asp Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser Asn Ile Gly Gly Lys
        275                 280                 285

Gln Ala Leu Glu Thr Val Gln Arg Leu Leu Pro Val Leu Cys Gln Asp
    290                 295                 300

His Gly Leu Thr Pro Glu Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Asp Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Ala Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Asp His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Arg Leu Leu Pro Val Leu Cys Gln Ala His Gly Leu Thr Pro Asp
465                 470                 475                 480
```

```
Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Ala Gln Val Val Ala Ile Ala Ser His Asp Gly Gly Lys Gln Ala
        515                 520                 525

Leu Glu Thr Val Gln Arg Leu Leu Pro Val Leu Cys Gln Asp His Gly
    530                 535                 540

Leu Thr Pro Asp Gln Val Val Ala Ile Ala Ser Asn Gly Gly Gly Lys
545                 550                 555                 560

Gln Ala Leu Glu Thr Val Gln Arg Leu Leu Pro Val Leu Cys Gln Asp
                565                 570                 575

His Gly Leu Thr Pro Glu Gln Val Val Ala Ile Ala Ser His Asp Gly
            580                 585                 590

Gly Lys Gln Ala Leu Glu Thr Val Gln Arg Leu Leu Pro Val Leu Cys
        595                 600                 605

Gln Ala His Gly Leu Thr Pro Glu Gln Val Val Ala Ile Ala Ser His
    610                 615                 620

Asp Gly Gly Arg Pro Ala Leu Glu Ser
625                 630

<210> SEQ ID NO 92
<211> LENGTH: 9
<212> TYPE: PRT
<213> ORGANISM: artificial sequence
<220> FEATURE:
<223> OTHER INFORMATION: QYD peptide

<400> SEQUENCE: 92

Gln Tyr Asp Pro Val Ala Ala Leu Phe
1               5

<210> SEQ ID NO 93
<211> LENGTH: 13
<212> TYPE: PRT
<213> ORGANISM: Homo sapiens

<400> SEQUENCE: 93

Cys Ala Glu Thr Pro Thr Asn Asp Tyr Lys Leu Ser Phe
1               5                   10

<210> SEQ ID NO 94
<211> LENGTH: 8
<212> TYPE: PRT
<213> ORGANISM: Homo sapiens

<400> SEQUENCE: 94

Ser Ser Gly Asn Gln Phe Tyr Phe
1               5

<210> SEQ ID NO 95
<211> LENGTH: 11
<212> TYPE: PRT
<213> ORGANISM: Homo sapiens

<400> SEQUENCE: 95

Cys Ala Asp Tyr Tyr Gly Gln Asn Phe Val Phe
1               5                   10

<210> SEQ ID NO 96
<211> LENGTH: 16
```

<212> TYPE: PRT
<213> ORGANISM: Homo sapiens

<400> SEQUENCE: 96

Cys Ala Ser Ser Glu Thr Glu Leu Leu Tyr Tyr Gly Tyr Thr Phe
1               5                   10                  15

<210> SEQ ID NO 97
<211> LENGTH: 15
<212> TYPE: PRT
<213> ORGANISM: Homo sapiens

<400> SEQUENCE: 97

Cys Ala Ser Ser Gln Gln Thr Gly Thr Ile Gly Gly Tyr Thr Phe
1               5                   10                  15

<210> SEQ ID NO 98
<211> LENGTH: 13
<212> TYPE: PRT
<213> ORGANISM: Homo sapiens

<400> SEQUENCE: 98

Cys Ala Ser Ser Phe Gln Gly Phe Thr Glu Ala Phe Phe
1               5                   10

<210> SEQ ID NO 99
<211> LENGTH: 11
<212> TYPE: PRT
<213> ORGANISM: Homo sapiens

<400> SEQUENCE: 99

Cys Ala Ser Pro Thr Gly Asn Gln Phe Tyr Phe
1               5                   10

<210> SEQ ID NO 100
<211> LENGTH: 13
<212> TYPE: PRT
<213> ORGANISM: Homo sapiens

<400> SEQUENCE: 100

Cys Ala Glu Ile Pro Ser Asn Asp Tyr Lys Leu Ser Phe
1               5                   10

<210> SEQ ID NO 101
<211> LENGTH: 11
<212> TYPE: PRT
<213> ORGANISM: Homo sapiens

<400> SEQUENCE: 101

Cys Ala Ser Gly Ser Gln Gly Asn Leu Ile Phe
1               5                   10

<210> SEQ ID NO 102
<211> LENGTH: 14
<212> TYPE: PRT
<213> ORGANISM: Homo sapiens

<400> SEQUENCE: 102

Cys Ala Gly Leu Thr Thr Asp Ser Trp Gly Lys Phe Gln Phe
1               5                   10

<210> SEQ ID NO 103
<211> LENGTH: 12
<212> TYPE: PRT
<213> ORGANISM: Homo sapiens

```
<400> SEQUENCE: 103

Cys Ala Thr Tyr Leu Thr Gly Asn Gln Phe Tyr Phe
1               5                   10

<210> SEQ ID NO 104
<211> LENGTH: 11
<212> TYPE: PRT
<213> ORGANISM: Homo sapiens

<400> SEQUENCE: 104

Cys Ala Val Cys Asn Phe Asn Lys Phe Tyr Phe
1               5                   10

<210> SEQ ID NO 105
<211> LENGTH: 16
<212> TYPE: PRT
<213> ORGANISM: Homo sapiens

<400> SEQUENCE: 105

Cys Ala Ser Ser Phe Thr Leu Gly Thr Gly Gly Val Glu Gln Tyr Phe
1               5                   10                  15

<210> SEQ ID NO 106
<211> LENGTH: 13
<212> TYPE: PRT
<213> ORGANISM: Homo sapiens

<400> SEQUENCE: 106

Cys Ser Ala Arg Gly Gln Asp Ile Tyr Glu Gln Tyr Phe
1               5                   10

<210> SEQ ID NO 107
<211> LENGTH: 14
<212> TYPE: PRT
<213> ORGANISM: Homo sapiens

<400> SEQUENCE: 107

Cys Ala Ser Gly Leu Thr Gly Phe Met Asp Glu Gln Tyr Phe
1               5                   10

<210> SEQ ID NO 108
<211> LENGTH: 16
<212> TYPE: PRT
<213> ORGANISM: Homo sapiens

<400> SEQUENCE: 108

Cys Ala Ser Ser Val Asp Val Ala Gly Gly Tyr Asn Glu Gln Phe Phe
1               5                   10                  15

<210> SEQ ID NO 109
<211> LENGTH: 13
<212> TYPE: PRT
<213> ORGANISM: Homo sapiens

<400> SEQUENCE: 109

Cys Ala Ser Ser Gln Ala Leu Pro Tyr Glu Gln Tyr Phe
1               5                   10

<210> SEQ ID NO 110
<211> LENGTH: 16
<212> TYPE: PRT
<213> ORGANISM: Homo sapiens

<400> SEQUENCE: 110
```

Cys Ala Ser Ser Ile Thr Leu Gly Thr Gly Gly Val Glu Gln Tyr Phe
1               5                   10                  15

<210> SEQ ID NO 111
<211> LENGTH: 34
<212> TYPE: PRT
<213> ORGANISM: artificial sequence
<220> FEATURE:
<223> OTHER INFORMATION: Exemplary amino acid sequence of Platinum
      TALEN DNA binding module

<400> SEQUENCE: 111

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 112
<211> LENGTH: 34
<212> TYPE: PRT
<213> ORGANISM: artificial sequence
<220> FEATURE:
<223> OTHER INFORMATION: Exemplary amino acid sequence of Platinum
      TALEN DNA binding module

<400> SEQUENCE: 112

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 113
<211> LENGTH: 34
<212> TYPE: PRT
<213> ORGANISM: artificial sequence
<220> FEATURE:
<223> OTHER INFORMATION: Exemplary amino acid sequence of Platinum
      TALEN DNA binding module

<400> SEQUENCE: 113

Leu Thr Pro Ala Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 114
<211> LENGTH: 34
<212> TYPE: PRT
<213> ORGANISM: artificial sequence
<220> FEATURE:
<223> OTHER INFORMATION: Exemplary amino acid sequence of Zhang TALEN
      DNA binding module

<400> SEQUENCE: 114

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 115
<211> LENGTH: 9
<212> TYPE: PRT
<213> ORGANISM: artificial sequence
<220> FEATURE:
<223> OTHER INFORMATION: HLA-A*0201-restricted NY-ESO-1157-165

<400> SEQUENCE: 115

Ser Leu Leu Met Trp Ile Thr Gln Cys
1               5

<210> SEQ ID NO 116
<211> LENGTH: 15
<212> TYPE: PRT
<213> ORGANISM: artificial sequence
<220> FEATURE:
<223> OTHER INFORMATION: 1G4 TCRA CDR3

<400> SEQUENCE: 116

Cys Ala Val Arg Pro Thr Ser Gly Gly Ser Tyr Ile Pro Thr Phe
1               5                   10                  15

<210> SEQ ID NO 117
<211> LENGTH: 14
<212> TYPE: PRT
<213> ORGANISM: artificial sequence
<220> FEATURE:
<223> OTHER INFORMATION: 1G4 TCRB CDR3

<400> SEQUENCE: 117

Cys Ala Ser Ser Tyr Val Gly Asn Thr Gly Glu Leu Phe Phe
1               5                   10

<210> SEQ ID NO 118
<211> LENGTH: 497
<212> TYPE: DNA
<213> ORGANISM: artificial sequence
<220> FEATURE:
<223> OTHER INFORMATION: 1G4 TCR Va casette

<400> SEQUENCE: 118
tggaggagaa ccctggacct atggagaccc tcttgggcct gctgatcctg tggctgcagc      60
tgcagtgggt gagcagcaag caggaggtga cccagattcc tgccgccctg agcgtgcctg     120
aaggcgagaa tctggtgctg aactgcagct tcaccgacag cgccatctac aacctgcagt     180
ggttcagaca ggaccccggc aagggcctga ccagcctgct gctgatccag agcagccaga     240
gagagcagac cagcggcaga ctgaacgcca gcctggacaa gagcagcggc agaagcaccc     300
tgtatatcgc cgccagccag ccaggcgata gcgccaccta cctgtgtgcc gtgagaccaa     360
ccagcggcgg cagctatatc cccacctttg gcagaggcac cagcctgatc gtgcacccct     420
acatccagaa ccccgacccc gccgtgtacc agctgagaga ctctaaatcc agtgacaagt     480
ctgtctgcct attcacc                                                   497

<210> SEQ ID NO 119
<211> LENGTH: 582
<212> TYPE: DNA
<213> ORGANISM: artificial sequence
<220> FEATURE:
<223> OTHER INFORMATION: 1G4 TCR Vb casette

<400> SEQUENCE: 119
tgccggatct agctagttaa ttaaggatcc gaattcctgc aggatgagca tcggcctgct      60

-continued

```
gtgttgtgcc gccctgtctc tgctgtgggc tggaccagtg aatgccggcg tgacacagac    120
ccctaagttc caggtgctga agaccggcca gagcatgacc ctgcagtgcg cccaggacat    180
gaaccacgag tacatgagct ggtacagaca ggaccccggc atgggcctga gactgatcca    240
ctacagcgtg ggcgccggaa tcacagacca gggcgaggtg ccaaacggct acaacgtgag    300
cagaagcacc accgaggatt tcccactgag actgctgtct gccgccccaa gccagaccag    360
cgtgtacttt tgcgccagca gctacgtggg caacaccggc gagctgttct cggcgaggg    420 cagcagactg accgtgctgg aggacctgaa gaacgtgttc cctcctgagg tggccgtgtt    480
tgagccaagc gaggccgaga tcagccacac ccaaaaggcc acactggtgt gcctggccac    540
aggcttcttc cccgaccacg tggagctgag ctggtgggtg aa                      582
```

<210> SEQ ID NO 120
<211> LENGTH: 60
<212> TYPE: DNA
<213> ORGANISM: artificial sequence
<220> FEATURE:
<223> OTHER INFORMATION: nucleotide sequence in figures 24 and 25

<400> SEQUENCE: 120

```
gtctgtctgc ctattcaccg attttgattc tcaaacaaat gtgtcacaaa gtaaggattc     60
```

<210> SEQ ID NO 121
<211> LENGTH: 60
<212> TYPE: DNA
<213> ORGANISM: artificial sequence
<220> FEATURE:
<223> OTHER INFORMATION: nucleotide sequence in figures 24 and 25

<400> SEQUENCE: 121

```
cagacagacg gataagtggc taaaactaag agtttgttta cacagtgttt cattcctaag     60
```

<210> SEQ ID NO 122
<211> LENGTH: 60
<212> TYPE: DNA
<213> ORGANISM: artificial sequence
<220> FEATURE:
<223> OTHER INFORMATION: nucleotide sequence in figures 24 and 25

<400> SEQUENCE: 122

```
gtctgtctgc ctattcaccg attgaagatt ttgattcaat gtgtcacaaa gtaaggattc     60
```

<210> SEQ ID NO 123
<211> LENGTH: 60
<212> TYPE: DNA
<213> ORGANISM: artificial sequence
<220> FEATURE:
<223> OTHER INFORMATION: nucleotide sequence in figures 24 and 25

<400> SEQUENCE: 123

```
cagacagacg gataagtggc taacttctaa aactaagtta cacagtgttt cattcctaag     60
```

<210> SEQ ID NO 124
<211> LENGTH: 60
<212> TYPE: DNA
<213> ORGANISM: artificial sequence
<220> FEATURE:
<223> OTHER INFORMATION: nucleotide sequence in figures 24 and 25

<400> SEQUENCE: 124

```
gtctgtctgc ctattcaccg attcaaacaa atgtgttaat gtgtcacaaa gtaaggattc     60
```

<210> SEQ ID NO 125
<211> LENGTH: 60
<212> TYPE: DNA
<213> ORGANISM: artificial sequence
<220> FEATURE:
<223> OTHER INFORMATION: nucleotide sequence in figures 24 and 25

<400> SEQUENCE: 125
cagacagacg gataagtggc taagtttgtt tacacaatta cacagtgttt cattcctaag        60

<210> SEQ ID NO 126
<211> LENGTH: 53
<212> TYPE: DNA
<213> ORGANISM: artificial sequence
<220> FEATURE:
<223> OTHER INFORMATION: nucleotide sequence in figures 24 and 25

<400> SEQUENCE: 126
gtctgtctgc ctattcaccg attttgattc aatgtgtcac aaagtaagga ttc              53

<210> SEQ ID NO 127
<211> LENGTH: 53
<212> TYPE: DNA
<213> ORGANISM: artificial sequence
<220> FEATURE:
<223> OTHER INFORMATION: nucleotide sequence in figures 24 and 25

<400> SEQUENCE: 127
cagacagacg gataagtggc taaaactaag ttacacagtg tttcattcct aag              53

<210> SEQ ID NO 128
<211> LENGTH: 52
<212> TYPE: DNA
<213> ORGANISM: artificial sequence
<220> FEATURE:
<223> OTHER INFORMATION: nucleotide sequence in figures 24 and 25

<400> SEQUENCE: 128
gtctgtctgc ctattcaccg attcaaacaa atgtgtcaca aagtaaggat tc               52

<210> SEQ ID NO 129
<211> LENGTH: 52
<212> TYPE: DNA
<213> ORGANISM: artificial sequence
<220> FEATURE:
<223> OTHER INFORMATION: nucleotide sequence in figures 24 and 25

<400> SEQUENCE: 129
cagacagacg gataagtggc taagtttgtt tacacagtgt ttcattccta ag               52

<210> SEQ ID NO 130
<211> LENGTH: 18
<212> TYPE: DNA
<213> ORGANISM: Mus musculus

<400> SEQUENCE: 130
tctgcctgtt caccgact                                                     18

<210> SEQ ID NO 131
<211> LENGTH: 20
<212> TYPE: DNA
<213> ORGANISM: Mus musculus

<400> SEQUENCE: 131
aatgtgccga aaaccatgga                                                   20

```
<210> SEQ ID NO 132
<211> LENGTH: 20
<212> TYPE: DNA
<213> ORGANISM: Mus musculus

<400> SEQUENCE: 132
tgactccacc caaggtctcc                                              20

<210> SEQ ID NO 133
<211> LENGTH: 20
<212> TYPE: DNA
<213> ORGANISM: Mus musculus

<400> SEQUENCE: 133
aaaagcagag attgcaaaca                                              20

<210> SEQ ID NO 134
<211> LENGTH: 20
<212> TYPE: DNA
<213> ORGANISM: Mus musculus

<400> SEQUENCE: 134
tgtgcttggc cagggcttc                                               20

<210> SEQ ID NO 135
<211> LENGTH: 20
<212> TYPE: DNA
<213> ORGANISM: Mus musculus

<400> SEQUENCE: 135
ggagctgagc tggtgggtga                                              20
```